US012460002B2

(12) United States Patent
Van Loo

(10) Patent No.: US 12,460,002 B2
(45) Date of Patent: Nov. 4, 2025

(54) CD3 BINDING MOLECULES

(71) Applicant: Merus N.V., Utrecht (NL)

(72) Inventor: Pieter Fokko Van Loo, Utrecht (NL)

(73) Assignee: Merus N.V., Utrecht (NL)

( * ) Notice: Subject to any disclaimer, the term of this patent is extended or adjusted under 35 U.S.C. 154(b) by 905 days.

(21) Appl. No.: 17/438,768

(22) PCT Filed: Mar. 27, 2020

(86) PCT No.: PCT/NL2020/050214
§ 371 (c)(1),
(2) Date: Sep. 13, 2021

(87) PCT Pub. No.: WO2020/204708
PCT Pub. Date: Oct. 8, 2020

(65) Prior Publication Data
US 2022/0356251 A1 Nov. 10, 2022

(30) Foreign Application Priority Data

Mar. 29, 2019 (EP) .................................... 19166345
Oct. 1, 2019 (EP) .................................... 19200931

(51) Int. Cl.
*C07K 16/28* (2006.01)
*A61P 35/00* (2006.01)

(52) U.S. Cl.
CPC .......... *C07K 16/2809* (2013.01); *A61P 35/00* (2018.01); *C07K 16/283* (2013.01); *C07K 16/2863* (2013.01); *C07K 2317/31* (2013.01); *C07K 2317/524* (2013.01); *C07K 2317/526* (2013.01); *C07K 2317/53* (2013.01);
(Continued)

(58) Field of Classification Search
CPC .. C07K 16/28; C07K 16/283; C07K 16/2863; C07K 2317/31; C07K 2317/524; C07K 2317/526; C07K 2317/53; C07K 2317/55; C07K 2317/565; C07K 2317/92;
(Continued)

(56) References Cited

U.S. PATENT DOCUMENTS 9,248,181 B2 2/2016 De Kruif et al.
9,358,286 B2 6/2016 De Kruif et al.
2014/0088295 A1 3/2014 Smith et al.

FOREIGN PATENT DOCUMENTS

CN 108026174 A 5/2018
EP 2604625 A1 6/2013
(Continued)

OTHER PUBLICATIONS

Lewandowska, A.M., et al.(2017) Environmental risk factors for cancer—review paper Ann. Agric. Environ. Med. 26(1); 1-7 (Year: 2017).*
(Continued)

*Primary Examiner* — Scarlett Y Goon
*Assistant Examiner* — Audrey L Buttice
(74) *Attorney, Agent, or Firm* — Sterne, Kessler, Goldstein & Fox P.L.L.C.

(57) ABSTRACT

The invention relates to heavy chain variable regions, binding domains and antibodies specific for human CD3, and CD3 binding proteins. The invention further relates to the use of a CD3 binding protein, preferably an antibody, of the invention in the treatment of cancer or autoimmune disease.

30 Claims, 57 Drawing Sheets

Specification includes a Sequence Listing.

(52) U.S. Cl.
CPC .... *C07K 2317/55* (2013.01); *C07K 2317/565* (2013.01); *C07K 2317/92* (2013.01)

(58) Field of Classification Search
CPC ............ C07K 2317/21; C07K 2317/73; C07K 2317/24; A61P 35/00; A61K 2039/505
See application file for complete search history.

(56) References Cited

FOREIGN PATENT DOCUMENTS

| | | | | |
|---|---|---|---|---|
| EP | 3115376 | A1 | 1/2017 | |
| JP | 2019506398 | A | 3/2019 | |
| WO | WO-2004009618 | A2 | 1/2004 | |
| WO | WO-2005118635 | A2 | 12/2005 | |
| WO | WO-2007145941 | A2 | 12/2007 | |
| WO | WO-2008027236 | A2 | 3/2008 | |
| WO | WO-2009126920 | A2 | 10/2009 | |
| WO | WO-2009015777 | A1 | 12/2009 | |
| WO | WO-2009157771 | A2 | 12/2009 | |
| WO | WO-2010108127 | A1 | 9/2010 | |
| WO | WO-2013157953 | A1 | 10/2013 | |
| WO | WO-2013157954 | A1 | 10/2013 | |
| WO | WO-2014051433 | A1 | 4/2014 | |
| WO | WO-2016210365 | A2 * | 12/2016 | ......... A61K 39/0011 |
| WO | WO-2017010874 | A1 | 1/2017 | |
| WO | WO-2017125831 | A1 | 7/2017 | |
| WO | WO-2019190327 | A2 | 10/2019 | |

OTHER PUBLICATIONS

DeCensi, A., et al (2015) Barriers to preventative therapy for breast and other major cancers and strategies to improve uptake ecancer 9(595); 1-12 (Year: 2015).*

Rosenblum, M.D., et al (2015) Mechanisms of human autoimmunity J Clin Invest 125(6); 2228-2233 (Year: 2015).*

Chiu, M.L., et al (2019) Antibody structure and function: The basis for engineering therapeutics Antibodies 8(55); 1-80 (Year: 2019).*

Rabia, L., et al (2018) Understanding and overcoming trade-offs between antibody affinity, specificity, stability, and solubility Biochem Eng. J. 15(137); 365-374 (Year: 2018).*

Bakker, A,B.H., et al., "C-Type Lectin-Like Molecule-1: A Novel Myeloid Cell Surface Marker Associated with Acute Myeloid Leukemia," Cancer Research, 64(22):8443-8450, American Association for Cancer Research, United States (Nov. 2004).

Chen, C.H., et al., "Dendritic-cell-associated C-type Lectin 2 (DCAL-2) Alters Dendritic-cell Maturation and Cytokine Production," Blood 107(4): 1459-1467, American Society of Hematology, United States (Feb. 2006).

De Haard, H.J., et al., "A Large Non-immunized Human Fab Fragment Phage Library That Permits Rapid Isolation and Kinetic Analysis of High Affinity Antibodies," Journal of Biological Chemistry 274(26):18218-18230, American Society for Biochemistry and Molecular Biology, United States (Jun. 1999).

Genbank, "*Homo sapiens* C-Type Lectin Protein CLL-1 mRNA, Complete Cds," Accession No. AF247788, accessed at https://www.ncbi.nlm.nih.gov/nuccore/AF247788, 1 page, (2000).

GenBank, "*Homo sapiens* Dendritic Cell Associated Lectin 2 mRNA, Complete Cds," Accession No. AY426759., accessed at https://www.ncbi.nlm.nih.gov/nuccore/AY426759.1, 1 page.

GenBank, "*Homo sapiens* chromosome 12, GRCh38.p14 Primary Assembly," ncbi.nlm.nih. gov, Accession No. NC_000012.12, accessed at <URL:https://www.ncbi.nlm.nih.gov/nuccore/NC_000012.12>, on Jul. 11, 2022, 3 pages.

GenBank, "*Homo sapiens* chromosome 12, alternate assembly CHM1_1.1, whole genome shotgun sequence," ncbi.nlm.nih.gov, Accession No. NC_018923.2, accessed at <URL:https://www.ncbi.nlm.nih.gov/nuccore/NC_018923.2?report=genbank>, on Jul. 11, 2022, 2 pages.

GenBank, "leucine-rich repeat-containing G-protein coupled receptor 5 isoform 2 precursor [*Homo sapiens*]," ncbi.nlm.nih.gov, Accession No. NP_001264155.1, accessed at <URL:https://www.ncbi.nlm.nih.gov/nuccore/NP_001264155.1>, on Jul. 11, 2022, 4 pages.

GenBank, "leucine-rich repeat-containing G-protein coupled receptor 5 isoform 3 precursor [*Homo sapiens*]," ncbi.nlm.nih.gov, Accession No. NP_001264156.1, accessed at <URL:https://www.ncbi.nlm.nih.gov/nuccore/NP_001264156.1>, on Jul. 11, 2022, 4 pages.

GenBank, "leucine-rich repeat-containing G-protein coupled receptor 5 isoform 1 precursor [*Homo sapiens*]," ncbi.nlm.nih.gov, Accession No. NP_003658.1, accessed at <URL:https://www.ncbi.nlm.nih.gov/nuccore/NP_003658.1>, on Jul. 11, 2022, 4 pages.

GenBank, "*Homo sapiens* chromosome 12 genomic scaffold, GRCh38.p14 Primary Assembly HSCHR12_CTG2_1," ncbi.nlm.nih.gov, Accession No. NT_029419.13, accessed at <URL:https://www.ncbi.nlm.nih.gov/nuccore/NT_029419.13>, on Jul. 11, 2022, 9 pages.

Han, Y., et al., "KLRLI, a novel killer celllectin like receptor, inhibits natural killer cell cytotoxicity," Blood, 104(9): 2858-2866, The American Society of Hematology, United States (2004).

Junttila, T.T., et al., "Superior In vivo Efficacy of Afucosylated Trastuzumab in the Treatment of HER2-Amplified Breast Cancer," Cancer Research, 70(11): 4481-4489, American Association for Cancer Research, United States (2010).

Kruskal, J. B., and Liberman, M., "Chapter Four—The Symmetric Time-Warping Problem: From Continuous to Discrete," in *Time Warps, String Edits, and Macromolecules: The Theory and Practice of Sequence Comparison*, Sankoff, D., and Kruskal, J. B., eds., Addison-Wesley Publishing Company, Inc., United States, 38 pages (1983).

Marks, J.D., et al., "By-passing Immunization. Human Antibodies from V-gene Libraries Displayed on Phage," Journal of Molecular Biology 222(3):581-597, Academic Press Limited, United States (Dec. 1991).

Marshall, A.S., et al., "Identification and Characterization of a Novel Human Myeloid Inhibitory C-type Lectin-like Receptor (MICL) That is Predominantly Expressed on Granulocytes and Monocytes," The Journal of Biological Chemistry 279(15):14792-14802, American Society for Biochemistry and Molecular Biology, United States (Apr. 2004).

Morrison, S.L., "Two Heads are Better Than One," Nature Biotechnology 25(11):1233-1234, Nature America Publishing, United States (Nov. 2007).

Moshaver, B., et al., "Identification of a Small Subpopulation of Candidate Leukemia-initiating Cells in the Side Population of Patients With Acute Myeloid Leukemia," Stem Cells 26(12):3059-3067, AlphaMed Press, United States (Dec. 2008).

Schaefer, G., et al., "A Two-in-one Antibody Against Her3 and Egfr Has Superior Inhibitory Activity Compared With Monospecific Antibodies," Cancer Cell 20(4):472-486, Cell Press, United States (Oct. 2011).

Spiess, C., et al., "Alternative Molecular Formats and Therapeutic Applications for Bispecific Antibodies," Molecular Immunology 67(2 Pt A):95-106, Pergamon Press, United Kingdom (Oct. 2015).

Thompson, J.D., et al., "Clustal W: Improving the Sensitivity of Progressive Multiple Sequence Alignment through Sequence Weighting, Position-specific Gap Penalties and Weight Matrix Choice," Nucleic Acids Research 22(22):4673-4680, Oxford University Press, United Kingdom (Nov. 1994).

Toft-Petersen, M., et al., "Unravelling the Relevance of Clec12a as a Cancer Stem Cell Marker in Myelodysplastic Syndrome," British Journal of Haematology 175(3):393-401, Wiley-Blackwell, United Kingdom (Nov. 2016).

UniProtKB, "Cell division cycle protein 123 homolog," UniProt.org, Accession No. O75794, accessed at <URL:https://www.uniprot.org/uniprotkb/075794/entry>, on Jul. 11, 2022, 6 pages.

UniProtKB, "Epidermal growth factor receptor," UniProt.org, Accession No. P00533, accessed at <URL:https://www.uniprot.org/uniprotkb/P00533/entry>, on Jul. 11, 2022, 13 pages.

UniProtKB, "T-cell surface glycoprotein CD3 delta chain," UniProt.org, Accession No. P04234, accessed at <URL:https://www.uniprot.org/uniprotkb/P04234/entry>, on Jul. 11, 2022, 9 pages.

UniProtKB, "Receptor tyrosine-protein kinase erbB-2," UniProt.org, Accession No. P04626, accessed at <URL:https://www.uniprot.org/uniprotkb/P04626/entry>, on Jul. 11, 2022, 14 pages.

(56) References Cited

OTHER PUBLICATIONS

UniProtKB, "Carcinoembryonic antigen-related cell adhesion molecule 5," UniProt.org, Accession No. P06731, accessed at <URL:https://www.uniprot.org/uniprotkb/P06731/entry>, on Jul. 11, 2022, 9 pages.
UniProtKB, "T-cell surface glycoprotein CD3 epsilon chain," UniProt.org, Accession No. P07766, accessed at <URL:https://www.uniprot.org/uniprotkb/P07766/entry>, on Jul. 11, 2022, 9 pages.
UniProtKB, "T-cell surface glycoprotein CD3 gamma chain," UniProt.org, Accession No. P09693, accessed at <URL:https://www.uniprot.org/uniprotkb/P09693/entry>, on Jul. 11, 2022, 9 pages.
UniProtKB, "B-lymphocyte antigen CD20," UniProt.org, Accession No. P11836, accessed at <URL:https://www.uniprot.org/uniprotkb/P11836/entry>, on Jul. 11, 2022, 10 pages.
UniProtKB, "Folate receptor alpha," UniProt.org, Accession No. P15328, accessed at <URL:https://www.uniprot.org/uniprotkb/P15328/entry>, on Jul. 11, 2022, 9 pages.
UniProtKB, "B-lymphocyte antigen CD19," UniProt.org, Accession No. P15391, accessed at <URL:https://www.uniprot.org/uniprotkb/P15391/entry>, on Jul. 11, 2022, 9 pages.
UniProtKB, "CD44 antigen," UniProt.org, Accession No. P16070, accessed at <URL:https://www.uniprot.org/uniprotkb/P16070/entry>, on Jul. 11, 2022, 13 pages.
UniProtKB, "Epithelial cell adhesion molecule," UniProt.org, Accession No. P16422, accessed at <URL:https://www.uniprot.org/uniprotkb/P16422/entry>, on Jul. 11, 2022, 9 pages.
UniProtKB, "Syndecan-1," UniProt.org, Accession No. P18827, accessed at <URL:https://www.uniprot.org/uniprotkb/P18827/entry>, on Jul. 11, 2022, 8 pages.
UniProtKB, "Myeloid cell surface antigen CD33," UniProt.org, Accession No. P20138, accessed at <URL:https://www.uniprot.org/uniprotkb/P20138/entry>, on Jul. 11, 2022, 9 pages.
UniProtKB, "T-cell surface glycoprotein CD3 zeta chain," UniProt.org, Accession No. P20963, accessed at <URL:https://www.uniprot.org/uniprotkb/P20963/entry>, on Jul. 11, 2022, 9 pages.
UniProtKB, "ADP-ribosyl cyclase/cyclic ADP-ribose hydrolase 1," UniProt.org, Accession No. P28907, accessed at <URL:https://www.uniprot.org/uniprotkb/P28907/entry>, on Jul. 11, 2022, 9 pages.
UniProtKB, "Tumor necrosis factor receptor superfamily member 8," UniProt.org, Accession No. P28908, accessed at <URL:https://www.uniprot.org/uniprotkb/P28908/entry>, on Jul. 11, 2022, 8 pages.
UniProtKB, "Folate receptor gamma," UniProt.org, Accession No. P41439, accessed at <URL:https://www.uniprot.org/uniprotkb/P41439/entry>, on Jul. 11, 2022, 8 pages.
UniProtKB, "Sperm mitochondrial-associated cysteine-rich protein," UniProt.org, Accession No. P49901, accessed at <URL:https://www.uniprot.org/uniprotkb/P49901/entry>, on Jul. 11, 2022, 6 pages.
UniProtKB, "Tumor necrosis factor receptor superfamily member 17," UniProt.org, Accession No. Q02223, accessed at <URL:https://www.uniprot.org/uniprotkb/Q02223/entry>, on Jul. 11, 2022, 8 pages.
UniProtKB, "Glutamate carboxypeptidase 2," UniProt.org, Accession No. Q04609, accessed at <URL:https://www.uniprot.org/uniprotkb/Q04609/entry>, on Jul. 11, 2022, 11 pages.
UniProtKB, "Bone marrow stromal antigen 2," UniProt.org, Accession No. Q10589, accessed at <URL:https://www.uniprot.org/uniprotkb/Q10589/entry>, on Jul. 11, 2022, 9 pages.
UniProtKB, "Mesothelin," UniProt.org, Accession No. Q13421, accessed at <URL:https://www.uniprot.org/uniprotkb/Q13421/entry>, on Jul. 11, 2022, 9 pages.
UniProtKB, "C-type lectin domain family 12 member A," UniProt.org, Accession No. Q5QGZ9, accessed at <URL:https://www.uniprot.org/uniprotkb/Q5QGZ9/entry>, on Jul. 11, 2022, 8 pages.
UniProtKB, "Delta-like protein 3," UniProt.org, Accession No. Q9NYJ7, accessed at <URL:https://www.uniprot.org/uniprotkb/Q9NYJ7/entry>, on Jul. 11, 2022, 8 pages.
UniProtKB, "Programmed cell death 1 ligand 1," UniProt.org, Accession No. Q9NZQ7, accessed at <URL:https://www.uniprot.org/uniprotkb/Q9NZQ7/entry>, on Jul. 11, 2022, 9 pages.
Van Rhenen, A., et al., "The Novel AML Stem Cell Associated Antigen Cll-1 Aids in Discrimination Between Normal and Leukemic Stem Cells," Blood 110(7):2659-2666, American Society of Hematology, United States (Oct. 2007).
Vecchio, C.A.D., et al., "EGFRvIII Gene Rearrangement is an Early Event in Glioblastoma Tumorigenesis and Expression Defines a Hierarchy Modulated by Epigenetic Mechanisms," Oncogene, 32(21):2670-2681, Nature Publishing Group, United Kingdom (May 2013).
Kuhn, C., et al., "Therapeutic anti-CD3 monoclonal antibodies: from bench to bedside," Immunotherapy 8(8):889-906, Future Medicine, United Kingdom (2016).
Merus, "Press Release: Merus Presents Preclinical Data on its Novel Bispecific Antibody MCLA-117 at EHA 2013," presented Jun. 17, 2013 in Utrecht Netherlands, 3 pages.
Rudikoff, S., et al., "Single amino acid substitution altering antigen-binding specificity," Immunology 79:1979-1983, Proc Natl. Acad. Sci, United States (1982).
Van Loo, P.F., et al., "Preclinical Evaluation of MCLA117, a CLEC12AxCD3 Bispecific Antibody Efficiently Targeting a Novel Leukemic Stem Cell Associated Antigen in AML," Blood 126(23):325, American Society of Hematologists, United States (2015).
Yang, Z., et al., "Construction of Anti-CD3 Human/Murine Chimeric Antibody Genes for Expression in Mammalian Cells," Chinese Journal of Cancer Biotherapy 2:108-111, Chinese Journal of Cancer Biotherapy, China (Jun. 1995).

* cited by examiner

| CD3 Fab | super cluster | CD3 binding (AUC) | lysis % max. (n=1) | BxPC3 lysis (AUC) n=1 | lysis EC50 (n=1) | lysis % max. (n=2) | BxPC3 lysis (AUC) n=2 | lysis EC50 (n=2) |
|---|---|---|---|---|---|---|---|---|
| MF8057 | 1 | 2171 | 64.7 | 209.3 | 26.81 | 58.6 | 236.0 | 23.9 |
| MF8058 | 1 | 9362 | 68.3 | 315.5 | 4.204 | 72.3 | 314.0 | 2.5 |
| MF8078 | 1 | 18723 | nd | nd | nd | 69.0 | 327.0 | 1.9 |
| MF8397 | 3 | 2264 | 22.6 | 97.5 | 48.0 | 33.0 | 114.0 | 25.9 |
| MF8508 | 4 | 2818 | 47.1 | 216.5 | 2.2 | 52.5 | 238.0 | 3.0 |
| MF9249 | 7 | 1994 | 26.0 | 115.5 | nd | 28.8 | 148.0 | 1.9 |
| MF9267 | 7 | 7220 | 26.8 | 162.5 | 0.3 | 39.7 | 192.5 | 1.5 |
| Pos. ref. | 8 | 20368 | 72.5 | 350.5 | 2.6 | 79.8 | 369.0 | 1.2 |
| MF6955 | R | 8383 | 40.7 | 211.0 | 1.1 | 61.9 | 224.5 | 7.6 |

Fig. 3

| MF nr. | super cluster | CD3 affinity (AUC HPB-ALL) | CD4+CD69+ (AUC) | CD4+CD25+ (AUC) | CD8+CD69+ (AUC) | CD8+CD25+ (AUC) |
|---|---|---|---|---|---|---|
| MF8057 | 1 | 2171 | 131 | 66.9 | 162.4 | 98.74 |
| MF8058 | 1 | 9362 | 197.8 | 108.7 | 202.8 | 189 |
| MF8078 | 1 | 18723 | 211.5 | 138.4 | 202.2 | 189 |
| MF8397 | 3 | 2264 | 48.75 | 17.26 | 120.5 | 21.4 |
| MF8508 | 4 | 2818 | 171.2 | 70.39 | 162.3 | 91.85 |
| MF9249 | 7 | 1994 | 80.28 | 29.19 | 123.6 | 33.44 |
| MF9267 | 7 | 7220 | 125.5 | 42.36 | 146.5 | 42.1 |
| Pos. ref. | 8 | 20368 | 225.7 | 148.6 | 183.8 | 186 |
| MF6955 | R | 8383 | 186.3 | 98.82 | 174.5 | 114.6 |

Fig. 5

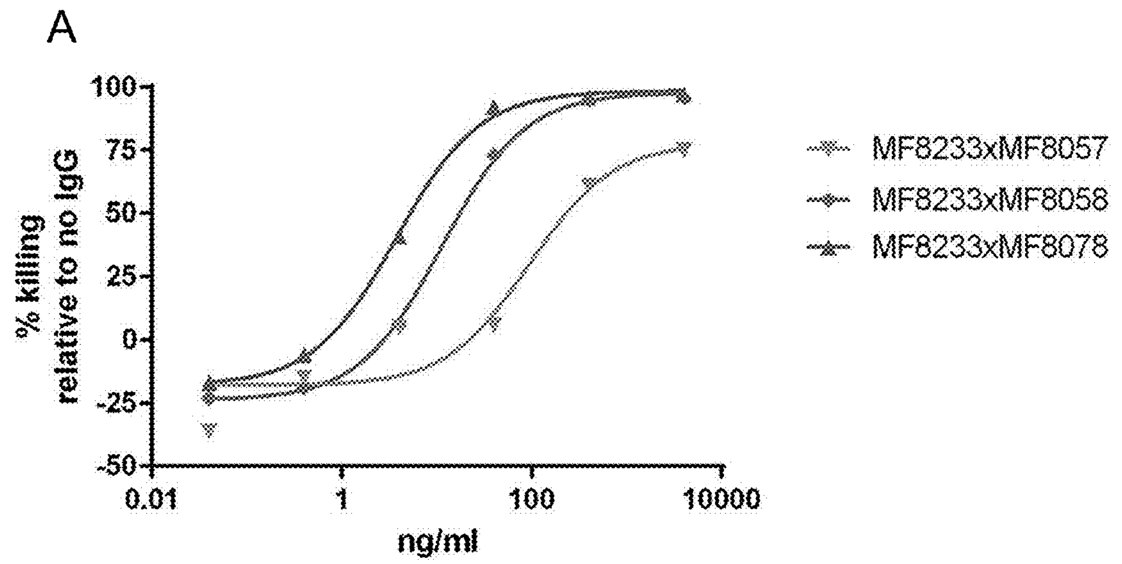
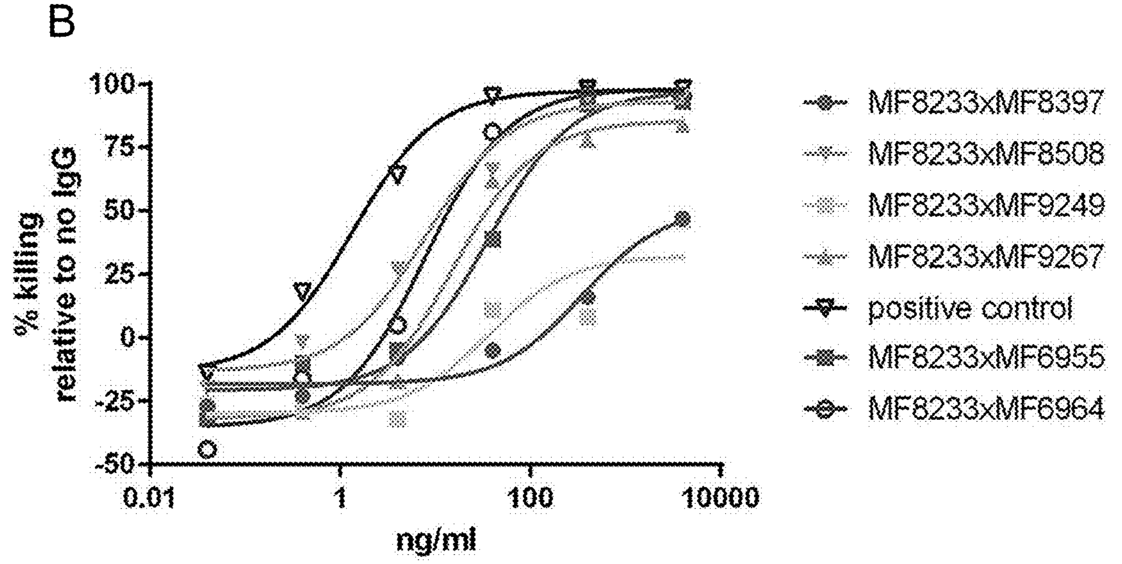
Fig. 8

| Super cluster | CD3 Fab | CD3 binding HPB-ALL (AUC) | HCT-116 lysis (AUC) | lysis EC50 |
|---|---|---|---|---|
| 1 | MF8057 | 2171 | 306.5 | 93.94 |
| 1 | MF8058 | 9362 | 421.5 | 11.34 |
| 1 | MF8078 | 18723 | 493 | 3.729 |
| 3 | MF8397 | 2264 | 220 | 354.1 |
| 4 | MF8508 | 2818 | 453.5 | 7.845 |
| 7 | MF9249 | 1994 | 199 | 36.34 |
| 7 | MF9267 | 7220 | 353 | 15.09 |
| 8 | Pos. ref. | 20368 | 547 | 1.34 |
| R | MF6955 | 8383 | 376.5 | 35.23 |
| R | MF6964 | 10151 | 421.5 | 7.761 |
| ref | MF5196 | 1578 | 158 | 1223 |

Fig. 9

Figure 11A:
DIQMTQSPSSLSASVGDRVTITCRASQSISSYLNWYQQKPGKAPKLLIYAASSLQSGVPSRFSGSGSGTDFTLTISS
LQPEDFATYYCQQSYSTPPTFGQGTKVEIK(SEQ ID NO 16)
RTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC(SEQ ID NO 18)

Figure 11B:
gacatccagatgacccagtctccatcctccctgtctgcatctgtaggagacagagtcacc
D I Q M T Q S P S S L S A S V G D R V T
atcacttgccgggcaagtcagagcattagcagctacttaaattggtatcagcagaaacca
I T C R A S Q S I S S Y L N W Y Q Q K P
gggaaagcccctaagctcctgatctatgctgcatccagtttgcaaagtggggtcccatca
G K A P K L L I Y A A S S L Q S G V P S
aggttcagtggcagtggatctgggacagatttcactctcaccatcagcagtctgcaacct
R F S G S G S G T D F T L T I S S L Q P
gaagattttgcaacttactactgtcaacagagttacagtacccctccaacgttcggccaa
E D F A T Y Y C Q Q S Y S T P P T F G Q
gggaccaaggtggagatcaaa(SEQ ID NO 15)
G T K V E I K (SEQ ID NO 16)

Figure 11C:
cgaactgtggctgcaccatctgtcttcatcttcccgccatctgatgagcagttgaaatct
R T V A A P S V F I F P P S D E Q L K S
ggaactgcctctgttgtgtgcctgctgaataacttctatcccagagaggccaaagtacag
G T A S V V C L L N N F Y P R E A K V Q
tggaaggtggataacgccctccaatcgggtaactcccaggagagtgtcacagagcaggac
W K V D N A L Q S G N S Q E S V T E Q D
agcaaggacagcacctacagcctcagcagcaccctgacgctgagcaaagcagactacgag
S K D S T Y S L S S T L T L S K A D Y E
aaacacaaagtctacgcctgcgaagtcacccatcagggcctgagctcgcccgtcacaaag
K H K V Y A C E V T H Q G L S S P V T K
agcttcaacaggggagagtgttag(SEQ ID NO 17)
S F N R G E C - (SEQ ID NO 18)

Figure 11D

DIQMTQSPSSLSASVGDRVTITCRASQSISSYLNWYQQKPGKAPKLLIYAASSLQSGVPSRFSGSGSGTDFTLTISS
LQPEDFATYYCQQSYSTPPITFGQGTRLEIK (SEQ ID NO 19)

Figure 11E

DIQMTQSPSSLSASVGDRVTITCRASQSISSYLNWYQQKPGKAPKLLIYAASSLQSGVPSRFSGSGSGTDFTLTISS
LQPEDFATYYCQQSYSTP(SEQ ID NO 20)

Figure 11F

CDR1 : QSISSY, (SEQ ID NO 21)
CDR2 : AAS, (SEQ ID NO 22)
CDR3 : QQSYSTP.(SEQ ID NO 23)

Figure 12A
CH1:
gctagcaccaagggcccatcggtcttccccctggcaccctcctccaagagcacctctggg
A S T K G P S V F P L A P S S K S T S G
ggcacagcggccctgggctgcctggtcaaggactacttccccgaaccggtgacggtgtcg
G T A A L G C L V K D Y F P E P V T V S
tggaactcaggcgccctgaccagcggcgtgcacaccttcccggctgtcctacagtcctca
W N S G A L T S G V H T F P A V L Q S S
ggactctactccctcagcagcgtcgtgaccgtgccctccagcagcttgggcacccagacc
G L Y S L S S V V T V P S S S L G T Q T
tacatctgcaacgtgaatcacaagcccagcaacaccaaggtggacaagagagtt (SEQ ID NO 24)
Y I C N V N H K P S N T K V D K R V (SEQ ID NO 25)

Figure 12B
Hinge:
gagcccaaatcttgtgacaaaactcacacatgcccaccgtgccca (SEQ ID NO 26)
E P K S C D K T H T C P P C P (SEQ ID NO 27)

Figure 12C
CH2:
gcacctgaactcctggggggaccgtcagtcttcctcttccccccaaaacccaaggacacc
A P E L L G G P S V F L F P P K P K D T
ctcatgatctcccggacccctgaggtcacatgcgtggtggtggacgtgagccacgaagac
L M I S R T P E V T C V V V D V S H E D
cctgaggtcaagttcaactggtacgtggacggcgtggaggtgcataatgccaagacaaag
P E V K F N W Y V D G V E V H N A K T K
ccgcgggaggagcagtacaacagcacgtaccgtgtggtcagcgtcctcaccgtcctgcac
P R E E Q Y N S T Y R V V S V L T V L H
caggactggctgaatggcaaggagtacaagtgcaaggtctccaacaaagccctcccagcc
Q D W L N G K E Y K C K V S N K A L P A
cccatcgagaaaaccatctccaaagccaaa (SEQ ID NO 28)
P I E K T I S K A K (SEQ ID NO 29)

Figure 12D
CH2 containing L235G and G236R silencing substitutions:
gcacctgaactcggcaggggaccgtcagtcttcctcttccccccaaaacccaaggacacc
A P E L G R G P S V F L F P P K P K D T
ctcatgatctcccggacccctgaggtcacatgcgtggtggtggacgtgagccacgaagac
L M I S R T P E V T C V V V D V S H E D
cctgaggtcaagttcaactggtacgtggacggcgtggaggtgcataatgccaagacaaag
P E V K F N W Y V D G V E V H N A K T K
ccgcgggaggagcagtacaacagcacgtaccgtgtggtcagcgtcctcaccgtcctgcac
P R E E Q Y N S T Y R V V S V L T V L H
caggactggctgaatggcaaggagtacaagtgcaaggtctccaacaaagccctcccagcc
Q D W L N G K E Y K C K V S N K A L P A
cccatcgagaaaaccatctccaaagccaaa (SEQ ID NO 30)
P I E K T I S K A K (SEQ ID NO 31)

Figure 12E
CH3: KK of DEKK (SEQ ID NO 36)
gggcagccccgagaaccacaggtgtacaccaagccccccatcccgggaggagatgaccaag
G Q P R E P Q V Y T K P P S R E E M T K
aaccaggtcagcctgaagtgcctggtcaaaggcttctatcccagcgacatcgccgtggag
N Q V S L K C L V K G F Y P S D I A V E
tgggagagcaatgggcagccggagaacaactacaagaccacgcctcccgtgctggactcc
W E S N G Q P E N N Y K T T P P V L D S
gacggctccttcttcctctatagcaagctcaccgtggacaagagcaggtggcagcagggg
D G S F F L Y S K L T V D K S R W Q Q G
aacgtcttctcatgctccgtgatgcatgaggctctgcacaaccactacacgcagaagagc
N V F S C S V M H E A L H N H Y T Q K S
ctctccctgtctccgggttga (SEQ ID NO 32)
L S L S P G - (SEQ ID NO 33)

Figure 12F
CH3: DE of DEKK (SEQ ID NO 36)
gggcagccccgagaaccacaggtgtacaccgaccccccatcccgggaggagatgaccaag
G Q P R E P Q V Y T D P P S R E E M T K
aaccaggtcagcctgacctgcgaggtcaaaggcttctatcccagcgacatcgccgtggag
N Q V S L T C E V K G F Y P S D I A V E
tgggagagcaatgggcagccggagaacaactacaagaccacgcctcccgtgctggactcc
W E S N G Q P E N N Y K T T P P V L D S
gacggctccttcttcctctatagcaagctcaccgtggacaagagcaggtggcagcagggg
D G S F F L Y S K L T V D K S R W Q Q G
aacgtcttctcatgctccgtgatgcatgaggctctgcacaaccactacacgcagaagagc
N V F S C S V M H E A L H N H Y T Q K S
ctctccctgtctccgggttga (SEQ ID NO 34)
L S L S P G - (SEQ ID NO 35)

Figure 13

- Supercluster 1:
  - MF8057,
    - DNA 1 ggcccagccg gccatggccg aggtgcagct ggtgcagtct ggagctgagg tgaagaagcc
61 tgggtcctcg gtgaaggtct cctgcaaggc ttctggaggc accttccgca gctttggtat
121 cagttgggtg cgacaggccc ctggacaagg acttgagtgg atgggaggat tcatccctgt
181 ccttggtaca gcaaactacg cacagaaatt ccagggcaga gtgacgatta tcgcggacaa
241 atccacgaac acagcctaca tggagctgag cagcctgaga tctgaggaca cggccgtgta
301 ttactgtgcg cgaaggggta actggaaccc gttcgacccc tggggccagg gaaccctggt
361 caccgtctcg agt (SEQ ID NO 37)

- AA

| | |
|---|---|
| FW1 | >MF8057.cep_FW1 -1AA in FW4<br>EVQLVQSGAEVKKPGSSVKVSCKASGGTFR (SEQ ID NO 38) |
| FW2 | >MF8057.cep_FW2 -1AA in FW4<br>WVRQAPGQGLEWMG (SEQ ID NO 39) |
| FW3 | >MF8057.cep_FW3 -1AA in FW4<br>RVTIIADKSTNTAYMELSSLRSEDTAVYYCAR (SEQ ID NO 40) |
| FW4 | >MF8057.cep_FW4 -1AA in FW4<br>WGQGTLVTVSS (SEQ ID NO 41) |
| CDR1 | >MF8057.cep_CDR1 -1AA in FW4<br>SFGIS (SEQ ID NO 42) |
| CDR2 | >MF8057.cep_CDR2 -1AA in FW4<br>GFIPVLGTANYAQKFQG (SEQ ID NO 43) |
| CDR3 | >MF8057.cep_CDR3 -1AA in FW4<br>RGNWNPFDP (SEQ ID NO 44) |
| VH | >MF8057.cep_VH -1AA in FW4<br>EVQLVQSGAEVKKPGSSVKVSCKASGGTFRSFGISWVRQAPGQGLEWMGGFIPVLGTANYAQKFQGRVTI<br>IADKSTNTAYMELSSLRSEDTAVYYCARRGNWNPFDPWGQGTLVTVSS (SEQ ID NO 45) |

- MF8058,
  - DNA 1 ggcccagccg gccatggccc aggtgcagct ggtgcagtct ggggctgagg tgaagaagcc
61 tgggtcctcg gtgaaggtct cctgcaaggc ttctggagac gccttcaaaa gcaaaacctt
121 tactatcagc tgggtgcgac aggcccctgg acaggggctt gagtggctgg gggggatcat
181 ccctcttttt ggtacaatta cctacgcaca gaagttccag ggcagagtca cgattaccgc
241 ggacaaatcc acgaacactg ccttcatgga actgagcagc ctgagatctg aggacacggc
301 catgtattat tgtacgcgac gggggaactg gaaccccttc gacccctggg gccagggaac
361 cctggtcacc gtctcgagt (SEQ ID NO 46)

- AA

| | |
|---|---|
| FW2 | >MF8058.cep_FW2 -1AA in FW4<br>WVRQAPGQGLEWLG (SEQ ID NO 47) |
| FW1 | >MF8058.cep_FW1 -1AA in FW4<br>QVQLVQSGAEVKKPGSSVKVSCKASGDAFK (SEQ ID NO 48) |
| FW3 | >MF8058.cep_FW3 -1AA in FW4<br>RVTITADKSTNTAFMELSSLRSEDTAMYYCTR (SEQ ID NO 49) |
| FW4 | >MF8058.cep_FW4 -1AA in FW4<br>WGQGTLVTVSS (SEQ ID NO 50) |
| CDR1 | >MF8058.cep_CDR1 -1AA in FW4<br>SKTFTIS (SEQ ID NO 51) |
| CDR2 | >MF8058.cep_CDR2 -1AA in FW4<br>GIIPLFGTITYAQKFQG (SEQ ID NO 52) |
| CDR3 | >MF8058.cep_CDR3 -1AA in FW4<br>RGNWNPFDP (SEQ ID NO 53) |
| VH | >MF8058.cep_VH -1AA in FW4<br>QVQLVQSGAEVKKPGSSVKVSCKASGDAFKSKTFTISWVRQAPGQGLEWLGGIIPLFGTITYAQKFQGRV<br>TITADKSTNTAFMELSSLRSEDTAMYYCTRRGNWNPFDPWGQGTLVTVSS (SEQ ID NO 54) |

Figure 13 Continued

- MF8078,
  - DNA 1 ggcccagccg gccatggccg aggtgcagct ggtgcagtct gggtctgagt tgaagaagcc
61 tgggtcctcg gtgaaggtct cctgcaaggc ttctggagtc accttcaaca gcagaacctt
121 tactatcagt tgggtgcgac aggcccctgg acaagggctt gagtggctgg ggagtatcat
181 ccctattttt ggtacaataa cctacgcaca gaagttccag ggcagagtca cgattaccgc
241 ggacaaatcc acgagcactg ccttcatgga actgaccagc ctgagatctg aggacacggc
301 catatattat tgtacgagac gggggaactg gaaccccttc gacccctggg gccagggcac
361 cctggtcacc gtctcgagt (SEQ ID NO 55)

- AA

| | |
|---|---|
| FW1 | >MF8078.cep_FW1 -1AA in FW4<br>EVQLVQSGSELKKPGSSVKVSCKASGVTFN (SEQ ID NO 56) |
| FW2 | >MF8078.cep_FW2 -1AA in FW4<br>WVRQAPGQGLEWLG (SEQ ID NO 57) |
| FW3 | >MF8078.cep_FW3 -1AA in FW4<br>RVTITADKSTSTAFMELTSLRSEDTAIYYCTR (SEQ ID NO 58) |
| FW4 | >MF8078.cep_FW4 -1AA in FW4<br>WGQGTLVTVSS (SEQ ID NO 59) |
| CDR1 | >MF8078.cep_CDR1 -1AA in FW4<br>SRTFTIS (SEQ ID NO 60) |
| CDR2 | >MF8078.cep_CDR2 -1AA in FW4<br>SIIPIFGTITYAQKFQG (SEQ ID NO 61) |
| CDR3 | >MF8078.cep_CDR3 -1AA in FW4<br>RGNWNPFDP (SEQ ID NO 62) |
| VH | >MF8078.cep_VH -1AA in FW4<br>EVQLVQSGSELKKPGSSVKVSCKASGVTFNSRTFTISWVRQAPGQGLEWLGSIIPIFGTITYAQKFQGRV<br>TITADKSTSTAFMELTSLRSEDTAIYYCTRRGNWNPFDPWGQGTLVTVSS (SEQ ID NO 63) |

Figure 13 Continued

MF8048

| | |
|---|---|
| FW1 | >MF8048.cep_FW1 -1AA in FW4<br>QVQLVQSGAEVKKPGSSVKVSCKASGGTFR (SEQ ID NO 64) |
| FW2 | >MF8048.cep_FW2 -1AA in FW4<br>WVRQAPGQGLEWVG (SEQ ID NO 65) |
| FW3 | >MF8048.cep_FW3 -1AA in FW4<br>RVTITADKSATTAYMELSSLRSEDTAIYYCAK (SEQ ID NO 66) |
| FW4 | >MF8048.cep_FW4 -1AA in FW4<br>WGQGTLVTVSS (SEQ ID NO 67) |
| CDR1 | >MF8048.cep_CDR1 -1AA in FW4<br>GSGIS (SEQ ID NO 68) |
| CDR2 | >MF8048.cep_CDR2 -1AA in FW4<br>GFIPFFGSANYAQKFRD (SEQ ID NO 69) |
| CDR3 | >MF8048.cep_CDR3 -1AA in FW4<br>RGNWNPLDP (SEQ ID NO 70) |
| VH | >MF8048.cep_VH -1AA in FW4<br>QVQLVQSGAEVKKPGSSVKVSCKASGGTFRGSGISWVRQAPGQGLEWVGGFIPFFGSANYAQKFRDRVTI<br>TADKSATTAYMELSSLRSEDTAIYYCAKRGNWNPLDPWGQGTLVTVSS (SEQ ID NO 71) |
| FW1 | >MF8048.cep_FW1 -1AA in FW4<br>caggtgcagctggtgcagtctggggctgaggtgaagaagcctgggtcctcggtgaaggtctcctgcaagg<br>cttctggaggcaccttcaga (SEQ ID NO 72) |
| FW2 | >MF8048.cep_FW2 -1AA in FW4<br>tgggtgcgacaggcccctggacaagggcttgagtgggtgggc (SEQ ID NO 73) |
| FW3 | >MF8048.cep_FW3 -1AA in FW4<br>agagtcacgattaccgcggacaaatccgcgaccacagcctacatggaactgagcagcctgagatctgagg<br>acacggccatatattactgtgcgaaa (SEQ ID NO 74) |
| FW4 | >MF8048.cep_FW4 -1AA in FW4<br>tggggccagggcaccctggtcaccgtctcgagt (SEQ ID NO 75) |
| CDR1 | >MF8048.cep_CDR1 -1AA in FW4<br>ggttctggtatcagc (SEQ ID NO 76) |
| CDR2 | >MF8048.cep_CDR2 -1AA in FW4<br>gggttcatccctttctttggttcagcaaactacgcacagaagttccgggac (SEQ ID NO 77) |
| CDR3 | >MF8048.cep_CDR3 -1AA in FW4<br>agaggaaattggaacccgctcgacccc (SEQ ID NO 78) |
| VH | >MF8048.cep_VH -1AA in FW4<br>caggtgcagctggtgcagtctggggctgaggtgaagaagcctgggtcctcggtgaaggtctcctgcaagg<br>cttctggaggcaccttcagaggttctggtatcagctgggtgcgacaggcccctggacaagggcttgagtg<br>ggtgggcgggttcatccctttctttggttcagcaaactacgcacagaagttccgggacagagtcacgatt<br>accgcggacaaatccgcgaccacagcctacatggaactgagcagcctgagatctgaggacacggccatat<br>attactgtgcgaaaagaggaaattggaacccgctcgacccctggggccagggcaccctggtcaccgtctc<br>gagt (SEQ ID NO 79) |

Figure 13 Continued

MF8101

| | |
|---|---|
| FW1 | >MF8101.cep_FW1 -1AA in FW4<br>QVQLVQSGAEVKKPGSSVKVSCKASGVTFK (SEQ ID NO 80) |
| FW2 | >MF8101.cep_FW2 -1AA in FW4<br>WVRQAPGQGLEWLG (SEQ ID NO 81) |
| FW3 | >MF8101.cep_FW3 -1AA in FW4<br>RVSITADKSTNTAYLELNSLRSEDTAIYYCAR (SEQ ID NO 82) |
| FW4 | >MF8101.cep_FW4 -1AA in FW4<br>WGQGTLVTVSS (SEQ ID NO 83) |
| CDR1 | >MF8101.cep_CDR1 -1AA in FW4<br>SKTLTIS (SEQ ID NO 84) |
| CDR2 | >MF8101.cep_CDR2 -1AA in FW4<br>GIIPIFGSITYAQKFQD (SEQ ID NO 85) |
| CDR3 | >MF8101.cep_CDR3 -1AA in FW4<br>RGNWNPFDP (SEQ ID NO 86) |
| VH | >MF8101.cep_VH -1AA in FW4<br>QVQLVQSGAEVKKPGSSVKVSCKASGVTFKSKTLTISWVRQAPGQGLEWLGGIIPIFGSITYAQKFQDRV<br>SITADKSTNTAYLELNSLRSEDTAIYYCARRGNWNPFDPWGQGTLVTVSS (SEQ ID NO 87) |
| FW1 | >MF8101.cep_FW1 -1AA in FW4<br>caggtgcagctggtgcagtctggggctgaggtgaagaagcctgggtcctcggtgaaggtctcctgcaagg<br>cttctggagtcaccttcaaa (SEQ ID NO 88) |
| FW2 | >MF8101.cep_FW2 -1AA in FW4<br>tgggtgcgacaggcccctggacaagggcttgagtggctggga (SEQ ID NO 89) |
| FW3 | >MF8101.cep_FW3 -1AA in FW4<br>agagtctcgattaccgcggacaaatccacgaacacagcctacttggaactgaacagcctgaggtctgagg<br>acacggccatttattattgtgcgaga (SEQ ID NO 90) |
| FW4 | >MF8101.cep_FW4 -1AA in FW4<br>tggggccagggcaccctggtcaccgtctcgagt (SEQ ID NO 91) |
| CDR1 | >MF8101.cep_CDR1 -1AA in FW4<br>agcaaaaccttaactatcagc (SEQ ID NO 92) |
| CDR2 | >MF8101.cep_CDR2 -1AA in FW4<br>gggatcatccctatttttggttcaataacctacgcacagaagttccaggac (SEQ ID NO 93) |
| CDR3 | >MF8101.cep_CDR3 -1AA in FW4<br>cgggggaactggaaccccttcgacccc (SEQ ID NO 94) |
| VH | >MF8101.cep_VH -1AA in FW4<br>caggtgcagctggtgcagtctggggctgaggtgaagaagcctgggtcctcggtgaaggtctcctgcaagg<br>cttctggagtcaccttcaaaagcaaaaccttaactatcagctgggtgcgacaggcccctggacaagggct<br>tgagtggctgggagggatcatccctatttttggttcaataacctacgcacagaagttccaggacagagtc<br>tcgattaccgcggacaaatccacgaacacagcctacttggaactgaacagcctgaggtctgaggacacgg<br>ccatttattattgtgcgagacgggggaactggaaccccttcgacccctggggccagggcaccctggtcac<br>cgtctcgagt (SEQ ID NO 95) |

Figure 13 Continued

MF8056

| | |
|---|---|
| FW1 | >MF8056.cep_FW1 -1AA in FW4<br>EVQLVQSGAEVKKPGSSVKVSCKASGGTFR (SEQ ID NO 96) |
| FW2 | >MF8056.cep_FW2 -1AA in FW4<br>WVRQAPGQGLEWVG (SEQ ID NO 97) |
| FW3 | >MF8056.cep_FW3 -1AA in FW4<br>RVTITADKSATTAYMELSSLRSEDTAIYYCAK (SEQ ID NO 98) |
| FW4 | >MF8056.cep_FW4 -1AA in FW4<br>WGQGTLVTVSS (SEQ ID NO 99) |
| CDR1 | >MF8056.cep_CDR1 -1AA in FW4<br>GSGIS (SEQ ID NO 100) |
| CDR2 | >MF8056.cep_CDR2 -1AA in FW4<br>GFIPFFGSANYAQKFRD (SEQ ID NO 101) |
| CDR3 | >MF8056.cep_CDR3 -1AA in FW4<br>RGNWNPFDP (SEQ ID NO 102) |
| VH | >MF8056.cep_VH -1AA in FW4<br>EVQLVQSGAEVKKPGSSVKVSCKASGGTFRGSGISWVRQAPGQGLEWVGGFIPFFGSANYAQKFRDRVTI<br>TADKSATTAYMELSSLRSEDTAIYYCAKRGNWNPFDPWGQGTLVTVSS (SEQ ID NO 103) |
| FW1 | >MF8056.cep_FW1 -1AA in FW4<br>gaggtgcagctggtgcagtctggagctgaggtgaagaagcctgggtcctcggtgaaggtctcctgcaagg<br>cttctggaggcaccttcaga (SEQ ID NO 104) |
| FW2 | >MF8056.cep_FW2 -1AA in FW4<br>tgggtgcgacaggcccctggacaagggcttgagtgggtgggc (SEQ ID NO 105) |
| FW3 | >MF8056.cep_FW3 -1AA in FW4<br>agagtcacgattaccgcggacaaatccgcgaccacagcctacatggaactgagcagcctgagatctgagg<br>acacggccatatattactgtgcgaaa (SEQ ID NO 106) |
| FW4 | >MF8056.cep_FW4 -1AA in FW4<br>tggggccagggcaccctggtcaccgtctcgagt (SEQ ID NO 107) |
| CDR1 | >MF8056.cep_CDR1 -1AA in FW4<br>ggttctggtatcagc (SEQ ID NO 108) |
| CDR2 | >MF8056.cep_CDR2 -1AA in FW4<br>gggttcatccctttctttggttcagcaaactacgcacagaagttccgggac (SEQ ID NO 109) |
| CDR3 | >MF8056.cep_CDR3 -1AA in FW4<br>agaggaaattggaacccgttcgacccc (SEQ ID NO 110) |
| VH | >MF8056.cep_VH -1AA in FW4<br>gaggtgcagctggtgcagtctggagctgaggtgaagaagcctgggtcctcggtgaaggtctcctgcaagg<br>cttctggaggcaccttcagaggttctggtatcagctgggtgcgacaggcccctggacaagggcttgagtg<br>ggtgggcgggttcatccctttctttggttcagcaaactacgcacagaagttccgggacagagtcacgatt<br>accgcggacaaatccgcgaccacagcctacatggaactgagcagcctgagatctgaggacacggccatat<br>attactgtgcgaaaagaggaaattggaacccgttcgacccctggggccagggcaccctggtcaccgtctc<br>gagt (SEQ ID NO 111) |

Figure 13 Continued

- Supercluster 3:
  - MF8397
    - DNA 1 caggtgcagc tggtgcagtc tgggggaggc ctggtacagc ctggggggtc cctgagactc
61 tcctgtgcaa cctctggatt caaattcagt agctatgccc tgagctgggt ccgccaggca
121 ccagggaagg gactggagtg ggtctcaggt attagtggta gtggtcgcac cacatggtat
181 gcagactccg tgaagggccg gttcaccatc tccagagaca attccaagaa cacgctgtat
241 ctgcaaatga acagcctgag agccgaggac acggccgtat attactgtgc gagagacggt
301 ggatacagct atggccctta ctggtacttc gatctctggg gccgtggaac cctggtcacc
361 cctggtcaccg tctccagt (SEQ ID NO 112)

- AA

| | |
|---|---|
| FW1 | >MF8397.cep_FW1<br>QVQLVQSGGGLVQPGGSLRLSCATSGFKFS (SEQ ID NO 113) |
| FW2 | >MF8397.cep_FW2<br>WVRQAPGKGLEWVS (SEQ ID NO 114) |
| FW3 | >MF8397.cep_FW3<br>RFTISRDNSKNTLYLQMNSLRAEDTAVYYCAR (SEQ ID NO 115) |
| FW4 | >MF8397.cep_FW4<br>WGRGTLVTVSS (SEQ ID NO 116) |
| CDR1 | >MF8397.cep_CDR1<br>SYALS (SEQ ID NO 117) |
| CDR2 | >MF8397.cep_CDR2<br>GISGSGRTTWYADSVKG (SEQ ID NO 118) |
| CDR3 | >MF8397.cep_CDR3<br>DGGYSYGPYWYFDL (SEQ ID NO 119) |
| VH | >MF8397.cep_VH<br>QVQLVQSGGGLVQPGGSLRLSCATSGFKFSSYALSWVRQAPGKGLEWVSGISGSGRTTWYADSVKGRFTI<br>SRDNSKNTLYLQMNSLRAEDTAVYYCARDGGYSYGPYWYFDLWGRGTLVTVSS (SEQ ID NO 120) |

Figure 13 Continued

MF8562

| | |
|---|---|
| FW1 | >MF8562.cep_FW1<br>QVQLVESGGGLVQPGGSLRLSCATSGFTFI (SEQ ID NO 121) |
| FW2 | >MF8562.cep_FW2<br>WVRQAPGKGLEWVS (SEQ ID NO 122) |
| FW3 | >MF8562.cep_FW3<br>RFTISRDNSKNTLFLQMNSLRAEDTAVYYCAR (SEQ ID NO 123) |
| FW4 | >MF8562.cep_FW4<br>WGRGTLVTVSS (SEQ ID NO 124) |
| CDR1 | >MF8562.cep_CDR1<br>SYALS (SEQ ID NO 125) |
| CDR2 | >MF8562.cep_CDR2<br>AISGSGRTTWYADSVKG (SEQ ID NO 126) |
| CDR3 | >MF8562.cep_CDR3<br>DGGYTYGPYWYFDL (SEQ ID NO 127) |
| VH | >MF8562.cep_VH<br>QVQLVESGGGLVQPGGSLRLSCATSGFTFISYALSWVRQAPGKGLEWVSAISGSGRTTWYADSVKGRFTI<br>SRDNSKNTLFLQMNSLRAEDTAVYYCARDGGYTYGPYWYFDLWGRGTLVTVSS (SEQ ID NO 128) |
| FW1 | >MF8562.cep_FW1<br>caggtgcagctggtggagtctgggggaggcctggtacagcctggggggtccctgagactctcctgtgcaa<br>cctctggattcacctttatc (SEQ ID NO 129) |
| FW2 | >MF8562.cep_FW2<br>tgggtccgccaggctccagggaaggggctggaatgggtctca (SEQ ID NO 130) |
| FW3 | >MF8562.cep_FW3<br>cggttcaccatctccagagacaattccaagaacacgctgtttctgcaaatgaacagcctgagagccgagg<br>acacggccgtatattactgtgcgaga (SEQ ID NO 131) |
| FW4 | >MF8562.cep_FW4<br>tggggccgtggcaccctggtcaccgtctcgagt (SEQ ID NO 132) |
| CDR1 | >MF8562.cep_CDR1<br>agctatgccctgagc (SEQ ID NO 133) |
| CDR2 | >MF8562.cep_CDR2<br>gctattagtggtagtggtcgtaccacatggtacgcagactccgtgaagggc (SEQ ID NO 134) |
| CDR3 | >MF8562.cep_CDR3<br>gacggtggatacacctatggcccttactggtacttcgatctc (SEQ ID NO 135) |
| VH | >MF8562.cep_VH<br>caggtgcagctggtggagtctgggggaggcctggtacagcctggggggtccctgagactctcctgtgcaa<br>cctctggattcacctttatcagctatgccctgagctgggtccgccaggctccagggaaggggctggaatg<br>ggtctcagctattagtggtagtggtcgtaccacatggtacgcagactccgtgaagggccggttcaccatc<br>tccagagacaattccaagaacacgctgtttctgcaaatgaacagcctgagagccgaggacacggccgtat<br>attactgtgcgagagacggtggatacacctatggcccttactggtacttcgatctctggggccgtggcac<br>cctggtcaccgtctcgagt (SEQ ID NO 136) |

Figure 13 Continued

- Supercluster 4:
  - MF8508
    - DNA 1 ggcccagccg gccatggccg aggtgcagct ggtggagtct gggggaggat tggtacagcc
61 tggcaggtcc ctgagactct cctgtgcaac ctctggattc aactttgatg attataccat
121 gcactgggtc cggcaagctc cagggaaggg cctggagtgg gtctcagata ttagttggag
181 tagtggtagc ataggctatg cggactctgt gaagggccga ttcaccatct ccagagacaa
241 cgccaagaac tccctgtggc tgcaaatgaa cagtctgaga actgaggaca cggccttgta
301 tttctgtgca aaagatcata gggggtacgg tgactacgag ggtggtggct ttgactactg
361 gggccaggga accctggtca ccgtctccag t (SEQ ID NO 137)

- AA

| | |
|---|---|
| FW1 | >MF8508.cep_FW1<br>EVQLVESGGGLVQPGRSLRLSCATSGFNFD (SEQ ID NO 138) |
| FW2 | >MF8508.cep_FW2<br>WVRQAPGKGLEWVS (SEQ ID NO 139) |
| FW3 | >MF8508.cep_FW3<br>RFTISRDNAKNSLWLQMNSLRTEDTALYFCAK (SEQ ID NO 140) |
| FW4 | >MF8508.cep_FW4<br>WGQGTLVTVSS (SEQ ID NO 141) |
| CDR1 | >MF8508.cep_CDR1<br>DYTMH (SEQ ID NO 142) |
| CDR2 | >MF8508.cep_CDR2<br>DISWSSGSIGYADSVKG (SEQ ID NO 143) |
| CDR3 | >MF8508.cep_CDR3<br>DHRGYGDYEGGGFDY (SEQ ID NO 144) |
| VH | >MF8508.cep_VH<br>EVQLVESGGGLVQPGRSLRLSCATSGFNFDDYTMHWVRQAPGKGLEWVSDISWSSGSIGYADSVKGRFTI<br>SRDNAKNSLWLQMNSLRTEDTALYFCAKDHRGYGDYEGGGFDYWGQGTLVTVSS (SEQ ID NO 145) |

Figure 13 Continued

MF8998

| | |
|---|---|
| FW1 | >MF8998.cep_FW1<br>EVQLVESGGGLVQPGRSLRLSCATSGFTFD (SEQ ID NO 146) |
| FW2 | >MF8998.cep_FW2<br>WVRQAPGKGLEWVS (SEQ ID NO 147) |
| FW3 | >MF8998.cep_FW3<br>RFTISRDNAKNSLYLQMNSLRAEDTALYFCAK (SEQ ID NO 148) |
| FW4 | >MF8998.cep_FW4<br>WGQGTLVTVSS (SEQ ID NO 149) |
| CDR1 | >MF8998.cep_CDR1<br>DYTMH (SEQ ID NO 150) |
| CDR2 | >MF8998.cep_CDR2<br>DISWSSGSIGYADSVKG (SEQ ID NO 151) |
| CDR3 | >MF8998.cep_CDR3<br>DHRGYGDYEGGGFDH (SEQ ID NO 152) |
| VH | >MF8998.cep_VH<br>EVQLVESGGGLVQPGRSLRLSCATSGFTFDDYTMHWVRQAPGKGLEWVSDISWSSGSIGYADSVKGRFTI<br>SRDNAKNSLYLQMNSLRAEDTALYFCAKDHRGYGDYEGGGFDHWGQGTLVTVSS (SEQ ID NO 153) |
| FW1 | >MF8998.cep_FW1<br>gaggtgcagctggtggagtctgggggaggcttggtacagcctggcaggtccctgagactctcctgtgcaa<br>cctctggattcacctttgat (SEQ ID NO 154) |
| FW2 | >MF8998.cep_FW2<br>tgggtccggcaagctccagggaagggcctggagtgggtctca (SEQ ID NO 155) |
| FW3 | >MF8998.cep_FW3<br>cgattcaccatctccagagacaacgccaagaactccctgtatctgcaaatgaacagtctgagagctgagg<br>acacggccttgtatttctgtgcaaaa (SEQ ID NO 156) |
| FW4 | >MF8998.cep_FW4<br>tggggccagggaaccctggtcaccgtctccagt (SEQ ID NO 157) |
| CDR1 | >MF8998.cep_CDR1<br>gattataccatgcac (SEQ ID NO 158) |
| CDR2 | >MF8998.cep_CDR2<br>gatattagttggagtagtggtagcataggctatgcggactctgtgaagggc (SEQ ID NO 159) |
| CDR3 | >MF8998.cep_CDR3<br>gatcataggggtacggtgactacgagggtggtggctttgaccac (SEQ ID NO 160) |
| VH | >MF8998.cep_VH<br>gaggtgcagctggtggagtctgggggaggcttggtacagcctggcaggtccctgagactctcctgtgcaa<br>cctctggattcacctttgatgattataccatgcactgggtccggcaagctccagggaagggcctggagtg<br>ggtctcagatattagttggagtagtggtagcataggctatgcggactctgtgaagggccgattcaccatc<br>tccagagacaacgccaagaactccctgtatctgcaaatgaacagtctgagagctgaggacacggccttgt<br>atttctgtgcaaaagatcataggggtacggtgactacgagggtggtggctttgaccactggggccaggg<br>aaccctggtcaccgtctccagt (SEQ ID NO 161) |

Figure 13 Continued

MF10401

| | |
|---|---|
| FW1 | >MF10401_FW1<br>EVQLVESGGVVVQPGGSLRLSCAASGFTFD (SEQ ID NO 162) |
| FW2 | >MF10401_FW2<br>WVRQAPGKGLEWVS (SEQ ID NO 163) |
| FW3 | >MF10401_FW3<br>RFTISRDNSKNSLYLQMNSLRTEDTALYYCAK (SEQ ID NO 164) |
| FW4 | >MF10401_FW4<br>WGRGTLVTVSS (SEQ ID NO 165) |
| CDR1 | >MF10401_CDR1<br>DYTMH (SEQ ID NO 166) |
| CDR2 | >MF10401_CDR2<br>DISWSGGSIYYADSVKG (SEQ ID NO 167) |
| CDR3 | >MF10401_CDR3<br>DHRGYGDYEGGGFDY (SEQ ID NO 168) |
| VH | >MF10401_VH<br>EVQLVESGGVVVQPGGSLRLSCAASGFTFDDYTMHWVRQAPGKGLEWVSDISWSGGSIYYADSVKGRFTI<br>SRDNSKNSLYLQMNSLRTEDTALYYCAKDHRGYGDYEGGGFDYWGRGTLVTVSS (SEQ ID NO 169) |
| FW1 | >MF10401_FW1<br>gaggtgcagctggtggagagcggcggcgtggtggtgcagcccggcggcagcctgagactgagctgcgccg<br>ccagcggcttcaccttcgac (SEQ ID NO 170) |
| FW2 | >MF10401_FW2<br>tgggtgagacaggcccccggcaagggcctggagtgggtgagc (SEQ ID NO 171) |
| FW3 | >MF10401_FW3<br>agattcaccatcagcagagacaacagcaagaacagcctgtacctgcagatgaacagcctgagaaccgagg<br>acaccgccctgtactactgcgccaag (SEQ ID NO 172) |
| FW4 | >MF10401_FW4<br>tggggcagaggcaccctggtcaccgtctcgagc (SEQ ID NO 173) |
| CDR1 | >MF10401_CDR1<br>gactacaccatgcac (SEQ ID NO 174) |
| CDR2 | >MF10401_CDR2<br>gacatcagctggagcggcggcagcatctactacgccgacagcgtgaagggc (SEQ ID NO 175) |
| CDR3 | >MF10401_CDR3<br>gaccacagaggctacggcgactacgagggcggcggcttcgactac (SEQ ID NO 176) |
| VH | >MF10401_VH<br>gaggtgcagctggtggagagcggcggcgtggtggtgcagcccggcggcagcctgagactgagctgcgccg<br>ccagcggcttcaccttcgacgactacaccatgcactgggtgagacaggcccccggcaagggcctggagtg<br>ggtgagcgacatcagctggagcggcggcagcatctactacgccgacagcgtgaagggcagattcaccatc<br>agcagagacaacagcaagaacagcctgtacctgcagatgaacagcctgagaaccgaggacaccgccctgt<br>actactgcgccaaggaccacagaggctacggcgactacgagggcggcggcttcgactactggggcagagg<br>caccctggtcaccgtctcgagc (SEQ ID NO 177) |

Figure 13 Continued

MF10428

| | |
|---|---|
| FW1 | >MF10428_FW1<br>EVQLVESGGGLVQPGRSLRLSCVTSGFTFD (SEQ ID NO 178) |
| FW2 | >MF10428_FW2<br>WVRQAPGKGLEWVS (SEQ ID NO 179) |
| FW3 | >MF10428_FW3<br>RFTISRDNAKDSLYLQMNSLRTEDTALYYCAK (SEQ ID NO 180) |
| FW4 | >MF10428_FW4<br>WGQGTLVTVSS (SEQ ID NO 181) |
| CDR1 | >MF10428_CDR1<br>DYTMH (SEQ ID NO 182) |
| CDR2 | >MF10428_CDR2<br>DISWSSGTTGYADSVKG (SEQ ID NO 183) |
| CDR3 | >MF10428_CDR3<br>DHMGYGDYEGGGFDY (SEQ ID NO 184) |
| VH | >MF10428_VH<br>EVQLVESGGGLVQPGRSLRLSCVTSGFTFDDYTMHWVRQAPGKGLEWVSDISWSSGTTGYADSVKGRFTI<br>SRDNAKDSLYLQMNSLRTEDTALYYCAKDHMGYGDYEGGGFDYWGQGTLVTVSS (SEQ ID NO 185) |
| FW1 | >MF10428_FW1<br>gaagtgcagctggtggagtctgggggaggcttggtacagcctggcaggtccctgagactctcctgtgtaa<br>cctctggattcacctttgat (SEQ ID NO 186) |
| FW2 | >MF10428_FW2<br>tgggtccggcaagctccggggaagggcctggagtgggtctca (SEQ ID NO 187) |
| FW3 | >MF10428_FW3<br>cgattcaccatctccagagacaatgccaaggactccctgtatctgcaaatgaacagtctgagaactgagg<br>acacggccttgtattactgtgcaaaa (SEQ ID NO 188) |
| FW4 | >MF10428_FW4<br>tggggccagggaaccctggtcaccgtctcgagc (SEQ ID NO 189) |
| CDR1 | >MF10428_CDR1<br>gattataccatgcac (SEQ ID NO 190) |
| CDR2 | >MF10428_CDR2<br>gatattagttggagtagtggcaccactggctatgcggactctgtgaagggc (SEQ ID NO 191) |
| CDR3 | >MF10428_CDR3<br>gatcatatggggtacggtgactacgagggtggtggctttgactac (SEQ ID NO 192) |
| VH | >MF10428_VH<br>gaagtgcagctggtggagtctgggggaggcttggtacagcctggcaggtccctgagactctcctgtgtaa<br>cctctggattcacctttgatgattataccatgcactgggtccggcaagctccggggaagggcctggagtg<br>ggtctcagatattagttggagtagtggcaccactggctatgcggactctgtgaagggccgattcaccatc<br>tccagagacaatgccaaggactccctgtatctgcaaatgaacagtctgagaactgaggacacggccttgt<br>attactgtgcaaaagatcatatggggtacggtgactacgagggtggtggctttgactactggggccaggg<br>aaccctggtcaccgtctcgagc (SEQ ID NO 193) |

Figure 13 Continued

- Supercluster 7:
  - MF9249
    - DNA

```
1   ggcccagccg gccatggccg aggtgcagct ggtgcagtct ggagcagaag tgaaaaagcc
61  cggggagtct ctgaagatct cctgtaaggg ttctggatac agttttacta ggttttggat
121 cggctgggtg cgccagatgc ccgggaaagg cctggagtgg atggggatca tctatcctgg
181 tgactctgat accagataca gcccgtcctt ccaaggccag gtcaccatct cagccgacaa
241 gtccaccagt accgcctacc tgcagtggag cagcctgaag gcctcggaca ccggcatgta
301 ttattgtgtg agacatatac gatattttga ctggtcggaa gactaccact attacctgga
361 cgtctggggc aaagggacca cggtcaccgt ctccagt  (SEQ ID NO 194)
```

- AA

| | |
|---|---|
| FW1 | >MF9249.cep_FW1<br>EVQLVQSGAEVKKPGESLKISCKGSGYSFT (SEQ ID NO 195) |
| FW2 | >MF9249.cep_FW2<br>WVRQMPGKGLEWMG (SEQ ID NO 196) |
| FW3 | >MF9249.cep_FW3<br>QVTISADKSTSTAYLQWSSLKASDTGMYYCVR (SEQ ID NO 197) |
| FW4 | >MF9249.cep_FW4<br>WGKGTTVTVSS (SEQ ID NO 198) |
| CDR1 | >MF9249.cep_CDR1<br>RFWIG (SEQ ID NO 199) |
| CDR2 | >MF9249.cep_CDR2<br>IIYPGDSDTRYSPSFQG (SEQ ID NO 200) |
| CDR3 | >MF9249.cep_CDR3<br>HIRYFDWSEDYHYYLDV (SEQ ID NO 201) |
| VH | >MF9249.cep_VH<br>EVQLVQSGAEVKKPGESLKISCKGSGYSFTRFWIGWVRQMPGKGLEWMGIIYPGDSDTRYSPSFQGQVTI<br>SADKSTSTAYLQWSSLKASDTGMYYCVRHIRYFDWSEDYHYYLDVWGKGTTVTVSS (SEQ ID NO 202) |

Figure 13 Continued

- Supercluster 7:
  - MF9267
    - DNA

```
1   gaggtgcagc tggtggagtc tggggcagag gtgaaaaagc ccggggagtc tctgaagatc
61  tcctgtaagg gttctggata cagttttact aggtattgga tcggctgggt gcgccagatg
121 cccgggaaag gcctggagtg gatggggatc atctatcctg gtgactctga taccagatac
181 agcccgtcct tccaaggcca ggtcaccatc tcagccgaca agtccatcag taccgcctac
241 ctgcagtgga gcagcctgaa ggcctcggac accgccatgt attattgtgt gagaaatata
301 cgatattttg tctggtcgga ggactaccac tactacatgg acgtctgggg caaagggacc
361 acggtcaccgt ctccagt (SEQ ID NO 203)
```

- AA

| | |
|---|---|
| FW1 | >MF9267.cep_FW1<br>EVQLVESGAEVKKPGESLKISCKGSGYSFT (SEQ ID NO 204) |
| FW2 | >MF9267.cep_FW2<br>WVRQMPGKGLEWMG (SEQ ID NO 205) |
| FW3 | >MF9267.cep_FW3<br>QVTISADKSISTAYLQWSSLKASDTAMYYCVR (SEQ ID NO 206) |
| FW4 | >MF9267.cep_FW4<br>WGKGTTVTVSS (SEQ ID NO 207) |
| CDR1 | >MF9267.cep_CDR1<br>RYWIG (SEQ ID NO 208) |
| CDR2 | >MF9267.cep_CDR2<br>IIYPGDSDTRYSPSFQG (SEQ ID NO 209) |
| CDR3 | >MF9267.cep_CDR3<br>NIRYFVWSEDYHYYMDV (SEQ ID NO 210) |
| VH | >MF9267.cep_VH<br>EVQLVESGAEVKKPGESLKISCKGSGYSFTRYWIGWVRQMPGKGLEWMGIIYPGDSDTRYSPSFQGQVTI<br>SADKSISTAYLQWSSLKASDTAMYYCVRNIRYFVWSEDYHYYMDVWGKGTTVTVSS (SEQ ID NO 211) |

Figure 13 Continued

PDL1 MFs

MF5377

DNA

```
  1 gaggtgcagct ggtgcagtct ggagctgagg tgaagaagcc
 61 tgggtcctcg gtgaaggtct cctgcaaggc ttctggaggc atcttcagca cctatgctat
121 cagctgggtg cgacaggccc ctggacaagg gcttgagtgg atgggaggga tcatccctat
181 ctttgataca ccaaactacg cacagaagtt ccagggcaga gtcacgatta ccgcggacaa
241 atccacgagc acagcctaca tggacctgag cagcctgaga tctgaggaca cggccgtata
301 ttactgtgcg aaaaacgtgc gtggatatag tgcctacgac cttgactact ggggccaggg
361 caccctggtc accgtctcca gt  (SEQ ID NO 212)
```

AA

| | |
|---|---|
| FW1 | FW1<br>EVQLVQSGAEVKKPGSSVKVSCKASGGIFS (SEQ ID NO 213) |
| FW2 | FW2<br>WVRQAPGQGLEWMG (SEQ ID NO 214) |
| FW3 | FW3<br>RVTITADKSTSTAYMDLSSLRSEDTAVYYCAK (SEQ ID NO 215) |
| FW4 | FW4<br>WGQGTLVTVSS (SEQ ID NO 216) |
| CDR1 | CDR1<br>TYAIS (SEQ ID NO 217) |
| CDR2 | CDR2<br>GIIPIFDTPNYAQKFQG (SEQ ID NO 218) |
| CDR3 | CDR3<br>NVRGYSAYDLDY (SEQ ID NO 219) |
| VH | VH<br>EVQLVQSGAEVKKPGSSVKVSCKASGGIFSTYAISWVRQAPGQGLEWM<br>GGIIPIFDTPNYAQKFQGRVTITADKSTSTAYMDLSSLRSEDTAVYYCAKNVRGYSAYDLDYWGQGTLVTVSS<br>(SEQ ID NO 220) |

Figure 13 Continued

MF5444

DNA c aggtgcagct ggtgcaatct gggtctgagt tgaagaagcc
61 tggggcctca gtgaaggttt cctgcaaggc ttctggatac accttcacta gctattctat
121 gaattgggtg cgacaggccc ctggacaagg gcttgagtgg atgggatgga tcaacaccaa
181 cactgggaac ccaacgtatg cccagggctt cacaggacgg tttgtcttct ccttggacac
241 ctctgtcagc acggcatatc tgcagatcag cagcctaaag gctgaggaca ctgccgtgta
301 ttactgtgcg agagatcacg attttcggac tgggagggct tttgatatct ggggccaagg
361 gaccacggtc accgtctcca gt(SEQ ID NO 220)

AA

| | |
|---|---|
| FW1 | FW1<br>QVQLVQSGSELKKPGASVKVSCKASGYTFT (SEQ ID NO 222) |
| FW2 | FW2<br>WVRQAPGQGLEWMG (SEQ ID NO 223) |
| FW3 | FW3<br>RFVFSLDTSVSTAYLQISSLKAEDTAVYYCAR (SEQ ID NO 224) |
| FW4 | FW4<br>WGQGTTVTVSS (SEQ ID NO 225) |
| CDR1 | CDR1<br>SYSMN (SEQ ID NO 226) |
| CDR2 | CDR2<br>WINTNTGNPTYAQGFTG (SEQ ID NO 227) |
| CDR3 | CDR3<br>DHDFRTGRAFDI (SEQ ID NO 228) |
| VH | VH<br>QVQLVQSGSELKKPGASVKVSCKASGYTFTSYSMNWVRQAPGQGLEWM<br>GWINTNTGNPTYAQGFTGRFVFSLDTSVSTAYLQISSLKAEDTAVYYCARDHDFRTGRAFDIWGQGTTVTVSS<br>(SEQ ID NO 229) |

Figure 13 Continued

MF5380

DNA g aggtgcagct ggtggagtct gggggagacg tggtccagcc
61 tgggaggtcc ctgagactct cctgtgcagc ctctggattc accttcagta gctatggcat
121 gcactgggtc cgccaggctc caggcaaggg gctggagtgg gtggcagtta tatcatatga
181 tggaagtaat aaatactatg cagactccgt gaagggccga ttcaccatct ccagagacaa
241 ctccaagagc acgctgtttc tgcaaatgaa cagcctgaga gctgaggaca cggctgtgta
301 tttctgtgtg agaggcctcc ccataactat ggttcgggga gcgtactcct ttgactactg
361 gggccagggc accctggtca ccgtctccag t (SEQ ID NO 230)

AA

| | |
|---|---|
| FW1 | FW1<br>EVQLVESGGDVVQPGRSLRLSCAASGFTFS (SEQ ID NO 231) |
| FW2 | FW2<br>WVRQAPGKGLEWVA (SEQ ID NO 232) |
| FW3 | FW3<br>RFTISRDNSKSTLFLQMNSLRAEDTAVYFCVR (SEQ ID NO 233) |
| FW4 | FW4<br>WGQGTLVTVSS (SEQ ID NO 234) |
| CDR 1 | CDR1<br>SYGMH (SEQ ID NO 235) |
| CDR 2 | CDR2<br>VISYDGSNKYYADSVKG (SEQ ID NO 236) |
| CDR 3 | CDR3<br>GLPITMVRGAYSFDY (SEQ ID NO 237) |
| VH | VH<br>EVQLVESGGDVVQPGRSLRLSCAASGFTFSSYGMHWVRQAPGKGLEWV<br>AVISYDGSNKYYADSVKGRFTISRDNSKSTLFLQMNSLRAEDTAVYFCVRGLPITMVRGAYSFDYWGQGTLVT<br>VSS (SEQ ID NO 238) |

Figure 13 Continued

EGFR MFs

MF8233

DNA c aggttcagct ggtgcagtct ggagctgagg tgaagaagcc
61 tggggcctca gtgaaggtct cctgcaaggc ttctggttac acctttacca gctatggtat
121 cagctgggtg cgacaggccc ctggacaagg gcttgagtgg atgggatgga tcagcgctta
181 caatgccaac acaaactatg cacagaagct ccagggcaga gtcaccatga ccacagacac
241 atccacgagc acagcctaca tggagctgag gagcctgaga tctgacgaca cggctgtgta
301 ttactgtgca aaagatcgtc attggcattg gtggctggac gcctttgatt attggggcca
361 aggtaccctg gtcaccgtct ccagt (SEQ ID NO 239)

AA

FW1: QVQLVQSGAEVKKPGASVKVSCKASGYTFT (SEQ ID NO 240)

FW2: WVRQAPGQGLEWMG (SEQ ID NO 241)

FW3: RVTMTTDTSTSTAYMELRSLRSDDTAVYYCAK (SEQ ID NO 242)

FW4: WGQGTLVTVSS (SEQ ID NO 243)

CDR1: SYGIS (SEQ ID NO 244)

CDR2: WISAYNANTNYAQKLQG (SEQ ID NO 245)

CDR3: DRHWHWWLDAFDY (SEQ ID NO 246)

VH: QVQLVQSGAEVKKPGASVKVSCKASGYTFTSYGISWVRQAPGQGLEWM
GWISAYNANTNYAQKLQGRVTMTTDTSTSTAYMELRSLRSDDTAVYYCAKDRHWHWWLDAFDYWGQGTLVTVSS
(SEQ ID NO 247)

Figure 13 Continued

MF9891

DNA

```
c aggttcagct ggtgcagtct ggagctgagg tgaagaagcc
     61 tggggcctca gtgaaggtct cctgcaaggc ttctggttac acctttacca gctatggtat
    121 cagctgggtg cgacaggccc ctggacaagg gcttgagtgg atgggatgga tcagcgctta
    181 caatgccaac acaaactatg cacagaagct ccagggcaga gtcaccatga ccacagacac
    241 atccacgagc acagcctaca tggagctgag gagcctgaga tctgacgaca cggctgtgta
    301 ttactgtgca aaagatctgt acggtcattg gtggctggat gcctttgatt attggggcca
    361 aggtaccctg gtcaccgtct ccagt (SEQ ID NO 248)
```

AA

| | |
|---|---|
| FW1 | FW1<br>QVQLVQSGAEVKKPGASVKVSCKASGYTFT (SEQ ID NO 249) |
| FW2 | FW2<br>WVRQAPGQGLEWMG (SEQ ID NO 250) |
| FW3 | FW3<br>RVTMTTDTSTSTAYMELRSLRSDDTAVYYCAK (SEQ ID NO 251) |
| FW4 | FW4<br>WGQGTLVTVSS (SEQ ID NO 252) |
| CDR 1 | CDR1<br>SYGIS (SEQ ID NO 253) |
| CDR 2 | CDR2<br>WISAYNANTNYAQKLQG (SEQ ID NO 254) |
| CDR 3 | CDR3<br>DLYGHWWLDAFDY (SEQ ID NO 255) |
| VH | VH<br>QVQLVQSGAEVKKPGASVKVSCKASGYTFTSYGISWVRQAPGQGLEWM<br>GWISAYNANTNYAQKLQGRVTMTTDTSTSTAYMELRSLRSDDTAVYYCAKDLYGHWWLDAFDYWGQGTLVTVS<br>S (SEQ ID NO 256) |

Figure 13 Continued

MF9886

DNA c aggttcagct ggtgcagtct ggagctgagg tgaagaagcc
61 tggggcctca gtgaaggtct cctgcaaggc ttctggttac acctttacca gctatggtat
121 cagctgggtg cgacaggccc ctggacaagg gcttgagtgg atgggatgga tcagcgctta
181 caatgccaac acaaactatg cacagaagct ccagggcaga gtcaccatga ccacagacac
241 atccacgagc acagcctaca tggagctgag gagcctgaga tctgacgaca cggctgtgta
301 ttactgtgca aaaggtccag gttctcattg gtggctggat gcctttgatt attggggcca
361 aggtaccctg gtcaccgtct ccagt (SEQ ID NO 257)

AA

| | |
|---|---|
| FW1 | FW1<br>QVQLVQSGAEVKKPGASVKVSCKASGYTFT (SEQ ID NO 258) |
| FW2 | FW2<br>WVRQAPGQGLEWMG (SEQ ID NO 259) |
| FW3 | FW3<br>RVTMTTDTSTSTAYMELRSLRSDDTAVYYCAK (SEQ ID NO 260) |
| FW4 | FW4<br>WGQGTLVTVSS (SEQ ID NO 261) |
| CDR 1 | CDR1<br>SYGIS (SEQ ID NO 262) |
| CDR 2 | CDR2<br>WISAYNANTNYAQKLQG (SEQ ID NO 263) |
| CDR 3 | CDR3<br>GPGSHWWLDAFDY (SEQ ID NO 264) |
| VH | VH<br>QVQLVQSGAEVKKPGASVKVSCKASGYTFTSYGISWVRQAPGQGLEWM<br>GWISAYNANTNYAQKLQGRVTMTTDTSTSTAYMELRSLRSDDTAVYYCAKGPGSHWWLDAFDYWGQGTLVTVS<br>S (SEQ ID NO 265) |

Figure 13 Continued

MF9873

DNA c aggttcagct ggtgcagtct ggagctgagg tgaagaagcc
61 tggggcctca gtgaaggtct cctgcaaggc ttctggttac acctttacca gctatggtat
121 cagctgggtg cgacaggccc ctggacaagg gcttgagtgg atgggatgga tcagcgctta
181 caatgccaac acaaactatg cacagaagct ccagggcaga gtcaccatga ccacagacac
241 atccacgagc acagcctaca tggagctgag gagcctgaga tctgacgaca cggctgtgta
301 ttactgtgca aaagatagag gttggcattg gtggctggat gcctttgatt attggggcca
361 aggtaccctg gtcaccgtct ccagt (SEQ ID NO 266)

AA

| | |
|---|---|
| FW1 | FW1<br>QVQLVQSGAEVKKPGASVKVSCKASGYTFT (SEQ ID NO 267) |
| FW2 | FW2<br>WVRQAPGQGLEWMG (SEQ ID NO 268) |
| FW3 | FW3<br>RVTMTTDTSTSTAYMELRSLRSDDTAVYYCAK (SEQ ID NO 269) |
| FW4 | FW4<br>WGQGTLVTVSS (SEQ ID NO 270) |
| CDR 1 | CDR1<br>SYGIS (SEQ ID NO 271) |
| CDR 2 | CDR2<br>WISAYNANTNYAQKLQG (SEQ ID NO 272) |
| CDR 3 | CDR3<br>DRGWHWWLDAFDY (SEQ ID NO 273) |
| VH | VH<br>QVQLVQSGAEVKKPGASVKVSCKASGYTFTSYGISWVRQAPGQGLEWM<br>GWISAYNANTNYAQKLQGRVTMTTDTSTSTAYMELRSLRSDDTAVYYCAKDRGWHWWLDAFDYWGQGTLVTVS<br>S (SEQ ID NO 274) |

Figure 13 Continued

MF9988

DNA c aggttcagct ggtgcagtct ggagctgagg tgaagaagcc
61 tggggcctca gtgaaggtct cctgcaaggc ttctggttac acctttacca gctatggtat
121 cagctgggtg cgacaggccc ctggacaagg gcttgagtgg atgggatgga tcagcgctta
181 caatgccaac acaaactatg cacagaagct ccagggcaga gtcaccatga ccacagacac
241 atccacgagc acagcctaca tggagctgag gagcctgaga tctgacgaca cggctgtgta
301 ttactgtgca aaagatcgtc attggcattg gtggctggac ggctttgatt attggggcca
361 aggtaccctg gtcaccgtct cgagtgtctc cagt (SEQ ID NO 275)

AA

| | |
|---|---|
| FW1 | FW1<br>QVQLVQSGAEVKKPGASVKVSCKASGYTFT (SEQ ID NO 276) |
| FW2 | FW2<br>WVRQAPGQGLEWMG (SEQ ID NO 277) |
| FW3 | FW3<br>RVTMTTDTSTSTAYMELRSLRSDDTAVYYCAK (SEQ ID NO 278) |
| FW4 | FW4<br>WGQGTLVTVSS (SEQ ID NO 279) |
| CDR 1 | CDR1<br>SYGIS (SEQ ID NO 280) |
| CDR 2 | CDR2<br>WISAYNANTNYAQKLQG (SEQ ID NO 281) |
| CDR 3 | CDR3<br>DRHWHWWLDGFDY (SEQ ID NO 282) |
| VH | VH<br>QVQLVQSGAEVKKPGASVKVSCKASGYTFTSYGISWVRQAPGQGLEWM<br>GWISAYNANTNYAQKLQGRVTMTTDTSTSTAYMELRSLRSDDTAVYYCAKDRHWHWWLDGFDYWGQGTLVTVS<br>S (SEQ ID NO 283) |

Figure 13 Continued

MF6744 anti-CD137 antibody sequence:

DNA g aggtgcagct ggtgcagtct ggagcagagg tgaaaaagcc 61 cggggagtca ctgaaaatct cctgtaaggg ttctggatac agctttacca gctactggat 121 cggctgggtg cgccagatgc ccgggaaagg cctggagtgg atggggatca tctttcctga 181 tgactctgat accagataca gtccgtcctt ccaaggccag gtcaccatct cagccgacaa 241 gtccatcagt accgcctacc tgcagtggag cagcctgaaa ccctcggaca ccgccatgta 301 ttactgtgtg agacttggtg gatatagtgg ctacgctgag gattttgttg acttctgggg 361 ccagggaacc ctggtcaccg tctccagt (SEQ ID NO 284)

AA

FW1: EVQLVQSGAEVKKPGESLKISCKGSGYSFT (SEQ ID NO 285)

FW2: WVRQMPGKGLEWMG (SEQ ID NO 286)

FW3: QVTISADKSISTAYLQWSSLKPSDTAMYYCVR (SEQ ID NO 287)

FW4: WGQGTLVTVSS (SEQ ID NO 288)

CDR1: SYWIG (SEQ ID NO 289)

CDR2: IIFPDDSDTRYSPSFQG (SEQ ID NO 290)

CDR3: LGGYSGYAEDFVDF (SEQ ID NO 291)

VH: EVQLVQSGAEVKKPGESLKISCKGSGYSFTSYWIGWVRQMPGKGLEWM
GIIFPDDSDTRYSPSFQGQVTISADKSISTAYLQWSSLKPSDTAMYYCVRLGGYSGYAEDFVDFWGQGTLVTVSS
(SEQ ID NO 292)

MF4327 (CLEC12A)

QVQLVQSGAEVKKPGASVKVSCKASGYTFTSYYMHWVRQAPGQGLEWMGIINPSGGSTSYAQKFQGRVTMTRDTSTST
VYMELSSLRSEDTAVYYCAKGTTGDWFDYWGQGTLVTVSS (SEQ ID NO 293)

H1H7232B (1129) VH - MF6955 in combination with common light chain

VH gene: IGHV3-9

DNA:

gcggcccagccggccatggccgaggtgcagctggtggagtcgggggaggcttggttcaccctggcaggtccctgaga
ctctcctgtgcagcctctggattcacctttgatgattataccatgcactgggtccggcaagctccagggaagggcctg
gaatgggtctcagatattagttggaatagtggtagcagaggctatgcggactctgtgaagggccgattcaccatctcc
agagataatgccgagaactccctgtacctgcaaatgaacagtctgagagctgaggacacggccttgtattactgtgca
aaagataaaagtggctacggccactactactactacgctatggacgtctggggccaagggaccacggtcaccgtctcc
tca (SEQ ID NO 294)

Protein:

AAQPAMAEVQLVESGGGLVHPGRSLRLSCAASGFTFDDYTMHWVRQAPGKGLEWVSDISWNSGSRGYADSVKGRFTIS
RDNAENSLYLQMNSLRAEDTALYYCAKDKSGYGHYYYYAMDVWGQGTTVTVSS (SEQ ID NO 295)

Figure 13 Continued

H1H7241B (1145) VH - MF6964 in combination with common light chain
VH gene: IGHV3-9
DNA:
gcggcccagccggccatggccgaggtgcagctggtggagtctgggggaggcttggttcagcctggcaggtccctgaga
ctctcctgtgcagcctctggatttacctttgctgactataccatgcactgggtccggcaaggtccagggaagggcctg
gagtgggtctcagatattggttggaatagtaatactataggctatgcggactctgtgaagggccgattcgccatctcc
agagacaacgccaagaactccctgtatcttcaaatgaacagtctgcgacctgaggacacggccttatattactgtgta
aaggataaaagtggctacgggaaattccaatacggtttggacgtctggggccaagggaccacggtcaccgtctcctca
(SEQ ID NO 296)
Protein:
AAQPAMAEVQLVESGGGLVQPGRSLRLSCAASGFTFADYTMHWVRQGPGKGLEWVSDIGWNSNTIGYADSVKGRFAIS
RDNAKNSLYLQMNSLRPEDTALYYCVKDKSGYGKFQYGLDVWGQGTTVTVSS (SEQ ID NO 297)

Figure 13 Continued

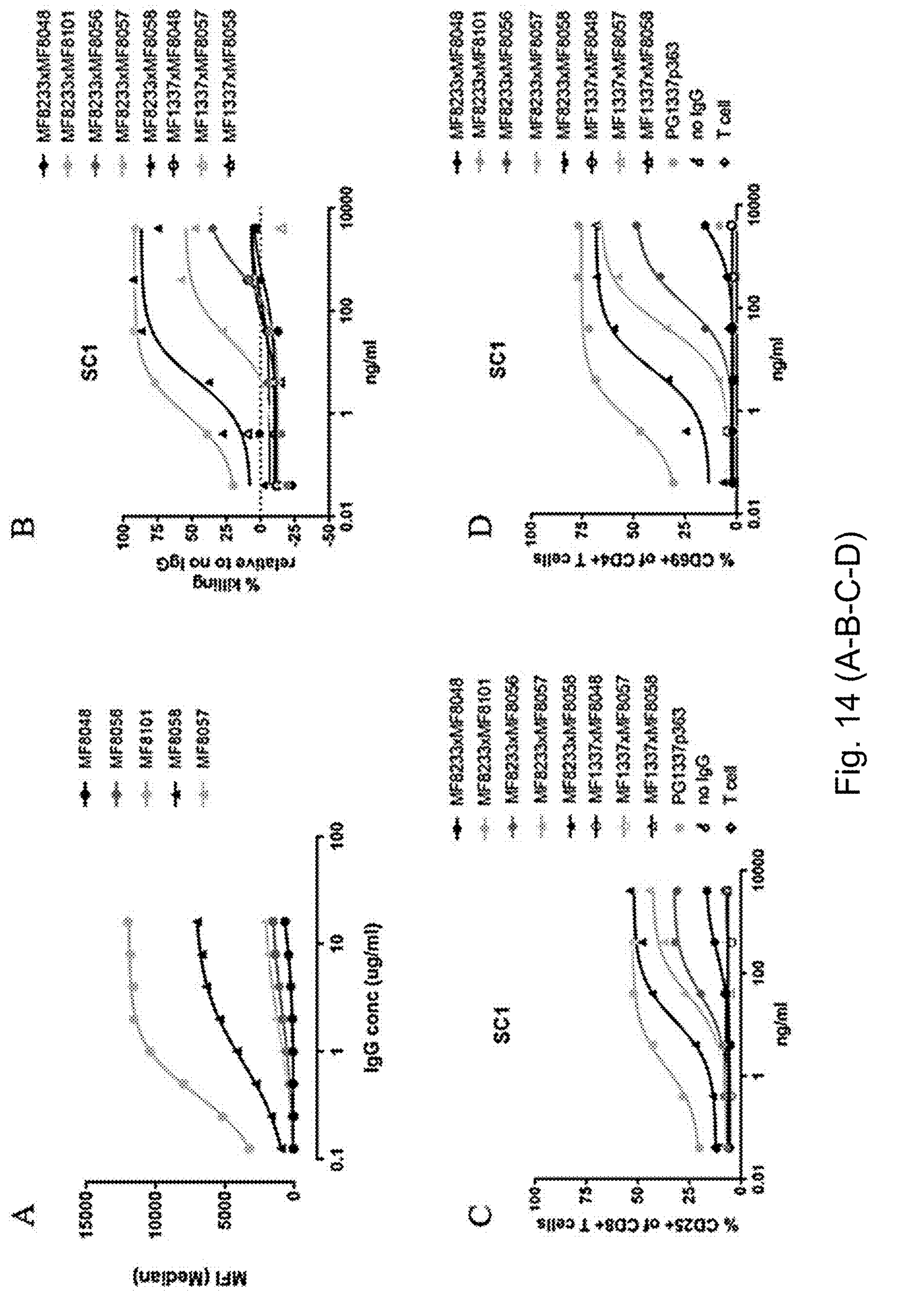
Fig. 14 (A-B-C-D)

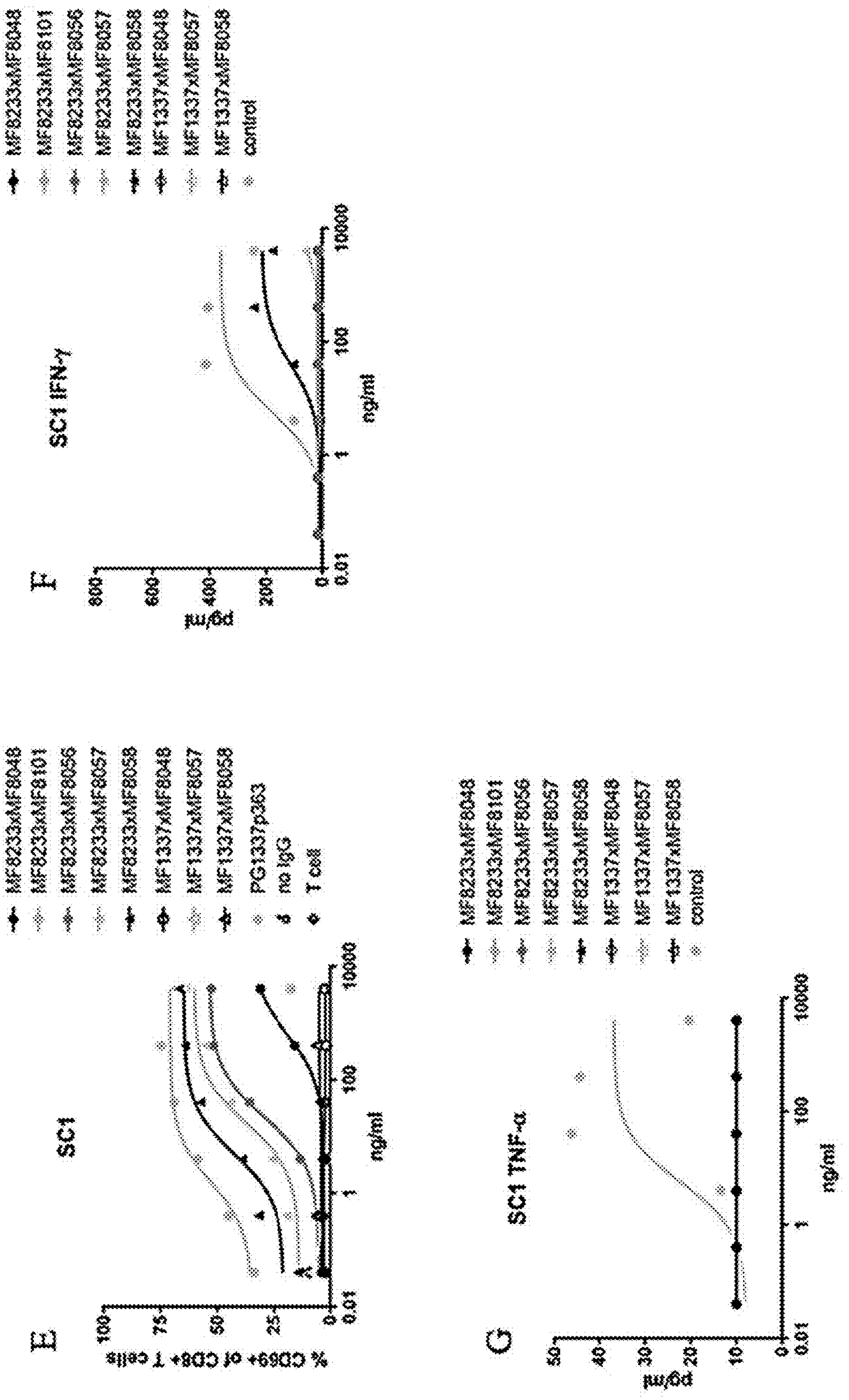
Fig. 14 (E-F-G)

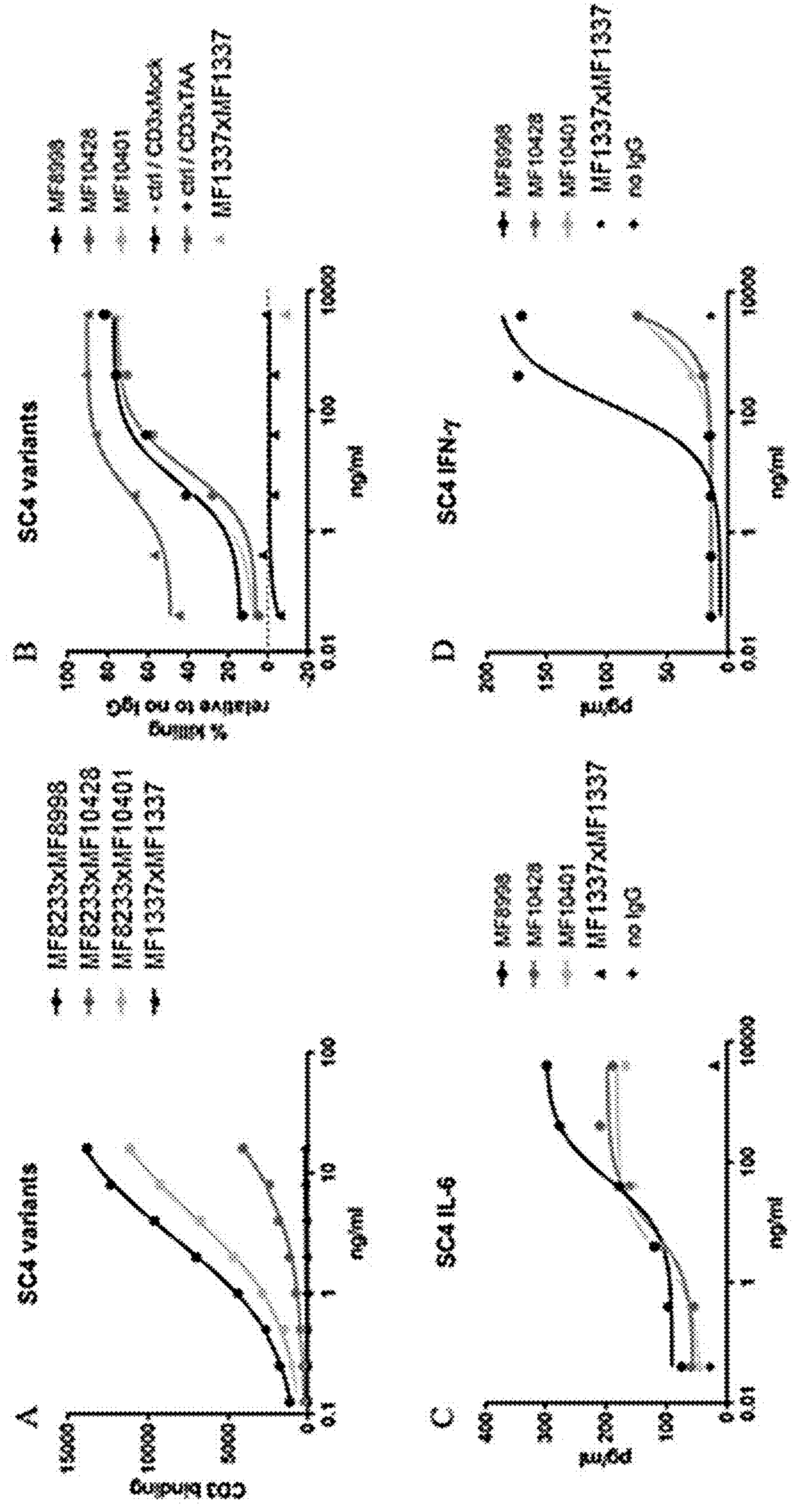
Fig. 15 (A-B-C-D)

Figure 19

CLEC12A (SEQ ID NO: 1)

>NC_000012.12:9951268-9995209 Homo sapiens chromosome 12, GRCh38.p13 Primary Assembly CTATTTAGCATTGCTGCTGCCAGCCCCAACCACATTTCTGATTGCCTAGGAAGAACAGCCTTTCAAATTT
GACTTCTGCATGTGGATAGGTGAGTGTCTTTTGTGGATACCGACAGTGGGAATGGCTCCTCTCAATTTGA
GAAATTCTGAAGGAATTTCCATTGGCAAGTTCAGCAAGGCCAACTGACGGAGAGAGGAAGCACCCTGACT
GTTCCAGTTCAGACACTCTTGGGGCTTGTTAGTAATTGAGTATGTGTCTGGATAAGTGAGTGTCATTTGT
GGGTCCAGACAGCAGGATCTGCTTTTCTCAATTTGAGAAATTCCGAAGGAATCTCCATTTGCAGATTGAA
CTAGCCCAACAAACAGGGAGAAAGCAACTCAACTGTTTCAGTTTGGACTCTCTTGGGACTTGCTTATTGT
TGCAGCAGTTAGATTGTATTCTGGTGGTTGTTTGTGTGTTGATGTAGTTGTGGGAGATCAGGGTTTGATC
TGAGTGCAGACCGCTTGGGTGTATTCTTCAGGGTTGGTCTGCATGTGGCTGTGGGCCAGTGGAGTGAGGG
AACATCTCTACCCGTATCACGCTGAACATGCCCAATCTCATCTGATCTCAGACAGTCTTTGAATTGTAGC
ACTGCCTTATATTTGGATTTATTTTGCTGTTGAATGTGAATATGGGATGGAAGTCCATGTCTCCAGGCTT
CTATGCTGCTGCTCTAAGGACAGGCAGGCCTGATTAGTATGTGCTGCTGTTTGGCTACAGAGTTCTTTGG
AGTCTGGAGAGATTTGGCCTTTAAAAATCAAACTGTCAGACCCTGTCTCAAGGAAAAAAAAAAAAACAGG
ATGTGAGCGCTCTCCCTCTCCCTCTCCCTCTCCCTCTCCGTCTCCCTCTCCCTCTCCCTCTCCGTCTCCC
TCTCCCTCTCCCTCTCCGTCTCCCTCTCCCTCTCCCCACGGTCTCCCTCTCATGTGGAGCCGAAGCTGGA
CTGTACTGCTGCCATCTCGGCTCACTGCAACCTCCCTGCCTGATTCTCCTGCCTCAGCCTGCCGAGTGCC
TGCGATTGCAGGCACGCACCACCACGCCTGACTGGTTTTGGTGGAGACGGGGTTTCGCTGTGTTGGCCGG
GCCGGTCTCCAGCCCCTAACCGCGAGTGATCCGCCAGCCTTGGCCTCCCGAGGTGCCGGGATTGCAGACG
GAGTCTCGTTCACTCAGTGCTCAATGGTGCCCAGGCTGGAGTGCAGTGGCGTGATCTCGGCTCACTACAA
CCTACACCTCCCAGCAACCTGCCTTGGCCTCCCAAAGTGCCGAGATTGCAGCCTCTGCCCGGCCGCCACC
CCGTCTGGGAAGTGAGGAGTGTCTCCGCCTGGCCACCCATCGTCTGGGATGTGAGGAGCCCCTCTGCCTG
GCTGCCCAGTCTGGAAAGTGAGGAGCGTCTCCGCCCGGCCGCCATCCCATCTAGGAAGTGAGGAGCGCCT
CTTCCCAGCCGCCATCACATCTAGGAAGTGAGGAGCGTCTCTGCCCGGCCGCCCATCGTCTGAGATGTGG
GGAGCGCCTCTGCCCCGCCGCCCCATCTGGGATGTGAGGAGCGCCTCTGCCCGGCCGAGACCCCGTCTGG
GAGGTGAGGAGCGTCTCTGCCCGGCCGCCCCGTCTGAGAAGTGAGGAGACCCTCTGCCTGGCAACCACCC
CGTCTGAGAAGTGAGGAGCCCCTCCGCCCGGCAGCCGCCCCGTCTGAGAAGTGAGGAGCCTCTCCGCCCG
GCAGCCACCCCATCTGGGAAGTGAGGAGCGTCTCCGCCCAGCAGCCACCCCGTCCGGGAGGGAGGTGGGG
GGGGTTAGCCCTCCGCCCGGCCAGCCGCCCCATCCGGGAGGGAGGTGGGGGGTCAGCCCCCCGCCTGGCC
AGCCATGCCGTCCGGGAGGGAGGTGGGGGGGTCAGCCCCCTGCCCGGCCAGCCGCCCCGTCCAGGAGGTG
AGGGGCGCCTCTGCCCGCCCCCCCCTACTGGGAAGTGAGGAGCCCCTCAGCCCGGCCAGCCACCCCGTCT
GGGACGGAGATGGGGGGTCAGCCCCCCCGCCCAGCCAGCTGCCCCGTCCGGGAGGGAGGTGGGGGGGTCA
GCCCCCCGCCTGGCCAGCCGCCCCGTCCGGGAGGGAGGTGGGGGGGTCAGCCCCCCGCCTGGCCAGCCGC
CCCGTCCGGGAGGGAGGTGGGGGGGGTCAGCCCCCCCGCCCAGCCAGCCGCCCCGTCCGGGAGGTGAGGG
GCGCCTCTGCCCGGCCGCCCCCTACTGGGAAGTGAGGAGCCCCTCTGCCTGGCCAGCCGCCCCGTCCGGG
AGGGAGGTGGGGGGGTCAGCCCCCTGCCCGGCCAGCCGCCCCGTCCGGGAGGTGAGGGGCGCCTCTGCCC
GGCCGCCCCTACTGGGAAGTGAGGAGCCCCTCTGCCCGGCCACCACCCCGTCTGGGAGGTGTGCCCAGCA
GCTCATTGAGAACGGGCCAGGATGACAATGGCGGCTTTGTGGAATAGAAAGGCGGGAAAGGTGGGGAAAA
GATTGAGAAATGGGATGGTTGCCGTGTCTGTGTAGAAAGAAGTAGACATGGGAGACTTTTCATTTTGTTC
TGCACTAAGAAAGATTCTTCTGCCTTGGGATCCTGTTGATCTGTGACCTTACCCCCAACCCTGTGCTCTC
TGAAACATGTGCTGTGTCCACTCAGGGTTAAATGGATTAAGGGCGGTGCAAGATGTGCTTTGTTAAACAG
ATGCTTGAAGGCAGCATGCTCGTTAAGAGTCATCACCAATCCCTAATCTCAAGTAATCAGGGACACAAAC
ACTGCGGAAGGCCGCAGGGTCCTCTGCCTAGGAAAACCAGAGACCTTTGTTCACTTGTTTATCTGCTGAC
CTTCCCTCCACTATTGTCCCATGACCCTGCCAAATCCCCTCTGTGAGAAACACCCAAGAATTATCAATAA
AAAAAAAAAAAAAAAAAAAAAAAAAATCAAACTGTCAGCTGGGCGCAAGAAACTGAGGTGGGCAGATACT
TGAGCCCAGGAGTTCGAGACCAGCCTGGGCAACATGGTGAAACCCTGTCTCTACAAAAAATACAAATATT
AGCTGGGTGTAATGGTGCATACCTGTAGTCCCAGCTACTCAGGAGGCTGAGGTGGGAGGATTACCTGAGC
CTGGGAGGTTGAGGCTGCAGTGAGCCTTGATCACACCACTGCACTTCCAGCCTGGGTGACGGAGATCCTG
TCTCAAAAAAAAAAATAATCAAACTATCATGGAAACTGCTTTATTCAAAATTTTGTTTCACAACCTTTAT
TGGATTACCTATCAGAACAAATAAAGTTCAACCATGTGAACATGTTCATAAACCAGTGAGTTTGCATTGC
TATCTCATGGCTGGAATTTAAAGGTAAAAGCTATTGGATCTTTGTGTGTATGTAGGTATATGTGTCTAGA
TGTTACGTGTTGTTTTTAGAGGGTAGCAAATTGGCTTATAAATTAAAAAGCGTTCATAAATTAAGTAAAT
GAGTCTAAGCATTTTTCAAGTTTACATGACTTAAGTAAATCTTTAATAAACAAGAGAGCTTTTAGATCAT
TTGTAAAATAAAAATAGAAATGCCTTTGGAATTGTCAGCATACTTTTTTTGTTTGGGTTTTACATTTGTC TCTGCTAGATATTTAAAGGTGTCAGGGTTTGACAAAGAGATTATAAGACTATAAACCCAGCCAAGAACAA
AATTATCTTTGTGTGATTTTTTGATAAATAAGACTAATTTAATGTCGTTAGGTTAATAAAAATAGCTGAA
ACTTTTGCATTATTGGTGCAAGTATCCATGTATTTTACTTTATGTTTCTTTTTTTTAAAAACGGAGTCTC
ACTCTGTCGCCCAGGCTGGAGTGCAGTGGCCCGATCTCGGCTCACTGCAAGCTCTGCCTCCCGGGTTCAC
GCCATTCTCCTGCCTCAGCCTCCTGAGTAGCTGGGACCACAGGCGCCCGCCACCACGCCCGGCTAATTTT
TTGTATTTTTTAGTAGAGAAGAGGTTTCACCATGTTAGCCAGGATGGTCTTGATCTCCTGACCTCATGAT
CCTCCTGCCTCAGCCTCCCAAAGTGCTGGGATTACAGGTGTAAGCAATCATGCCCAGCCAACTTTATGTT
TCTTACTTAGGTGAACATCTAATATATACAAGTTATAAAAATGGTTAACAAGGAAATAATGAATAGCTTT
GATATCTCTTTTCTCATAAGTAATATAGATAATTGCTAAAAAAGTGAATGAAATATAAATGGCATAAATG
CTCTAAGTGAACTTTTTGTGTAATTTAATATCTTGAAGTTATTTTGGATGCTCATGAGATGTGTGGGTCA
TTTCCAATTATGAAAGGGTTTCAATACAGAAAGTTAAATGATGTAAAAACCTTAATTCCTTTAAATCTCA
GTTTTCCTAAGCAATCAAAAACCCAATAACAATGACATAGAAATTATTTTGATAAAATGTAAAATTTGTT
TCTCAGGTCAGTTACCAAAAGGCAAAGAAAAACCTCCTGCAGTGTGATTGCTTCTCCTATCAGAGTCCCA
TCTCGAAAACCTGAAAATCAAACCTGATAAATGATGTAGACATATCAAGAAAAGCCAAGAGGACAGAATC
AAGCTATACTGGAGGAAAACGTTGCTTCTCTAGAATTTTAAAATAAATATTTCAGCATCAGACCATGACA
GCAGTTAAGGCAAGAGGGAAAAAAAAGATACAAGAACTGACAAAGTTGAAGGAGATAGTTTCATTTCAGG
TTCCTTCAAGGGGAGACAAGCTGACAGCAACAAAACACAAGAAAGCTGCACTTTGGAGATATAGATCTGA
GAAGTATTCAAAAAGTAACAGATTATAGAGTCAAAATCAAAACCTCTCATCCAATCAATATTTTAAGAAA
ACCTTGTTCTAACCCAGGGGACTAATCTATATCTCTCTCCCCTAGTTACTGGATCCTTTCTACCCTGTTT
CATAAACAACCTAAGTCTATAATTTGAATTAACCTTTAGATAACTTCTGAGTTAAACAAAATTATTTCTT
TAATCAATAAGAACACATCTTCTTTGGCACATTGTACATGGAATCATACAATTTGCTGGAATTCTTATTC
TTAGTAATCCTAAATTTTAATGGAAACCTAGGAAGCAAGAAATCCTGGGCTGTCTATCAGATATTAACAT
TTTATAGATGAGAAACATGAATGTTCTCAGGCCCAGAAAACTCAAGTTGTTTTGGGACCTCAAGAAAAGA
GGAATTCACCCAATTCATACAGGTATCTGCAAGCACAGATCAATTATTGGTTGTGCTCGAGAGGCCTTTA
AAAATCAAATCTGAGATTCCTTATGAAAAGTTCCAGCAAAGCCAATTTAAAAAAGCCTATATGAACAATA
ATTCTTGCTTCAGTTTATGCAAATAATCAGGCAAACTATAATAAGATTAAAACAGATTTTGCAAATAAAT
TGGTCCTACTGTGATTTGCCTTTCATGGAAATGGGGAGCTGGAGAGAGAAACATTATGTTTTGGAAGAAA
ACTGCAGTACACCTGTTATTAGATTAATCTTTGACCTATGGCAACCTGGTCATCCATGGTATGGAGATAC
ATCTGTGCTGTGCTGCATTCAGTTATTAAAAGTATAAGTTACCAGTGGAATTTAGATATGGATTCATCAC
CTCAGAAGTTGGTTCACTGGATGCATAAGGAAATAAAAACTAATTTTTAAAAAAGCAAAATTTTCAATCC
CTTGGTTTTTGTTATCGATATAAACCAAAATGTATCTGAGGTAGGTCTCAATTAATTTCAAAGTTTATTT
TGCCAAGGGTAGGGATATGTGCCTGAAACACAAGTCTGTGCCTTTCTCCAAAGATGCTTTTGAGGGCTTC
AATATTTAAAGGGGAAAGGGCAGATATTGGGGAAAGAGGAAGAAATTTTAAAAAGGTGTGGGTAGGGCGG
TGGCTCATGCCTGTAATCCCAGTAATTTGGGAGGCCAAGGTGGGCAGATCACCTGAGGTCAGGAGTTTGA
GACTAGCCTGACCAACATGGACAAACCCCATCTCTACTAAAAATACAAAAATTAGCTGGGTGTGGTGGTG
CACGGCTGTAATCCCAGCTACTCAGGAGGCTGAGGCAGGAGAATCACTTGAACTCGGGAGACAGAGGTTG
CAGTGAGCCAAAATCGTGCCACTGCATTCCAGCCTGGGTGATGACAGAGTGAGACTTCATCTCAAAAAAA
AAAAAAACAAAAAAACAAAAAAAAGGTGTGGGTAGATAAGAGACAAATGGTTGTATTCTTTTGAGATTTT
GATCAGACTTTCACTAAATACACAATTACATGTGAGAGTGGGGTAAAGAAATAGTCACTTATGCCTCAGT
CTAGATCAGTGAATCTGCATTTTTATACAAACGAAAGGGCAGAGGAAGCAATCAGATATGCATTTGTTTC
AGATGAGCAGAGGGTTGACTTCAAGTTCTATCCTTTGTCCCATACCTGTGAAGATAAGCTATCAATTTAC
ATTGCCAGGGTGAAATTCAATCGAATAAAATGGGAGCCAGGTTTGCCTGACACAATTCCCAGCTTGACTT
CTCTCTTTGGCTTAGTGATTTGGGGACCCCAAGATTTATTTTCCTTTCACATCTGTAATAGCTAAAATTA
AAGTAGGAGAATATTGGGTCAGGCTTTGAGGCCAAACCAAGCCTAGATGTGGGTCTGTCTGAACTCAGAT
CACTAGCCTCAAGGCTGCTCATGAAGAAGAAAATTATGCCAGGAAACCAGAAAGTACCTCTGAGATCTGT
GGTTTCCTGGAAGGTAGTCAATGTGGGGAAGGAGTGAATTAAAGTGACTTCTGAAACTAGAGGGTATAAT
GTGAAGGAATTGTTCTATTTTGCAAATCAGTATCATTAGCTTCCTGAACCTTTACTAAAATAAATTGTGA
GAGTAATTACTTTAGGCACAATGTCTTTGGTTTTAAATGCTGCAGAGTGGAAGATCCGGTTGATACAGAA
CCCACGGCTCACAATTGAACAGTTGCAGATGGGTACATATAATCCGGGCACACAGGAGGTTATTCCCAAA
AGAACAGCCTACTTGGTGGACTGGATAAAACACTGTGAGAACTATTTACTCTGAGAAGGAGAATTGTCCC
ACTCCACCTATAAATGCCAAGTGGAGCACTCCAGATGAAGCAACAGATATGCTTCAAATGTAAGCCACGG
GGGACTGGCTTTATAATGATGTGGCAGGCCAGGTCACTAATGCAGGCCTCCATAACAACTGTTTCAGTAC
TGACTGAGTGGTTAAGTTAAATGTTAAAAGGTAAAAAAGCCAGTGGCCTTATACAAACTCTGGATTGTAA
CAAAAGCCCACCACGAGTTTTGCCTAGGACTTTCCTGGGGCTTGGACCCATGACAAGATAATGAAGGAAT
TCTTAACAGGACCAGATTAGGATTAAACAAGTTTTACCGGCAGTCTGAAGAAACTTCCCAGGCTTCCACA
GACAAGTTTATTGGAGATCTCAAGGAAGTTCCCAAACCTCCATGATTTAGCAGGAGACAAGATAGGGTAA
TCACCCCAGCACCTGGACCCATATAGATTAAGTAAATTTACTAAGCCTCCAGAGGAAGGTCTTCAGAACT

Figure 19 Continued

CAGATCTCAGTTATAGATTACAAGAAGTTAATCACTCATGTTTTTAGATGAATGCACTTACACACAGACA
TATAACTTAGAAGGTAATAAGCTCTGGAAGACTTTGTAATTTTGAGTTGGTCTGGCAATATTTTCCAGGC
CTTCTCCCTATAACTTGTTAAAGAAATAAAAACTCTTCCTCCCCAGTTCATCTGCATCTTGTTACTGGGC
TGGAAGAAATAGCAGTCTGACCCTCAGTTTGGTCCAGGAACAATGATAGAAATATTAACTTGGCTGGGCG
TGGTGGCTCACTCCTGTGATCCCTGCACTTTGGGAGGCTGAGGCGGGTGGATCACATGAGGTCAGGAGTT
TGAGACCAGCCTGGCCAACATGATGAAACCCCATGTCTACTAAAAATACAAAAAATTAGCTGGGCGTGGT
GGCGGGCACCTGTAACCCCAGCTACTCTGGAGGCTGAGGCAGGAGAATCTCTTGAACCAGTGAGGCGGAG
GTTGCAGTGAGTAGAGATTGTGCCACTGCACTCCAGCCTGGGAGAGAAGAGCGAAACTCTGTCTCAAAAA
AAAAAAAAAAGAAGAAAGAAATATTAACCTTACTTTTTGGTTTTTGGCTCTTTCGTTGCTTTGAGTTTTA
ATGGTAATGAGTCCCTGGCACCTCTATTCTTGTGTGGCCTAGAATGTTTAATTGACTATAAGTCTTTTTT
GACTCTAAGTCCCTTGGTTACAGGGGTCCCACTGACGAACAGGATGGACTCGGGGCAGGTAGTCATACCA
CCTTGGAAATGATATGGAACAAAATAAAGTTTGGCAATCAATGCTCCCTCTGGCATATTCCAAGGAGACC
TCAGTTTCCAAGAGATAAATCTTACCTGGGAAAAGGTCTTGCCCCTTGCCCTGCTGAGGGTACTGGTAGC
TCCCAGAAATGGATTAGCTCTTAGCCCCTTTCAAAATGTTTACTTGGAGACTGTTTTCCTGGACTCTCTG
ATGCTTGAGGATTTTTTCCTCCCCTGAAACAGAAGCTATGTCATACATGAAACAATTAGGGAATATATTA
ACTAGTCTCTCCAACAGACTTCATTTCTGTATGGACTTGCCTCTTCCCTGTTTGAAACCAGGGAATCGAA
TCATACTGAAGACCTGGAAATCCCATCAGGCTGAAGACTAGCTGCAACCACAATAGGTCAGTCTTTTTAA
GGTGCTGCTGACCACCCACTCGTCTATCAAGTTAGCCAGTGTTAAACCATGAATTCAACATACTCAGTAA
AACTAGTCACTGTGGGATCCCTCCAGGGGAAACAGTCATGCTCTTGTGAACCTATACATGGCCTTAAGTT
AATATTGAAAGCCCAGCCAAAGATCCTAGATAAGAAACTGTAAAAGGAATATGCATTTTTCAGTTATTAT
TCTCTTTAAACCCACAGCTTTTCACATATAAGATATAATGAATCAGGAATACTTTTTGGTAGGCTTAGGA
TTGTTCTCTTGGATTCCCCAAGGGATCCACTCCAAATTCTCTGGTATTTTAAAATTGGTTTATCTATATT
ATTTATCATCCTTGTTCAATGTGGCCTAAAACGTTGTTCTAAAACTGAAATAAAAGTACCCAGATCATAG
TGCTCCAATGACTACTTCTGATTATAGTGCCACATTTCCATTCCTTATCATTATTCCACCTCACACGTCC
TCAGCATGAAGCAGCCAGAAGGATCAATGACCAGATTCTCCATGATTGAGGAAGTGATAAATAGAAAAGA
GAGACTGAAACCGGCCCCGTTATCTTATAGAACTAATATTTACAGTTGTTTTTGTTTGTTTTGCTTTGGA
ACATAGAAATGGACCCTGTCTGGTCTTAAAACTTGAAACTTGTTTGTTTTCCTGAGTTTCTTGCTTAGAA
AACCGACTTTCAGGCAAGGAACTGAAACTCATCAGAGCACCACACCCAGGCAATGAGACTGCAGATCCTT
CACCCAGCATGATTTTTTCCCTACCTCTGCCTAATTTCTATTTTTCCCCTGTCCACGTAGCATCAAACTC
TGTAAAATATTTGAAGAGATTTATTCTGAGCCAAATATGAGTGACCATGCCCGTGACACAGCCCTCAGGA
GGCCCTGCGAACATGCACCCAAGGTGGTTCAGGTACACATTGGTTTTGTACATTTTAGGGAGACACGAGG
CTTCAATCAACTATAAACATTTACTGATTGGCAATTGGTTGAGTTTATCTAAAGGTCTGGAATCAATAGA
AAAGAAATGTCTGGGTTGTGGTAAGAGGTTGTAGAGACCAAGGTTTTATCATGCAAATGAAGCCTCCAGA
CAGCAGACTTGAGAGAGACTTAAGTATTAATGCCTGAGAGATATAATGAAGCGTGTTCGACACGCACTTC
CTGTCATGGCCTGAACCCATCTCTCAGGTTAAATTTTCAAAGAGCTGTGGTTGAAGAGGGAGTCCATTCA
GATGGTTGAGGGGCCTTAGAATTTCATTTTTGGTTTACACTCCCCACACAGCTACATTTCTGCCTGCACA
TAGCTACATTCCTTCCTCACTATATAACCTCCCAATTTTAGTTTGTTGGAGAACAAAGCCAGAATAAAGC
CAATCCTAGTCATAGCATTGCAACTTGTATCAGATGAAAGAAACCTACAAAAAGATAATTATAAAATTTA
GATAAAATGTATAAAACAACTGAGAAGGCAAAATTTGAGGGGCTCCAATTAATCAAGGTTTACCGCTTAT
ATTCTGTGTGACTGCCAGAAAAAAAGAAACAAAACTTTTTGGTAGGAAGATCATTTAAAATTTCTGTTTT
TAATACATAAGGCCTGTTATTTAATAAAAAATTATGAGACAACCTAAAAAAAAAGAATTAAATATCAAAA
CACCAATTGACAAGCCAAATGATAAAAACTGGCCTACATATGGTTCAGAAAATGATTTCAATAAATCTAC
TCTTCACCATTCTAATCCCTTTGCAGTGCCCTAGGATGGTGACTGACTCTCATGTATAATATCCCTGGAC
ACTATTGTCCTGAAGCTCTAGGTATGTTTGTGCTAATAGGAAGAATAGGCAAAAGATTTAAAGGTGGGAG
AATCCTTCCCTACAGCACTAGGAAATGGATATGGAGTTGTTCTCGCTGAGTGTACCTCCAGGGAGGCAGC
CTTCATCAGCTATAGTTTCTGCTGCTTCAGTTAATTGCTACCAGCAATGTTCTCTCAGGCCTAATGTAGT
AATGGCTTCCGGCAGTAGCTAGCCCTGGGGTATTTCACTATCCCTCATGGTTTCCTTTGGTCTTATCTCT
ATCTTGTAAATTGTCCTGTTATTTTATCTTCTTAAATTTTCCTTTTAATGTATAACCGGTTTTTTCTTTT
TTTTTTTTTTTTTTGGATCCCAAGTGTGTGTTTCTTTTTGGTACCTGAGTATATCACTGTCACTGTGGTC
TCTCAACTTTTAAATTATGTGACTCTGAAGGTGTGTGTCTCCAAATTTTTATCCCTGTGCACTTTTCTTC
ACCTGTCTTCATTTCTTTCCCTTTTTTCCGTTATAACTTTCACTCACATCCGTGTGAAGAGACCACCAAA
CAGGCTTTGTGTGAGCAACAAGGCTGTTTATTTCACCTGGGTGCAGGTGGGCTGAGTCCGAAAAGAGAGT
CAGCGAAGGGAGATAGGGGTGGAGCTGTTTTATAAGATTTGGGTAGGTAGTGGGAAATTACAGTCAAAGG
GGGCTTGTTCTCTGGCGGACAGGAGTGGGGGCCACAAGGTGCTCAGTGGGGGAGCTTTTGAGCCAGGATG
AGCCAGGAGAAGGAATTTTATAATGTCATCAGTTAAGGCAGGAACAGACCATTTTCACTTCTTTTGTAGT
GGAATGTCATCTGTTAAGGCAGGAACCGGCCATCTGGATGTGTATGTGCAGGTCACAGGGGATAGGATGG
TTTAGCTTGGGCTCAGAGGCCTGACATTCCTGTCTCCTTATATTAATAAGAAAATAAAAATGAAATAGTG

Figure 19 Continued

GTAAAGTGTTGGGACGGCAAAAATTTTGGGGGCTTGGTATGGAGAGATAACGGGCGATATTTCTCAGGGC
TGCTTCCAGCGGGATTAGGGGCGATGTGGGAACCTAGAGTGGGAGAGATTAAGCTGAAGGAAGATTTCAT
GCTAAGGGGTGATATTGTGGAGTTGCTAGAAGAAACATTTGTCATTTAGAATTATTCGTGATGGCCTGGA
TACGGTTTTGTATGAATTGAAAAACTAAACAGAATAAGAGAAGGAGAAAAACAGGTATTAAAGGACTAAG
AATTGGGAGGACCTAGGACATCTAATTAGAGAGTGTCCAAGGGGGTTCAGCATAATTACTTACTTGGTTG
GCAAGTTTTTGGGCTCTATCCTTGAGTTTTTTATGTTGTCATACACCAGGCCAGATTGATTTAGGTAGAA
ACAACACTCTTCATTTAAGAATATACAGAGTCCTCCTTTTTCAGCAGTGACTAAGTCAAGGCCTCAGCGG
TTTTGGAGGACAACTGCAGCTAAAGAGTCAACTTGGGCCTGGAGGACTGATAAAGTTTGTGATATGTCTG
TGATGCTAGCAGAGAAGACACTAGAGAGGCTATGGAAGGTCGTGACAGAGGTTGAAATGCCTCCTATTCC
AGTACCGAGAGCAATAGTGGAGGCAGAAAGTCTTAAACTGATAAGCAAGGGAATTAGTGGAATAACTCTT
TTTTGTCGTGTCGGTGTCATGAGGGGAACAGGGAGCTCTTCGGTCCTATTTGCAAATTGAATTTTAGGAG
TAAGGAAAACTAGTGTGCATGTACCTGTCCAATTAGCAGGTAGACACATGGAGGTAGAGGATCCACAGAG
GAAGAAGAGACCTTGTGCGAGGCAAAACTGGAGAAGCAAAGTAAAAAGATGAGAAGGAGTGCTGAAAGGG
GTGTCTTGTACCCAGACTCCTGGGGATCCAGCTAGGGCAGCAGCCATCAGAGGTTGTAATGGGGACTGGT
GGGGTAACTGCGTAGAGGGGGAGGTTCGATTTTCATGGTGTATGAGAAAATGTTGAGTGTCTATGAGCTA
CCTTTCACTGTTATTTATGGGGCTGGGTATAAGTAAACAACAAGAGGGCTTTGGAGATGAAGAGTAAAGG
AACATCAAAGTGAAAGGTTACCCAGGGGAATTCCAGTGGGTCTTTGCTGAGAGATACATAAAGGAGCAGC
CACAGGAATAGTAGTTTGTGTTGTGAGAGGTAAATACGGGGGGAGTAGAGTTGATACAAGGAGAAAGGTT
TTTTAAGTAAGTGTGGAGGAGGGCGGCAGCTTGCTGACGTGAAATGTCTGGGGAGGTCTAGCTGGACCTG
TCTAGAAAGTAAATGAGTTCATCAGGAGGGTAAAGGTGAGGGCTGTTAAAGGAAGTTTGGAGGTGTAGGA
GACAGGAGATGTTGCCTAGTCTGCATGTAAGGTGGGGACAGCTGTGTAGGCATTGGAAGAAAGGGAAATG
CAAAGCTAGAGTTTGTTCGCTAAGGAGGGATTAGAAACAGCTAGGAGAGAATGAGTAATGTTTATAGTGT
GGTGGAGATAGCTGGGGAGAGGTAGAGGGTGGCATAAGAATGGGAATGAGAATAAGATTGAGTATAAAAG
TAAAGAATAGAACTTCATCAGGGTGAAAGTATTGGAGGGTCCCCTGCCAGCAAAGATTATCTATCCCCTC
TGAGAGGGAGTTAAGAGTTGCCAGTCCTGGGTGGGGGCAAATCCTCGAGCTTGATGTGTAGGGAAAGGAG
GGGGCCTGAATAATCTATGAGGAGGAGTAGAATAGTAGATGGAACAGAAGTTATTTCCTTGAGGATAGAT
TTCCACGATGGAAAGGAAATGAGAGGTTCTAAGAGGTGGGCTGGTGACTTGTACTATAGCATAGCCTGCC
TTTGCTGGTGTGTGGCGATTAGGCCTGGTGGAACTACTATGAATAAACTAAGTGTGTTCAGGGTGAGGAA
CACGAAAGAAGGAAATATGAGGAAAAGGGGTGAATGTCAGGTGAATCAGAGAGATACAGTCATAGGGGTC
AGGTGTGGTATCCAGAATACTGTGGGAGGCTGGATTGAAGTCTGGGCCAGGAACAATGGTAATTGTCAGA
GACTTAACAAAAAGGGAGTGTAGCTGAAGGAGCCAGGGAGCAGAAAGTGTATGCGTCAGGTGGGAGAAAG
AAAATAGATTTTGGAAATTATGAGAACCGTAGAGAATGAGTTGGGCATAGTTTGTGATTTTTTGGGCCTC
TAAAAGTATTAAAGCAGCGGCAGCCACTGCATGCAGACATGAGGGCTAGGCTAAAATGGTAAGGTCAAGT
TGTTTGGACAGAAAGGCTACAGGGTGCGGTCCCAGCTCTTGTGTAAGAATTCTGACTGCCCTAACCATGC
CTAGGAAGGAAAGGAGTTGTTGTTTTGTAGAAGGGATTGGGGTTTGGGAAATTAGCCGGACATGATCAGC
AGGGAGAGCACATGTGTTTTTATGAGAATTATGCTGAGATAGGTAAGAGATGAGGAAGAAATTTGGGCTT
GACTGAAGTAATGGGGGCTGTCTGTGAAGCCTTGCGGCAATACAGCCTAGGTAATTTGCTGAGTCTGATG
GGTGTCAGGGTCAGTCCAAGTGAAAGTGAAGAGAGGCTGGGATGACGGGTGCAAAGGAATAGTAAAGAAA
GCATGTTTGAGACCCAGAACAGAATAATGGGTTGTGGAGGGAGATATTGAGGATAGGAGAGTATATGGAT
TTGGCACCATGGGGTGGTTAGGCAAAACAATTTGGTTGATAAGGCACAGATCCTGAACTAACCTGTAAGC
CTTGTCTGGTTTTAGGACAGGTAAAATGGGGGAATTGTAAGGGGAGTTTATAGGCTTTAAAAGGCCATGC
TGTAGCAGGAGAGTGATAATAGGCTGTAATCCTTTTAAAGCGTGCTGTGGGATAGGATATTGGCATTGAG
CGGGGTAAGGTGATTAGGTTTTAATGGGATGGTAAGGGGTGCAGGATCAGTCGCTAAGGAGGCAGTAGAG
GTGTCCTATACTTGTGGGTTAAGGTGGGGAGATACAAGGGGAGGATGTGAAGGAGGCTTTGACCTGGGGG
AAAAGGTGGCAATGAGGTGTGGCTGTAGCCTAGGAATAGTTAGGGAAGCAGATAATTTAGTTAAAGTGTC
TCAGCCTAATAAGGGAACTAGGCAGGTGGGGATAACTAAAAAGGAGTGCTTAAAAGAGTATTGTCTAAGT
TGGCACAAGAGTTGGGGAGTTTTAAGAGGTTTAGAAGCCTGGCCATCAGTACTTACAACAGTTATGAAGG
CAAGGGAAACAGGCCTTTGAAAAGAAGGTAATGTGGAGTGGGTAGCCTCCGTATTGATTAAGAAGGGGAC
GGGCTTACCCTCCACTGTGAGAGTTACCTAGAGTGTCTGTGATGGTCCTGTAGGCTTCTGAGGTGATTGG
GCAGTGACAGTCTTCAGTTGTTAAGCCGAGAAGATCTGGGAAGGAGTCAGTCAGAGAGCCTTGGGGCAGA
GTTCCAGGGGCTATGGGAGTGGCTGCCGGTGAGATGGACAGTCTGATTTCCAGTGGGGTCTTGCACAGAT
GGGACATGGCTTAGGAGGAATCTTGGGCTGCGGGCATTCTCTGGCCAGGTGGCCAGATTTCTGGCACTTT
TAGCAAGCTCCTGGGGGAGGCAGGCCTGGAGGAATGCCTGGCCACTGTGGTTTAGGCGTTTGGAAGTTCT
TGCGTGCTGGAGATGTGGCTGGGGTTTGTCTCACAGTGGAGGCAAGGAATTGCAACTCAGAAATATGTTG
CTACTTTGCTGCCTCTACTTTATTATTGTACACTTTGAAGGCGAGGTTAATTAAGTCCTGTTGTGGGGTT
TGAGGACTGGAATTTAATTTTTGGAGTTTTATTTAATGTCGGGAGCAGATTGGGTAATAAAATGTATATT
GAGAATAAGACGGCCTTTTGACCTTTTAGGATCTAGGGCTGTAAAGCGTCTCAGGGTTGCTGCCAAACGA

Figure 19 Continued

GCCATGAACTGGGCTGGGTTATTATATTTGATGAAAAAGAGCCTAAACGCTATCTGATTTGGGATAAAGA
AAAAGGAACATTAACCTTGACTATGCCTTTAGCTCCAGCCACCTTTTTAAGAGGAAATTGCTGAACAGGT
TGGGGAGGGCTAGTCATGGAATGAAACTGTAAGCTGGGCCAGGTGTGAGGAGAGGAGGTGATAAAAGGAT
TACAGGGTGGAGAAGTGGAGGCTGAGGAAGAATTGGGACCTAGCTCGGCCTGGTGAGGAGGCGAGAGGTC
ACATGGGTTTGTAGAAAAGGAAGATTAGAAAGACTCAGCGATGCTTGGGGTTGGGACTGAGGGGACAGGC
GGGAGGGAAAGAAGGAAGATTTGGGATGAGTTGCATTGGGAACAGAGACTAGGGAGGGACCAATGTGTAA
AAGAATGCCTGGACGTCAGGCACCTCAGACCGTTTGCCTATTTTACAACAAGAATTATTTAGATCTTGTA
GGATGGAAAAATGGAAAGTGACATTTTCTGGCTATGTGGAACTACTGTCGAGTTTGTATTGGGGTCAAGT
GGCATTGCAGAAGAAAATAAGGCATTTAGGTTTTAGGTCAGCTGTGAATTGAAGAGGTTTTAGGTTTTTA
AGAGCACAGGCTAAGGGAGAAGAAGGGGGAATGGAGGGCGGAAGCTTGCCCATAGTGAAGGAGGCAAGCC
CAGAGAGAAGAGAGAGTAGAGACATGGAGAGAAGGGGTTGGGGGTTCTTGCCCCCAAGAAGAGCGGTACT
TGCCGCTAAGGGTGAAGGAGAAGGGGTTGGGGGGTTCTTGCCCCCCAGAAAAGCGGAGAAGGGGTAGAGA
CATGGAGAAAAGCGGTGGGGTTCTTGCCCCCCAGAAAAGCAGAGAAGGAGTAGAGACACGGAGAGAAGGG
GTTGGGGGTTCTTGCTCCCAAGAAAAGCAGTACTTGTCGCTAAGGGTGAAGGACCAAGGCAGGTGTCCCC
ACATGGTCAGACACCTCTGAAACATGGGTGAATAATCAGGCAGGCATCCCTGCCTGATTCCAAAGGGAAG
ACTGTCTTCCCAATTCCGTGACTGGTGCCGGAGTTTTGGGTCTATGAATAAAACGCGTCTCCTTCATCTC
TGTCAGAAAAGGAAAGGAACTGAAATTAAGAGAGAGATTGAAGGGTGATGCCAAGATTGAAAGGAGAAAG
AGGTTGAGGGATAGTGAGAGAGGTTGGAGAAGAGAGTAAAAAGAGGCCACTTACTGGATTTAAAATTGGT
GAGATGTTCCTTGGGCTAGTTGGTCTGAGGACCAGAGGTCATAGGTGGATCTTTCTCATGGAATAAAGAG
CAGGAGGACAGGGGATTGATCTCCCAAGGGAGGTCCCCTGATCCGAGTCACAGCACCAAATTTCACTCGC
ATCCGTGTGAAGAGACCACAAAACAGGCTTTGTGTGAGCAACAAGGCTGTTTATTTCACCTGGGTGCAGG
TGGGCTGAGTCTGCAAAGAGAGTCAGCGAAGGGAGATGGGGTGGGGCTGTTTTATAAGATTTGGGTAGGT
AAAGGAAAATTACATCAAAGGGGGGTTGTTCTCTGGCGGGCAGGAGTGGGGGTAACAAGGTGCTCAATAG
GGGAGCTTTTGAGCCAAGATGAGCCAGGAGAAGGAATTTCAGAAGATAATGTCATCAGTTAAGGCAGGAA
CAGGCCATTTTCACTTCTTTTGTGGTGGAATGTCATCAGTTAACGCAGGAACCGGCCATCTGGATGTGTA
CATGCAGGTCATAGGCATATACACAGGCATATGATGGCTTAGCTTGGGCTCAGAGGCCTGACAATAACAA
CCCACAAAAAATATATAATTTAGGTAATGGATAATGTATCACTTATGTTTAATATTGGAAGACATCTGTA
ATTATATTTGCAGATTGTCTCTTAGTATTCAACTAGAATGAAAATTGATATAGGTTGATTTCATATCTTG
TCTATTGCAAATAGTGCTGCAATAAACATGGGAGTGCAGGTATCTATAGTATATATACACAATGGAATAT
TATTTGGCCATAGAAGGAAATGAAATCCTGTCATTTGCAGAAACAGGAGTGGAACTGAAGGTCATTATGT
TAACTGAAATAAGCCAGGCACAGAAAGACAAATATCACATGTTTCCACTCATATGTGAGAGCTAAAAGAA
TGAATCTCATGGAAGCAGAGAGTAGAATTGTGGTTACCAGAGGCTTAGAAAGGGGTGGTGGGGGATAAAG
ATAAGTTGGTTGGGTACAAAAATAAAATTAGATAGAAGGAACAAATTCTAGTATTTGATAGTACAGTGGG
AAAACTATAGTTGACAATAATTTATTGTATATTTCAAAATAGCTAAAAGAGAAGAAATGTACTATTCCCA
ACAGAAGGAAAAGGTAAGTGTTTGACGGAATGAATATTCTTATTACCCTGATTTGGTCATTACACATTGT
ATACAGGTTTCAAAATATCACATGTACCTCCAAAATACATACAACTATTTTGTATCAATAACAAAATTTT
TAAAAAACTGATATAGGCTGTGAAGGGCAAACCATGTAGTCATCTCAGAGCTCAGCTTATTCTTGTGGAT
ATAAATGTTTTAGCTGGCTCTAAACCAAGGATTTTGTATGAAGTAATACTTATTCAAATATTTTCAACAA
AATAGAGTACCTTGCAAACAGGACTTTGAGATTTTTCATTTGTTTCCCTTTACAGTTCGTCATATACGCT
TCATCTTCTAGTGTTGATTGATGAAACAACGTTCCACATGAGACAGCAGAGCAATAGAACACAGAACAGG
ACTCTGCCTGTGTGGTGGCCGGTTTCCATCCTTTCACAAACAAAGAGATATTTATAAACAAATATTTATA
TGCAAATATTTGATCCACCTAGGAAAAATAGAGGGCTACTCTTTCCCACCAGGAGAGGCCTTATAGCCTG
TGCACATATTTGAACAAGGCAACCAGAGACTTTGATGGTCTCAACTCTACCACTCACCAACTGTGTGATG
TTGGATACAAACTTAACCACTTTGCAACTCACTTCCGCATCTGTAAAATAAGGGTGATAATAATAGCACC
TGGTTTAGAGAGTTGTAAAGATAAAAGCAACATTAGTAAAGTACTTAGGATGAAGTAATCATGTTTTGAA
TATATTTTCCTTTAAATGTGGCTGCCAATATTTTCATGGTAATATTTTCAAATGTATTCAATAGCTTTTT
CTTTATCAGGAGAAAATCAGTTGTTTTAATTAAATTGACATTGAATTTTTGATACATTTAGGAGAATTTA
GTTTCTTTTTATACAGTATTGACGCTTCTAATCCCACAGCATGTTTTTCTATTTTTTTCTTTTCTTCAAT
AGTTTTAAAATTTTTTTGTTCATTTTGGTTATGCAAATATCTAGTTAATTTCTATCTGTAATATTTTCCT
ATTTATTTTTAGTAGCTCTTATAAAGGGAGCATTTTGTTTTTCCTGTCTATCCTGACATAATAAAGCAAT
TAGTTTTTAATTGATTTTTAAAAATATTTATGCATTCTCTTTCATATGTATAATAATAATACCTAACCAT
TTTATGATTTACATGTGGCAATGTCAAGAAGAATTTTAAAGTAAGATTTACTAACGAATATTAGAGAACA
TGCTCAAAAACAGTCCTCTCCACCCCCTCACTTCCACTTGCATTCTTGATCAAGAAGTGAAATAAAAAAT
ACTAAGACTATTGAGTCAAACTAATAAGACACAAATCTGGACTTTGGAGACTCATTTCCCTCCCACTTTT
GATAGCTTAGCTGAGGAGGAGATCAAATGGTTGAGTCAGTCTGTAGAGAGATAGCAAGGCTGATTATAGT
TTTCCTGGCCTGCAAAGCTGTTTCCAGAGCCCTCAGTATACAGACCTTGGCCATCAGTATGCATACTCTC
TGGTGTGGTTTCTGGGCATCAGATCCCTTAATATATAGGTTGGCGCTAAAGTAATTTTGTAACTTTTAA

Figure 19 Continued

TGGCAAAAACCACAATTACTTTTGCTTTTAATGGCAAAAACCAGAATTACTTTAGCACCAACCTATATAT
TGTTATTTAGAGAAACTAGGCATTCCCTACCTCTCTTAGGCAAACCTATAGCTATGTAACATGGCAACGG
AATGACACTAACTGTCTCATTCTCCTTGGGAGTGCTCTCTGTATGTTCAGTCTCCCAGTGAAGAGAACCC
TTCTATCAGGACCTTCATCATCATACAAAAGGAATATCTATGCCAGGCCACAGCTGCAGATTAGTGAGTG
TCTGAGAACTGCATCTTTTCTGTTATTTTTCTGCTTGAAAGTTTTTCACCAATAAATCCTACACTATGTC
TGCACCATGTGGTGCTAGTTATTTGTGTTCTCTTGCATGACACTGATGATGTTATCCAAACACAATTTCA
AAAACTACTTTCTGTAGTTGGTAAATATATAGAAATTGAGAAAAAGGAAGAAATATGAGGAAGAAAGATG
TTATCTGTTGCAACAGTTCAATGTTCTTAACTGAAGCCACAGATGAGATTTGGCTCATTTGCAGACATAT
GGGTGATTGGTACAGTAGGTTTATAAACAGAAGTTTAAACTTGTAAGCTTAAGCTTCCGTTTATAAACAG
AAGTTTAAAATTATAGGTCCTGTTTAACATTCAGCTCTGTTAACTCACTCATCTTTTTGTGTTTTTACAC
TTTGTCAAGATTTCTTTACATATTCATCAATGTCTGAAGAAGTTACTTATGCAGATCTTCAATTCCAGAA
CTCCAGTGAGATGGAAAAAATCCCAGAAATTGGCAAATTTGGGGAAAAAGGTAAGATTTTGAGTTATGGA
TGTGTTGTAAGTTTGTATAATAGAAGTGGTTATAGACTTGCATCTTCAATATTAGTGATATAGTTACTAT
TCAACTTAAATTTTCAATTAAGTCTCTTATGTTTAAGCAAAGGAACAAAAAGTGTATGAACAAAATGATT
AGAAAAAAGGGTTTTGTAAAAACACTTATCTCTGCATTGAATAATCAATCTTTTACATTTTTGAAATTTT
TTATTATCACACTCAATATAATTGGGACAGAATTTTTCAAATGATTGGGTTGTATGAAGATTTTATTTCT
TTATGAGATGAAGCCATGGAAAAAGAAACATGTTCAGGAAAGTCATGATTTCATATGTGTGTGTGTGTGT
GTGTTTTTTTTTTTATAAGAAAATGCTTTGTGTCAGACAGAGAGACCTTTATAGGATTTCATTTGACTAT
CTACCAAACTAAGCATAAATCACCCTAAAATTTCTCCTACTTCTTTTGGAGATTTTTTACTAACTTACTA
AAAAATAAAACATGTTAAGTTAAATGAAATGAATCATTAAGGAATAAAGGAAGAAAAGAGGTAAAGAAAT
ATCAGAAGACATAATATATTCATAATATTCAAAACCACATTATATCAAGTAACTTTGTATTTTTCAATTC
AAATTAAAATCATGAAATAAGTGGTCCATCTGTGTTGACTTTCACTTAAACAAAACTACTCTTCATCTTA
CTCAGAATCCTATAGTTTTCCTATTATGTATGGTTCTTGCCTTCTGGCTCCTAGCCTTTTGGGAGTGAAA
TCTGCCCTAGCGAATCCATAGTTTAAATCAGTGTATTTGAGTTAAAAATAACTTAAACAGTGATAGTGGA
GAACACAAAGAAGGGTGATAGAAACAGAAAAATAAGGAGAGAAGAGTGCCAAAATTCTCACATATTATTT
AAGTTGTTGTCCTCTCTCCTCTCCCCACACAGAATATAACATCTTTAATATTCTAGCATTGCTATAAACA
GAAATTTCACTGTTACATCTTGGATCCATTTATGATGAGCATTGTAAATCTTGAGAAAGGATAGCAGATT
AATTCTGTTGGCTTCTTTTTTAATACTGAAATTTTTTTTTAGAAAGAAGAAGGGTTTAAGAATTTTACAA
TATTTTCTGTCTTTATTTCCTTGTTTATATTTCTTCTTTTATACACTGAAAGAGAATGGGCATATCATGA
GCCTAATATTACCAACAATTGCCCTTTACTTGTCCTCTCACACCCTTTCCCACCTCTTTTCCTGCCAATC
CACCTTAAGTTCCCACCACAAGAATTCCCTGAATTCACGGAAATATTGAATCCATGTCTTCTTCATGTTC
TTAATCTCATCTAATTTTCTCATTATCGAGCTTAGAATCTACATTATGTAATATAACATTGTATTATGTA
ATGTCTACTCTTAGTCTCTTACACTTCTCCTCTTCAATGTGTGTTAATTTTTCCTTAAAAACTCCAGCTC
TGGCTAGGTGCAGTGGCTCATACCCATAGTCCTAGCACTTTGAGAGGCCAAGATGGGAGGATTATTTGAG
GCCAGAAGTTTGAGACCAGCCTGGGGAAAGTAGAGATATGCCATGTCTATAAAAAAAAAATTTTTTTAAT
TAACTGGGCACCCATAGTCTCAGCTGCTTGGGAGGCTGAGGAAAGAGGATTACTTGAGTCCAGGAGTTGG
AGGCTCTAGTAAGCTAAGATCAGGCGAGTGTACTCCAGTCTGGGTGACACAGCAAGATCCTGCCTCAAAC
AAATCAAAACAAAACAAGACAAAAACCCCAAAAACAAACAAATAAAAACAACTCCAGTTCTGGTTAAACC
CGAATATCCACCCAGTCTGCCCCAGAGTTGAATATTGCTGGTGAAAAATACACAAATTTTCAACCCCAGT
TACTCTCACCTTTCCTCTGGTAAGAAAAAAGCATCCATCTACACTTTTTTTTGTTGTTATTTAAATGTCT
ATCCTACCATGTCCTTACTGATACTCTGCTTTCCTTCCAGATAGTATTTACGATAAGTATGTACTTATGA
AGGGACGGCTCCTCATTTTGCTCTGAATTTCAGTCCATGTGTCGTTTTCAAAGACAGACTTCCGTAATTT
TTTCCTTTCTCTCCTGTGTCATTATTCTCTCTTCCTTCTCTGCTTTTCCTTTTTGGTGCACCAACATACT
CTACTACTCACCAATATACTCTGCTACTCCTTTTATAACAAAACACAATCCTTGCTTGACCACTTAAGCC
TTTCCATTATTATTTAACTTCTTTGTTTCCTTTCACAACTCAACTTTTGAAAGCATTTTCTTTGGCCACT
GACTCTCAGTTCTTCACCTCTCATTCTGTTCTCAACCAACTCTATTAGGCTTCTGCCCCCTTGGTGCCAT
AGAGACTGAGCTTTAGGTCACTGATGTCCTGCCTGTTTCATCCCAATAGTCACATGTCTCTTCCATTACT
TCACTTCCCTGCAGCATTGAAAAAGTTGAACAGTCCTCTAAATGCTTTCTTTGCACATCCCTCCTGACAC
ATCCTCATGGCTTCTCCTGTCACCATGCCTGCCTCTCCTCATTCTTTGTTGATTCCTCCTCCTAGATGAA
ACTCTACAAGATGGAATACTCTGAAGCCCTGTCCTGGGTCCCGTTTTATTGCATCACTCAGTACACTCTT
CTAATCTACCTCATTCAGTTGTTTGACTTTAAATAGAGTGACTCCCCAATATCTCTGTATGACCTTTCCC
TGAATCTCAAGACTAGAAAATACATGTGCCACTTTCACATTTCCATAAGGAGTTCTAATCTCATTTTAAA
CTTAAAATGTCAAAAATAGTAATATTTATTTTTCTTCTAAAATTGTCTCTCTCTCCAGACAGCCTCATCT
CATTAAATACACATATAAATATATATTTAAATACAATTTTCAAGTGTTTTCTCTGTGCCAGTTCTGTTCT
AATTGCATTATAAATATTAAATTATTTAGTGTCTGATACTTTGCAGTCTTTCTGTCTCCCATGCTTTAAC
CATATTGAAACTCAGACACAGAGATGTTAAAAGGTGTTAAATAATTTTCCCGAGGTTTCACAAGCAATAA
GCAGCAGAACCAGAATTCAAACCAAAACATACTGATATGGTTTGACTGTGTCTCCACCCAAATCTCATCT

Figure 19 Continued

TGAATTGTAGCTCCCATAAGTCCCACATGCTGTAGGAGGGACATGGTGGGAGGTAATTGAATCATGGGAG
CGGGTTTTTCCCATGCTGTTCTTGTGATAGTGAATAAGTCTCATGAGATCTGATGGTTTTATAAAGAGGA
GTTTTCCTGCACAAGTTCTCTCTTGTCTGTGGCCATGTGAGATGTGCCTTTCACCTTCCACCATGAGTGT
GAGGCCTCTCCAGCCACATGGAACCATGAGTCCATTAAACCTCTTTTTACTTATAAATTACCCAGTTGTG
GGTATGTCTTTATCAGTCGTGTGAAAATGAACTAATGCAGTAAATTGGTACCAATAGAGTAGGGCGCTGC
TGTAAAGATACCCAAAAATCTGAAAGAGACTTTGGGACTGGGCAACAGGCAGAGGTTGGAATACTTTGGA
GGGCTCAGAAGAAGACAGAAAAATGTGGGACAGTTTGGCACTTCCTAGAGACTTCTTGAATGGCTTTGAC
AAAAATGGTGATAAGGCTGAGGTGGTCTCAGATGGAGATGAGGAATTTGTTGGGAACGGGAGCAAAGGTG
ACTCTTGTTATGTTTTAGCAAAGTGACTGGTAGCATTTTGCTCCTGCCCTAGAAATTTGTGGAACATTGA
ACTTGAGAGGGATGATTTAGGATATCTGGCAGAAGAAATTTCTAAGCAGCAAAGCATTAAAGACGTGACT
CGGGTGCTGTTAAAAGCATTCAGTTTTATAAGGGAAGCAGAGCATAAAAGTTCAGAAAATTTGTGGCTTG
ACAATGATAAATAAAAGAAAATCCCATTTTCTGAGGAGAAATTCAAGCCAGCTGAAGAAATTTCTAAAGT
CATGGGAAGCCAAATGATAATCGCCAAGGCAATGGGGAAAATGACTCCAGGGCATATCAGAGGTCTTCCC
AGCAGCCCCTCCCATCACATGCCCAGAGGCCTAGGAGGAATAAATGGTATTATGGACTGAGCCCAGGGTC
CCTCTGCTGTGTGCAGTCTAGGAACTTGGTGCCCTGCATCCCAGCTGCTCCAGCCATGACTAAAAGAGGC
TAAGGTACAGCTCAGGTCATGGCTTCGGAGAGGGTGCAAACCCCAAGCCTTGGTAGCTTCCATGTGGTGT
TGAGCCTTTGAGTGCACAGAAGTCAAGAGTTGGGTTTTGGGAACCTCTGTCTAGATTTCAGAGGATGTAT
GGAAATGCCTGGATGTCCAGGCAGAAGTTTGCTGCAGGCATGGGGTGCTCATGGATAACCTCTGCTAGGA
CAGTGCAGAAGGGAAATGTGAGGTCAGAAGCTCCACACAGAGTCCCCACTGGGGTACTGTCCAGTGGAGC
AGTGAGAAGTGGACCACCGTCCTCCAGCTCTCAGAATGGTAGATCCACTGACAGCATGCACTGTCCACTT
GGAAAAGCTGCAGACACTCAATATCAGCCCATGAAAGCAGCCATGAGGGAGACTGTACCTTGCAAAGCCA
CAGGAGCAGAGCTGCCCAAAGACATGGGAGCCTACCTCTTGCATCAGCATGACCTGGATGTGAGATATAG
AGCCAAAGGAGATGATTTTGGAGCTTTAAGATTTGGTGCCCTTTGGACTTGCATGGGGCCTGTAGCCCCT
TTGTTTTGGCCAATTTCTCCCATTTGGAATGACCGTATTTATCCAATGCCTGTACTCTCATTGTATCTAG
GAAGTAACTAACTTTCTTTTGAATTTACTGGCTCATAGGTGGAAGGGACTTGCCTTGTCTCAGATGGACT
GTGGACTTTTGAGTTAATGATGAAATGAGTTAAGTCTTTTGGGGACTGTTGGGAAGGCATGATTGGTTTT
GAAATGTGAGACATGAGATTTGGGAGAGGTCAGGGTGGAATGATATGGTTTGGCTGTGTCCACACCCAAA
TCTCATCTTGAATTATAGCTCCCACAATTTCCACGTGTTGTTGGAGGGACCTCGTGGGAGGTAATTGAAT
CATATGGTAGGGGTGTTTCTCGTGCTGTTCCTGTGATAGTGAATAAGTGTCATGAGATCTGATGGTTTTA
TAAAGGGGAGTTTCCCTGCACAAGTTCTTTCTTCTCTTGTCTGCTGCCATATGAGGTGTGCCTTTCACCT
TCCACCATGATTGTGAGGCCTCCCCAGCCGCGTGAAACTGTGAATCCATTAAACCTCTCTTTCCTTATAA
ATTGCCCAGTCTTGGGTATGTCTTATTAGCAATGTGAAAATGGACTAATACACATGCTAACCCTAAAGAT
GGTGTTTTGCTTTTTATCACTATGAGATACTGCCTACAAATGTGCATATCTACCAACTTTCTCTAAAGAA
AAATTTCAGAAATTTTTGCAATAGATTTTAGCTTAGAAATGTATACTTAATTTATCCATGGGTCATCAAA
TTCCCTAGTACTAGCTAGTCAAACTTCTGTTCTCTTTCACATGTCATACTGTAACAGATTTCTTACTGAT
AAAACAACTCTGTTATTTTGCCCTCCTAGATTAAATTCTTCCAGTGGTTTCCCCAAAAATCTAACTTATT
CTGGCTAGAAAAGGCTGTAAATAATGTCTCCTCCTTGTTATTTTAAAAACAAAACAAAAGAAAACAAATA
AAACCTTTAACATCATTTTTCACATTGGCCACAATTCTTCTGCCCCTCTGAATATATTCTGTTTTTCAAA
TAGAAATCTTTTCCTTAAATTATTGTCTTTGAACTTCATGTAATTGCTACCTGTAATGTTCTTCCTACTT
ATTTTGCATGCTGGTTCCTATTCATAAGATTTGAACTGCCTGCTCTCTATAACAGCTTAGTTTTAAATCT
CTGCACAACATCGCCAAATTTGAGATCTTTTCTCCCTTTCTTTCTTTCTCCCTGTCTCACTTATATATCT
ATTTATCTATTTCCTCCTACAATTAAAATTTATAGCTGTGAAAACAGGAACTTGTACATCTTGCTCACTT
TGATATTGTTAGCACCCAGGATAATGTCTAATAAATACAAGGCACTCAAAAGATAACTTTTGAATAATTG
AACTTTTTAATAATTGAATAAGTTCATTGAATAAATAAACTTGAATAATTGAATACACATATAAATAAGA
AAATAATTTTAAGAAAGATAGCACTGGCATTTATAATTCTAATCTTAGATAAAATCTTGAACATGTAGTT
CTTTCAGTAGTAACTATTTTCTAAAGTCTATATAAGTTAAGTTTACTATTTATTAGTAATTGTCTCTGG
ATTTCACAATATTATTGCACCATCAACTATGAGATGTAAGACATAGCTCAGAAGTATAGTGAGATTATTA
TGGTATCCCTGAATTGGATTTTCTTGAAATATCTAGCTAGTCTTTACCTAATGTATAATAGCTTTATACA
TAATGATGATTTAAATAACATAGTCACAATAATAATTCACTCACAAAGTTTATAATTCCTGTTTTTTTTT
TAAATAGAGAAATGATCTATTCTGGGCTTCACTATTCATTAAAAAGGAAGTATTCAATAAAAGTTTCTTG
CAAAAACACATGAAAATTTTTTTGAAAAATTGCAATAAAAATGGTGTAGATCTGGACTGATTAAGATCAA
AAGCTAACGGGAGGACACCCAAAGACATTATGAAAAGACAGCCTATCTTGTTCATTCTGCAGCTAAATTC
TCATAATTGCCTGGGGGGATACATAAACAACTGAAACTGTTTTTCTTGACATGCCACAATTGTCTACTCA
AGCAAAGACTTCTCCTATTGGCTTCTCTGTTAATTTCCAGCTACTCACTTTTCCCAAATTTGTACAAACA
AAATACACTATATCTAGGTTGACTGGTTTTCTCCATTCTCTATTATAAATTCTGTTTTTGCTTATCTGTT
TTTTTAAATCAGTCTACCAGTTAACAGCTTCTCCTGCCAGAATCAATTTACATACAAAACAATTAAGTGA
TTTTGATTTATTCTTGACATATTCTTCAAAAATATTTTTTGAATATTCTTGAATGGCTAGCAAATCCATT

Figure 19 Continued

TCTTTCCAATAGGCATATTAGGAAATAAAGGTAAAATGAATGAATGAATGAATGAGTAAATAATCCAAAT
GAAAGTTATACCATTTTTAGGCCTCTCTGTTAATTTTGCTTTCCACAGCACCTCCAGCTCCCTCTCATGT
ATGGCGTCCAGCAGCCTTGTTTCTGACTCTTCTGTGCCTTCTGTTGCTCATTGGATTGGGAGTCTTGGCA
AGCATGTGTATGTACTGCCCCTGTTTTTGTCAAGAGGAAGTATCTAGAATTTCAAATATTTAGCAACAAA
AGTTTATTCCTTCAGTGGAAGATTTATAATAATGATAGGTGATAGGCCCACAAGGAGGACTTACAATGTG
GAACTTAGTCTCTTTCCCTCACTCCTGTAGAGTAATTGCTTTCCCTACCCCTTTAATCTTTATACTACTT
CTGCAAATGATAAAGGATGATGGCTCTATTGAGAATTTACAATTTTTTGTCATTTTTTTAATGTGGAGTT
CACGTAACTTTGAAGATAGAAATGAAAAAAATGAACAAACTACAAAACATCAGTGAAGAGCTCCAGAGAA
ATATTTCTCTACAACTGATGAGTAACATGAATATCTCCAACAAGATCAGGAACCTCTCCACCACACTGCA
AACAATAGCCACCAAATTATGTCGTGAGCTATATAGCAAAGAACAAGGTAATCTTGTATTCTCTTGGAGT
TATTTATTGGACAATAAACTAAACCACTGAGTCTCTTAAGAATCATTTTATAATTAGCTAGCAGCCTTTC
TCTAGGGAGTCATAATTTGGGGGAAAGAATTACATGTGGTTGATGGAGAATTCATTGATATTTCCACGCA
GTTAGAAGAAAAACAGAAAAAGTAGTAACAACAATAGGCCCCCAAATTATCAGGAGATAATGGTTACATA
ATAAAATGTTAGACAAGACAGTTTCTCTAATCTGTCACTTACTATAATTATTCTGGGCACTGAGGTTAAT
AGAAGACAGGGAGGAAGTGACACCTCTTTACAGGTGACTTCATTCTTAAATTTCAGTCAGTGATTGATAA
CAAAGTCCATAGAAAAAAATAAATTGAGACTTCACCTTTGGGATCGGGGAGTTGGTCTTTTAGTGTCTCC
ATAAGTTTCTATAGTCATAGTTGCTAAAACATATTCCTTTTGCTCCTGAGAAACCTCAAAGTTTCAACAT
TTCAGAGAACAAAAATTAAAGAAGATAAGATTGGTATAGATAGGTGGGGTTAATTCTTACTATACAGAAT
GTTTCCAGTAATTAGTTTTTATTGTCTTTAAAGAATATACAAAATAACAAAGAGGAATTGACATAGGAAG
ACACACTTGAATCCAAGTGCTTAATTTGAAATTTTTTTGTTCAAGTTATGTGTCTGACACATTATGGTGG
TATATAAGGAACTAGAATACAGGATTCACTTACTTCCCCTTCGATGTAAAAAAAAAAGAAACGGCATGTA
ATCCCAGCTACTTGGGTGGCTGAGGCAGGAGAGTCACTTGAATCCAGGAGGTGGAGGCTGCTGTGAGCTG
AGATCACGCCACTGCTCTCCAGTTTGGGCAATAGAGCAAGACTCTGTCAAAAAAAAAAAAAGGGGGAAAG
AGAGAAAGAAAAAGAAAGAAGAATAAACAGCAAATGTGATCAATGTCACACAGAGAGGAAAGGAAATAAT
AAGAATTATTATGACTATCAACAAAACCCAAATAAAACTATGTTCTTCTTCCAGAGCACAAATGTAAGCC
TTGTCCAAGGAGATGGATTTGGCATAAGGACAGCTGTTATTTCCTAAGTGATGATGTCCAAACATGGCAG
GAGAGTAAAATGGCCTGTGCTGCTCAGAATGCCAGCCTGTTGAAGATAAACAACAAAAATGCATTGGTAA
AGCCCAGGTGTTTCTACCATCATGGGATAGAGAGGGGTGTGGCATGTTGGAGAAGACTTCAATCAACCCA
CTCATGATTCTGGTTTATTTCAGTTGGGGTGTGAAGTGACTGAAACTTTGTACACTTATCTCAAGATATC
ATAGGCAAGGTAAAACATACAAGTTTAGGACCTTAGCATAAGAGAAATATTACTAGCTGACAGGTAGATG
AGTATTACAGGGCACCCAGAATCTATAGGTCTGTAAGCATTTCCAAATTAGAATCTAGAACCAAATCTCA
GAACTTAATTTATAAACATTTATCTAAAAACAGAGGATACAGAGATTATTCCCCAGGATTAGCAATTCCA
TAAGAACTACATGGGAGAATATGTTTTGTTTCTACCATTTTGTATTTTTTAATTCACTAAGAGAAATAGG
CAAGTTATAGTAGGTTAGCATAAAATATGTACAAACAAGAAGAACTGAAGTAAGATGGCACAGGCAAGTG
TCAGATATATTGTACTGAGTCCTTGAATCCCAGGAAAAATGTGTTTTCTGGTAGCTTTATTGATTTATTC
ATTTTCTTAGTTTTCCATGTCTAAATAATGTTTCCATGTTACACTTATTACATAGCATTTTTGGTCTCTC
ACATAGCAATCATATATTTTTAAGCAAAATTACCTTTTCTAAAATTCTCTGCTTCCCCACAATAAGAAAC
TTTCATCATCCTTTATAGAAGAGAGATAAATCAACCCACAATCTCTTCCTCATCAGATCATTGTCAAGTG
ACCCATTCACAGTTACTTACTCTAGAAAAAATTTTTAAAGGCTAGAATAAGAAAAAAACCTGTTATTTGG
CTACAAAATTCTGGACTGGTTCTGAATTCTGTTCTGTAACCACTCACATCTGAGTGTGTGGCATTTTTTT
CCTACTCTTTCTGTTTCTATTAACTCTTGTTTATAGCCATTACCCACCTCCTTTGGCCCTGGACACAATA
TTTACTGCTCAAATTTTTTAATCTTGAACTTGTCATTGTGAACTCTTCACTGACTGTAAATTAAGGTTGT
ACATGGATTAGTAGGGCCTCTCTTCTTGTGAGACCAGCAATGATATTGTTAAAAATATTGAAATTTTGTA
GTAAGGAGTACTTTCTTTCAATTTCTTATAATGACATTTAATAGTAGTAGTGCAATGTCCAGTATGTTAC
CTTAAAACAGCAATTTGTAAGAAATTACATTATAATGTAAAATACAAAAGTAGGAGACTGTTTCTTAAAC
AGACTATCTGTATTTCCTGTAGGAATTTATAAAATCCCAGAGTAGATCATATGACTATTGGCTGGGATTA
TCTCCTGAAGAAGATTCCACTCGTGGTATGAGAGTGGATAATATAATCAACTCCTCTGCCTGGTAAGTGT
CTATTCTTGTTAGAATTTTATAGCTGGGTTTGAGTAGAGGTATTTTCCTTAGGAGCACTGTAGATTCAAA
TTAAAACCAGCTTCAATTGAAATTGCATGCTAAAAGAACCCTTTTCTATCATGCTTCTTTGATGTATTTT
CTAATACATAAAGTTACCATAAATGCCTTCTCATAATTTTGACAAGTAACTAACAAAATTACAGCAGCCA
AATTATGGAGAACTCTGTAAATAATTTTATCTAAGAAAAATTGTGGAAGCCCAGAAAAGTCATTGGACTA
ACAAGTACTTAATATTGTGATAAGTTCTAGGGTTCAAAGATGAATGAAATATTGATTCATCATTAAAGTT
ACTTAACCATCAATTTTATGTGCAGACTGATTGAATTATGCTAGAGATAAAGAGAATATAGTGTGATAAA
TGCTTCAGTAAGAATACACAGACTAACAAAACATAAATTTTTGCAATGATACTTTTGTTATAAATGACAC
TTCAAATGGGCATTTTAAAAAGTTTATGGATTTAGGGGGTACGATTGCAATTTTGTTATATAAATATATT
GCATAATGATGAAGTCAGTGTTTTCAGTGTAACCATAACCTGGATAGTGTACACTGTACCCAACAGGTAA
TTTCTCATTCTTTATTTTCTTCCCACCCTCCTACTTTTTGGAGTCTCCAATGTCTATTATTCCACTTTTT

Figure 19 Continued

ATGTGCATGTGTACATATTATTTAGCTCCCACTTAAGTGAGAATATGCAGTATTTAAATTTACGTTCCTG
AGTTATTTCATTTAAGAGAATGGTCTCCAGCTCCATCCATTTTGCTGCAAAGTCATGATTTCCTTCTTTT
TTATACTTGAGTAGTATTTCATGGTGTATACACTCTAAAAGAAAGCATGGTTTCATGTTTTCTTATGCAA
TAATCCGTTGATGGACACTTAGGACAGTTCCATGACTTTGCTATTGTAAATAGTTCTACAACAAACATTT
AAGTGTAGGTGTCTTTTTTTTAATATAATAATTCCTTTCCCTTTGGTTAGATACCCAATAGTGGAATTGC
TGGATCAAATGGTAATTCTATTTTTAGTTCTTTGAAAAATTGCCATAGAGTTTACACTAACTTCCATTCT
GAAATGGGCATTTTTGAATGAAAAATTTAAAGACTGGTTTAGAAGAGCACTTCAGGTGAAAGAATATAAA
CTTCAGCTTAATATATCACATATATAGTATAGATAAAATAATTTGTTGTGTAGTATAATGAGGAATGTGG
TTATAAATATACTATTTTAAGTGGATTTATACGTTGTATTTGTTCTGCTTATAATGGGAAAAAAAGTCTT
TACATATAAAAATAGTGGCAAATTCCATTTGTATTTTTTAATCTCTGAAATTTGGGAAGCAGAAAATATC
AAACGAAGAAAGAAACCAGAGTCTCAACCTGCTGGACACTATTGGAAGTCCATCATTTAACACGTTTTTA
GTATATACTTTTAGCAGGAGACAGCTCTGAGTCAACTGTGTTGAGGTGCCACCACAGCGAGTTTAGGCAC
TCAGATCCCTGCATACTCATCACATTGGGCCATAATGGCAAATAGAATTTTTTGTTTTGTTTTGTTTGTT
TGCTTTTTCTTTCACATAGAAATAGTAAGTGTAGGAGTGTGGGTCAGAAAGAAAAGGTGGCCCTACCTCT
GATGGTTGGCAATGATAGGATACAATGGGAGATAAGCTATCTACAAATGGAGTGGAGAAGGATATATATT
TCAAAGGCCTAATTTGTAGTGAAAGACTAGAGACAAAGGTAATGTGTGTGTCAGGAGAGAGTACAGATGG
AATCTTGTTTTGCAAACGTAGAATATGTATGTGTTTGTAATTATTGCAAATGGAATGGTAATCTATAATG
GAATGGAAAACATTGTAGATATTTTCAGTTATCAAAAAGAAAACTGAAAAAGTATATAATAATTGTATGT
ATGATATATATATGTGTGTGTGTGTGTATATATATCTTCACTTTATAACTCTGTGTTGTTTTGGGGTTTG
TTTCTGAAAGGGGGTTGTAATAAATGACATCTGTACTATGTCACCACAAATAAATCTCATTCTTAAACAT
TTAATTGATGAACTTATTTACTGGTTGATATCATTATTTTTTTACCCAAGTATTGATGCTAAATTAATCT
AAAAGGTAATATTTTTTAATTTATAAATTTGTTTTTAGTGCATAGTCCCTGATCACTAATCTAGTATTTAT
GGGCTGGTCATTAGAACTTCAGAGTAAAATCTTTTGCCAAGTGTCACTTAGAGATGATGTTGAACTTCAG
GTGTCATATATCTCAGGTGAATTCCTGACTTTGATGATTATAAAAAGCACTTGAGGGAGAAAGGGTCCAA
GTCTTACTACTCCTAGCCAGTTAGACTAGGAGAATCTTATGGAATGGTATTATTCCAAATTATATTATAT
ATGAAGGGGCTGGGGTGCTAACTCTGTAAGCAAAGGACAGCAAATATCAGATGTTAGAAAGTGGAAAAAG
CAGGGAGAAATGAAGCAGTATTTGACATTGCATATGTGTTAACATAAACAATTAACTCGGACATTCTTGA
TACTCTGAACATTAAATTAGATTTAGTTTAAACAACACAGAGTCTAGGGCAATAATATCATGTTGGAAGT
GTAATTTTTTTTTCTGTGAATATGTTTCAAATATCTGACTTGCCAAGTGTAATTCTTTACTTTCTCTTTC
AGGGTTATAAGAAACGCACCTGACTTAAATAACATGTATTGTGGATATATAAATAGACTATATGTTCAAT
ATTATCACTGCACTTATAAAAAAAGAATGATATGTGAGAAGATGGCCAATCCAGTGCAGCTTGGTTCTAC
ATATTTTAGGGAGGCATGAGGCATCAATCAAATACATTTAAGGAGTGTAGGGGGTGGGGGTTCTAGGCTA
TAGGTAAATTTAAATATTTTCTGGTTGACAATTAGTTGAGTTTGTCTGAAGACCTGGGATTTTATCATGC
AGATGAAACATCCAGGTAGCAAGCTTCAGAGAGAATAGACTGTGAATGTTAATGCCAGAGAGGTATAATG
AAGCATGTCCCACCTCCCACTTTCCATCATGGCCTGAACCCTGGAGGAAGAGGAAGTCCATTCAGATAGT
TGTGGGGGGCCTTCGAATTTTCATTTTCATTTACGTTCTTCCCCTTCTGGCCAAGATTTGCCAGAGGCAA
CATCAAAAACCAGCAAATTTTAATTTTGTCCCACAGCGTTGCTAGGGTGGCATGGCTCCCCATCTCGGGT
CCATCCTATACTTCCATGGGACTCCCTATGGCTGAAGGCCTTATGAGTCAAAGGACTTATAGCCAATTGA
TTGTTCTAGGCCAGGTAAGAATGGATATGGACATGCATTTATTACCTCTTAAAATTATTATTTTAAGTAA
AAGCCAATAAACAAAAACGAAAAGGCAAGTTACGAGACTGACTTATTTTTAACTTCTGTGTGTTGAGCTA
CTGTAAGCTTGGCTTTTGTTAAAGACATACAGCAATTAGCTATGCAAACATAAGCATTGTTCTGAAAAAA
AATATATAGATAGATATGTTTATCTCCATAACTCATAACTGGGAGTATTATACCCAAGAGGCTTTGTTAC
AAGGTATTTTTTATCCTGTTAGTAAATATTTTCCTGTAATTCTATAATAAGCAAATAAATTTTCATGGTT
GGGGTAGATGCAAAAGTGACACATAATCGTTTAGAAAGCAACTAAACTTGTTTTACCAGCTGTTTAGGCA
TTTTTGTAACCCCTCCTTGATTTGGAGGTTTGACCTTGACCTAATTTTTTTCTTTAAAACCAGCCCTTAC
AATCTTCTGCCCCCTCCTCTTCTGTGACAGTAGCTGGGCCTAGAGGGAAGGGGGCTTGTATAGTTTGTGC
AGCAGAGCATTCTCAGTGAAATACAGATCCCGGCCCAGTGGGATGCCAAAATGACGGAGAGCCACATCTC
TGATCTTCAAAATATCATGATTTGGGTTTTCCTGGAAGTAAAACAAGAAGAGATAAATAACATTTACAGT
TTGATCATTAAAAGAGCAATTTGTGCGTCAGAACAGAAAAAGGAACCTATTCCATTAGGGTACCAACTAA
AAATACGAAGAAAAATTATAATCTGGTACTTGCTAGTGGATTACCATAGCCAAAAAATGATGTTTCAGTC
TCCACTGAAAAAAAAAAAAAAAAAGATTAGGACTGAAATTGAGTATTAAATGTTTTCCTTTGAAGCAATT
CCTTTATCCCCCCCCCCCTTTTTTTCTATTAAAGAGAAATTATAGCAAGACCAATTTGTGTGCAAAATAA
GTTTTCGGCTTATTATACTTGGCCTGGTAATTTTGCATAAAAGGCAGCAAGGGTTGGGTATGGTGGCTTA
TGCCTGTAATCCCAGCACGTTGGGAGGCCAAGGCAGGTGGATTGCCTGAGGTCAGGAGTTCAAGACCAGA
CTGGCTAACATGGTGAAATCCCATTTCTACTAAAAATACAAAAATCAGCCAGGCGTGGTGACACACGCCT
ACAGTCCCAGCTACTCGGGAGGCTGAGGCAGGAGAATCGCTTGAACCCGGGAGGCAAAGGTGCCAGTGAG
GTGAGATTGCACCACTGCACTCCAGCCTGGGTGACAGAGCAAGATTCCATCTCCAAAAAAAATTAATTAA

Figure 19 Continued

TTAATTTAAAATGCAGCAAGAATTGATTGGCCATATAGGCTTCTTTAAGTTGACCTTGACTGAACTTTAC
CTAAAAATATGCTATTTTAGTTAAAGTCTTAGTAAAATAACCAGTGTCTCAAATTCTTTTATTTTAAAAG
ATGCTTTTTGAATTTATGCAAATGACTATACTGTCATAAAATCACAATCCAAATTTTAGAACTCAAAGAG
AAATATAAATTTGCTTACAAAAACATACTTCACTCAAATAACTCAAAAGAAAAAGATTTTGTTGACCCTG
CTTTAACCAGAGCCAGAGCTTTCAAACAATGTTTATTTGGGAAATGCCATTTACAAGCCAACAGCTCATG
AAAGCTGTCTATCAGGCATGGTAGAATCTAGGAAAGAGGCCCCCTACTTATCAGTATTTTCTCCTAATAT
CCCCAGGTAGCAAGATTCTATGTAAATCATTTTTATTTTTTTATGGAACTCTTTTGGGCACCATCATTTT
TATTAGCATAGGGGTGGCTTCAGTTAAAATTCCATAGCAAGGCAGTACATGGCTCTCAGGTGGAAATTCT
CTGTTCAATATTGTCATTGGGAAATATTTACAGTTTTTTGCCATCAGCCCCAATAAATGTGCCACAAATG
CCACAAATGAAATGGAGGATTTGTCCTGACTAGCGCTCTAGCTTCTACCCAATACTTTGTGGGCTGAGGC
AATTTTACTAGTTCCCATTCAGCATGTTCAATTAACATTTACTAAAAGAGCAGATTTTTATGCCTTCAGC
TTTATAGTACTAGAAAGGGGAAACATCTCCCAGTCAGATATAGTACCCATTTTCACATGACATTTAGGTA
AAGGGCTTACAACTACCTTCCATAAAGTTTGTTTAAACATCTTAAATTTTATAATTCTGTTAACCTGTAT
GTTTTTGTTTGTTTTTTTGTTTTGTTTTGTTTTTAGCCCCAGATCATTTTACCTTTTCTTTCTTTCTTTT
ATTTATTTATTTTTTTTTGAGACAGAGTCTCGCTCTTGTCACCCAGGCTGGAGTGCAGTGGCATGATCTT
GGCTCACTGCAACCTCCGCCTCCTTGGTTCAAGTGATTCTCCTGCCTCAGCCTACCAACTAGCTGGGATT
ACAGGTGCCCACCATCACACCTGGCTAATTTTTGTATTTTTTTGGGCTGTGGACTGTTGAGTTAATGCTAA
AATGAGTTAAGACTTTGGGGGACTTTTGGGAAGACATGATTGATTTTGAAATGTGAGGACATGAGATTTG
GGAGGTCCAGGGATGGAGTGATATGGTTTGGCTGTGTCTCCACCCAAATCTAATCTTGAATTGTAGCTCC
CATAATTCAACATGATGCAGGAGGGGACCTGGTGGGAGATAATTAAATCATGAGGGTGGTTCCCCTATAC
TGTTCTCATGTTAGACCTAAAACCATAAAAATCCTAGAAGAAAACCTAGGCATTACCATTCAGGACACAG
GCATGGGCAAGGACTTCATGTCTAAAACACCAAAAGCAATGGCATCAAAAGCCAAAATTGACAAATGGGA
TCTAATTAAACTCAAGAGCTTCTGCACAGCAAAAGAAACTACCATCAGAGTGTACAGGCAACCTACAAAA
TGGGAGAAAGTTTTTGCAATCTACTCATCTGACAAAGGGCTAATATCCAGAATCTACGAAGAACTCAAAC
AAATTTACAAGAAAAAAACAAACAACCCCATCAAAAAGTGGGCAAAGGATATGAACAGACACTTCTCAAAA
GAAGACATTTATGCAGCCAAAAGACACATGTAAAAGTGCTCATCATCACTGGCCATCAGAGAAATGCAAA
TCAAAACCACAATGAGATACCATCCCACACCAGTTAGAATGGTGATCATTAAAAAGTCAGGAGACAACAG
GTGCTGGAGAGGATGTGGAGAAATAGGAACACTTTTACACTGTTGGTGGGACGTAAACTAGTTCAACCAT
TATGGAAGTCAGTGTGGCGATTCCTCAGGGATCTAGAACTAGAAATACCATTTGACCCAGCCATCCCATT
GCTGGGTATATACCCAAAGGATTATAAAACATGTTGCTATAAAGACACATGCACATGTATGTTTATTGCA
GCACTATTCACAATAGCAAAGACTTGGAACCAACCCGAATGTCCAACAGTGATAGACTGGATTAAGAAAA
TGTGGCACATATACACCATGGAATACTATGCAGCCATAAAAAAGGATGAGTTCATGTCCTTTGTAGGGAC
ATGGATGAAGCTGGAAACCATCATTCTCAGCAAAGTATTGCAAGGACAAAAAACCAAACACCGCATGTTC
TCACTCATAGGTGGGAATTGAACAATGAGAACACCTGGACACAGGAAGGGGAACATCACACACCGGGGCC
TGTTGTGGGATGGGGGGAGGGGGGAGGGATAGCATTAGGAGATACACCTAATGTTAAATGACGAGTTAAT
GGGTGCAGCACACCAACATGGCACATGTATAAATATGTAACTAACCTGCACGTTGTGCACATGTACCCTA
AAACTTAAAGTATAATAATAAAAAAAAAGAAATTACAAGTGCTGCTCCAATGAACACACAAATAGTAAGA
AAACAAGATAGCCTTATTGCTGATATGGAGAAAGTTTGGTGGTCTGGATACAAGACGAAACCAATCACAA
CGTTCTCTTAAGTCAAAGCCTAATCCAGAGCAAGGCCCTAACTCTTGTCAATTCTGTGATGGGTGAGAGA
GGTGAAGAAGCTACAGAAGAAATGTTGGAAGCTAGCAGAGGTTGGTTCATCAGGTTTAAGGAAAGAAGCC
TTCTCTCTAACATAAAAATGAAAGATGAAGCAGCAAGTTGTGATGTAGAAACTGGAGCAAGTTATCCAGA
AGATATAGCTAAGATAGCTGAAGGTGTCTAGATGAAACAGCTTTGTATTGGAAAGACATGTCATCTAGGA
TTTTTATACCTAGAGAGGAAAAGTCAATGGCTGGCTTGAAAGCTTCAAAGGACAAGCTGACTCTCTTGTT
AGGGACTAATGCAGCTGATGACTTTAAGTTAAAGCCAGTAGTCTTTTATCATTTCAAACGTCCTAGGGAC
CTTAATAATTATGCTAAATGTACCTGCCAATGCTCTATGAATGAAACAATGACGTCTAGATGAAAGCACA
TTTGTTTATAGCATTGTTTACTGAGTATTTTAAGCCCATTGTTGAGAAACACTGCTCAGAAAAAAAAAAG
GTCTTTTTTTCAAAATATTACAGCTCATTGACAATGCACCTAGTCACCCAAGAGCTCTTATAGACATGTA
CCGGGAGGTTAATGTTTTCAGTCCTGCTAACACAGCATCCTTTTCTGCAACCAACAAATCAAGGAGTAAT
TTTGACTTTCAAGTTTTATTCTTTAAGAAATACACATCATAAGGCTATAACTCCCACAGATACTGATTCT
TCTTATATATCAGAGCAAAGTAAATTGAAAACCACCTGGAGACAACTTACCATTCTAGATGCCATTAAAA
AGATTTGTGATTCATGGAAGGAAGACAAAGTGTCAACATTAACAGACACTTGGAAGAAGTTGAATCAAAC
CCTCATGGATAACTTGCAGGCGTTCAAGACTTCAGTGGTGGAAGTAACTGCAGATGTGGTGGAAATAGCA
AGAGAACTAGAACTGGAAGTGGAGCCTGAAGATGTGGCTGAATTGATGCAATTTTATCAGGAAACTTTAA
CAAATGAGGAGTTGCTTTTTATGGATGAGCAAAGAAAATGGTTCTTGAGACAAATATTATTCCTGGTGAA
CATGCTGTGAACATTGTTGAAATGCTAATAAAGTATTCTGAATATTGCATAAACTTAGTTGATAAAGCAG
TAGCAGGATTTGAGAGGACTGACTTCAATTTTGAAAGAAGTTTACGATGAGTAAAATGCTATTTAACAGC
ATCGCATTCTACAGATAAAAATTTCATAAAAGGAAGACTAAATTGATGCTACAAACTTCACCATTGTCTT

Figure 19 Continued

ATTTTAAAAATAGCCACATCTACCCCATCCTTCAGCAACCACTGCTGTGATCCATCAGCAGCCATCAACA
TCAAGGCAAGACGCTACACCAGCAAAAAGATTTTCACTCACTAAAGACTCAAATAATCAGCATTTTTAGC
AATAAACTATTTTTAATAAAACTATGTACATTTTCCAGACATAATGCTGTTGTATACTTAATAGAAGACG
TTGTAGCTCAAACATAACTTTTACACGAATTGGGAAAGCAAATAATTAATGTGACTCACTTTATTGCAAT
AATTGCTTTATTGTGGTGGTCTGGAACTGAACCCACAATATTTCCGAGGCATGCCTGTAAGTTAGTTTTA
AATTGAAGAAGACAGAAGTCAAATTTTGCTGGAGTTCACTTAGATGACATGTAGAAGATTTAGTATTTGA
AATGAGGTGGTCTGATCTGTGCTACTAACGTTTGTGCTATTTTGATTTTATGTATAAGATACTTTAGATA
TGAATACCAGAAAAAGAATCACAGTGATTGGCCTACATTTTTAATTGTATTGTTGCCATGCACTAAGATA
TTATTCTTCTAAGTTTATGTGTGCTATAGGGATGTATACACATATGTTTTTCCATTTTAGGGAGATGAAA
CAAAGTTGAGTTGCTAATTTTGTACAGTTTTCTGAATTATTGGTTCCTATTTAGTTTCTCTAAATAGACA
ATTCAAAATAAAAAACATACTGATACCATCACCCAAATCCAAGATCTCCAGACATTTGAAGTAACAAGTA
AAATTTGAGGTATTTCTATTATTTTTCCTAAGCCCTCCAAATCTGCTTAATTATTGATAGGCTAGAAAAA
AGATAAAGATTCAAGTGTCTTTCAGTGTTAGCGCACAAAGCTTTAAGAGTAACACATATTTATTGAGTAT
GTATTACATACTTGGTATTCTGATCGATACTTTATATAATCATATTAAATGAGCTTCACAATTAACTTAT
GAGCAAGGTAATAATATTAAACCCATTTCAAGGTGAGAACATTACTTATCCAAAGCCAGATAGAGAGTAA
GTTCTAAAGTAGTGATATTTCTCTAACTGTATTAAAGACTACTTGTATGAGAATTGTGTCGTGATGCTGG
TAAAAACCCAGGTCTCTGTGTCTCCTCAGTCTTCCCACTGAGTAACATCAGCATTTGAGTTTCCTATTTG
GTTTCTCTATGTTTTAACCAAAACCTCCGTTGAGATGTTTGAGAATCATGTTCGTAAATGGTAGCCACTA
GTTAAAAAAGGGAAGCTGTGGGAAAGAAATGCAATTTTTTCCTATTATCCTGTAAAAGGGTGCCTTTCCA
CATATTCTGTAAATACTTCCTGAGTTACTCAGCAAAAATAAAGCACAGAACTGTTAGGAAAATACTAATT
AAAGCATTTTTACTTGTCCTTCTGTCTAGTAGCCTCTGAAACTTAAGAAGCATTTATTCATTTTACAAAC
CCAGTGAGTTTTCTTGCAAACTTTCTTTTCCTTCTCTAGCGCAGAAAATTACTACTGTTGAATCTAACCA
GAGGTAGACTTGGAATAGTAATTCTATTTGCGTAATGTTTTAATGATTGAGCTATTTTTCTCATGAACTA
TCTTATACAAAGAGAAACAAATATCTCTCTGTTTTGTGAGCCAGGGTTTCGGGTTGGTGCTGGTAAGAGA
ATAGTGAATGGGGAAGTCATAGTGTTCGCTTTCATGGAGTTTCTGGTACAGTTAACACTCTAAAGTTCTA
TTTTAGGTTGTAGAACTGTGAGATATAAAAGATGGTTGTTATTATTCCTATTTTAAATATGAGAAAAGGG
AAGTTAAAGAGGTTATGAAACTTGTTCATGATTGTAATTTAGTTAATTGACATCTAAATTATTTTGCTGA
TTCTAAGTTTAATATTCTTTTTACTATCTTACACCGCCTTTCAAACTTAGATATTTTGGACAGATTTCAA
ACATAGATATTTTGCACAACTTATATTAATTAAGCCCTAACCTATATTGGCCTGATTTTGATGTTATATG
TGTATATCTGAAGATGCAGTAAATCATACCATGTTCAGGTAATTAGAAATGAAGGACAAGAAGAAAGAAA
ATTAAAGGAAAATAGAACAATTGGGAAGCAAATGATAAACTCACGTGATGGCTTCTGTATATTCAAAGAA
GGGACTAGGTAATTCTGATAGGAAAGATAATATTAAAAATAACTCCAGTGAGAAGAAAGGGAGAAATAAG
CAATTTTCAGCTACTGATGCATTCATACATATCTTTTATTGTACAATAAAGCCCTTATCTGTGTTATCCT
GTCCACCTCTTTGCATTAAGGTAGTTGGTCCACCTTGGTCATGCCAGCCTTCCTCTCACACATTAAATAA
TGTTTGTTCTCACAGAAGGTAGGGTGCATTTTCCCATTATGAAAATAAGCACAATTCATATTTCCTTTTC
CATCTTCCAAAAACTCAAACCTGTGAAGGGAAAGTTAGAATAAATTCCTTTGAAAACTGAGCAAACAATC
AGTAATCAGACTCTGCGTATAGTAGTTTGATGCACCAAATAGAGACTGAGGAAAATAGGAAAAAAAAACA
AAAAAAAAAACGATTCTCATTGTTGAGAAAGTTCCACCCTGCTTGGCAGTACAAGATATGCATATTTAAA
AAGCCCAATATCAATTTCATTTAGCATAAAATTAGGAGCAAGGGAACAGTAGGTACAATAGGAGCCCTGA
AGAAGTGATGGAGATGGCTCCAAAATAATGGGAAAACGCATTATCTACAAGATCAGACTTTAGTTCGGTA
TTGATGGAAGGTCAGGACTCAGATGAACTGACAGGAGATGGAAGAGCCCTACAGGACAAGTAGCTGCACT
AGATGGGAATACGCTCATGGAAAAGTGAGTTGATTCAGTAGTTTTGAAATCAGGATTTATGTTGCAAGAT
AAATCATCTAACACAGCAGGCTGTATTGTAATTGTCTGTTAAGTTATATTTCTTTCTTTCTAAACTGCTT
ATAATGAGATGACAAGGAATATATACTTATTGGTTTATTTGGAGAATACCTGCAGAACTATGTGACAAAG
TTGTTCTATGTGCTGAGGATACACTGATAAAGAAAGACAAGAAAGCTAATGTCTTTCTTGTTGGGGAACT
TTCATTTAAGTGGGGCGATACCGGTAAGAAGCCCACAAAAAATAGACAAGAAAAATTGAGACAGTGGTAA
GAGTTACAAAGAAACAAAACAGTGGTGGACTGTATGGATATGGGTTTAAGGGAGGCTAATTTAGTTTGGG
TAGAGTTAGGTTCACTGAAGAAGTGATGTTTAAATAGAGACTTGAGTCTCAGTGGAGAGATGGTCATGGA
GTTGTGGAGGCAGAGCATTCTAGAAGAAAATAGCAAGACAAAAGCCTTAAGGTAACAAAACGAGTTTGAT
TTGTTGGAAGAATGTAAAGAACACTAAGTTGCCTGCAATATTGTAAATGAGGCAGCAAGCAATAGGAGAT
AGGAGATAAAGCCCAAGGTCTGTGAAGAGGCTTGCTTGTAGTTGTAGTATCCTAAGATCCTATCTATAGT
AAATACTTAATAAATATTTGTTTAAAAATTTAATTCATAATTTGAGTAATAATCAGATTATATAAGTTTT
GGTTATCAGTTTAAATTTTAATTGAAGAGAGACTGCAGTTTTGATATACAGGATGAACAAAAGATGTTGA
GACTGCAGATTGGAAAGCCATATAGGAAGCAACTCCACTCAATGCAATCAGTCCCTTTGCCTGGATTGTT
TGTAGAAGGACAAAGCTTCGTTAATGGACATTGGAATTATCTTGTGAAATACAATGTATCGAATTCTTGG
AGACTCCCAGAATAGAGGAATAGGCAAAACAATATTGAAAACTCAAAAGGACTCTCAAGATAACAACTTT
CAACTGTAAAATAATGATATGAAATTTTGTTTTAAAAATATGTGAAGATAATCAGAACAAGCAAAACACA

Figure 19 Continued

AAAACACACACACATGTGCATGCGCGCACACACACACACACACTCACACATACACATACATGCACACAGT
GTTCCATGGTAAGGTTGAATGTAAAAATGAATGGGAATAATATCAGAGATAAAGGTGGATTGTGGCTTAG
ATAAAGAGCAAAGTAATGGGAGAGAGGGGAAAGAATTGTCTTATGACCAGCGCTGTCTTGTTTGAATTAG
CAGGTAAGTGACCCAGCTGCTGCTTCTATAACCCATAGTAGTGACTTGGACTGAGAGAAGAGGGAATCTC
AAGAATAAGAGTTTCCAGTACTCCCTCCTATTCTAAGTGTCCAGTGACTTACATATTTTCTGAGATAACC
GAGCCATCCTCCCACTTCCAGACCTCATTCGACTTCTGGCGAGATAATCCGA

Figure 19 Continued

Figure 20

CD3γ chain (SEQ ID NO: 2)

```
MEQGKGLAVL ILAIILLQGT LAQSIKGNHL VKVYDYQEDG SVLLTCDAEA KNITWFKDGK  60
MIGFLTEDKK KWNLGSNAKD PRGMYQCKGS QNKSKPLQVY YRMCQNCIEL NAATISGFLF 120
AEIVSIFVLA VGVYFIAGQD GVRQSRASDK QTLLPNDQLY QPLKDREDDQ YSHLQGNQLR 180
RN                                                               182
```

CD3δ chain (SEQ ID NO: 3)

```
MEHSTFLSGL VLATLLSQVS PFKIPIEELE DRVFVNCNTS ITWVEGTVGT LLSDITRLDL  60
GKRILDPRGI YRCNGTDIYK DKESTVQVHY RMCQSCVELD PATVAGIIVT DVIATLLLAL 120
GVFCFAGHET GRLSGAADTQ ALLRNDQVYQ PLRDRDDAQY SHLGGNWARN K          171
```

CD3ε chain (SEQ ID NO: 4)

```
MQSGTHWRVL GLCLLSVGVW GQDGNEEMGG ITQTPYKVSI SGTTVILTCP QYPGSEILWQ  60
HNDKNIGGDE DDKNIGSDED HLSLKEFSEL EQSGYYVCYP RGSKPEDANF YLYLRARVCE 120
NCMEMDVMSV ATIVIVDICI TGGLLLLVYY WSKNRKAKAK PVTRGAGAGG RQRGQNKERP 180
PPVPNPDYEP IRKGQRDLYS GLNQRRI                                    207
```

CD3ζ chain (SEQ ID NO: 5)

```
MKWKALFTAA ILQAQLPITE AQSFGLLDPK LCYLLDGILF IYGVILTALF LRVKFSRSAD  60
APAYQQGQNQ LYNELNLGRR EEYDVLDKRR GRDPEMGGKP QRRKNPQEGL YNELQKDKMA 120
EAYSEIGMKG ERRRGKGHDG LYQGLSTATK DTYDALHMQA LPPR                 164
```

CD3 BINDING MOLECULES

CROSS-REFERENCE TO RELATED APPLICATIONS

This application is the 35 U.S.C. § 371 National Phase of International Application No. PCT/NL2020/050214, filed Mar. 27, 2020, which claims priority to EP 19200931.4, filed Oct. 1, 2019 and EP 19166345.9, filed Mar. 29, 2019. The entire contents of International Application No. PCT/NL2020/050214 are hereby incorporated by reference.

REFERENCE TO A SEQUENCE LISTING SUBMITTED ELECTRONICAL VIA EFS WEB

This application includes a Sequence Listing submitted electronically via EFS-web Name: 4096 0390002 Seqlisting ST25.txt, File Size: 193,189 bytes, and Created On: Apr. 28, 2025), which is hereby incorporated by reference in its entirety.

FIELD OF THE INVENTION

The invention relates to the field of antibodies, in particular to the field of therapeutic antibodies. The antibodies can be used in the treatment of humans. More in particular the invention relates to antibodies and preferably bispecific or multispecific antibodies for the treatment of a tumor.

BACKGROUND TO THE INVENTION

Monoclonal antibodies that bind to human CD3 were among the first antibodies developed for therapeutic use in humans. Monoclonal CD3 binding antibodies are typically used for their immune suppressive qualities, for instance in transplant rejection. Antibodies which are bispecific for CD3 on T cells and for a surface target antigen on cancer cells, are capable of connecting any kind of T cell to a cancer cell, independently of T-cell receptor specificity, costimulation, or peptide antigen presentation. Such bispecific T-cell engaging antibodies show great promise in the treatment of various cancers and neoplastic growths.

It is an object of the invention to provide new antibodies with CD3 binding properties in kind, not necessarily in amount, with improved characteristics, having relatively low affinity, with higher cytotoxicity, which are amenable for immuno-oncology applications for T-cell and effector cell engagement, and conversely, new antibodies with CD3 binding that have relatively high affinity, with lower cytotoxicity, which are amenable for auto-immune applications for T-cell and effector cell down-regulation. It is a further object of the invention to provide T-cell engaging CD3 binding proteins and antibodies with the above properties that bind at least one further membrane associated molecule.

SUMMARY OF THE INVENTION

The invention provides an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1: SEQ ID NO 42
SFGIS;

CDR2: SEQ ID NO 43
GFIPVLGTANYAQKFQG;

CDR3: SEQ ID NO 44
RGNWNPFDP;

or comprising the amino acid sequence:

CDR1: SEQ ID NO 6
SX$_1$FTIS;

CDR2: SEQ ID NO 7
GIIPX$_2$FGTITYAQKFQG;

CDR3: SEQ ID NO 44
RGNWNPFDP;

wherein $X_1$=K or R;

$X_2$=L or I.

In a preferred embodiment $X_1$=K; and $X_2$=L; In another preferred embodiment $X_1$=R; and $X_2$=I.

In a preferred embodiment, the invention provides an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1: SEQ ID NO 84
SKTLTIS;

CDR2: SEQ ID NO 85
GIIPIFGSITYAQKFQD;

CDR3: SEQ ID NO 44
RGNWNPFDP;

comprising the amino acid sequence:

CDR1: SEQ ID NO 100
GSGIS;

CDR2: SEQ ID NO 101
GFIPFFGSANYAQKFRD;

CDR3: SEQ ID NO 8
RGNWNPX$_{13}$DP;

wherein $X_{13}$=L or F.

The invention further provides an antigen-binding protein, preferably an antibody, that binds human CD3 comprising an antibody variable domain comprising a heavy chain variable region and a light chain variable region wherein the heavy chain variable region comprises the amino acid sequence SEQ ID NO 45
EVQLVQSGAEVKKPGSSVKVSCKASGGTFRSFGISWVRQAPGQGLEWMG
GFIPVLGTANYAQKFQGRVTIIADKSTNTAYMELSSLRSEDTAVYYCAR
RGNWNPFDPWGQGTLVTVSS;

SEQ ID NO 54
QVQLVQSGAEVKKPGSSVKVSCKASGDAFKSKTFTISWVRQAPGQGLEW
LGGIIPLFGTITYAQKFQGRVTITADKSTNTAFMELSSLRSEDTAMYYC
TRRGNWNPFDPWGQGTLVTVSS;

SEQ ID NO 63
EVQLVQSGSELKKPGSSVKVSCKASGVTFNSRTFTISWVRQAPGQGLEW
LGSIIPIFGTITYAQKFQGRVTITADKSTSTAFMELTSLRSEDTAIYYC
TRRGNWNPFDPWGQGTLVTVSS;

SEQ ID NO 71
QVQLVQSGAEVKKPGSSVKVSCKASGGTFRGSGISWVRQAPGQGLEWVG
GFIPFFGSANYAQKFRDRVTITADKSATTAYMELSSLRSEDTAIYYCAK
RGNWNPLDPWGQGTLVTVSS;

SEQ ID NO 87
QVQLVQSGAEVKKPGSSVKVSCKASGVTFKSKTLTISWVRQAPGQGLEW
LGGIIPIFGSITYAQKFQDRVSITADKSTNTAYLELNSLRSEDTAIYYC
ARRGNWNPFDPWGQGTLVTVSS;
or

SEQ ID NO 103
EVQLVQSGAEVKKPGSSVKVSCKASGGTFRGSGISWVRQAPGQGLEWVG
GFIPFFGSANYAQKFRDRVTITADKSATTAYMELSSLRSEDTAIYYCAK
RGNWNPFDPWGQGTLVTVSS;

with 0-10, preferably 0-5 amino acid variations, insertions, deletions, substitutions, additions or a combination thereof at one or more positions other than the CDRs.

Further provided is an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
SEQ ID NO 9
$RX_3WIG$;

CDR2:
SEQ ID NO 200
IIYPGDSDTRYSPSFQG;

CDR3:
SEQ ID NO 10
$X_4IRYFX_5WSEDYHYYX_6DV$;

wherein $X_3$=F or Y;

$X_4$=H or N;

$X_5$=D or V;

$X_6$=L or M.

In one embodiment $X_3$=F; $X_4$=H; $X_5$=D; and $X_6$=L. In another embodiment $X_3$=Y; $X_4$=N; $X_5$=V; and $X_6$=M.

The invention further provides an antigen-binding protein, preferably an antibody, that binds human CD3 comprising an antibody variable domain comprising a heavy chain variable region and a light chain variable region wherein the heavy chain variable region comprises the amino acid sequence SEQ ID NO 298
EVQLVQSGAEVKKPGESLKISCKGSGYSFTRFWIGWVRQMPGKGLEWMG
IIYPGDSDTRYSPSFQGQVTISADKSTSTAYLQWSSLKASDTGMYYCVR
HIRYFDWSEDYHYYLDVWGKGTTVTVSS;
or SEQ ID NO 211
EVQLVESGAEVKKPGESLKISCKGSGYSFTRYWIGWVRQMPGKGLEWMG
IIYPGDSDTRYSPSFQGQVTISADKSISTAYLQWSSLKASDTAMYYCVR
NIRYFVWSEDYHYYMDVWGKGTTVTVSS;

with 0-10, preferably 0-5 amino acid variations, insertions, deletions, substitutions, additions or a combination thereof at one or more positions other than the CDRs.

Further provided is an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
SEQ ID NO 117
SYALS;

CDR2:
SEQ ID NO 118
GISGSGRTTWYADSVKG;

CDR3:
SEQ ID NO 119
DGGYSYGPYWYFDL.

Further provided is an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
SEQ ID NO 117
SYALS;

CDR2:
SEQ ID NO 126
AISGSGRTTWYADSVKG;

CDR3:
SEQ ID NO 127
DGGYTYGPYWYFDL.

Further provided is an antigen-binding protein, preferably an antibody, that binds human CD3 comprising an antibody variable domain comprising a heavy chain variable region and a light chain variable region wherein the heavy chain variable region comprises the amino acid sequence

SEQ ID NO 120
QVQLVQSGGGLVQPGGSLRLSCATSGFKFSSYALSWVRQAPGKGLEWVS

GISGSGRTTWYADSVKGRFTISRDNSKNTLYLQMNSLRAEDTAVYYCAR

DGGYSYGPYWYFDLWGRGTLVTVSS;
or

SEQ ID NO 128
QVQLVESGGGLVQPGGSLRLSCATSGFTFISYALSWVRQAPGKGLEWVS

AISGSGRTTWYADSVKGRFTISRDNSKNTLFLQMNSLRAEDTAVYYCAR

DGGYTYGPYWYFDLWGRGTLVTVSS;

with 0-10, preferably 0-5 amino acid variations, insertions, deletions, substitutions, additions or a combination thereof at one or more positions other than the CDRs.

Also provided is an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
SEQ ID NO 142
DYTMH;

CDR2:
SEQ ID NO 143
DISWSSGSIGYADSVKG;

CDR3:
SEQ ID NO 144
DHRGYGDYEGGGFDY.

Also provided is an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
SEQ ID NO 142
DYTMH;

CDR2:
SEQ ID NO 11
DISWS$X_7$G$X_8X_9X_{10}$YADSVKG;

CDR3:
SEQ ID NO 12
DH$X_{11}$GYGDYEGGGFD$X_{12}$;

wherein $X_7$=S or G;
$X_8$=S or T;
$X_9$=I or T;
$X_{10}$=G or Y;
$X_{11}$=R or M;
$X_{12}$=H or Y.

In one embodiment. $X_7$, $X_8$, $X_9$ and $X_{10}$ are S, S, I and G, and $X_{11}$ and $X_{12}$ are R and H. In another embodiment, $X_7$, $X_8$, $X_9$ and $X_{10}$ are G, S, I and Y, and $X_{11}$ and $X_{12}$ are R and Y. In another embodiment, $X_7$, $X_8$, $X_9$ and $X_{10}$ are S, T, T and G, and $X_{11}$ and $X_{12}$ are M and Y.

Further provided is an antigen-binding protein, preferably an antibody, that binds human CD3 comprising an antibody variable domain comprising a heavy chain variable region and a light chain variable region wherein the heavy chain variable region comprises the amino acid sequence (SEQ ID NO 145)
EVQLVESGGGLVQPGRSLRLSCATSGFNFDDYTMHWVRQAPGKGLEWVS

DISWSSGSIGYADSVKGRFTISRDNAKNSLWLQMNSLRTEDTALYFCAK

DHRGYGDYEGGGFDYWGQGTLVTVSS;
or (SEQ ID NO 153)
EVQLVESGGGLVQPGRSLRLSCATSGFTFDDYTMHWVRQAPGKGLEWVS

DISWSSGSIGYADSVKGRFTISRDNAKNSLYLQMNSLRAEDTALYFCAK

DHRGYGDYEGGGFDHWGQGTLVTVSS;
or (SEQ ID NO 169)
EVQLVESGGVVVQPGGSLRLSCAASGFTFDDYTMHWVRQAPGKGLEWVS

DISWSGGSIYYADSVKGRFTISRDNSKNSLYLQMNSLRTEDTALYYCAK

DHRGYGDYEGGGFDYWGRGTLVTVSS;
or (SEQ ID NO 185)
EVQLVESGGGLVQPGRSLRLSCVTSGFTFDDYTMHWVRQAPGKGLEWVS

DISWSSGTTGYADSVKGRFTISRDNAKDSLYLQMNSLRTEDTALYYCAK

DHMGYGDYEGGGFDYWGQGTLVTVSS;

with 0-10, preferably 0-5 amino acid variations, insertions, deletions, substitutions, additions or a combination thereof at one or more positions other than the CDRs.

The light chain variable region in an antigen-binding protein, preferably an antibody, of the invention preferably comprises a common light chain variable region. The common light chain variable region preferably comprises an IgVκ1-39 light chain variable region. Said light chain variable region is preferably a germline IgVκ1-39*01 variable region. The light chain variable region preferably comprises the kappa light chain IgVκ1-39*01/IGJκ1*01 or IgVκ1-39*01/IGJκ5*01. In one embodiment the light chain variable region comprises the human germline kappa light chain IgVκ1-39*01/IGJκ1*01 or IgVκ1-39*01/IGJκ5*01. Said light chain variable region preferably comprises the amino acid sequence (SEQ ID NO 16)
DIQMT QSPSS LSASV GDRVT ITCRA SQSIS SYLNW YQQKP

GKAPK LLIYA ASSLQ SGVPS RFSGS GSGTD FTLTI SSLQP

EDFAT YYCQQ SYSTP PTFGQ GTKVE IK
or (SEQ ID NO 19)
DIQMT QSPSS LSASV GDRVT ITCRA SQSIS SYLNW YQQKP

GKAPK LLIYA ASSLQ SGVPS RFSGS GSGTD FTLTI SSLQP

EDFAT YYCQQ SYSTP PITFG QGTRL EIK with 0-5 amino acid variations, insertions, deletions, substitutions, additions or a combination thereof.

The antigen-binding protein, is preferably an antibody, preferably a bispecific or multispecific antibody.

Said antibody preferably comprises a H/L chain combination that binds human CD3 as indicated herein and a H/L chain combination that binds a tumor-antigen. Said H/L chain combination that binds a tumor-antigen preferably binds human BCMA, CD19, CD20, CD30, CD33, CD38, CD44, CD123, CD138, CEA, CLEC12A, CS-1, EGFR, EGFRvIII, EPCAM, DLL3, LGR5, MSLN, FOLR1, FOLR3, HER2, HM1.24, MCSP, PD-L1, PSMA protein or a variant thereof, in a preferred embodiment EGFR, PD-L1 or CLEC12A.

The antibody, bispecific or multispecific antibody is preferably a human or humanized antibody.

The bispecific or multispecific antibody preferably comprises two different immunoglobulin heavy chains with compatible heterodimerization domains. Said compatible heterodimerization domains are preferably compatible immunoglobulin heavy chain CH3 heterodimerization domains.

The bispecific or multispecific antibody is preferably an IgG antibody with a mutant CH2 and/or lower hinge domain such that interaction of the bispecific or multispecific IgG antibody to a Fc-gamma receptor is reduced. The mutant CH2 and/or lower hinge domain preferably comprise an amino substitution at position 235 and/or 236 (according to EU numbering), preferably an L235G and/or G236R substitution.

The bispecific or multispecific antibody preferably comprises a common light chain.

The invention further provides an antigen-binding protein or antibody as indicated herein, for use in the treatment of a subject in need thereof. The subject preferably has cancer or is treated for cancer. An antigen-binding protein or antibody having the CDRs and/or the VH sequence of MF8057, MF8058, MF8078, or MF8508, or a variant thereof having 0-10 amino acids substitutions, variations, insertions, additions or deletions, are preferred for treatment, in particular for a treatment comprising the local administration and/or local release of the antigen-binding protein or antibody. An antigen-binding protein or antibody having the CDRs and/or the VH sequence of MF9249, MF9267, MF8397, or a variant thereof having 0-10 amino acids substitutions, variations, insertions, additions or deletions, are preferred for a treatment of a subject with an over-active immune system, such as an auto-immune disease.

An antibody of the invention is, unless otherwise specifically specified, preferably a bispecific antibody. The bispecific antibody preferably binds at least human CD3. In addition, the bispecific antibody preferably binds at least a surface molecule that is preferentially expressed on human tumor cells. In a preferred embodiment, the bispecific antibody binds to BCMA, CD19, CD20, CD30, CD33, CD38, CD44, CD123, CD138, CEA, CLEC12A, CS-1, EGFR, EGFRvIII, EPCAM, DLL3, LGR5, MSLN, PD-L1, FOLR1, FOLR3, HER2, HM1.24, MCSP, or PSMA. In a more preferred embodiment, the bispecific antibody binds to EGFR or CLEC12A. In a more preferred embodiment, the multispecific antibody binds to EGFR and PD-L1.

The invention further provides a pharmaceutical composition comprising an antibody according to the invention.

Further provided is an antibody according to the invention that further comprises a label, preferably a label for in vivo imaging.

The invention also provides a method for the treatment of a subject having a tumor or at risk of having a tumor, comprising administering to the subject a bispecific or multispecific antibody according to the invention. Also provided is a bispecific or multispecific antibody according to the invention for use in the treatment of a subject having a tumor or at risk of having a tumor. Further provided is the use of an antibody of the invention for the preparation of a medicament for the treatment of a subject having a tumor or at risk of having a tumor. In a preferred embodiment, the tumor is an EGFR or a CLEC12A positive tumor or an EGFR and PD-L1 positive tumor.

DETAILED DESCRIPTION OF THE INVENTION

An "antibody" is a proteinaceous molecule belonging to the immunoglobulin class of proteins, containing one or more domains that bind an epitope on an antigen, where such domains are derived from or share sequence homology with the variable region of an antibody. Antibody binding has different qualities including specificity and affinity. The specificity determines which antigen or epitope thereof is specifically bound by the binding domain. The affinity is a measure for the strength of binding to a particular antigen or epitope. It is convenient to note here that the 'specificity' of an antibody refers to its selectivity for a particular antigen, whereas 'affinity' refers to the strength of the interaction between the antibody's antigen binding site and the epitope it binds. Antibodies are typically made of basic structural units—each with two heavy chains and two light chains. Antibodies for therapeutic use are preferably as close to natural antibodies of the subject to be treated as possible (for instance human antibodies for human subjects). An antibody according to the present invention is not limited to any particular format or method of producing it.

Thus, the "binding specificity" as used herein refers to the ability of an individual antibody binding site to react with an antigenic determinant. Typically, the binding site of the antibody of the invention is located in the variable domain, in the Fab portion comprising the variable domain and is constructed from the hypervariable regions of the heavy and light chains.

An antibody of the invention is preferably an IgG antibody, preferably an IgG1 antibody. Full length IgG antibodies may be preferred because of their favorable half-life and the desire to stay as close to fully autologous (human) molecules for reasons of immunogenicity. IgG1 is favored based on its long circulatory half-life in man. In order to prevent or avoid immunogenicity in humans it is preferred that a bispecific full length IgG antibody according to the invention is a human IgG1.

A "bispecific antibody" is an antibody as described herein wherein one variable domain of the antibody binds to a first antigen whereas a second variable domain of the antibody binds to a second antigen, wherein said first and second antigens are not identical. The term "bispecific antibody" also encompasses biparatopic antibodies, wherein one variable domain of the antibody binds to a first epitope on an antigen whereas a second variable domain of the antibody binds a second epitope on the antigen. The term further includes antibodies wherein at least one VH is capable of specifically recognizing a first antigen and a VL, paired with the at least one VH in an immunoglobulin variable domain, is capable of specifically recognizing a second antigen. The resulting VH/VL pair will bind either antigen 1 or antigen 2, and are called "two-in-one antibodies", described in for instance WO 2008/027236, WO 20101108127 and Schaefer et al (Cancer Cell 20, 472-486, October 2011). A bispecific antibody according to the present invention is not limited to any particular bispecific format or method of producing it. A bispecific antibody is a multispecific antibody.

Multispecific multimers or antibodies as referred to herein, encompass proteinaceous molecules belonging to the immunoglobulin class of proteins, containing two or more domains that bind an epitope on an antigen, where such domains are derived from or share sequence homology with the variable region of an antibody, and include proteinaceous molecules binding three antigens or more as known in the art, including as described in WO2019/190327.

An "antigen" is a molecule capable of inducing an immune response (to produce an antibody) in a host organism and/or being targeted by an antibody. At the molecular level, an antigen is characterized by its ability to be bound by the antigen-binding site of an antibody.

Also mixtures of antigens can be regarded as an 'antigen', i.e. the skilled person would appreciate that sometimes a lysate of tumor cells, or viral particles may be indicated as 'antigen' whereas such tumor cell lysate or viral particle preparation exists of many antigenic determinants. An antigen comprises at least one, but often more, epitopes. For binding proteins and antibodies as disclosed herein, the antigen is typically associated with a cell membrane and present on the extracellular portion of the cell membrane.

An "epitope" or "antigenic determinant" is a site on an antigen to which an immunoglobulin or antibody specifically binds. Epitopes can be formed from contiguous amino acids or noncontiguous amino acids juxtaposed by tertiary folding of a protein (so-called linear and conformational epitopes, respectively). Epitopes formed from contiguous, linear amino acids are typically retained on exposure to denaturing solvents, whereas epitopes formed by tertiary folding, conformation is typically lost on treatment with denaturing solvents. An epitope may typically include 3, 4, 5, 6, 7, 8, 9, 10, 11, 12, 13, 14 or 15 amino acids in a unique spatial conformation.

The term "heavy chain" or "immunoglobulin heavy chain" includes an immunoglobulin heavy chain constant region sequence from any organism, and unless otherwise specified includes a heavy chain variable domain. The term heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen and that comprises at least one CDR.

The term "light chain" includes an immunoglobulin light chain variable domain, or $V_L$(, or a functional fragment thereof; and an immunoglobulin constant domain, or $C_L$, or functional fragment thereof, sequence from any organism. Unless otherwise specified, the term light chain may include a light chain selected from a human kappa, lambda, and a combination thereof. Light chain variable ($V_L$) domains typically include three light chain CDRs and four framework (FR) regions, unless otherwise specified. Generally, a full-length light chain includes, from N-terminus to C-terminus, a VL domain that includes FR1-CDR1-FR2-CDR2-FR3-CDR3-FR4, and a light chain constant domain. Light chains that can be used with this invention include those, e.g., that do not selectively bind an epitope selectively bound by the heavy chains.

Suitable light chains for use in an antibody of the invention include a common light chain (cLC), such as those that can be identified by screening for the most commonly employed light chains in existing antibody libraries (wet libraries or in silico), where the light chains do not substantially interfere with the affinity and/or selectivity of the epitope-binding domains of the heavy chains, but are also suitable to pair with an array of heavy chains. For example, a suitable light chain includes one from a transgenic animal, such as MeMo® having a common light chain integrated into its genome and which can be used to generate large panels of common light chain antibodies having diversity at the heavy chain and capable of specifically binding an antigen upon exposure to said antigen.

The term "common light chain" according to the invention refers to light chains which may be identical or have some amino acid sequence differences while the binding specificity of an antibody of the invention is not affected, i.e. the differences do not materially influence the formation of functional binding regions.

It is for instance possible within the scope of the definition of common chains as used herein, to prepare or find variable chains that are not identical but still functionally equivalent, e.g., by introducing and testing conservative amino acid changes, changes of amino acids in regions that do not or only partly contribute to binding specificity when paired with a cognate chain, and the like. Such variants are thus also capable of binding different cognate chains and forming functional antigen binding domains. The term 'common light chain' as used herein thus refers to light chains which may be identical or have some amino acid sequence differences while retaining the binding specificity of the resulting antibody after pairing with a heavy chain. A combination of a certain common light chain and such functionally equivalent variants is encompassed within the term "common light chain". Reference is made to WO 2004/009618 and WO2009/157771 for a detailed description of the use of common light chains.

A "Fab" means a binding domain comprising a variable region, typically a binding domain comprising a paired heavy chain variable region and light chain variable region. A Fab may comprise constant region domains, including a CH1 and a VH domain paired with a constant light domain (CL) and VL domain. Such pairing may take place, for example, as covalent linkage via a disulfide bridge at the CH1 and CL domains.

A "single-chain variable fragment" (scFv) means a binding domain comprising a VH domain and a VL domain which are connected via a linker, for example a peptide linker, for example from about 10 to about 25 amino acids in length.

The term 'full length IgG' or 'full length antibody' according to the invention is defined as comprising an essentially complete IgG, which however does not necessarily have all functions of an intact IgG. For the avoidance of doubt, a full length IgG contains two heavy and two light chains. Each chain contains constant (C) and variable (V) regions, which can be broken down into domains designated CH1, CH2, CH3, VH, and CL, VL. An IgG antibody binds to antigen via the variable region domains contained in the Fab portion, and after binding can interact with molecules and cells of the immune system through the constant domains, mostly through the Fc portion. Full length antibodies according to the invention encompass IgG molecules wherein mutations may be present that provide desired characteristics. Full length IgG should not have deletions of substantial portions of any of the regions. However, IgG molecules wherein one or several amino acid residues are deleted, without essentially altering the binding characteristics of the resulting IgG molecule, are embraced within the term "full length IgG". For instance, such IgG molecules can have a deletion of between 1 and 10 amino acid residues, preferably in non-CDR regions, wherein the deleted amino acids are not essential for the binding specificity of the IgG.

"Percent (%) identity" as referring to nucleic acid or amino acid sequences herein is defined as the percentage of residues in a candidate sequence that are identical with the residues in a selected sequence, after aligning the sequences for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley).

For the purposes of inventions and sequences set out herein, percent sequence identity between two nucleic acid sequences may be determined using the AlignX application of the Vector NTI Program Advance 10.5.2 software using the default settings, which employ a modified ClustalW algorithm (Thompson, J. D., Higgins, D. G., and Gibson T. J. (1994) Nuc. Acid Res. 22: 4673-4680), the swgapdnarnt score matrix, a gap opening penalty of 15 and a gap extension penalty of 6.66. Amino acid sequences may be aligned with the AlignX application of the Vector NTI Program Advance 11.5.2 software using default settings, which employ a modified ClustalW algorithm (Thompson, J. D., Higgins, D. G., and Gibson T. J., 1994), the blosum62mt2 score matrix, a gap opening penalty of 10 and a gap extension penalty of 0.1.

The term "super-cluster" or "supercluster" is used herein to refer to a group of clones, and the binding domains they are capable of producing, based on the same VH V-gene segment usage and having at least 70% sequence identity in HCDR3 and the same HCDR3 length.

Thus, in a preferred embodiment, there is provided by the present invention, a "super-cluster" or "supercluster" comprising a group of clones, and the binding domains they are capable of producing, based on the same VH V-gene segment usage and having at least 70% sequence identity in HCDR3 and the same HCDR3 length. In a preferred embodiment, said sequence identity is 80%, more preferably 90%, most preferably 95% sequence identity, with the proviso that a clone comprising nucleic acid coding for HCDR3 sequence DGGYSYGPYWYFDL (SEQ ID NO 199) and DHRGYGDYEGGGFDY (SEQ ID NO 144), clones comprising nucleic acid coding for HCDR2 sequences GFIPVLGTANYAQKFQG, GIIPLFGTITYAQKFQG (SEQ ID NO 43), and SIIPIFGTITYAQKFQG (SEQ ID NO 52) are excluded, or with the proviso that clones comprising nucleic acid coding for VH sequences

```
                                                  (SEQ ID NO 120)
QVQLVQSGGGLVQPGGSLRLSCATSGFKFSSYALSWVRQAPGKGLEWVS

GISGSGRTTWYADSVKGRFTISRDNSKNTLYLQMNSLRAEDTAVYYCAR

DGGYSYGPYWYFDLWGRGTLVTVSS;

                                                  (SEQ ID NO 145)
EVQLVESGGGLVQPGRSLRLSCATSGFNFDDYTMHWVRQAPGKGLEWVS

DISWSSGSIGYADSVKGRFTISRDNAKNSLWLQMNSLRTEDTALYFCAK

DHRGYGDYEGGGFDYWGQGTLVTVSS;

                                                   (SEQ ID NO 45)
EVQLVQSGAEVKKPGSSVKVSCKASGGTFRSFGISWVRQAPGQGLEWMG

GFIPVLGTANYAQKFQGRVTIIADKSTNTAYMELSSLRSEDTAVYYCAR

RGNWNPFDPWGQGTLVTVSS;

                                                   (SEQ ID NO 54)
QVQLVQSGAEVKKPGSSVKVSCKASGDAFKSKTFTISWVRQAPGQGLEW

LGGIIPLFGTITYAQKFQGRVTITADKSTNTAFMELSSLRSEDTAMYYC

TRRGNWNPFDPWGQGTLVTVSS;
and

                                                   (SEQ ID NO 63)
EVQLVQSGSELKKPGSSVKVSCKASGVTFNSRTFTISWVRQAPGQGLEW

LGSIIPIFGTITYAQKFQGRVTITADKSTSTAFMELTSLRSEDTAIYYC

TRRGNWNPFDPWGQGTLVTVSS
```

are excluded or with the proviso that clones from said group comprise nucleic acid that code for a HCDR3 that is comprised by or designed to be comprised by a bispecific antibody.

The term "super-cluster 1" or "supercluster 1" is used herein to refer to a group of clones, and the binding domains they are capable of producing, based on the same VH V-gene segment usage (VH1-69) and having at least 70% sequence identity in HCDR3 and the same HCDR3 length to members of that supercluster. Included are for instance MF8048, MF8056, MF8057, MF8058, MF8078 and MF8101. In another preferred embodiment, an anti-CD3 antibody herein is based on the same VH V-gene segment usage of VH1-69 and/or having at least 80% identity in HCDR3 and the same HCDR3 length, more preferably 90% or most preferably 95% identity in the HCDR3. In another preferred embodiment, an anti-CD3 antibody herein is based on the same VH V-gene segment usage of VH1-69 and/or having at least 80% identity in HCDR3 and the same HCDR3 length compared to the encoded CDR3 segment RGNWNPFDP, preferably at least 90% sequence identity in HCDR3 and the same HCDR3 length, more preferably 95% or most preferably 98% identity and the same HCDR3 length, with the proviso that clones comprising nucleic acid coding for HCDR2 sequences GFIPVLGTANYAQKFQG (SEQ ID NO 43), GIIPLFGTITYAQKFQG (SEQ ID NO 52) and SIIPIFGTITYAQKFQG (SEQ ID NO 61)are excluded, or with the proviso that clones comprising nucleic acid coding for VH sequences

```
                                                   (SEQ ID NO 45)
EVQLVQSGAEVKKPGSSVKVSCKASGGTFRSFGISWVRQAPGQGLEWMG

GFIPVLGTANYAQKFQGRVTIIADKSTNTAYMELSSLRSEDTAVYYCAR

RGNWNPFDPWGQGTLVTVSS;
```

-continued (SEQ ID NO 54)
QVQLVQSGAEVKKPGSSVKVSCKASGDAFKSKTFTISWVRQAPGQGLEW

LGGIIPLFGTITYAQKFQGRVTITADKSTNTAFMELSSLRSEDTAMYYC

TRRGNWNPFDPWGQGTLVTVSS;

(SEQ ID NO 63)
EVQLVQSGSELKKPGSSVKVSCKASGVTFNSRTFTISWVRQAPGQGLEW

LGSIIPIFGTITYAQKFQGRVTITADKSTSTAFMELTSLRSEDTAIYYC

TRRGNWNPFDPWGQGTLVTVSS;

are excluded or with the proviso that clones from said group comprise nucleic acid that code for a HCDR3 that is comprised by or designed to be comprised by a bispecific antibody. The term "super-cluster 3" or "supercluster 3" is used herein to refer to a group of clones, and the binding domains they are capable of producing, based on the same VH V-gene segment usage (VH3-23) and having at least 70% sequence identity in HCDR3 and the same HCDR3 length to members of that supercluster. Included are for instance MF8397, and MF8562. In another preferred embodiment, an anti-CD3 antibody herein is based on the same VH V-gene segment usage of VH3-23 and/or having at least 80% identity in HCDR3 and the same HCDR3 length, more preferably 90% or most preferable 95% identity in the HCDR3. In another preferred embodiment, an anti-CD3 antibody herein is based on the same VH V-gene segment usage of VH3-23 and/or having at least 80% identity in HCDR3 and the same HCDR3 length compared to the encoded CDR3 segment DGGYSYGPYWYFDL (SEQ ID NO 119), preferably at least 90% sequence identity in HCDR3 and the same HCDR3 length, more preferably 95% or most preferably 98% identity and the same HCDR3 length, with the proviso that a clone comprising nucleic acid encoding HCDR3 sequence DGGYSYGPYWYFDL (SEQ ID NO 119) is excluded or with the proviso that a clone comprising nucleic acid coding for VH sequence (SEQ ID NO 120)
QVQLVQSGGGLVQPGGSLRLSCATSGFKFSSYALSWVRQAPGKGLEWVS

GISGSGRTTWYADSVKGRFTISRDNSKNTLYLQMNSLRAEDTAVYYCAR

DGGYSYGPYWYFDLWGRGTLVTVSS is excluded or with the proviso that clones from said group comprise nucleic acid that code for a HCDR3 that is comprised by or designed to be comprised by a bispecific antibody.

The term "super-cluster 4" or "supercluster 4" is used herein to refer to a group of clones, and the binding domains they are capable of producing, based on the same VH V-gene segment usage (VH3-9) and having at least 70% sequence identity in HCDR3 and the same HCDR3 length to members of that supercluster. Included are for instance MF8508, MF8998, MF10401 and MF10428. In another preferred embodiment, an anti-CD3 antibody herein is based on the same VH V-gene segment usage of VH3-9 and/or having at least 80% identity in HCDR3 and the same HCDR3 length, more preferably 90% or most preferable 95% identity in the HCDR3. In another preferred embodiment, an anti-CD3 antibody herein is based on the same VH V-gene segment usage of VH3-9 and/or having at least 80% identity in HCDR3 and the same HCDR3 length compared to the encoded CDR3 segment DHRGYGDYEGGGFDY (SEQ ID NO 144), preferably at least 90% sequence identity in HCDR3 and the same HCDR3 length, more preferably 95% or most preferably 98% identity and the same HCDR3 length, with the proviso that a clone comprising nucleic acid coding for HCDR3 sequence DHRGYGDYEGGGFDY (SEQ ID NO 168) is excluded or with the proviso that a clone comprising nucleic acid coding for VH sequence (SEQ ID NO 145)
EVQLVESGGGLVQPGRSLRLSCATSGFNFDDYTMHWVRQAPGKGLEWVS

DISWSSGSIGYADSVKGRFTISRDNAKNSLWLQMNSLRTEDTALYFCAK

DHRGYGDYEGGGFDYWGQGTLVTVSS is excluded or with the proviso that clones from said group comprising nucleic acid that code for a HCDR3 that is comprised by or designed to be comprised by a bispecific antibody.

The term "super-cluster 7" or "supercluster 7" is used herein to refer to a group of clones, and the binding domains they are capable of producing, based on the same VH V-gene segment usage (VH5-51) and having at least 70% sequence identity in HCDR3 and the same HCDR3 length to members of that supercluster. Included is for instance MF9249, and MF9267. In another preferred embodiment, an anti-CD3 antibody herein is based on the same VH V-gene segment usage of VH5-51 and/or having at least 80% identity in HCDR3 and the same HCDR3 length, more preferably 90% or most preferable 95% identity in the HCDR3. In another preferred embodiment, an anti-CD3 antibody herein is based on the same VH V-gene segment usage of V H5-51 and/or having at least 80% identity in HCDR3 and the same HCDR3 length compared to the encoded CDR3 segment HIRYFDWSEDYHYYLDV (SEQ ID NO 201), preferably at least 90% sequence identity in HCDR3 and the same HCDR3 length, more preferably 95% or most preferably 98% identity and the same HCDR3 length The invention further provides a bispecific antibody comprising a variable domain with a VH encoded by V-gene segment VH1-69; or a variant of V-gene segment VH1-69 comprising at least 70%, preferably at least 80%, more preferably at least 90% and more preferably at least 95% sequence identity to the sequence of said V-gene segment;

wherein the VH further comprises a HCDR3 of MF8048, MF8056, MF8057, MF8058, MF8078 or MF8101;

or a variant of said HCDR3 comprising at least 70% sequence identity to said HCDR3 and the same length of said HCDR3.

In a preferred embodiment said variant of said HCDR3 comprises the same length as said HCDR3 and at least 80% sequence identity to said HCDR3, more preferably at least 90% and more preferably at least 95% sequence identity to the sequence of said HCDR3.

In some embodiments said bispecific antibody does not have a VH encoded by V-gene segment VH1-69; or a variant of V-gene segment VH1-69 with a HCDR2 sequence (SEQ ID NO 43)
GFIPVLGTANYAQKFQG,
or -continued (SEQ ID NO 52)
GIIPLFGTITYAQKFQG
or (SEQ ID NO 61)
SIIPIFGTITYAQKFQG.

In some embodiments said bispecific antibody does not have a VH encoded by V-gene segment VH1-69; or a variant of V-gene segment VH1-69 with a VH sequence (SEQ ID NO 45)
EVQLVQSGAEVKKPGSSVKVSCKASGGTFRSFGISWVRQAPGQGLEWMG
GFIPVLGTANYAQKFQGRVTIIADKSTNTAYMELSSLRSEDTAVYYCAR
RGNWNPFDPWGQGTLVTVSS;
or (SEQ ID NO 54)
QVQLVQSGAEVKKPGSSVKVSCKASGDAFKSKTFTISWVRQAPGQGLEW
LGGIIPLFGTITYAQKFQGRVTITADKSTNTAFMELSSLRSEDTAMYYC
TRRGNWNPFDPWGQGTLVTVSS;
or (SEQ ID NO 63)
EVQLVQSGSELKKPGSSVKVSCKASGVTFNSRTFTISWVRQAPGQGLEW
LGSIIPIFGTITYAQKFQGRVTITADKSTSTAFMELTSLRSEDTAIYYC
TRRGNWNPFDPWGQGTLVTVSS.

The invention further provides a bispecific antibody comprising a variable domain with a VH encoded by

- V-gene segment VH3-23; or
- a variant of V-gene segment VH2-23 comprising at least 70%, preferably at least 80%, more preferably at least 90% and more preferably at least 95% sequence identity to the sequence of said V-gene segment;

wherein the VH further comprises

- a HCDR3 of MF8397; or MF8562;
- or a variant of said HCDR3 comprising at least 70% sequence identity to said HCDR3 and the same length of said HCDR3.

In a preferred embodiment said variant of said HCDR3 comprises the same length as said HCDR3 and at least 80% sequence identity to said HCDR3, more preferably at least 90%, more preferably at least 93% and more preferably at least 95% sequence identity to the sequence of said HCDR3.

In some embodiments said bispecific antibody does not have a VH encoded by V-gene segment VH3-23; or a variant of V-gene segment VH3-23 with a HCDR3 sequence (SEQ ID NO 119)
DGGYSYGPYWYFDL.

In some embodiments said bispecific antibody does not have a VH encoded by V-gene segment VH3-23; or a variant of V-gene segment VH3-23 with a VH sequence (SEQ ID NO 120)
QVQLVQSGGGLVQPGGSLRLSCATSGFKFSSYALSWVRQAPGKGLEWVSG
ISGSGRTTWYADSVKGRFTISRDNSKNTLYLQMNSLRAEDTAVYYCARDG
GYSYGPYWYFDLWGRGTLVTVSS.

The invention further provides a bispecific antibody comprising a variable domain with a VH encoded by

- V-gene segment VH3-9; or
- a variant of V-gene segment VH3-9 comprising at least 70%, preferably at least 80%, more preferably at least 90% and more preferably at least 95% sequence identity to the sequence of said V-gene segment;

wherein the VH further comprises

- a HCDR3 of MF8508; MF8998; MF1041; or MF10428;
- or a variant of said HCDR3 comprising at least 70% sequence identity to said HCDR3 and the same length of said HCDR3.

In a preferred embodiment said variant of said HCDR3 comprises the same length as said HCDR3 and at least 80% sequence identity to said HCDR3, more preferably at least 90% and more preferably at least 95% sequence identity to the sequence of said HCDR3.

In some embodiments said bispecific antibody does not have a VH encoded by V-gene segment VH3-9; or a variant of V-gene segment VH3-9 with a HCDR3 sequence (SEQ ID NO 144)
DHRGYGDYEGGGFDY.

In some embodiments said bispecific antibody does not have a VH encoded by V-gene segment VH3-9; or a variant of V-gene segment VH3-9 with a VH sequence (SEQ ID NO 145)
EVQLVESGGGLVQPGRSLRLSCATSGFNFDDYTMHWVRQAPGKGLEWVS
DISWSSGSIGYADSVKGRFTISRDNAKNSLWLQMNSLRTEDTALYFCAK
DHRGYGDYEGGGFDYWGQGTLVTVSS.

The invention further provides a bispecific antibody comprising a variable domain with a VH encoded by

- V-gene segment VH5-51; or
- a variant of V-gene segment VH5-51 comprising at least 70%, preferably at least 80%, more preferably at least 90% and more preferably at least 95% sequence identity to the sequence of said V-gene segment;

wherein the VH further comprises

- a HCDR3 of MF9249 or MF9267;
- or a variant of said HCDR3 comprising at least 70% sequence identity to said HCDR3 and the same length of said HCDR3.

In a preferred embodiment said variant of said HCDR3 comprises the same length as said HCDR3 and at least 80% sequence identity to said HCDR3, more preferably at least 90% and more preferably at least 95% sequence identity to the sequence of said HCDR3.

A bispecific antibody as provided by the invention defined herein is preferably not a bispecific antibody comprising a CD3 binding variable domain as defined in PCT/NL2019/050199.

The invention further provides a VH encoded by

- V-gene segment VH1-69; or
- a variant of V-gene segment VH1-69 comprising at least 70%, preferably at least 80%, more preferably at least 90% and more preferably at least 95% sequence identity to the sequence of said V-gene segment;

wherein the VH further comprises

- a HCDR3 of MF8048, MF8056, MF8057, MF8058, MF8078 or MF8101;
- or a variant of said HCDR3 comprising at least 70% sequence identity to said HCDR3 and the same length of said HCDR3.

In a preferred embodiment said variant of said HCDR3 comprises the same length as said HCDR3 and at least 80% sequence identity to said HCDR3, more preferably at least 90% and more preferably at least 95% sequence identity to the sequence of said HCDR3.

In some embodiments said VH is not a VH encoded by V-gene segment VH1-69; or a variant of V-gene segment VH1-69 with a HCDR2 sequence GFIPVLGTANYAQKFQG (SEQ ID NO 43), or GIIPLFGTITYAQKFQG (SEQ ID NO 52) or SIIPIFGTITYAQKFQG (SEQ ID NO 61).

In some embodiments said VH is not a VH encoded by V-gene segment VH1-69; or a variant of V-gene segment VH1-69 with a VH sequence

```
(SEQ ID NO 45)
EVQLVQSGAEVKKPGSSVKVSCKASGGTFRSFGISWVRQAPGQGLEWMG

GFIPVLGTANYAQKFQGRVTIIADKSTNTAYMELSSLRSEDTAVYYCAR

RGNWNPFDPWGQGTLVTVSS;
or

(SEQ ID NO 54)
QVQLVQSGAEVKKPGSSVKVSCKASGDAFKSKTFTISWVRQAPGQGLEW

LGGIIPLFGTITYAQKFQGRVTITADKSTNTAFMELSSLRSEDTAMYYC

TRRGNWNPFDPWGQGTLVTVSS;
or

(SEQ ID NO 63)
EVQLVQSGSELKKPGSSVKVSCKASGVTFNSRTFTISWVRQAPGQGLEW

LGSIIPIFGTITYAQKFQGRVTITADKSTSTAFMELTSLRSEDTAIYYC

TRRGNWNPFDPWGQGTLVTVSS.
```

The invention further provides a VH encoded by V-gene segment VH3-23; or a variant of V-gene segment VH2-23 comprising at least 70%, preferably at least 80%, more preferably at least 90% and more preferably at least 95% sequence identity to the sequence of said V-gene segment;

wherein the VH further comprises a HCDR3 of MF8397; or MF8562;

or a variant of said HCDR3 comprising at least 70% sequence identity to said HCDR3 and the same length of said HCDR3.

In a preferred embodiment said variant of said HCDR3 comprises the same length as said HCDR3 and at least 80% sequence identity to said HCDR3, more preferably at least 90%, more preferably at least 93% and more preferably at least 95% sequence identity to the sequence of said HCDR3.

In some embodiments said VH is not a VH encoded by V-gene segment VH3-23; or a variant of V-gene segment VH3-23 with a HCDR3 sequence DGGYSYGPYWYFDL. (SEQ ID NO 119)

In some embodiments said VH is not a VH encoded by V-gene segment VH3-23; or a variant of V-gene segment VH3-23 with a VH sequence

```
(SEQ ID NO 120)
QVQLVQSGGGLVQPGGSLRLSCATSGFKFSSYALSWVRQAPGKGLEWVS

GISGSGRTTWYADSVKGRFTISRDNSKNTLYLQMNSLRAEDTAVYYCAR

DGGYSYGPYWYFDLWGRGTLVTVSS.
```

The invention further provides a VH encoded by V-gene segment VH3-9; or a variant of V-gene segment VH3-9 comprising at least 70%, preferably at least 80%, more preferably at least 90% and more preferably at least 95% sequence identity to the sequence of said V-gene segment;

wherein the VH further comprises a HCDR3 of MF8508; MF8998; MF10401; or MF10428;

or a variant of said HCDR3 comprising at least 70% sequence identity to said HCDR3 and the same length of said HCDR3.

In a preferred embodiment said variant of said HCDR3 comprises the same length as said HCDR3 and at least 80% sequence identity to said HCDR3, more preferably at least 90% and more preferably at least 95% sequence identity to the sequence of said HCDR3.

In some embodiments said VH is not a VH encoded by V-gene segment VH3-9; or a variant of V-gene segment VH3-9 with a HCDR3 sequence DHRGYGDYEGGGFDY (SEQ ID NO 144).

In some embodiments said VH is not a VH encoded by V-gene segment VH3-9; or a variant of V-gene segment VH3-9 with a VH sequence

```
(SEQ ID NO 145)
EVQLVESGGGLVQPGRSLRLSCATSGFNFDDYTMHWVRQAPGKGLEWVS

DISWSSGSIGYADSVKGRFTISRDNAKNSLWLQMNSLRTEDTALYFCAK

DHRGYGDYEGGGFDYWGQGTLVTVSS.
```

The invention further provides a VH encoded by V-gene segment VH5-51; or a variant of V-gene segment VH5-51 comprising at least 70%, preferably at least 80%, more preferably at least 90% and more preferably at least 95% sequence identity to the sequence of said V-gene segment;

wherein the VH further comprises a HCDR3 of MF9249 or MF9267;

or a variant of said HCDR3 comprising at least 70% sequence identity to said HCDR3 and the same length of said HCDR3.

In a preferred embodiment said variant of said HCDR3 comprises the same length as said HCDR3 and at least 80% sequence identity to said HCDR3, more preferably at least 90% and more preferably at least 95% sequence identity to the sequence of said HCDR3.

A VH as provided by the invention defined herein is preferably not a VH of a CD3 binding variable domain as defined in PCT/NL2019/050199.

Also provided is an antigen-binding protein or antibody, preferably a bispecific antibody, wherein the CDRs have 70%, preferably 80%, more preferably 90% identity to the CDRs as claimed. In a preferred embodiment the antigen-binding protein or antibody is a bispecific antibody that comprises CDRs with at most 2, preferably at most 1 and more preferably at most 0 amino acid residue variations, insertions, substitutions, deletions or additions with respect to the CDRs as claimed.

Antigen binding by an antibody is typically mediated through the complementarity regions of the antibody and the specific three-dimensional structure of both the antigen and the variable domain allowing these two structures to bind together with precision (an interaction similar to a lock and key), as opposed to random, non-specific sticking of antibodies. As an antibody typically recognizes an epitope of an antigen, and as such epitope may be present in other proteins as well, antibodies according to the present invention that bind CD3 or CLEC12A may recognize other proteins as well, if such other proteins contain the same epitope. Hence, the term "binding" does not exclude binding of the antibodies to another protein or protein(s) that contain the same epitope. A heavy/light chain combination that binds CD3 in an antibody of the invention does not bind to other proteins on the membrane of cells in a post-natal, preferably adult human. A heavy/light chain combination that binds CLEC12A, EGFR, PD-L1 or tumor cell antigens of the invention does not bind other proteins on the membrane of cells in a post-natal, preferably adult human. Suitable tumor antigen specific arms are disclosed in PCT/NL2019/050199.

"Plurality" means two or more.

A "variant" of an antibody as described herein may comprise a functional part, derivative and/or analogue of an antibody. This includes antibody mimetics, monobodies and aptamers.

A variant typically maintains the binding specificity of the antibody, for example the specificities of a bispecific antibody. A variant may be a functional part or derivative of a binding domain, multimer or antibody as described herein.

A functional part of a binding domain, multimer or antibody as described herein is a part comprising a variable domain that binds the same target as such binding domain, multimer or antibody.

A functional derivative of an antibody as described herein is a protein comprising a variable domain that binds one target and a variable domain that binds a second target that are linked by a linking region. The variable domains may be variable domains as such, or Fab fragments or variable domain like molecules such as single chain Fv (scFv) fragments comprising a VH and a VL linked together via a linker. Antibody variable domains or antibody variable domain like molecules can be linked to each other in different ways. Various linkers and carrier structures have been described that can bind one, two or more variable domains. An antigen-binding protein as described herein is a protein comprising at least one of such variable domain. In the case of bispecific or multispecific antigen binding proteins, such proteins comprise two or more variable domains of which at least two bind a different target. The variable domains are linked to each other via a linking portion. This is typically a stretch of 0-15, preferably 3-12, more preferably around 5-8 amino acid residues. Other examples of variable domain like molecules are so-called single domain antibody fragments. A single-domain antibody fragment (sdAb) is an antibody fragment with a single monomeric variable antibody region. Like a whole antibody, it is able to bind selectively to a specific antigen. With a molecular weight of only 12-15 kDa, single-domain antibody fragments are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable regions, one from a light and one from a heavy chain). Single-domain antibodies by themselves are not much smaller than normal antibodies (being typically 90-100 ka). Single-domain antibody fragments may be engineered from heavy-chain antibodies found in camelids; these are called VHH fragments (Nanobodies®). Some fishes also have heavy-chain only antibodies (IgNAR, 'immunoglobulin new antigen receptor'), from which single-domain antibody fragments called VNAR fragments can be obtained. An alternative approach is to split the dimeric variable domains from common immunoglobulin G (IgG) from humans or mice into monomers. Although most research into single-domain antibodies is currently based on heavy chain variable domains, nanobodies derived from light chains have also been shown to be capable of binding to target epitopes. Other non-limiting examples of variable domain-like molecules are VHH, Human Domain Antibodies (dAbs) and Unibodies. Preferred functional parts are parts that comprise variable domains comprising a heavy chain variable region and a light chain variable region. Non-limiting examples of such variable domains are F(ab)-fragments and Single chain Fv fragments. Bispecific formats for variable domain(-like) linkage are for instance Human Serum Albumin (HSA) bound to two different scFv; bispecific mini-antibodies comprising two different scFv bound together via dimerization motifs or self-associating secondary structures such as helix bundles or coiled coils to bring about dimerization of the scFv fragments (Morrison (2007) Nat. Biotechnol. 25:1233-34). Examples of suitable HSA linkers and method for coupling scFv to the linker are described in WO2009/126920.

A functional derivative can be an antibody mimetic, a polypeptide, an aptamer or a combination thereof. These proteins or aptamers typically bind to one target. The protein of the invention binds to two or more targets. It is to be understood that any combination of these antibodies, antibody mimetics, polypeptides and aptamers can be linked together by methods known in the art. For example, in some embodiments the binding molecule of the invention is a conjugate or a fusion protein.

An antibody mimetic is a polypeptide that, like antibodies, can specifically bind an antigen, but that is not structurally related to antibodies. Antibody mimetics are usually artificial peptides or proteins with a molar mass of about 3 to 20 kDa. Non-limiting examples of antibody mimetics are affibody molecules (typically based on the Z domain of Protein A); affilins (typically based on Gamma-B crystalline or Ubiquitin); affimers (typically based on Cystatin); affitins (typically based on Sac7d from *Sulfolobus acidocaldarius*); alphabodies (typically based on Triple helix coiled coil); anticalins (typically based on Lipocalins); avimers (typically based on A domains of various membrane receptors); DARPins (typically based on ankyrin repeat motif); fynomers (typically based on SH3 domain of Fyn 7); kunitz domain peptides (typically based on Kunitz domains of various protease inhibitors); and monobodies (typically based on type Ill domain of fibronectin).

Monobodies are synthetic binding proteins that are constructed using a fibronectin type III domain (FN3) as a molecular scaffold. Monobodies are an alternative to antibodies for creating target-binding proteins.

Monobodies and other antibody mimetics are typically generated from combinatorial libraries in which portions of the scaffold are diversified using molecular display and directed evolution technologies such as phage display, mRNA display and yeast surface display.

Aptamers are oligonucleotide or peptide molecules that bind to a specific target molecule. Aptamers are usually created by selecting them from a large random sequence pool, but natural aptamers also exist in riboswitches. Aptamers can be used for both basic research and clinical purposes as macromolecules.

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

An antibody of the invention is preferably a bispecific or multispecific antibody. The bispecific or multispecific antibody preferably binds at least human CD3.

An antigen-binding protein or antibody of the invention is preferably a bi- or multispecific antigen binding protein or antibody. The bi- or multispecific antigen binding protein or antibody preferably binds at least human CD3 and in addition, preferably at least a surface molecule that is expressed on human tumor cells. In a preferred embodiment the bi- or multispecific antigen binding protein or antibody binds to BCMA, CD19, CD20, CD30, CD33, CD38, CD44, CD123, CD138, CEA, CLEC12A, CS-1, EGFR, EGFRvIII, EPCAM, DLL3, LGR5, MSLN, PD-L1, FOLR1, FOLR3, HER2, HM1.24, MCSP, or PSMA. In a particularly preferred embodiment, the bispecific antibody binds to CLEC12A. In a particularly preferred embodiment, the multispecific antibody binds to CD3, PD-L1 and EGFR.

As used herein, the term "CLEC12A" refers to C type lectin domain family 12 member A. CLEC12A is also referred to as C-Type Lectin Protein CLL-1; MICL; Dendritic Cell-Associated Lectin 2; C-Type Lectin Superfamily; Myeloid Inhibitory C-Type Lectin-Like Receptor; C-Type Lectin-Like Molecule-1; DCAL2; CLL1; C-Type Lectin-Like Molecule 1; DCAL-2; Killer cell lectin like receptor subfamily L, member 1 (KLRL1); CD371(cluster of differentiation 371) (Bakker A. et al. Cancer Res. 2004, 64, p8843 50; GenBank™ access.no: AY547296; Zhang W. et al. GenBank™ access.no: AF247788; A. S. Marshall, et al. J Biol Chem 2004, 279, p14792-802; GenBank™ access.no: AY498550; Y. Han et al. Blood 2004, 104, p2858 66; H. Floyd, et al. GenBank™ access.no: AY426759; C. H. Chen, et al. Blood 2006, 107, p1459 67). Ids: HGNC: 31713; Entrez Gene: 160364; Ensembl: ENSG00000172322; OMIM: 612088; UniProtKB: Q5QGZ9.

CLEC12A is an antigen that is expressed on leukemic blast cells and on leukemic stem cells in acute myeloid leukemia (AML), including the CD34 negative or CD34 low expressing leukemic stem cells (side population) (A. B. Bakker et al. Cancer Res 2004, 64, p8443 50; Van Rhenen et al. 2007 Blood 110:2659; Moshaver et al. 2008 Stem Cells 26:3059), as well as in myelodysplastic syndromes (MDS) (Bakker et al. 2004, supra and Toff-Peterson et al., Br. J. Haematol. 175(3):393-401, 2016). Expression of CLEC12A is otherwise thought to be restricted to cells of the hematopoietic lineage, particularly to myeloid lineage in peripheral blood and bone marrow, i.e., granulocytes, monocytes and dendritic cell precursors. More importantly, CLEC12A is absent on normal hematopoietic stem cells. Where reference is made to CLEC12A herein, the reference is to human CLEC12A (SEQ ID NO: 1; FIG. 19), unless specifically stated otherwise.

The term "CLEC12A" means all variants (such as splice and mutation) that are referenced herein and isoforms thereof that retain the myeloid expression profile (both at surface expression level and mRNA level) including as described in Bakker et al. Cancer Res 2004, 64, p8443-50 and Marshall 2004—J Biol Chem 279(15), p14792-802. While accession numbers are primarily provided as a further method of identification, the actual sequence of the protein may vary, for instance because of a mutation in the encoding gene such as those occurring in some cancers or the like.

The term "CD3" (cluster of differentiation 3) refers a protein complex, which is composed of a CD3γ chain (SwissProt P09693), a CD3δ chain (SwissProt P04234), CD3ε chains (SwissProt P07766), and a CD3 zeta chain homodimer (SwissProt P20963). CD3ε is known under various aliases some of which are: "CD3e Molecule, Epsilon (CD3-TCR Complex)"; "CD3e Antigen, Epsilon Polypeptide (TiT3 Complex)"; T-Cell Surface Antigen T3/Leu-4 Epsilon Chain; T3E; T-Cell Antigen Receptor Complex, Epsilon Subunit Of T3; CD3e Antigen; CD3-Epsilon 3; IMD18; TCRE. Ids for CD3E Gene are HGNC: 1674; Entrez Gene: 916; Ensembl: ENSG00000198851; OMIM: 186830 and UniProtKB: P07766. These chains associate with the T-cell receptor (TCR) and the ζ-chain to form a TCR complex that can upon mitogenic signaling generates an activation signal in T lymphocytes. CD3 is expressed on T cells and NK T cells. Where reference is made to CD3 herein, the reference is to human CD3 (SEQ ID NOs: 2-5; FIG. 20), unless specifically stated otherwise.

BCMA is also referred to as Tumor Necrosis Factor Receptor Superfamily, Member 17 (TNFRSF17); TNFRSF13A2; B Cell Maturation Antigen; BCM; B-Cell Maturation Factor; B-Cell Maturation Protein; CD269 or CD269 Antigen. Ids: HGNC: 11913; Entrez Gene: 608; Ensembl: ENSG00000048462; OMIM: 109545; UniProtKB: Q02223.

CD19 is also referred to as CD19 Molecule; T-Cell Surface Antigen Leu-12; CD19 Antigen; CVID3; Differentiation Antigen CD19; B4; B-Lymphocyte Surface Antigen B4; B-Lymphocyte Antigen CD19. Ids: HGNC: 1633; Entrez Gene: 930; Ensembl: ENSG00000177455; OMIM: 107265; UniProtKB: P15391.

CD20 is also referred to as Membrane-Spanning 4-Domains, Subfamily A, Member 1 (MS4A1); MS4A2; CD20; S7; Leukocyte Surface Antigen Leu-16; B-Lymphocyte Antigen CD20; Bp35; B-Lymphocyte Cell-Surface Antigen B1; CD20 Antigen; CD20 Receptor; CVID5; B-Lymphocyte Surface Antigen B1; B1; Membrane-Spanning 4-Domains Subfamily A Member 1; LEU-16. Ids: HGNC: 7315; Entrez Gene: 931; Ensembl: ENSG00000156738; OMIM: 112210; UniProtKB: P11836.

CD30 is also referred to as Tumor Necrosis Factor Receptor Superfamily, Member 8 (TNFRSF8); Ki-1 Antigen; CD30; Ki-1; D1S166E; Cytokine Receptor CD30; Lymphocyte Activation Antigen CD30; Tumor Necrosis Factor Receptor Superfamily Member 8; CD30L Receptor; CD30 Antigen. Ids: HGNC: 11923; Entrez Gene: 943; Ensembl: ENSG00000120949; OMIM: 153243; UniProtKB: P28908.

CD33 is also referred to as CD33 Molecule; SIGLEC-3; CD33 Antigen (Gp67); Myeloid Cell Surface Antigen CD33; Sialic Acid Binding Ig-Like Lectin 3; Siglec-3; SIGLEC3; CD33 Antigen and gp67. Ids: HGNC: 1659; Entrez Gene: 945; Ensembl: ENSG00000105383; OMIM: 159590; UniProtKB: P20138.

CD38 is also referred to as CD38 Molecule; T10; CD38 Antigen (P45); CADPr Hydrolase 1; ADP-Ribosyl Cyclase 1; ADP-Ribosyl Cyclase/Cyclic ADP-Ribose Hydrolase; NAD(+) Nucleosidase; EC 3.2.2.5; Cyclic ADP-Ribose Hydrolase 1; CD38 Antigen. Ids: HGNC: 1667; Entrez Gene: 952; Ensembl: ENSG00000004468; OMIM: 107270; UniProtKB: P28907.

CD44 is also referred to as CD44 Molecule (Indian Blood Group); IN; MDU2; CD44 Antigen (Homing Function And Indian Blood Group System); MDU3; CDW44; MIC4; CSPG8; Chondroitin Sulfate Proteoglycan 8; HCELL; Hematopoietic Cell E- And L-Selectin Ligand; MC56; Extracellular Matrix Receptor III; Pgp1; Heparan Sulfate Proteoglycan; Cell Surface Glycoprotein CD44; Hyaluronate Receptor; epican; Phagocytic Glycoprotein 1; Homing Function And Indian Blood Group System; ECMR-III; CDw44; HUTCH-I; Epican; LHR; PGP-1; CD44 Antigen;

PGP-I; CP90 Lymphocyte Homing/Adhesion Receptor; Phagocytic Glycoprotein I; Hermes Antigen. Ids: HGNC: 1681; Entrez Gene: 960; Ensembl: ENSG00000026508; OMIM: 107269; UniProtKB: P16070.

CD123 is also referred to as Cell Division Cycle 123; Cell Division Cycle 123 Homolog; C10orf7; Cell Division Cycle Protein 123 Homolog; D123; Protein D123; HT-1080; CCEP123; PZ32; CEP89; Cell Division Cycle 123 Homolog (*S. Cerevisiae*); FLJ14640; Chromosome 10 Open Reading Frame 7. Ids: HGNC: 16827; Entrez Gene: 8872; Ensembl: ENSG00000151465; OMIM: 615470; UniProtKB: 075794.

CD138 is also referred to as Syndecan 1 (SCD1); CD138; SDC; Heparan Sulfate Proteoglycan Fibroblast Growth Factor Receptor; Syndecan Proteoglycan 1; syndecan; SYND1; syndecan-1; CD138 Antigen. Ids: HGNC: 10658; Entrez Gene: 6382; Ensembl: ENSG00000115884; OMIM: 186355; UniProtKB: P18827.

CEA is also referred to as Carcinoembryonic Antigen-Related Cell Adhesion Molecule 5 (CEACAM5); Meconium Antigen 100; CD66e; Carcinoembryonic Antigen; CD66e Antigen. Ids: HGNC: 1817; Entrez Gene: 1048; Ensembl: ENSG00000105388; OMIM: 114890; UniProtKB: P06731.

EGFR is also referred to as Epidermal Growth Factor Receptor; Erythroblastic Leukemia Viral (V-Erb-B) Oncogene Homolog (Avian); ERBB1; PIG61; Proto-Oncogene C-ErbB-1; Avian Erythroblastic Leukemia Viral (V-Erb-B) Oncogene Homolog; Receptor Tyrosine-Protein Kinase ErbB-1; Cell Growth Inhibiting Protein 40; Cell Proliferation-Inducing Protein 61; HER1; mENA; EC 2.7.10.1; EC 2.7.10; Epidermal Growth Factor Receptor (Avian Erythroblastic Leukemia Viral (V-Erb-B) Oncogene Homolog). Ids: HGNC: 3236; Entrez Gene: 1956; Ensembl: ENSG00000146648; OMIM: 131550; UniProtKB: P00533.

EGFRvIII is a common variant of EGFR (Oncogene. 2013 May 23; 32(21):2670-81. doi: 10.1038/onc.2012.280. Epub 2012 Jul. 16).

Delta like 3 (DLL3) is also referred to as Delta-Like 3); *Drosophila* Delta Homolog 3; Delta3; Delta (*Drosophila*)-Like 3; SCDO1. Ids for DLL3 are: HGNC: 2909; Entrez Gene: 10683; Ensembl: ENSG00000090932; OMIM: 602768 and UniProtKB: Q9NYJ7.

LGR5 is Leucine-Rich Repeat Containing G Protein-Coupled Receptor 5 Alternative names for the gene or protein are Leucine-Rich Repeat Containing G Protein-Coupled Receptor 5; Leucine-Rich Repeat-Containing G Protein-Coupled Receptor 5; G-Protein Coupled Receptor HG38; G-Protein Coupled Receptor 49; G-Protein Coupled Receptor 67; GPR67; GPR49; Orphan G Protein-Coupled Receptor HG38; G Protein-Coupled Receptor 49; GPR49; HG38 and FEX. A protein or antibody of the invention that binds LGR5, binds human LGR5. The LGR5 binding protein or antibody of the invention may, due to sequence and tertiary structure similarity between human and other mammalian orthologs, also bind such an ortholog but not necessarily so. Database accession numbers for the human LGR5 protein and the gene encoding it are (NC_000012.12; NT_029419.13; NC_018923.2; NP_001264155.1; NP_001264156.1; NP_003658.1).

MSLN or mesothelin is also referred to as Mesothelin; Pre-Pro-Megakaryocyte-Potentiating Factor; CAK1 Antigen; MPF; Soluble MPF Mesothelin Related Protein; Megakaryocyte Potentiating Factor and SMRP. Ids for MSLN are: HGNC: 7371; Entrez Gene: 10232; Ensembl: ENSG00000102854; OMIM: 601051; UniProtKB: Q13421.

Folate receptor 1 is also referred to as FOLR1; Folate Receptor 1; Ovarian Tumor-Associated Antigen MOv18; Adult Folate-Binding Protein; Folate Receptor, Adult; KB Cells FBP; FR-Alpha; FOLR; FBP; Folate Binding Protein; and Folate Receptor 1. Ids for FOLR1 are HGNC: 3791; Entrez Gene: 2348; Ensembl: ENSG00000110195; OMIM: 136430; UniProtKB: P15328.

Folate receptor 3 is also referred to as FOLR3; Folate Receptor 3 (Gamma); FR-Gamma; Folate Receptor 3; Gamma-HFR; and FR-G. Ids for FOLR3 are HGNC: 3795; Entrez Gene: 2352; Ensembl: ENSG00000110203; OMIM: 602469; and UniProtKB: P41439.

EPCAM is also referred to as Epithelial Cell Adhesion Molecule; EGP40; M4S1; ESA; MIC18; KS1/4; Tumor-Associated Calcium Signal Transducer 1; MK-1; TACSTD1; Human Epithelial Glycoprotein-2; TROP1; Membrane Component, Chromosome 4, Surface Marker (35 kD Glycoprotein); Adenocarcinoma-Associated Antigen; EGP; Cell Surface Glycoprotein Trop-1; Ep-CAM; Epithelial Glycoprotein 314; GA733-2; Major Gastrointestinal Tumor-Associated Protein GA733-2; M1S2; EGP314; CD326 Antigen; KSA; Epithelial Cell Surface Antigen; DIAR5; Epithelial Glycoprotein; HNPCC8; hEGP314; Antigen Identified By Monoclonal Antibody AUA1; KS 1/4 Antigen; EGP-2; ACSTD1. Ids: HGNC: 11529; Entrez Gene: 4072; Ensembl: ENSG00000119888; OMIM: 185535; UniProtKB: P16422.

HER2 is also referred to as V-Erb-B2 Avian Erythroblastic Leukemia Viral Oncogene Homolog 2; ERBB2; CD340; NGL; HER-2; HER-2/neu2; NEU2; TKR1; Neuro/Glioblastoma Derived Oncogene Homolog; C-Erb B2/Neu Protein; Metastatic Lymph Node Gene 19 Protein; herstatin; Proto-Oncogene C-ErbB-2; Neuroblastoma/Glioblastoma Derived Oncogene Homolog; Proto-Oncogene Neu; Receptor Tyrosine-Protein Kinase ErbB-2; Tyrosine Kinase-Type Cell Surface Receptor HER2; V-Erb-B2 Erythroblastic Leukemia Viral Oncogene Homolog 2, Neuro/Glioblastoma Derived Oncogene Homolog; MLN 19; MLN19; p185erbB2; CD340 Antigen; EC 2.7.10.1; EC 2.7.10; V-Erb-B2 Avian Erythroblastic Leukemia Viral Oncogene Homolog 2 (Neuro/Glioblastoma Derived Oncogene Homolog). Ids:

HGNC: 3430; Entrez Gene: 2064; Ensembl: ENSG00000141736; OMIM: 164870; UniProtKB: P04626.

HM1.24 is also referred to as BST2; Bone Marrow Stromal Cell Antigen 2; TETHERIN; BST-2; Bone Marrow Stromal Antigen 2; HM1.24 Antigen; Tetherin; CD317; CD317 Antigen; NPC-A-7. Ids: HGNC: 1119; Entrez Gene: 684; Ensembl: ENSG00000130303; OMIM: 600534; UniProtKB: Q10589.

MCSP is also referred to as Sperm Mitochondria-Associated Cysteine-Rich Protein (SMCP); MCSP; MCS; Mitochondrial Capsule Selenoprotein; HSMCSGEN1; Sperm Mitochondrial-Associated Cysteine-Rich Protein. Ids: HGNC: 6962; Entrez Gene: 4184; Ensembl: ENSG00000163206; OMIM: 601148; UniProtKB: P49901.

PD-L1 is a type 1 transmembrane protein that plays a role in suppressing an immune response during particular events such as pregnancy, tissue allografts, autoimmune disease and other disease states such as hepatitis. The binding of PDL1 to PD-1 or B7.1 (CD80) transmits an inhibitory signal which reduces the proliferation of the PD-1 expressing T cells. PD-1 is thought to be able to control the accumulation of foreign antigen specific T cells through apoptosis. PD-L1 is expressed by a variety of cancer cells and the expression thereof is thought to be at least in part responsible for a dampening of an immune response against the cancer cell. PD-L1 is a member of the B7-family of protein and is known under a variety of other names such as CD274 Molecule; CD274 Antigen; B7 Homolog 1; PDCD1 Ligand 1;

PDCD1LG1; PDCD1 L1; B7H1; PDL1; Programmed Cell Death 1 Ligand 1; Programmed Death Ligand 1; B7-H1; and B7-H. External Ids for CD274 are HGNC: 17635; Entrez Gene: 29126; Ensembl: ENSG00000120217; OMIM: 605402; UniProtKB: Q9NZQ7.

PSMA is also referred to as Folate Hydrolase (Prostate-Specific Membrane Antigen) 1; FOLH1; NAALAD1; FOLH; mGCP; Glutamate Carboxypeptidase II; N-Acetylated-Alpha-Linked Acidic Dipeptidase I; PSM; NAALADase I; PSMA; EC 3.4.17.21; Glutamate Carboxylase II; GCP2; Cell Growth-Inhibiting Gene 27 Protein; NAALAdase; Folylpoly-Gamma-Glutamate Carboxypeptidase; Glutamate Carboxypeptidase 2; Membrane Glutamate Carboxypeptidase; N-Acetylated Alpha-Linked Acidic Dipeptidase 1; Pteroylpoly-Gamma-Glutamate Carboxypeptidase; Prostate Specific Membrane Antigen Variant F; FGCP; Folate Hydrolase 1; GCPII; Prostate-Specific Membrane Antigen. Ids: HGNC: 3788; Entrez Gene: 2346; Ensembl: ENSG00000086205; OMIM: 600934; UniProtKB: Q04609.

PSMA is not to be confused with Proteasome (Prosome, Macropain) Subunit, Alpha Type, 1 which is also known under the alias PSMA1.

Accession numbers are primarily given to provide a further method of identification of a target, the actual sequence of the protein bound may vary, for instance because of a mutation in the encoding gene such as those occurring in some cancers or the like. The antigen binding site binds the antigen and a variety of variants thereof, such as those expressed by some antigen positive immune or tumor cells.

When herein reference is made to a gene, a protein, the reference is preferably to the human form of the gene or protein. When herein reference is made to a gene or protein reference is made to the natural gene or protein and to variant forms of the gene or protein as can be detected in tumours, cancers and the like, preferably as can be detected in human tumours, cancers and the like.

A bispecific or multispecific antibody of the invention preferably binds to the human BCMA, CD19, CD20, CD30, CD33, CD38, CD44, CD123, CD138, CEA, CLEC12A, CS-1, EGFR, EGFRvIII, EPCAM, DLL3, LGR5, MSLN, FOLR1, FOLR3, HER2, HM1.24, MCSP, PD-L1, PSMA protein or a variant thereof. The antigen binding heavy/light chain combination preferably binds the extracellular part of the antigen. A bispecific antibody according to the invention preferably binds to human CLEC12A or a variant thereof. A preferred bispecific antibody according to the invention binds to human CD3 and human CLEC12A or a variant thereof. In a preferred embodiment, the multispecific antibody binds to CD3, PD-L1 and EGFR.

HGNC stands for the HUGO Gene nomenclature committee. The number following the abbreviation is the accession number with which information on the gene and protein encoded by the gene can be retrieved from the HGNC database. Entrez Gene provides the accession number or gene ID with which information on the gene or protein encoded by the gene can be retrieved from the NCBI (National Center for Biotechnology Information) database. Ensemble provides the accession number with which information on the gene or protein encoded by the gene can be obtained from the Ensemble database. Ensembl is a joint project between EMBL-EBI and the Wellcome Trust Sanger Institute to develop a software system which produces and maintains automatic annotation on selected eukaryotic genomes.

The invention provides an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1: (SEQ ID NO 42)
SFGIS;

CDR2: (SEQ ID NO 43)
GFIPVLGTANYAQKFQG;

CDR3: (SEQ ID NO 44)
RGNWNPFDP or comprising the amino acid sequence:

CDR1: (SEQ ID NO 6)
SX$_1$TFTIS;

CDR2: (SEQ ID NO 7)
GIIPX$_2$FGTITYAQKFQG;

CDR3: (SEQ ID NO 44)
RGNWNPFDP;

wherein $X_1$=K or R; $X_2$=L or I.

In a preferred embodiment $X_1$=K; and $X_2$=L. In another preferred embodiment $X_1$=R; and $X_2$=I.

The invention provides an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1: SKTLTIS; (SEQ ID NO 84) CDR2: GIIPIFGSITYAQKFQD (SEQ ID NO 85); CDR3: RGNWNPFDP (SEQ ID NO 86); or comprising the amino acid sequence: IDC-50 DNA

CDR1: (SEQ ID NO 100)
GSGIS;

CDR2: (SEQ ID NO 101)
GFIPFFGSANYAQKFRD;

CDR3: (SEQ ID NO 8)
RGNWNPX$_{13}$DP;

wherein $X_{13}$=or L or F.

The invention further provides an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
(SEQ ID NO 9)
$RX_3WIG$;

CDR2:
(SEQ ID NO 200)
IIYPGDSDTRYSPSFQG;

CDR3:
(SEQ ID NO 10)
$X_4IRYFX_5WSEDYHYYX_6DV$;

wherein $X_3$=F or Y; $X_4$=H or N; $X_5$=D or V; and $X_6$=L or M.

In a preferred embodiment $X_3$=F; $X_4$=H; $X_5$=D; and $X_6$=L; or $X_3$=Y; $X_4$=N; $X_5$=V; and $X_6$=M.

The invention further provides an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
(SEQ ID NO 117)
SYALS;

CDR2:
(SEQ ID NO 118)
GISGSGRTTWYADSVKG;

CDR3:
(SEQ ID NO 119)
DGGYSYGPYWYFDL.

The invention further provides an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
(SEQ ID NO 117)
SYALS;

CDR2:
(SEQ ID NO 126)
AISGSGRTTWYADSVKG;

CDR3:
(SEQ ID NO 127)
DGGYTYGPYWYFDL.

The invention further provides an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
(SEQ ID NO 2)
DYTMH;

CDR2:
(SEQ ID NO 143)
DISWSSGSIGYADSVKG;

-continued

CDR3:
(SEQ ID NO 144)
DHRGYGDYEGGGFDY.

The invention further provides an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
(SEQ ID NO 142)
DYTMH;

CDR2:
(SEQ ID NO 11)
$DISWSX_7GX_8X_9X_{10}YADSVKG$;

CDR3:
(SEQ ID NO 12)
$DHX_{11}GYGDYEGGGFDX_{12}$;

wherein $X_7$=S or G;
$X_8$=S or T;
$X_9$=I or T;
$X_{10}$=G or Y;
$X_{11}$=R or M;
$X_{12}$=H or Y, preferably $X_7$, $X_8$, $X_9$ and $X_{10}$ are S, S, I and G or G, S, I and Y or S, T, T and G, and preferably $X_{11}$ and $X_{12}$ are R and H, or R and Y, or M and Y, more preferably $X_7$, $X_8$, $X_9$, $X_{10}$, $X_{11}$ and $X_{12}$ are S, S, I, G, R and H or G, S, I, Y, R and Y or S, T, T, G, M and Y, or, in other words, preferably $X_7$, $X_8$, $X_9$ and $X_{10}$ are S, S, I and G, and $X_{11}$ and $X_{12}$ are R and H; or $X_7$, $X_8$, $X_9$ and $X_{10}$ are G, S, I and Y, and $X_{11}$ and $X_{12}$ are R and Y; or $X_7$, $X_8$, $X_9$ and $X_{10}$ are S, T, T and G, and $X_{11}$ and $X_{12}$ are M and Y.

In a preferred embodiment the light chain variable region comprises the amino acid sequence of an IgVκ1-39*01 gene segment as depicted in FIG. 11A with 0-10, preferably 0-5 amino acid variations, insertions, deletions, substitutions, additions or a combination thereof. The amino acid sequence of the IgVκ1-39*01 is depicted in FIG. 11A. IgVκ1-39 is short for Immunoglobulin Variable Kappa 1-39 Gene. The gene is also known as Immunoglobulin Kappa Variable 1-39; IGKV139; IGKV1-39. External Ids for the gene are HGNC: 5740; Entrez Gene: 28930; Ensembl: ENSG00000242371. A preferred amino acid sequence for IgVκ1-39 is given in FIG. 11A. This lists the sequence of the V-region. The V-region can be combined with one of five J-regions. FIGS. 11B and 11C describe two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org).

It is preferred that the IgVκ1-39*01 comprising light chain variable region is a germline sequence. It is further preferred that the IGJκ1*01 or/IGJκ5*01 comprising light chain variable region is a germline sequence. In a preferred embodiment, the IGKV1-39/jk1 or IGKV1-39/jk5 light chain variable regions are germline sequences.

In a preferred embodiment the light chain variable region comprises a germline IgVκ1-39*01. In a preferred embodiment the light chain variable region comprises the kappa light chain IgVκ1-39*01/IGJκ1*01 or IgVκ1-39*01/

IGJκ5*01. In a preferred embodiment a IgVκ1-39*01/IGJκ1*01. The light chain variable region preferably comprises a germline kappa light chain IgVκ1-39*01/IGJκ1*01 or germline kappa light chain IgVκ1-39*01/IGJκ5*01, preferably a germline IgVκ1-39*01/IGJκ1*01.

Mature B-cells that produce an antibody with a light chain often produce a light chain that has undergone one or more mutations with respect to the germline sequence, i.e. the normal sequence in non-lymphoid cells of the organism. The process that is responsible for these mutations is often referred to as somatic (hyper)mutation. The resulting light chain is referred to as an affinity matured light chain. Such light chains, when derived from a germline IgVκ1-39*01 sequence are IgVκ1-39*01 derived light chains. In this specification, the phrase "IgVκ1-39*01" will include IgVκ1-39*01-derived light chains, The mutations that are introduced by somatic hypermutation can also be introduced artificially in the lab. In the lab also other mutations or variations to a light chain can be introduced without affecting the properties of the light chain in kind, not necessarily in amount. A light chain is at least an IgVκ1-39*01 light chain if it comprises a sequence as depicted in FIG. 11A, FIG. 11D or FIG. 11E with 0-10, preferably 0-5 amino acid variations, insertions, deletions, substitutions, additions or a combination thereof. In a preferred embodiment the IgVκ1-39*01 light chain is a light chain comprising a sequence as depicted in FIG. 11A, FIG. 11B or FIG. 11C with 0-9, 0-8, 0-7, 0-6, 0-5, 0-4 amino acid variations, insertions, deletions, substitutions, additions or a combination thereof. In a preferred embodiment the IgVκ1-39*01 light chain is a light chain comprising a sequence as depicted in FIG. 11A, FIG. 11B or FIG. 11C with 0-5, preferably 0-4, more preferably 0-3 amino acid variations, insertions, deletions, substitutions, additions or a combination thereof. In a preferred embodiment the IgVκ1-39*01 light chain is a light chain comprising a sequence as depicted in FIG. 11A, FIG. 11B or FIG. 11C with 0-2, more preferably 0-1, most preferably 0 amino acid variations, insertions, deletions, substitutions, additions or a combination thereof. In a preferred embodiment the IgVκ1-39*01 light chain is a light chain comprising a sequence as depicted in FIG. 11A or FIG. 11B with the mentioned amino acid variations, insertions, deletions, substitutions, additions or a combination thereof. In a preferred embodiment the light chain comprises the sequence of FIG. 11B.

The light chain preferably comprises a common light chain variable region. Said common light chain variable region preferably comprises an IgVκ1-39 light chain variable region. Said light chain variable region is preferably a germline IgVκ1-39*01 variable region. Said light chain variable region preferably comprises the kappa light chain IgVκ1-39*01/IGJκ1*01 or IgVκ1-39*01/IGJκ5*01. The light chain variable region preferably comprises the germline kappa light chain IgVκ1-39*01/IGJκ1*01 or IgVκ1-39*01/IGJκ5*01. Said light chain variable region preferably comprises the amino acid sequence DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PTFGQ GTKVE IK (SEQ ID NO 16) or DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PITFG QGTRL EIK (SEQ ID NO 19) with 0-5 amino acid variations, insertions, deletions, substitutions, additions or a combination thereof.

The light chain variable region preferably comprises a CDR1, CDR2, and CDR3 region comprising the amino acid sequence CDR1-QSISSY (SEQ ID NO 21), CDR2-AAS (SEQ ID NO 22), CDR3-QQSYSTP (SEQ ID NO 23), i.e. the CDRs of IGKV1-39 (according to IMGT). The amino acid variations, insertions, deletions, substitutions, additions or combination thereof are preferably not in the CDR3 region of the light chain variable region, preferably not in the CDR1 or CDR2 region of the light chain variable region. In a preferred embodiment the light chain variable region does not comprise a deletion, addition or variations, insertion with respect to the sequence indicated. In this embodiment the light chain variable region can have 0-5 amino acid substitutions with respect to the indicated amino acid sequence. An amino acid substitution is preferably a conservative amino acid substitution. The CDR1, CDR2 and CDR3 of a light chain of an antibody of the invention preferably comprises respectively the amino acid sequence CDR1-QSISSY (SEQ ID NO 21), CDR2-AAS (SEQ ID NO 22), CDR3-QQSYSTP (SEQ ID NO 23), i.e. the CDRs of IGKV1-39 (according to IMGT).

The antigen-binding protein is preferably an antibody, preferably a bispecific or multispecific antibody. The antibody preferably comprises a common light chain including a common light variable region as defined herein and a light chain constant region as defined herein.

An antibody of the invention is, as mentioned, preferably a bispecific antibody. A "bispecific antibody" is an antibody as described herein wherein one domain of the antibody binds to a first antigen whereas a second domain of the antibody binds to a second antigen, wherein said first and second antigens are not identical. The term "bispecific antibody" also encompasses antibodies wherein one heavy chain variable region/light chain variable region (VH/VL) combination binds a first epitope on an antigen and a second VH/VL combination that binds a second epitope. The term further includes antibodies wherein VH is capable of specifically recognizing a first antigen and the VL, paired with the VH in an immunoglobulin variable region, is capable of specifically recognizing a second antigen. The resulting VH/VL pair will bind either antigen 1 or antigen 2. Such so called "two-in-one antibodies", described in for instance WO 2008/027236, WO 2010/108127 and Schaefer et al (Cancer Cell 20, 472-486, October 2011). A bispecific antibody according to the present invention is not limited to any particular bispecific format or method of producing it.

The bispecific antibody preferably has one heavy chain variable region/light chain variable region (VH/VL) combination that binds CD3 and a second VH/VL combination that binds an antigen other than an antigen on CD3. In a preferred embodiment the antigen is a tumor antigen. In a preferred embodiment the VL in said first VH/VL combination is similar to the VL in said second VH/VL combination. In a more preferred embodiment, the VLs in the first and second VH/VL combinations are identical. In a preferred embodiment, the bispecific antibody is a full length antibody which has one heavy/light (H/L) chain combination that binds CD3 and one H/L chain combination that binds another antigen, preferably a tumor antigen. In a preferred embodiment the light chain in said first H/L chain combination is similar to the light chain in said second H/L chain combination. In a more preferred embodiment, the light chains in the first and second H/L chain combinations are identical, i.e. a similar or identical human light chain is a so-called 'common light chain', which is a light chain that can combine with different heavy chains to form antibodies with functional antigen binding domains. In a preferred embodiment the light chain in said first H/L chain combination comprises a light chain variable region that is similar to the light chain variable region in said second H/L chain combination. In a more preferred embodiment, the light chain variably regions in the first and second H/L chain combinations are identical, i.e. a similar or identical human light chain variable region is a so-called 'common light chain variable region', which is a light chain variable region that can combine with different heavy chain variable regions to form antibodies with functional antigen binding domains. The light chain comprising a common light chain variable region is preferably a common light chain. The common light chain of the bispecific antibody is preferably an IgVκ1-39 light chain as indicated herein above.

The invention also provides alternative bispecific formats, such as those described in Spiess, C., et al., (Alternative molecular formats and therapeutic applications for bispecific antibodies. Mol. Immunol. (2015). Bispecific antibody formats that are not classical antibodies with two H/L combinations, have at least a variable domain comprising a heavy chain variable region and a light chain variable region of the invention. This variable domain may be linked to a single chain Fv-fragment, monobody, a VHH and a Fab-fragment that provides the second binding activity.

In a bispecific antibody of the invention the light chain in the CD3-binding H/L chain combination is preferably similar to the light chain in H/L chain combination that can bind an antigen other than CD3, preferably a tumor antigen. In a more preferred embodiment, the light chain in both H/L chain combinations is identical, i.e. said human light chain is a so-called 'common light chain', which is a light chain that can combine with different heavy chains to form antibodies with functional antigen binding domains. Preferably, the common light chain has a germline sequence. A preferred germline sequence is a light chain variable region that is frequently used in the human repertoire and has good thermodynamic stability, yield and solubility. A preferred germline light chain is IgVκ1-39, preferably the rearranged germline human kappa light chain IgVκ1-39*01/IGJκ1*01 or a fragment or a functional equivalent (i.e. same IgVκ1-39 gene segment but different IGJκ gene segment) thereof (nomenclature according to the IMGT database worldwide web at imgt.org).

The term 'aberrant cells' as used herein includes tumor cells, more specifically tumor cells of hematological origin including also pre-leukemic cells such as cells that cause myelodysplastic syndromes (MDS) and leukemic cells such as acute myeloid leukemia (AML) tumor cells or chronic myelogenous leukemia (CML) cells.

The term 'immune effector cell' or 'effector cell' as used herein refers to a cell within the natural repertoire of cells in the mammalian immune system which can be activated to affect the viability of a target cell. Immune effector cells include cells of the lymphoid lineage such as natural killer (NK) cells, T cells including cytotoxic T cells, or B cells, and including cells of the myeloid lineage, such as monocytes or macrophages, dendritic cells and neutrophilic granulocytes. Hence, said effector cell is preferably an NK cell, a T cell, a B cell, a monocyte, a macrophage, a dendritic cell or a neutrophilic granulocyte. The recruitment of effector cells to aberrant cells means that immune effector cells are brought in proximity to the aberrant target cells such that the effector cells can directly kill, or indirectly initiate the killing of the aberrant cells.

As used herein, the terms "subject" and "patient" are used interchangeably and refer to a mammal such as a human, mouse, rat, hamster, guinea pig, rabbit, cat, dog, monkey, cow, horse, pig and the like (e.g., a patient, such as a human patient, having cancer).

The terms "treat," "treating," and "treatment," as used herein, refer to any type of intervention or process performed on, or administering an active agent or combination of active agents to the subject with the objective of reversing, alleviating, ameliorating, inhibiting, or slowing down or preventing the progression, development, severity or recurrence of a symptom, complication, condition or biochemical indicia associated with a disease.

As used herein, "effective treatment" or "positive therapeutic response" refers to a treatment producing a beneficial effect, e.g., amelioration of at least one symptom of a disease or disorder, e.g., cancer. A beneficial effect can take the form of an improvement over baseline, including an improvement over a measurement or observation made prior to initiation of therapy according to the method. For example, a beneficial effect can take the form of slowing, stabilizing, stopping or reversing the progression of a cancer in a subject at any clinical stage, as evidenced by a decrease or elimination of a clinical or diagnostic symptom of the disease, or of a marker of cancer. Effective treatment may, for example, decrease in tumor size, decrease the presence of circulating tumor cells, reduce or prevent metastases of a tumor, slow or arrest tumor growth and/or prevent or delay tumor recurrence or relapse.

The term "therapeutic amount" refers to an amount of an agent or combination of agents that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In some embodiments, a therapeutic amount is an amount sufficient to delay tumor development. In some embodiments, a therapeutic amount is an amount sufficient to prevent or delay tumor recurrence. A therapeutic amount can be administered in one or more administrations. The therapeutic amount of the drug or composition may: (i) reduce the number of cancer cells; (ii) reduce tumor size; (iii) inhibit, retard, slow to some extent and may stop cancer cell infiltration into peripheral organs; (iv) inhibit tumor metastasis; (v) inhibit tumor growth; (vi) prevent or delay occurrence and/or recurrence of tumor; and/or (vii) relieve to some extent one or more of the symptoms associated with the cancer. In one example, an "therapeutic amount" is the amount of a CLEC12A/CD3 bispecific antibody that effects a decrease in a cancer (for example a decrease in the number of cancer cells) or slowing of progression of a cancer, such as acute myeloid leukemia, myelodysplastic syndrome or chronic myelogenous leukemia.

The invention also provides an antigen-binding protein, preferably an antibody, that binds human CD3 comprising an antibody variable domain comprising a heavy chain variable region and a light chain variable region wherein the heavy chain variable region comprises the amino acid sequence (SEQ ID NO 45)

EVQLVQSGAEVKKPGSSVKVSCKASGGTFRSFGISWVRQAPGQGLEWMGG

FIPVLGTANYAQKFQGRVTIIADKSTNTAYMELSSLRSEDTAVYYCARRG

NWNPFDPWGQGTLVTVSS;

-continued (SEQ ID NO 54)
QVQLVQSGAEVKKPGSSVKVSCKASGDAFKSKTFTISWVRQAPGQGLEWL
GGIIPLFGTITYAQKFQGRVTITADKSTNTAFMELSSLRSEDTAMYYCTR
RGNWNPFDPWGQGTLVTVSS;

(SEQ ID NO 63)
EVQLVQSGSELKKPGSSVKVSCKASGVTFNSRTFTISWVRQAPGQGLEWL
GSIIPIFGTITYAQKFQGRVTITADKSTSTAFMELTSLRSEDTAIYYCTR
RGNWNPFDPWGQGTLVTVSS;

(SEQ ID NO 71)
QVQLVQSGAEVKKPGSSVKVSCKASGGTFRGSGISWVRQAPGQGLEWVGG
FIPFFGSANYAQKFRDRVTITADKSATTAYMELSSLRSEDTAIYYCAKRG
NWNPLDPWGQGTLVTVSS;

(SEQ ID NO 87)
QVQLVQSGAEVKKPGSSVKVSCKASGVTFKSKTLTISWVRQAPGQGLEWL
GGIIPIFGSITYAQKFQDRVSITADKSTNTAYLELNSLRSEDTAIYYCAR
RGNWNPFDPWGQGTLVTVSS;
or (SEQ ID NO 103)
EVQLVQSGAEVKKPGSSVKVSCKASGGTFRGSGISWVRQAPGQGLEWVGG
FIPFFGSANYAQKFRDRVTITADKSATTAYMELSSLRSEDTAIYYCAKRG
NWNPFDPWGQGTLVTVSS with 0-10, preferably 0-5 amino acid variations, insertions, deletions, substitutions, additions or a combination thereof at one or more positions other than the CDRs.

Further provided is an antigen-binding protein, preferably an antibody, that binds human CD3 comprising an antibody variable domain comprising a heavy chain variable region and a light chain variable region wherein the heavy chain variable region comprises the amino acid sequence (SEQ ID NO 298)
EVQLVQSGAEVKKPGESLKISCKGSGYSFTRFWIGWVRQMPGKGLEWMGI
IYPGDSDTRYSPSFQGQVTISADKSTSTAYLQWSSLKASDTGMYYCVRHI
RYFDWSEDYHYYLDVWGKGTTVTVSS;
or (SEQ ID NO 211)
EVQLVESGAEVKKPGESLKISCKGSGYSFTRYWIGWVRQMPGKGLEWMGI
IYPGDSDTRYSPSFQGQVTISADKSISTAYLQWSSLKASDTAMYYCVRNI
RYFVWSEDYHYYMDVWGKGTTVTVSS;

with 0-10, preferably 0-5 amino acid variations, insertions, deletions, substitutions, additions or a combination thereof at one or more positions other than the CDRs.

Also provided is an antigen-binding protein, preferably an antibody, that binds human CD3 comprising an antibody variable domain comprising a heavy chain variable region and a light chain variable region wherein the heavy chain variable region comprises the amino acid sequence (SEQ ID NO 120)
QVQLVQSGGGLVQPGGSLRLSCATSGFKFSSYALSWVRQAPGKGLEWVSG
ISGSGRTTWYADSVKGRFTISRDNSKNTLYLQMNSLRAEDTAVYYCARDG
GYSYGPYWYFDLWGRGTLVTVSS;
or (SEQ ID NO 128)
QVQLVESGGGLVQPGGSLRLSCATSGFTFISYALSWVRQAPGKGLEWVSA
ISGSGRTTWYADSVKGRFTISRDNSKNTLFLQMNSLRAEDTAVYYCARDG
GYTYGPYWYFDLWGRGTLVTVSS with 0-10, preferably 0-5 amino acid variations, insertions, deletions, substitutions, additions or a combination thereof at one or more positions other than the CDRs.

The invention further provides an antigen-binding protein, preferably an antibody, that binds human CD3 comprising an antibody variable domain comprising a heavy chain variable region and a light chain variable region wherein the heavy chain variable region comprises the amino acid sequence (SEQ ID NO 145)
EVQLVESGGGLVQPGRSLRLSCATSGFNFDDYTMHWVRQAPGKGLEWVSD
ISWSSGSIGYADSVKGRFTISRDNAKNSLWLQMNSLRTEDTALYFCAKDH
RGYGDYEGGGFDYWGQGTLVTVSS;

(SEQ ID NO 153)
EVQLVESGGGLVQPGRSLRLSCATSGFTFDDYTMHWVRQAPGKGLEWVSD
ISWSSGSIGYADSVKGRFTISRDNAKNSLYLQMNSLRAEDTALYFCAKDH
RGYGDYEGGGFDHWGQGTLVTVSS;

(SEQ ID NO 185)
EVQLVESGGGLVQPGRSLRLSCVTSGFTFDDYTMHWVRQAPGKGLEWVSD
ISWSSGTTGYADSVKGRFTISRDNAKDSLYLQMNSLRTEDTALYYCAKDH
MGYGDYEGGGFDYWGQGTLVTVSS;
or (SEQ ID NO 169)
EVQLVESGGVVVQPGGSLRLSCAASGFTFDDYTMHWVRQAPGKGLEWVSD
ISWSGGSIYYADSVKGRFTISRDNSKNSLYLQMNSLRTEDTALYYCAKDH
RGYGDYEGGGFDYWGRGTLVTVSS;

with 0-10, preferably 0-5 amino acid variations, insertions, deletions, substitutions, additions or a combination thereof at one or more positions other than the CDRs.

The amino acid variations, insertions, deletions, substitutions, additions or combination thereof are preferably not in the CDR3 region of the heavy chain variable region, preferably not in the CDR1 and/or CDR2 region of the heavy chain variable region. In a preferred embodiment the heavy chain variable region does not comprise a deletion, addition or variation, insertion with respect to the sequence indicated. In one embodiment the heavy chain variable region can have 0-10, preferably 0-5 amino acid substitutions with respect to the indicated amino acid sequence. In a preferred embodiment the heavy chain variable region comprises 0-9, 0-8, 0-7, 0-6, 0-5, 0-4, preferably 0-3, preferably 0-2, preferably 0-1 and preferably 0 amino acid variations, insertions, deletions, substitutions, additions with respect to the indicated amino acid sequence, or a combination thereof at positions other than the CDRs. A combination of an insertion, addition, deletion or substitution is a combination as claimed if aligned sequences do not differ at more than 10, preferably no more than 5 positions. A gap in one of the aligned sequences counts for as many amino acids as skipped in the other sequence. An amino acid substitution, if any, is preferably a conservative amino acid substitution.

The invention further provides an antigen-binding protein, preferably an antibody, that binds human CD3 comprising an antibody variable domain comprising a heavy chain variable region and a light chain variable region wherein the heavy chain variable region comprises the amino acid sequence of MF8057; MF8058 or MF8078 as depicted in FIG. 13.

The invention further provides an antigen-binding protein, preferably an antibody, that binds human CD3 comprising an antibody variable domain comprising a heavy chain variable region and a light chain variable region wherein the heavy chain variable region comprises the amino acid sequence of MF8397 as depicted in FIG. 13.

The invention further provides an antigen-binding protein, preferably an antibody, that binds human CD3 comprising an antibody variable domain comprising a heavy chain variable region and a light chain variable region wherein the heavy chain variable region comprises the amino acid sequence of MF8508 as depicted in FIG. 13.

The invention further provides an antigen-binding protein, preferably an antibody, that binds human CD3 comprising an antibody variable domain comprising a heavy chain variable region and a light chain variable region wherein the heavy chain variable region comprises the amino acid sequence of MF9249 or MF9267 as depicted in FIG. 13.

The light chain preferably comprises the CDR1, CDR2 and CDR3 region as defined elsewhere herein. It preferably comprises a common light chain variable region and preferably a common light chain as defined elsewhere herein. The bispecific antibody preferably further comprises a heavy chain and light chain combination that binds another antigen, preferably a tumor antigen. The light chain of the heavy chain and light chain combination that binds another antigen is preferably a common light chain as defined elsewhere herein. The heavy chain of the heavy chain and light chain combination that binds another antigen preferably comprises a heavy chain variable region comprising an amino acid sequence: MF8233 (EGFR) QVQLVQSGAEVKKPGASVKVSCKASGYTFTSYGISWVRQAPGQGLEWMGWISAYNANTNYA QKLQGRVTMTTDTSTSTAYMELRSLRSDDTAVYYCAKDRHWHWWLDAFDYWGQGTLVTVSS (SEQ ID NO 247) with 0-10, preferably 0-5 amino acid variations, insertions, deletions, substitutions, additions or a combination thereof at one or more positions other than the CDRs; or MF4327 (CLECI2A) QVQLVQSGAEVKKPGASVKVSCKASGYTFTSYYMHWVRQAPGQGLEWMGIINPSGGSTSYA QKFQGRVTMTRDTSTSTVYMELSSLRSEDTAVYYCAKGTTGDWFDYWGQGTLVTVSS (SEQ ID NO 293) with 0-10, preferably 0-5 amino acid variations, insertions, deletions, substitutions, additions or a combination thereof at one or more positions other than the CDRs.

Variable domains that bind CLEC12A that have a heavy chain variable region and a common light chain region as defined herein are described among others in WO2014/051433 and WO2017/010874 which are specifically referred to for this purpose herein and which are incorporated by reference herein. The heavy chain variable region of the heavy/light chain combination that binds human EGFR or CLEC12A can have 0-10, preferably 0-5 amino acid variations, insertions, deletions, substitutions, additions with respect to the indicated amino acid sequence, or a combination thereof. In a preferred embodiment the heavy chain variable region comprises 0-9, 0-8, 0-7, 0-6, 0-5, 0-4, preferably 0-3, preferably 0-2, preferably 0-1 and preferably 0 amino acid variations, insertions, deletions, substitutions, additions with respect to the indicated amino acid sequence, or a combination thereof. A combination of an insertion, deletion, addition or substitution is a combination as claimed if aligned sequences do not differ at more than 5 positions. A gap in one of the aligned sequences counts for as many amino acid as skipped in the other sequence.

An amino acid variation, insertion, deletion, substitution, addition or combination thereof is preferably not done/present in the binding interface of the heavy and light chain. If an amino acid is changed in the interface of the H/L chain interaction, it is preferred that the corresponding amino acids in the other chain are changed to accommodate the change. An insertion or addition of an amino acid preferably does not entail the insertion or addition of a proline.

An addition of an amino acid can in principle be regarded to be the same as an insertion. Adding an amino acid to one of the ends of a polypeptide chain is sometimes not considered an insertion but as a strict addition (prolongation). For the present invention both an addition within a chain or to one of the ends, are considered to be an insertion.

The amino acid variations, insertions, deletions, substitutions, additions or combination thereof are preferably not in the CDR3 region of the heavy chain variable region, preferably not in the CDR1 or CDR2 region of the heavy chain variable region. In a preferred embodiment the heavy chain variable region does not comprise a deletion, addition or variations, insertion with respect to the sequence indicated. In this embodiment the heavy chain variable region can have 0-5 amino acid substitutions with respect to the indicated amino acid sequence. An amino acid substitution is preferably a conservative amino acid substitution. The CDR1, CDR2 and CDR3 of a CD3 binding VH of the invention preferably comprises a CDR1, CD2 and CDR3 combination of a CD3 binding VH depicted in FIG. 13, preferably of the VH of one of MF8057; MF8058; MF8078; MF8397; MF8508; MF9249 or MF9267.

The constant region of an antibody of the present invention, including a bispecific or multispecific antibody, is preferably a human constant region. The constant region may contain one or more, preferably not more than 10, preferably not more than 5 amino-acid differences with the constant region of a naturally occurring human antibody. Various variable domains of antibodies produced herein are derived from a human antibody variable domain library. As such these variable domains are human. The unique CDR regions may be derived from humans, be synthetic or derived from another organism. An antibody or bispecific antibody of the invention is preferably a human or humanized antibody. Suitable heavy chain constant regions are non-limitingly exemplified in FIG. 12.

In the art various methods exist to produce antibodies. Antibodies are typically produced by a cell that expresses nucleic acid encoding the antibody. Suitable cells for antibody production are a hybridoma cell, a Chinese hamster ovary (CHO) cell, an NS0 cell or a PER-C6 cell. In a particularly preferred embodiment said cell is a CHO cell.

Various institutions and companies have developed cell lines for the large scale production of antibodies, for instance for clinical use. Non-limiting examples of such cell lines are CHO cells, NS0 cells or PER.C6 cells. These cells are also used for other purposes such as the production of proteins. Cell lines developed for industrial scale production of proteins and antibodies are herein further referred to as industrial cell lines. In a preferred embodiment the invention provides an industrial cell line that produces and an antibody of the invention.

The invention in one embodiment provides a cell comprising an antibody according to the invention and/or a nucleic acid according to the invention. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Preferably said cell (typically an in vitro, isolated or recombinant cell) produces said antibody. In a preferred embodiment said cell is a hybridoma cell, a Chinese hamster ovary (CHO) cell, an NS0 cell or a PER.C6 cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NS0 cells or PER.C6 cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention. The invention further provides a cell for producing an antibody comprising a nucleic acid molecule that codes for a VH, a VL, and/or a heavy and light chain of an antibody as claimed. Preferably said nucleic acid molecule encodes a VH identified in FIG. 13, a nucleic acid molecule encoding a VH as identified by numeral 4327 or identified by numeral 8233 or a combination thereof.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, a 293F cell, an NS0 cell or another cell type known for its suitability for antibody production for clinical purposes. In a particularly preferred embodiment said cell is a human cell. Preferably a cell that is transformed by an adenovirus E1 region or a functional equivalent thereof. A preferred example of such a cell line is the PER.C6 cell line or equivalent thereof. In a particularly preferred embodiment said cell is a CHO cell or a variant thereof. Preferably a variant that makes use of a Glutamine synthetase (GS) vector system for expression of an antibody.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

Bispecific antibodies are typically also produced by cells that express nucleic acid encoding the antibody. In this case the cell expresses the different light and heavy chains that make up the bispecific antibody. To this end the cell expresses two different heavy chains and at least one light chain. As unmodified heavy chains can pair with each other to form dimers such cells typically produce the two monospecific antibodies (homodimers), in addition to the bispecific antibody (heterodimer). This principle also applies to unmodified heavy chains that comprise a first heavy chain having one heavy chain variable region and a second heavy chain having at least two heavy chain variable regions, such that cells expressing these two heavy chains produce a monospecific antibody (homodimer of the pairing of the two first heavy chain), a quadrovalent antibody (homodimer of the pairing of two of the second heavy chains) and a trispecific antibody (heterodimer of the first and second heavy chain). The number of possible heavy/light chain combinations in the produced antibodies increases when the cell expresses two or more light chains. To reduce the number of different antibody species (combinations of different heavy and light chains) produced the afore mentioned "common light chain" is preferred.

An antibody producing cell that expresses a common light chain and equal amounts of the two heavy chains typically produces 50% bispecific antibody and 25% of each of the monospecific antibodies (i.e. having identical heavy light chain combinations). Alternatively in the above, example concerning a first heavy chain having one variable region and a second heavy chain having two variable regions, the two heavy chains typically produces 50% trispecific, 25% monospecific and 25% quadrospecific.

Several methods have been published to favor the production of the bispecific antibody or vice versa, the monospecific antibodies, which can further be employed for favoring multispecific antibody production. In the present invention it is preferred that the cell favors the production of the bispecific antibody over the production of the respective monospecific antibodies. Such is typically achieved by modifying the constant region of the heavy chains such that they favor heterodimerization (i.e. dimerization with the heavy chain of the other heavy/light chain combination) over homodimerization. In a preferred embodiment the bispecific antibody of the invention comprises two different immunoglobulin heavy chains with compatible heterodimerization domains. Various compatible heterodimerization domains have been described in the art. The compatible heterodimerization domains are preferably compatible immunoglobulin heavy chain CH3 heterodimerization domains. The art describes various ways in which such hetero-dimerization of heavy chains can be achieved, including use of 'knob into hole' bispecific antibodies.

In U.S. Ser. No. 13/866,747 (now issued as U.S. Pat. No. 9,248,181), U.S. Ser. No. 14/081,848 (now issued as U.S. Pat. No. 9,358,286) and PCT/NL2013/050294 (published as WO2013/157954); incorporated herein by reference) methods and means are disclosed for producing bispecific antibodies using compatible heterodimerization domains. These means and methods can also be favorably employed in the present invention. Specifically, preferred mutations to produce essentially only bispecific full length IgG molecules are the amino acid substitutions L351K and T366K (according to EU numbering) in the first CH3 domain (the 'KK-variant' heavy chain) and the amino acid substitutions L351D and L368E in the second domain (the 'DE-variant' heavy chain), or vice versa. It was previously demonstrated in our U.S. Pat. Nos. 9,248,181 and 9,358,286 patents as well as the WO2013/157954 PCT application that the DE-variant and KK-variant preferentially pair to form heterodimers (so-called 'DEKK' (SEQ ID NO 36) bispecific molecules). Homodimerization of DE-variant heavy chains (DEDE homodimers) or KK-variant heavy chains (KKKK homodimers) hardly occurs due to strong repulsion between the charged residues in the CH3-CH3 interface between identical heavy chains. In one embodiment the heavy chain/light chain combination that comprises the variable domain that binds CD3, comprises a KK variant of the heavy chain. In this embodiment the heavy chain/light chain combination that comprises the variable domain that binds an antigen other than CD3 comprises a DE variant of the heavy chain. In a preferred embodiment the antigen other than CD3 is CLEC12A. In a preferred embodiment the VH of the variable domain that binds CLEC12A is MF4327 as depicted in FIG. 13.

Some antibodies are modified in CH2/lower hinge region, for instance to reduce Fc-receptor interaction or to reduce C1q binding. In some embodiments the antibody of the invention is an IgG antibody with a mutant CH2 and/or lower hinge domain such that interaction of the bispecific IgG antibody to a Fc-gamma receptor is reduced. Such a mutant CH2 and/or lower hinge domain preferably comprise an amino substitution at position 235 and/or 236 (according to EU numbering), preferably an L235G and/or G236R substitution.

Alternatively, some antibodies are modified for instance to enhance Fc receptor interaction or enhance C1q binding. For embodiments directed to auto-immune indications, such a modification may be preferred.

The invention further provides a method of treating a subject comprising administering an antigen-binding protein, preferably an antibody of the invention to the subject in need thereof. The invention further provides an antigen-binding protein, preferably an antibody of the invention for use in the treatment of a subject in need thereof. The subject preferably has cells that are to be removed from the body. The cells can be aberrant immune cells directing an auto-immune response or cancer cells or the like. Variable domains that are suited for this purpose are among others those with a common light chain and the VH of MF9249, and MF8397. These have a suitably low affinity and low cell kill activity but are functional under auto-immune response conditions. Variable domains that are suited for this purpose are among others those with a common light chain and the VH of MF9267, MF8057, MF8058, MF8078 and MF8508. These variable domains have a suitable affinity and a suitable cell kill activity for anticancer purposes.

Further, an invention set out herein, includes an antigen-binding protein or antibody with a high affinity variable domain having a high cell kill activity, which can be administered locally or be expressed locally, including the binding domain MF8078. The invention further provides a method of treating a subject comprising administering an antigen-binding protein, preferably an antibody of the invention to the subject in need thereof through a localized means of administration, as known to those of skill in the art, including, for example, an oncolytic virus, topical treatments for melanoma or other cancers in separate compartments such as the brain.

The invention further provides an antigen-binding protein, preferably an antibody, of the invention for use in the treatment of a subject in need thereof, which preferably has moderate to high affinity and relative high cytotoxicity such as those described herein. Variable domains that are suited for this purpose are among others those with a common light chain and the VH of MF8057, MF8058, MF9267, MF8508 and MF8078.

The invention further provides a method of treating cancer or a risk of cancer in a subject comprising administering to the subject in need thereof an antigen-binding protein, preferably an antibody that binds human CD3 comprising an antibody variable domain comprising a heavy chain variable region and a light chain variable region wherein the heavy chain variable region comprises a CDR1, CDR2 and CDR3 comprising the amino acid sequence:

```
CDR1:
                              (SEQ ID NO 42)
SFGIS
CDR2:
                              (SEQ ID NO 43)
GFIPVLGTANYAQKFQG
CDR3:
                              (SEQ ID NO 44)
RGNWNPFDP;
```

comprising the amino acid sequence:

CDR1: (SEQ ID NO 6)
$SX_1TFTIS$;

CDR2: (SEQ ID NO 7)
$GIIPX_2FGTITYAQKFQG$;

CDR3: (SEQ ID NO 44)
RGNWNPFDP;

wherein $X_1$=K or R;

$X_2$=L or I.

In a preferred embodiment $X_1$=K; and $X_2$=L. In another preferred embodiment $X_1$=R; and $X_2$=I.

The invention further provides an antigen-binding protein, preferably an antibody, of the invention for use in the treatment of a subject in need thereof, which preferably has moderate to high affinity and relative high cytotoxicity such as those described herein. Variable domains that are suited for this purpose are among others those with a common light chain and the VH of MF8048, MF8056 and MF8101.

The invention further provides a method of treating cancer or a risk of cancer in a subject comprising administering to the subject in need thereof an antigen-binding protein, preferably an antibody that binds human CD3 comprising an antibody variable domain comprising a heavy chain variable region and a light chain variable region wherein the heavy chain variable region comprises aa CDR1, CDR2 and CDR3 comprising the amino acid sequence:

```
CDR1:
                              (SEQ ID NO 84)
SKTLTIS;
CDR2:
                              (SEQ ID NO 85)
GIIPIFGSITYAQKFQD;
```

-continued

CDR3: (SEQ ID NO 44)
RGNWNPFDP;

comprising the amino acid sequence:

CDR1: (SEQ ID NO 100)
GSGIS;

CDR2: (SEQ ID NO 101)
GFIPFFGSANYAQKFRD;

CDR3: (SEQ ID NO 8)
RGNWNP$X_{13}$DP;

wherein $X_{13}$=or L or F.

The invention further provides a method of treating cancer or a risk of cancer in a subject comprising administering to the subject in need thereof an antigen-binding protein, preferably an antibody, that binds human CD3 comprising an antibody variable domain comprising a heavy chain variable region and a light chain variable region wherein the heavy chain variable region comprises the amino acid sequence (SEQ ID NO 45)
EVQLVQSGAEVKKPGSSVKVSCKASGGTFRSFGISWVRQAPGQGLEWMGG
FIPVLGTANYAQKFQGRVTIIADKSTNTAYMELSSLRSEDTAVYYCARRG
NWNPFDPWGQGTLVTVSS;

(SEQ ID NO 54)
QVQLVQSGAEVKKPGSSVKVSCKASGDAFKSKTFTISWVRQAPGQGLEWL
GGIIPLFGTITYAQKFQGRVTITADKSTNTAFMELSSLRSEDTAMYYCTR
RGNWNPFDPWGQGTLVTVSS;

(SEQ ID NO 63)
EVQLVQSGSELKKPGSSVKVSCKASGVTFNSRTFTISWVRQAPGQGLEWL
GSIIPIFGTITYAQKFQGRVTITADKSTSTAFMELTSLRSEDTAIYYCTR
RGNWNPFDPWGQGTLVTVSS;

(SEQ ID NO 71)
QVQLVQSGAEVKKPGSSVKVSCKASGGTFRGSGISWVRQAPGQGLEWVGG
FIPFFGSANYAQKFRDRVTITADKSATTAYMELSSLRSEDTAIYYCAKRG
NWNPLDPWGQGTLVTVSS;

(SEQ ID NO 87)
QVQLVQSGAEVKKPGSSVKVSCKASGVTFKSKTLTISWVRQAPGQGLEWL
GGIIPIFGSITYAQKFQDRVSITADKSTNTAYLELNSLRSEDTAIYYCAR
RGNWNPFDPWGQGTLVTVSS;
or (SEQ ID NO 103)
EVQLVQSGAEVKKPGSSVKVSCKASGGTFRGSGISWVRQAPGQGLEWVGG
FIPFFGSANYAQKFRDRVTITADKSATTAYMELSSLRSEDTAIYYCAKRG
NWNPFDPWGQGTLVTVSS;

with 0-10, preferably 0-5 amino acid variations, insertions, deletions, substitutions, additions or a combination thereof at one or more positions other than the CDRs.

The invention further provides a method of treating cancer or a risk of cancer in a subject comprising administering to the subject in need thereof an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1: (SEQ ID NO 9)
R$X_3$WIG;

CDR2: (SEQ ID NO 200)
IIYPGDSDTRYSPSFQG;

CDR3: (SEQ ID NO 10)
$X_4$IRYF$X_5$WSEDYHYY$X_6$DV;

wherein $X_3$=F or Y;

$X_4$=H or N;

$X_5$=D or V;

$X_6$=L or M.

In one embodiment $X_3$=F; $X_4$=H; $X_5$=D; and $X_6$=L. In a further embodiment $X_3$=Y; $X_4$=N; $X_5$=V; and $X_6$=M.

The invention further provides a method of treating cancer or a risk of cancer in a subject comprising administering to the subject in need thereof an antigen-binding protein, preferably an antibody, that binds human CD3 comprising an antibody variable domain comprising a heavy chain variable region and a light chain variable region wherein the heavy chain variable region comprises the amino acid sequence (SEQ ID NO 298)
EVQLVQSGAEVKKPGESLKISCKGSGYSFTRFWIGWVRQMPGKGLEWMGI
IYPGDSDTRYSPSFQGQVTISADKSTSTAYLQWSSLKASDTGMYYCVRHI
RYFDWSEDYHYYLDVWGKGTTVTVSS;
or (SEQ ID NO 211)
EVQLVESGAEVKKPGESLKISCKGSGYSFTRYWIGWVRQMPGKGLEWMGI
IYPGDSDTRYSPSFQGQVTISADKSISTAYLQWSSLKASDTAMYYCVRNI
RYFVWSEDYHYYMDVWGKGTTVTVSS;

with 0-10, preferably 0-5 amino acid variations, insertions, deletions, substitutions, additions or a combination thereof at one or more positions other than the CDRs.

The invention further provides a method of treating cancer or a risk of cancer in a subject comprising administering to the subject in need thereof an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1: (SEQ ID NO 117)
SYALS;

-continued

CDR2:

(SEQ ID NO 118)

GISGSGRTTWYADSVKG;

CDR3:

(SEQ ID NO 119)

DGGYSYGPYWYFDL.

The invention further provides a method of treating cancer or a risk of cancer in a subject comprising administering to the subject in need thereof an antigen-binding protein, preferably an antibody, that binds human CD3 comprising an antibody variable domain comprising a heavy chain variable region and a light chain variable region wherein the heavy chain variable region comprises a CDR1, CDR2 and CDR3 comprising the amino acid sequence:

CDR1:

(SEQ ID NO 117)

SYALS;

CDR2:

(SEQ ID NO 126)

AISGSGRTTWYADSVKG;

CDR3:

(SEQ ID NO 127)

DGGYTYGPYWYFDL.

The invention further provides a method of treating cancer or a risk of cancer in a subject comprising administering to the subject in need thereof an antigen-binding protein, preferably an antibody, that binds human CD3 comprising an antibody variable domain comprising a heavy chain variable region and a light chain variable region wherein the heavy chain variable region comprises the amino acid sequence (SEQ ID NO 120)

QVQLVQSGGGLVQPGGSLRLSCATSGFKFSSYALSWVRQAPGKGLEWVSG

ISGSGRTTWYADSVKGRFTISRDNSKNTLYLQMNSLRAEDTAVYYCARDG

GYSYGPYWYFDLWGRGTLVTVSS;

or (SEQ ID NO 128)

QVQLVESGGGLVQPGGSLRLSCATSGFTFISYALSWVRQAPGKGLEWVSA

ISGSGRTTWYADSVKGRFTISRDNSKNTLFLQMNSLRAEDTAVYYCARDG

GYTYGPYWYFDLWGRGTLVTVSS;

with 0-10, preferably 0-5 amino acid variations, insertions, deletions, substitutions, additions or a combination thereof at one or more positions other than the CDRs.

The invention further provides a method of treating cancer or a risk of cancer in a subject comprising administering to the subject in need thereof an antigen-binding protein, preferably an antibody that binds human CD3 comprising an antibody variable domain comprising a heavy chain variable region and a light chain variable region wherein the heavy chain variable region comprises a CDR1, CDR2 and CDR3 comprising the amino acid sequence:

CDR1:

(SEQ ID NO 142)

DYTMH;

-continued

CDR2:

(SEQ ID NO 143)

DISWSSGSIGYADSVKG;

CDR3:

(SEQ ID NO 144)

DHRGYGDYEGGGFDY.

The invention further provides a method of treating cancer or a risk of cancer in a subject comprising administering to the subject in need thereof an antigen-binding protein, preferably an antibody that binds human CD3 comprising an antibody variable domain comprising a heavy chain variable region and a light chain variable region wherein the heavy chain variable region comprises a CDR1, CDR2 and CDR3 comprising the amino acid sequence:

CDR1:

(SEQ ID NO 142)

DYTMH;

CDR2:

(SEQ ID NO 11)

DISWS$X_7$G$X_8X_9X_{10}$YADSVKG;

CDR3:

(SEQ ID NO 12)

DH$X_{11}$GYGDYEGGGFD$X_{12}$;

wherein $X_7$=S or G;

$X_8$=S or T;

$X_9$=I or T;

$X_{10}$=G or Y;

$X_{11}$=R or M;

$X_{12}$=H or Y, preferably $X_7$, $X_8$, $X_9$ and $X_{10}$ are S, S, I and G or G, S, I and Y or S, T, T and G, and preferably $X_{11}$ and $X_{12}$ are R and H, or R and Y, or M and Y, more preferably $X_7$, $X_8$, $X_9$, $X_{10}$, $X_{11}$ and $X_{12}$ are S, S, I, G, R and H or G, S, I, Y, R and Y or S, T, T, G, M and Y, or, in other words, preferably $X_7$, $X_8$, $X_9$ and $X_{10}$ are S, S, I and G, and $X_{11}$ and $X_{12}$ are R and H; or $X_7$, $X_8$, $X_9$ and $X_{10}$ are G, S, I and Y, and $X_{11}$ and $X_{12}$ are R and Y; or $X_7$, $X_8$, $X_9$ and $X_{10}$ are S, T, T and G, and $X_{11}$ and $X_{12}$ are M and Y.

The invention further provides a method of treating cancer or a risk of cancer in a subject comprising administering to the subject in need thereof an antigen-binding protein, preferably an antibody that binds human CD3 comprising an antibody variable domain comprising a heavy chain variable region and a light chain variable region wherein the heavy chain variable region comprises the amino acid sequence (SEQ ID NO 145)

EVQLVESGGGLVQPGRSLRLSCATSGFNFDDYTMHWVRQAPGKGLEWVSD

ISWSSGSIGYADSVKGRFTISRDNAKNSLWLQMNSLRTEDTALYFCAKDH

RGYGDYEGGGFDYWGQGTLVTVSS;

(SEQ ID NO 153)

EVQLVESGGGLVQPGRSLRLSCATSGFTFDDYTMHWVRQAPGKGLEWVSD

ISWSSGSIGYADSVKGRFTISRDNAKNSLYLQMNSLRAEDTALYFCAKDH

RGYGDYEGGGFDHWGQGTLVTVSS;

-continued (SEQ ID NO 185)
EVQLVESGGGLVQPGRSLRLSCVTSGFTFDDYTMHWVRQAPGKGLEWVSD

ISWSSGTTGYADSVKGRFTISRDNAKDSLYLQMNSLRTEDTALYYCAKDH

MGYGDYEGGGFDYWGQGTLVTVSS;
or (SEQ ID NO 169)
EVQLVESGGVVVQPGGSLRLSCAASGFTFDDYTMHWVRQAPGKGLEWVSD

ISWSGGSIYYADSVKGRFTISRDNSKNSLYLQMNSLRTEDTALYYCAKDH

RGYGDYEGGGFDYWGRGTLVTVSS;

with 0-10, preferably 0-5 amino acid variations, insertions, deletions, substitutions, additions or a combination thereof at one or more positions other than the CDRs.

The antigen-binding protein, preferably an antibody in a treatment as indicated herein above preferably comprises a heavy chain-light chain (H/L) combination that binds a tumor-antigen.

The antibody is preferably a human or humanized antibody. Preferably the antibody comprises two different immunoglobulin heavy chains with compatible heterodimerization domains. Said compatible heterodimerization domains are preferably compatible immunoglobulin heavy chain CH3 heterodimerization domains. Said bispecific antibody is preferably an IgG antibody with a mutant CH2 and/or lower hinge domain such for immuno-oncology applications that interaction of the bispecific or multispecific IgG antibody to a Fc-gamma receptor is reduced. The mutant CH2 and/or lower hinge domain preferably comprise an amino substitution at position 235 and/or 236 (according to EU numbering), preferably an L235G and/or G236R substitution. Alternatively, for auto-immune applications, the interaction of the bispecific or multispecific to a Fc-gamma receptor is enhanced or ADCC and CDC is enhanced by modification to the CH2 and/or CH3 domain. For example, by engineering Fc regions (through introducing amino acid substitutions) that bind to activating receptors with greater selectivity, antibodies can be created that have greater capability to mediate cytotoxic activities desired by an anti-cancer Mab or CD3 targeting binding arm for the treatment of auto-immune related maladies. For instance, a reported technique for enhancing ADCC of an antibody is afucosylation. (See for instance Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489). Further provided is therefore a bispecific antibody according to the invention, which is afucosylated. Alternatively, or additionally, multiple other strategies are reported to be used to achieve ADCC enhancement, for instance including glycoengineering (Kyowa Hakko/Biowa, GlycArt (Roche) and Eureka Therapeutics) and mutagenesis (Xencor and Macrogenics), all of which seek to improve Fc binding to low-affinity activating FcγRIIIa, and/or to reduce binding to the low affinity inhibitory FcγRIIIb.

The antibody preferably comprises a common light chain.

The invention further provides a bispecific antigen-binding protein, preferably a bispecific antibody, that comprises a variable domain that binds a tumor-antigen and a variable domain that binds human CD3 wherein the variable domains each comprise a different heavy chain variable region and a common light chain variable region and wherein the heavy chain variable region of the variable domain that binds human CD3 comprises a CDR1, CDR2 and CDR3 comprising the amino acid sequence:

CDR1:
(SEQ ID NO 42)
SFGIS

CDR2:
(SEQ ID NO 43)
GFIPVLGTANYAQKFQG

CDR3:
(SEQ ID NO 44)
RGNWNPFDP;

or comprising the amino acid sequence:

CDR1:
(SEQ ID NO 6)
$SX_1TFTIS$;

CDR2:
(SEQ ID NO 7)
$GIIPX_2FGTITYAQKFQG$;

CDR3:
(SEQ ID NO 44)
RGNWNPFDP;

wherein $X_1$=K or R;

$X_2$=L or I.

In a preferred embodiment $X_1$=K; and $X_2$=L. In another preferred embodiment $X_1$=R; and $X_2$=I.

The invention further provides a bispecific antigen-binding protein, preferably a bispecific antibody, that comprises a variable domain that binds a tumor-antigen and a variable domain that binds human CD3 wherein the variable domains each comprise a different heavy chain variable region and a common light chain variable region and wherein the heavy chain variable region of the variable domain that binds human CD3 comprises a CDR1, CDR2 and CDR3 comprising the amino acid sequence:

CDR1:
(SEQ ID NO 84)
SKTLTIS;

CDR2:
(SEQ ID NO 85)
GIIPIFGSITYAQKFQD;

CDR3:
(SEQ ID NO 44)
RGNWNPFDP;

or comprising the amino acid sequence:

CDR1:
(SEQ ID NO 100)
GSGIS;

CDR2:
(SEQ ID NO 101)
GFIPFFGSANYAQKFRD;

CDR3:
(SEQ ID NO 8)
$RGNWNPX_{13}DP$;

wherein $X_{13}$=or L or F.

The invention further provides a bispecific antigen-binding protein, preferably a bispecific antibody, that comprises a variable domain that binds a tumor-antigen and a variable domain that binds human CD3 wherein the variable domains each comprise a different heavy chain variable region and a common light chain variable region and wherein the heavy chain variable region of the variable domain that binds human CD3 comprises the amino acid sequence (SEQ ID NO 45)
EVQLVQSGAEVKKPGSSVKVSCKASGGTFRSFGISWVRQAPGQGLEWMGG
FIPVLGTANYAQKFQGRVTIIADKSTNTAYMELSSLRSEDTAVYYCARRG
NWNPFDPWGQGTLVTVSS;

(SEQ ID NO 54)
QVQLVQSGAEVKKPGSSVKVSCKASGDAFKSKTFTISWVRQAPGQGLEWL
GGIIPLFGTITYAQKFQGRVTITADKSTNTAFMELSSLRSEDTAMYYCTR
RGNWNPFDPWGQGTLVTVSS;

(SEQ ID NO 63)
EVQLVQSGSELKKPGSSVKVSCKASGVTFNSRTFTISWVRQAPGQGLEWL
GSIIPIFGTITYAQKFQGRVTITADKSTSTAFMELTSLRSEDTAIYYCTR
RGNWNPFDPWGQGTLVTVSS;

(SEQ ID NO 71)
QVQLVQSGAEVKKPGSSVKVSCKASGGTFRGSGISWVRQAPGQGLEWVGG
FIPFFGSANYAQKFRDRVTITADKSATTAYMELSSLRSEDTAIYYCAKRG
NWNPLDPWGQGTLVTVSS;

(SEQ ID NO 87)
QVQLVQSGAEVKKPGSSVKVSCKASGVTFKSKTLTISWVRQAPGQGLEWL
GGIIPIFGSITYAQKFQDRVSITADKSTNTAYLELNSLRSEDTAIYYCAR
RGNWNPFDPWGQGTLVTVSS;
or (SEQ ID NO 103)
EVQLVQSGAEVKKPGSSVKVSCKASGGTFRGSGISWVRQAPGQGLEWVGG
FIPFFGSANYAQKFRDRVTITADKSATTAYMELSSLRSEDTAIYYCAKRG
NWNPFDPWGQGTLVTVSS with 0-10, preferably 0-5 amino acid variations, insertions, deletions, substitutions, additions or a combination thereof at one or more positions other than the CDRs.

The invention further provides a bispecific antigen-binding protein, preferably a bispecific antibody, that comprises a variable domain that binds a tumor-antigen and a variable domain that binds human CD3 wherein the variable domains each comprise a different heavy chain variable region and a common light chain variable region and wherein the heavy chain variable region of the variable domain that binds human CD3 comprises a CDR1, CDR2 and CDR3 comprising the amino acid sequence:

CDR1:
(SEQ ID NO 9)
R$X_3$WIG;

-continued

CDR2:
(SEQ ID NO 200)
IIYPGDSDTRYSPSFQG;

CDR3:
(SEQ ID NO 10)
$X_4$IRYF$X_5$WSEDYHYY$X_6$DV;

wherein
$X_3$=F or Y;
$X_4$=H or N;
$X_5$=D or V;
$X_6$=L or M.

In one embodiment $X_3$=F; $X_4$=H; $X_5$=D; and $X_6$=L. In a further embodiment $X_3$=Y; $X_4$=N; $X_5$=V; and $X_6$=M.

The invention further provides a bispecific antigen-binding protein, preferably a bispecific antibody, that comprises a variable domain that binds a tumor-antigen and a variable domain that binds human CD3 wherein the variable domains each comprise a different heavy chain variable region and a common light chain variable region and wherein the heavy chain variable region of the variable domain that binds human CD3 comprises the amino acid sequence (SEQ ID NO 298)
EVQLVQSGAEVKKPGESLKISCKGSGYSFTRFWIGWVRQMPGKGLEWMGI
IYPGDSDTRYSPSFQGQVTISADKSTSTAYLQWSSLKASDTGMYYCVRHI
RYFDWSEDYHYYLDVWGKGTTVTVSS;
or (SEQ ID NO 211)
EVQLVESGAEVKKPGESLKISCKGSGYSFTRYWIGWVRQMPGKGLEWMGI
IYPGDSDTRYSPSFQGQVTISADKSISTAYLQWSSLKASDTAMYYCVRNI
RYFVWSEDYHYYMDVWGKGTTVTVSS;

with 0-10, preferably 0-5 amino acid variations, insertions, deletions, substitutions, additions or a combination thereof at one or more positions other than the CDRs.

The invention further provides a bispecific antigen-binding protein, preferably a bispecific antibody, that comprises a variable domain that binds a tumor-antigen and a variable domain that binds human CD3 wherein the variable domains each comprise a different heavy chain variable region and a common light chain variable region and wherein the heavy chain variable region of the variable domain that binds human CD3 comprises a CDR1, CDR2 and CDR3 comprising the amino acid sequence:

CDR1:
(SEQ ID NO 117)
SYALS;

CDR2:
(SEQ ID NO 118)
GISGSGRTTWYADSVKG;

CDR3:
(SEQ ID NO 119)
DGGYSYGPYWYFDL.

The invention further provides a bispecific antigen-binding protein, preferably a bispecific antibody, that comprises a variable domain that binds a tumor-antigen and a variable domain that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
(SEQ ID NO 117)
SYALS;

CDR2:
(SEQ ID NO 126)
AISGSGRTTWYADSVKG;

CDR3:
(SEQ ID NO 127)
DGGYTYGPYWYFDL.

The invention further provides a bispecific antigen-binding protein, preferably a bispecific antibody, that comprises a variable domain that binds a tumor-antigen and a variable domain that binds human CD3 wherein the variable domains each comprise a different heavy chain variable region and a common light chain variable region and wherein the heavy chain variable region of the variable domain that binds human CD3 comprises the amino acid sequence (SEQ ID NO 120)
QVQLVQSGGGLVQPGGSLRLSCATSGFKFSSYALSWVRQAPGKGLEWVSG

ISGSGRTTWYADSVKGRFTISRDNSKNTLYLQMNSLRAEDTAVYYCARDG

GYSYGPYWYFDLWGRGTLVTVSS;

or (SEQ ID NO 128)
QVQLVESGGGLVQPGGSLRLSCATSGFTFISYALSWVRQAPGKGLEWVSA

ISGSGRTTWYADSVKGRFTISRDNSKNTLFLQMNSLRAEDTAVYYCARDG

GYTYGPYWYFDLWGRGTLVTVSS with 0-10, preferably 0-5 amino acid variations, insertions, deletions, substitutions, additions or a combination thereof at one or more positions other than the CDRs.

The invention further provides a bispecific antigen-binding protein, preferably a bispecific antibody, that comprises a variable domain that binds a tumor-antigen and a variable domain that binds human CD3 wherein the variable domains each comprise a different heavy chain variable region and a common light chain variable region and wherein the heavy chain variable region of the variable domain that binds human CD3 comprises a CDR1, CDR2 and CDR3 comprising the amino acid sequence:

CDR1:
(SEQ ID NO 142)
DYTMH;

CDR2:
(SEQ ID NO 143)
DISWSSGSIGYADSVKG;

CDR3:
(SEQ ID NO 144)
DHRGYGDYEGGGFDY.

The invention further provides a bispecific antigen-binding protein, preferably a bispecific antibody, that comprises a variable domain that binds a tumor-antigen and a variable domain that binds human CD3 comprising an antibody variable domain comprising a heavy chain variable region and a light chain variable region wherein the heavy chain variable region comprises a CDR1, CDR2 and CDR3 comprising the amino acid sequence:

CDR1:
(SEQ ID NO 142)
DYTMH;

CDR2:
(SEQ ID NO 11)
DISWS$X_7$G$X_8X_9X_{10}$YADSVKG;

CDR3:
(SEQ ID NO 12)
DH$X_{11}$GYGDYEGGGFD$X_{12}$;

wherein $X_7$=S or G;

$X_8$=S or T;

$X_9$=I or T;

$X_{10}$=G or Y;

$X_{11}$=R or M;

$X_{12}$=H or Y, preferably $X_7$, $X_8$, $X_9$ and $X_{10}$ are S, S, I and G or G, S, I and Y or S, T, T and G, and preferably $X_{11}$ and $X_{12}$ are R and H, or R and Y, or M and Y, more preferably $X_7$, $X_8$, $X_9$, $X_{10}$, $X_{11}$ and $X_{12}$ are S, S, I, G, R and H or G, S, I, Y, R and Y or S, T, T, G, M and Y, or, in other words, preferably $X_7$, $X_8$, $X_9$ and $X_{10}$ are S, S, I and G, and $X_{11}$ and $X_{12}$ are R and H; or $X_7$, $X_8$, $X_9$ and $X_{10}$ are G, S, I and Y, and $X_{11}$ and $X_{12}$ are R and Y; or $X_7$, $X_8$, $X_9$ and $X_{10}$ are S, T, T and G, and $X_{11}$ and $X_{12}$ are M and Y.

The invention further provides a bispecific antigen-binding protein, preferably a bispecific antibody, that comprises a variable domain that binds a tumor-antigen and a variable domain that binds human CD3 wherein the variable domains each comprise a different heavy chain variable region and a common light chain variable region and wherein the heavy chain variable region of the variable domain that binds human CD3 comprises the amino acid sequence (SEQ ID NO 145)
EVQLVESGGGLVQPGRSLRLSCATSGFNFDDYTMHWVRQAPGKGLEWVSDI

SWSSGSIGYADSVKGRFTISRDNAKNSLWLQMNSLRTEDTALYFCAKDHRG

YGDYEGGGFDYWGQGTLVTVSS;

(SEQ ID NO 153)
EVQLVESGGGLVQPGRSLRLSCATSGFTFDDYTMHWVRQAPGKGLEWVSDI

SWSSGSIGYADSVKGRFTISRDNAKNSLYLQMNSLRAEDTALYFCAKDHRG

YGDYEGGGFDHWGQGTLVTVSS;

(SEQ ID NO 185)
EVQLVESGGGLVQPGRSLRLSCVTSGFTFDDYTMHWVRQAPGKGLEWVSDI

SWSSGTTGYADSVKGRFTISRDNAKDSLYLQMNSLRTEDTALYYCAKDHMG

YGDYEGGGFDYWGQGTLVTVSS;

or (SEQ ID NO 169)
EVQLVESGGVVVQPGGSLRLSCAASGFTFDDYTMHWVRQAPGKGLEWVSDI

SWSGGSIYYADSVKGRFTISRDNSKNSLYLQMNSLRTEDTALYYCAKDHRG

YGDYEGGGFDYWGRGTLVTVSS;

with 0-10, preferably 0-5 amino acid variations, insertions, deletions, substitutions, additions or a combination thereof at one or more positions other than the CDRs.

In one embodiment the heavy chain variable region of the variable domain that binds a tumor antigen preferably comprises the amino acid sequence of MF8233 (EGFR) QVQLVQSGAEVKKPGASVKVSCKASGYTFTSY-GISWVRQAPGQGLEWMGWISAYNANTNYA QKLQGRVTMTTDTSTSTAYMELRSLRSDDTAVYY-CAKDRHWHWWWLDAFDYWGQGTLVTVSS (SEQ ID NO 247)

with 0-10, preferably 0-5 amino acid variations, insertions, deletions, substitutions, additions or a combination thereof at one or more positions other than the CDR.

In another embodiment the heavy chain variable region of the variable domain that binds a tumor antigen preferably comprises the amino acid sequence of

```
MF4327(CLEC12A)
                                  (SEQ ID NO 293)
QVQLVQSGAEVKKPGASVKVSCKASGYTFTSYYMHWVRQAPGQGLEWMGI

INPSGGSTSYAQKFQGRVTMTRDTSTSTVYMELSSLRSEDTAVYYCAKGT

TGDWFDYWGQGTLVTVSS
```

with 0-10, preferably 0-5 amino acid variations, insertions, deletions, substitutions, additions or a combination thereof at one or more positions other than the CDRs.

The invention further provides an antibody of the invention or a derivative thereof or a pharmaceutical composition of the invention, for use in the treatment of a subject in need thereof. For the treatment of a subject that has or is at risk of having a tumor it is preferred that the antibody is a bispecific antibody of the invention. Preferably wherein the CD3 binding antibody comprises a heavy/light chain combination that binds a tumor antigen.

Provided are CD3/tumor antigen bispecific antibodies and pharmaceutical compositions comprising such bispecific antibodies for use in the treatment of solid or hematological tumors. Preferred solid tumors are of epithelial origin; gynecological cancer such as ovarian and endometrial tumors; prostate cancer, brain cancer or any other solid tumor.

Provided is also a CD3/tumor antigen bispecific antibody of the invention or a derivative thereof or pharmaceutical compositions comprising such bispecific antibody or derivative thereof for use in the treatment of various leukemias and pre-leukemic diseases of myeloid origin but also B cell lymphomas. Diseases that can be treated according to the invention include myeloid leukemias or pre-leukemic diseases such as acute myeloid leukemia (AML), myelodysplastic syndrome (MDS) and chronic myelogenous leukemia (CML), and Hodgkin's lymphomas and most non-Hodgkin's lymphomas. Also B-ALL; T-ALL, mantle cell lymphoma are also preferred targets for treatment with antibody of the invention. Thus the invention provides a bispecific full length IgG antibody according to the invention for use as a pharmaceutical in the treatment of myelodysplastic syndrome (MDS), chronic myelogenous leukemia (CML), multiple myeloma (MM) or preferably acute myeloid leukemia (AML). Also provided is a use of a bispecific IgG antibody according to the invention in the preparation of a medicament for the treatment or prevention of MDS, CML, MM or preferably AML.

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred.

Approximately 30.000 patients are diagnosed each year with AML in Europe and US. The majority of these patients are 60 years of age or older. Older age is a major negative determinant of outcome in AML and long term survival (at 5 years) of intensively treated older AML patients is approximately 10%. In almost all patients that have achieved remission upon induction chemotherapy, disease progression is observed within 3 years. Current post remission treatment has shown limited, if any, value in older patients with AML. Therefore, a significant load of residual resistant leukemia remains, and the surviving subpopulation of drug resistant leukemic cells rapidly generates recurrence. Novel types of drugs with entirely different modes of action are needed to target these chemotherapy non responsive AML tumor cells in efforts to induce and sustain complete remissions. Although complete remission (CR) can be achieved with a number of intensive chemotherapy combinations in more than 50% of elderly AML patients and around 80% in younger patients, advancements of response or survival have remained a major investigational challenge. In a recently published network meta-analysis of 65 randomized clinical trials (15.110 patients) in older patients with AML most of the amended investigational induction regimens have similar or even worse efficacy profiles as compared to the conventional 3+7 induction regimen with daunorubicin and cytarabine. This standard treatment of AML is associated with high morbidity and even mortality. The majority of the patients in CR relapse due to remaining leukemic stem cells after chemotherapy. Further dose intensification is limited due to unacceptable toxicity. An urgent need for new treatment modalities preferably with less toxicity is thus emerging especially in elderly patients with AML.

Treatment of chemotherapy unresponsive AML could be achieved by redirecting T cells from the patient's own immune system to AML tumor cells and subsequent tumor target-specific activation of T cells using a bispecific antibody. This process is also known as a so-called "T-cell engaging approach". In this manner, the patients' immune system is strengthened and retargeted to attack and eradicate the AML tumor cells. For example, CD3×CLEC12A bispecific IgG antibodies efficiently redirect T cells towards the AML tumor cells, thereby inducing AML tumor cell lysis.

Figure 1:
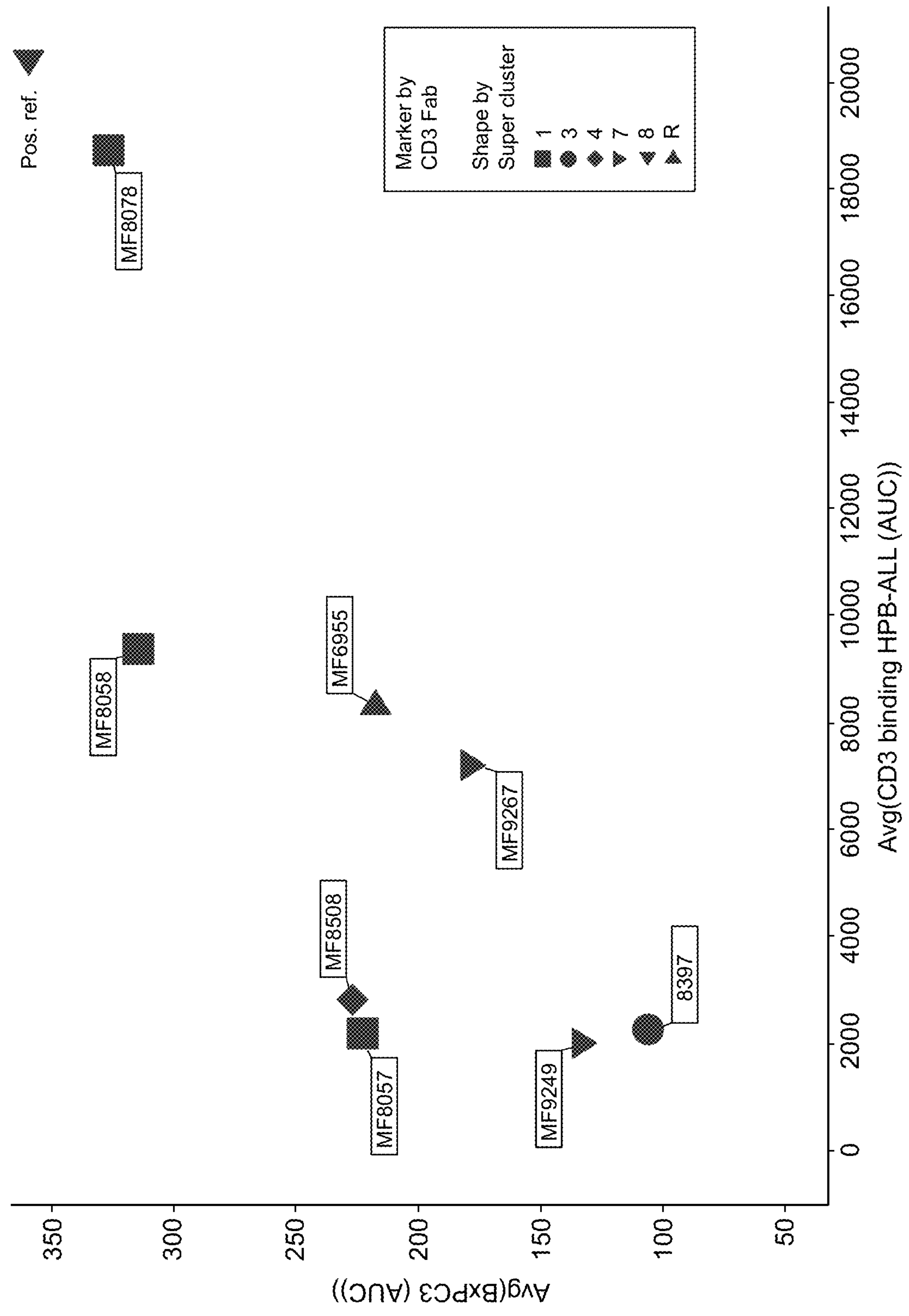
FIG. 1
Figure 2:
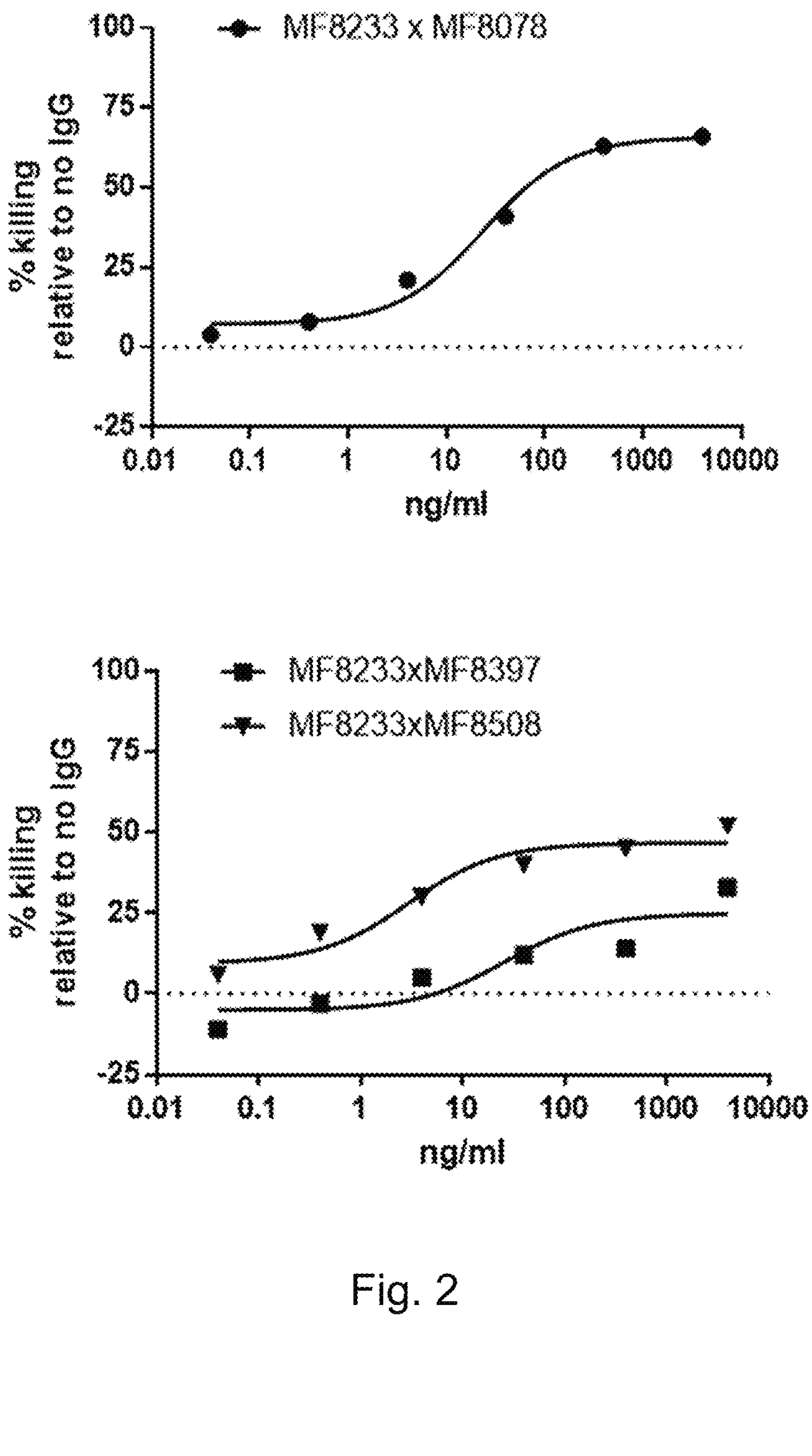

Evaluation of functional activity: T cell cytotoxicity assay with BxPC3 target cells upon treatment with EGFRxCD3 bispecific antibodies. Each bispecific antibody comprises a CD3 binding domain comprised of a heavy chain variable region designated by MF number, and an EGFR binding domain comprising a heavy chain variable region MF8233. These variable regions are paired with a common light chain to form an EGFRxCD3 bispecific antibody. Affinity (HPB-ALL binding) versus BxPC3 lysis. Certain antibodies of the invention exhibit a relative low level of binding to HPB-ALL cells indicating that the CD3 binding domain of the antibody binds human CD3 with a comparatively low affinity. It is clear that the relative lower affinity does not necessarily prohibit tumor antigen mediated T cell cytotoxicity of BxPC3 cells (BxPC3 lysis, vertical axis). The bispecific antibodies MF8233 x MF8508 and MF8233 x MF8057 can efficiently lyse BxPC3 cells whereas the bispecific antibodies MF8233 x MF8397 and MF8233 x MF9249 do not do so efficiently while having similar binding. Further, a comparison of the bispecific antibody MF8233 x MF6955 binds HPB-ALL (i.e. human CD3) with a higher affinity but does not lyse BxPC3 cells more efficiently than the bispecific antibodies MF8233 x MF8508 and MF8233 x MF8057 that bind CD3 to a lesser extent. MF6955 is a heavy chain variable region combined with a common light chain and used as comparator sequences, and corresponds to H1H7232B (1129) VH, in US2014/0088295 A1. The comparator bispecific antibody having MF6955 and the same EGFR binding domain separately has a higher affinity for human CD3 than MF9267, and exhibits more efficient killing than MF9267. In contrast, other antibodies incorporating a CD3 binding domain of the invention, such as MF8058, have approximately the same binding activity as MF6955, yet demonstrate more efficient killing of BxPC3 cells, such as MF8233 x MF8058. Other bispecific antibodies comprising a binding domain of the invention capable of binding CD3 demonstrate relative high binding and more efficient killing, such as MF8233 x MF8078, which are useful for particular applications described herein. Whereas other bispecific antibodies comprising a binding domain of the invention capable of binding CD3 demonstrate relative low affinity and low killing, such as MF8233 x MF9249 and MF8233 x MF8397, which are useful for alternative applications described herein.

FIG. 2

Antibody titration curves indicating their capacity to induce T cell mediated % killing of BxPC3 target cells compared to no antibody control. Curves for the antibodies MF8233 x MF8078, MF8233 x MF8397; and MF8233 x MF8508 are shown.

FIG. 3

Summary of the titration curve data of various bispecific antibodies in T cell cytotoxicity with BxPC3 target cells. The CD3 Fab column indicates the MF number of the CD3 binding arm. The EGFR arm has the indicated MF8233 number. The column indicates the supercluster numbers to set out variants based on the same VH gene segment. The column indicating CD3 binding reflect the results of the HBP-ALL binding experiment.

The results of two independent cytotoxicity assays to determine capacity to induce T cell mediated lysis of BxPC3 target cells are shown.

FIG. 4

T cell activation in T cell cytotoxicity assay with BxPC3 target cells on CD8+ T cells with the expression. Antibody titration curves of various supercluster numbers, which set out variant CD3 binding domains. The other arm of the bispecific antibody has the heavy chain binding domain of MF8233. For comparison the bispecific antibodies MF8233 x MF6955 and MF8233 x MF6964 were tested as well, where MF6955 and MF6964 are heavy chain variable regions combined with a common light chain and used as comparator sequences, and correspond to H1H7232B (1129) VH and HH7241B (1145) respectively, in US2014/0088295 A1

FIG. 5

Summary of the titration curve data of various antibodies in T cell activation T cell cytotoxicity assay with BxPC3 target cells. The MF nr. column indicates the MF number of the CD3 binding domain. The EGFR binding domain has the indicated MF8233 number. The supercluster information of the various CD3 binding domain sequences is indicated in column "supercluster"; The column indicating CD3 affinity reflects the results of the HBP-ALL binding experiment.

The results of CD4+ and CD8+ cells are shown for the markers CD69 and CD25. The indicated bispecific antibodies are examples from a larger pool of bispecific antibodies.

FIG. 6

Evaluation of functional activity: T cell cytotoxicity assay with BxPC3 target cells. Affinity (HPB-ALL binding) versus CD8+ T cell activation measured by CD69 expression. Certain antibodies of the invention exhibit a relative low level of binding to HPB-ALL cells indicating that the CD3 binding domain of the antibody binds human CD3 with a relative low affinity. Such affinity does not necessarily prohibit tumor antigen mediated T-cell activation as exemplified by the results of the CD8 positive CD69 activation analysis. The bispecific antibodies MF8233 x MF8508 and MF8233 x MF8057 can efficiently activate T cells whereas the bispecific antibodies MF8233 x MF8397 and MF8233 x MF9249 do not do so as efficiently. Certain CD3 binding domains that do not bind efficiently to these cells also do not activate T cells (see lower left corner). Whereas other CD3 binding domains MF8508 and MF8057, which bind HPB-ALL cells less than comparator CD3 binding domain MF6955, for example, activate T cells to a similar degree. Other bispecific antibodies comprising a binding domain of the invention capable of binding CD3 demonstrate relative high binding and high levels of activation, such as MF8078, which has use in particular applications described herein. Whereas other bispecific antibodies comprising a binding domain of the invention capable of binding CD3 demonstrates relative low affinity and low activation, such as MF9249 and MF8397, which are useful for alternative applications described herein.

FIG. 7

Evaluation of functional activity: T cell cytotoxicity assay with HCT116 target cells. Affinity (HPB-ALL binding) versus HCT-116 lysis.

Certain bispecific antibodies of the invention exhibit a low level of binding to HPB-ALL cells indicating that the CD3 binding domain of the antibody binds human CD3 with a comparatively low affinity. It is clear that the low affinity does not necessarily prohibit tumor antigen mediated cell lysis of HCT-116 cells (vertical axis). The bispecific antibodies MF8233 x MF8508 and MF8233 x MF8057 can efficiently lyse HCT-116 cells whereas the bispecific antibodies MF8233 x MF8397 and MF8233 x MF9249 do not do so efficiently. For comparison the bispecific antibodies MF8233 x MF6955 and MF8233 x MF6964 bind HPB-ALL (i.e. human CD3) with a higher affinity than, for example, MF8233 x MF8508, MF8233 x MF8057 and MF8233 x MF9267, but do not lyse HCT-116 cells more efficiently than MF8233 x MF8508 or MF8233 x MF9267, or significantly more than MF8233 x MF8057 relative to the difference in binding, in a test as presented here. Another bispecific antibodies comprising a binding domain of the invention capable of binding CD3 demonstrates relative high binding and high levels of killing, such as MF8078, which has use in particular applications described herein. Whereas other bispecific antibodies comprising a binding domain of the invention capable of binding CD3 demonstrate relative low affinity and low killing, such as MF9249 and MF8397, which are useful for alternative applications described herein.

FIG. 8

Antibody titration curves in T cell cytotoxicity assay with HCT-116 target cells indicating the % killing of HCT-116 cells compared to no antibody control. Curves for various bispecific antibodies are shown.

FIG. 9

Summary of the titration curve data of various antibodies in T cell cytotoxicity assay with HCT-116 target cells. The CD3 Fab column indicates the MF number of the CD3 binding domain. The EGFR binding domain has the indicated MF8233 number. The column indicates the supercluster numbers to set out variants based on the same VH gene segment. The column indicating CD3 binding reflect the results of the HBP-ALL binding experiment.

Percentage lysis of HCT-116 cells and EC50 values for lysis (ng/mL) are indicated in the next columns. The indicated bispecific antibodies are examples from a larger pool of bispecific antibodies.

FIG. 10

Figure 10:
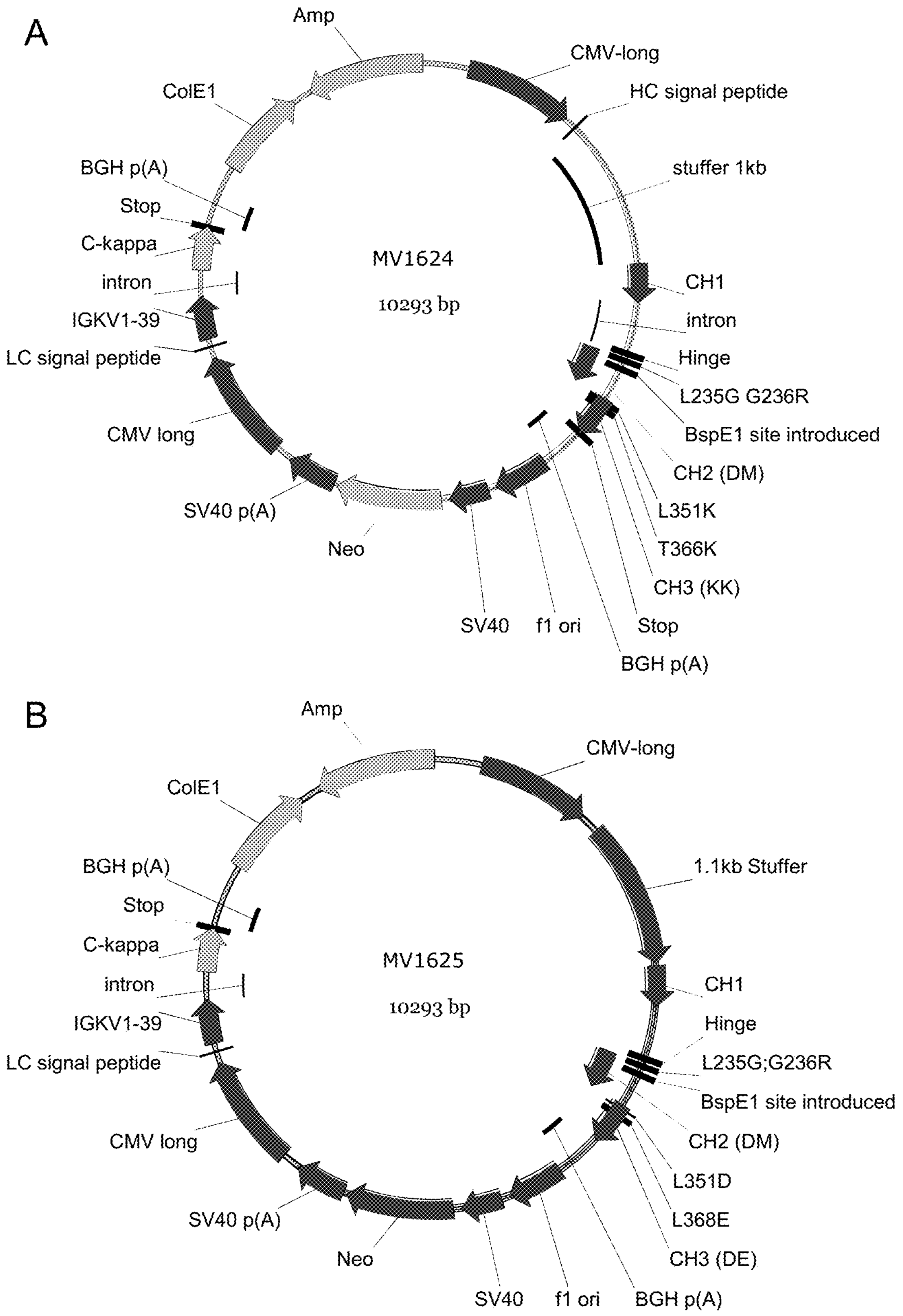

FIGS. 10*a* and 10*b* set out a schematic diagram of the MV1624 expression vector and the MV1625 expression vector.

FIG. 11

Common light chain used in mono- and bispecific IgG. FIG. 11A: Common light chain amino acid sequence. FIG. 11B: Common light chain variable domain DNA sequence and translation (IGKV1-39/jk1). FIG. 11C: Common light chain constant region DNA sequence and translation. FIG. 11D: IGKV1-39/jk5 common light chain variable domain translation. FIG. 11E: V-region IGKV1-39A; FIG. 11F: CDR1, CDR2 and CDR3 of the common light chain.

FIG. 12

IgG heavy chains for the generation of bispecific molecules. FIG. 12A: CH1 region. FIG. 12B: hinge region. FIG. 12C: CH2 region. FIG. 12D: CH2 containing L235G and G236R silencing substitutions. FIG. 12E: CH3 domain containing substitutions L351K and T366K (KK). FIG. 12F; CH3 domain containing substitutions L351D and L368E (DE).

FIG. 13

Sequences of various DNA encoding and amino acid sequences of the heavy chain variable regions and parts thereof described in the specification.

FIG. 14

Characterization of additional clones from supercluster 1 in comparison with clones MF8057 and MF8058. A: Binding of selected MF clones with HPB-ALL human cells expressing a human CD3-TCR complex in a FACS assay. B: T-cell cytotoxicity assay with HCT-116 cells indicating the % killing of HCT-116 cells. C-E: Quantification of activation markers CD25 and CD69 in FACS indicating T-cell activation. F-G: Cytokine production in the supernatants from the cytotoxicity assay.

FIG. 15

Characterization of clones from supercluster 4. A: Binding of the selected MF clones to HPB-ALL human cells. B: T cell cytotoxicity assay with BxPC3 cells indicating % killing of BXP3 cells. C-E: Cytokine production in the supernatants from the cytotoxicity assay.

FIG. 16

Evaluation of CD3 functional activity. A: Affinity (HPB-ALL) on X-axis versus HCT-116 Lysis on Y-axis for additional clones from supercluster 1 (MF8048, MF8101, MF8056), supercluster 3 (MF8562) and supercluster 4 (MF8998). B: Antibodies belonging to supercluster 1 and supercluster 4 which show similar activity in cytotoxicity assay and different binding affinity. C: Antibodies belonging to supercluster 1 and supercluster 3 which exhibit similar binding affinity and differential lysis activity.

FIG. 17

Activity of CD3 Fabs MF8998 and MF8058 in bispecific CD3xEGFR format.

FIG. 18

FACS binding data of a large panel of IgGs specific for CD3. For antibodies MF5196, MF6955 and MF6964, binding was determined by BIAcore™ on CD3δε-Fc antigen, whereas FACS binding data to HPB-ALL cells is shown for the remainder of the clones.

FIG. 19

Nucleotide sequence of human CLEC12A.

FIG. 20

Amino acid sequences of the human CD3γ-, δ-, ε- and ζ-chain.

The following Examples illustrate the invention:

EXAMPLES

Cell Lines

BxPC3 human pancreatic cancer cell line.

HCT-116 human colon carcinoma cell line.

Immunization of Memo® Mice with CD3

For generation of human antibodies binding to CD3, mice transgenic for the human common light chain and for a human heavy chain (HC) minilocus (comprising a selection of human V gene segments, all human Ds and all human Js) (see WO2009/157771 incorporated herein by reference) were immunized with TCR/CD3 containing lipoparticles (Intergral Molecular). These mice are referred to as 'MeMo®' mice. For specific heavy chain variable regions, or trivalent multimers having the sequences disclosed herein, they can be produced by any means known to persons of ordinary skill in the art.

MeMo® mice were immunized with Hek293T-derived human 5D5M TCR/CD3 containing lipoparticles, followed by human T-cells for the generation of an anti-TCR/CDR3 immune response and anti-TCR/CD3 antibody panel generation.

Lipoparticles concentrate conformationally intact membrane proteins directly from the cell surface, permitting these complex proteins to be manipulated as soluble, high-concentration proteins for antibody immunization and screening The lipoparticles used in the present study for immunisation contain the 5D5M TCRαβ combination. Vectors comprising the 5D5M TCRαβ combination were synthesized, cloned and used to generate lipoparticles containing this TCR/CD3 combination by transient transfection into HEK293T cells (Intergral Molecular).

```
5D5M TCRα
                                     (SEQ ID NO 13)
MWGVFLLYVSMKMGGTTGQNIDQPTEMTATEGAIVQINCTYQTSGFNGLF

WYQQHAGEAPTFLSYNVLDGLEEKGRFSSFLSRSKGYSYLLLKELQMKDS

ASYLCAVMDSNYQLIWGAGTKLIIKPDIQNPDPAVYQLRDSKSSDKSVCL

FTDFDSQTNVSQSKDSDVYITDKTVLDMRSMDFKSNSAVAWSNKSDFACA

NAFNNSIIPEDTFFPSPESSCDVKLVEKSFETDTNLNFQNLSVIGFRILL

LKVAGFNLLMTLRLWSS

5D5M TCRβ
                                     (SEQ ID NO 14)
MRIRLLCCVAFSLLWAGPVIAGITQAPTSQILAAGRRMTLRCTQDMRHNA

MYWYRQDLGLGLRLIHYSNTAGTTGKGEVPDGYSVSRANTDDFPLTLASA
```

-continued

VPSQTSVYFCASSEAGGNTGELFFGEGSRLTVLEDLNKVFPPEVAVFEPS

EAEISHTQKATLVCLATGFFPDHVELSWWVNGKEVHSGVSTDPQPLKEQP

ALNDSRYCLSSRLRVSATFWQNPRNHFRCQVQFYGLSENDEWTQDRAKPV

TQIVSAEAWGRADCGFTSVSYQQGVLSATILYEILLGKATLYAVLVSALV

LMAMVKRKDF

MeMo® mice were used for immunizations using TCR/CD3 lipoparticles and primary human T cells.

The immunization schedule contains points on day 35, 56, 77 and 98, where the antigen-specific Ig serum titer was determined by ELISA using QTG-derived 3SDX TCR/CD3 positive and -negative lipoparticles using anti mouse IgG detection and by ELISA using CD3c5E-Fc fusion protein as a positive control. The reactivity was observed in sera drawn at day 35 will determine which mice developed a relevant anti-TCR/CD3 response.

For all immunized mice, lymphoid material for antibody discovery was collected and stored when:

Titers are 1/300 for human TCR/CD3 (in ELISA using lipoparticles), or:

Titers are <1/300 and >1/100 for human TCR/CD3 and did not increase during the last booster immunization.

Priming Immunisation Using Lipoparticles

To prime the humoral immune response in the MeMo® mice for TCR/CD3, lipoparticles containing the human 5D5M TCRαβ combination was used for immunization. Lipoparticles were used together with Gerbu adjuvant for the first and second injection.

Booster Immunizations Using Polyclonal T-Cells

Mice were immunised by sub-cutaneous injection of cell suspension. The first booster immunisations (day 28) comprised a mix of cells in PBS with adjuvant and all subsequent injections are only composed of cells in PBS. Mice that have developed at day 35 serum IgG titers of 1/300 against human TCR/CD3 (determined by ELISA using lipoparticles) received additional injections with cells on days 42, 43 and 44. Mice that failed to meet these criteria receive booster immunisations (day 42 and 49) with cells. All subsequent immunisations are given as sub-cutaneous injections of cells in PBS. After the final immunisation, mice are sacrificed, bled for serum and the spleen and left inguinal lymph nodes are collected.

Screening Sera from Immunised Mice in ELISA

Interim serum IgG titers were screened by ELISA using TCR/CD3-containing lipoparticles and 'null' lipoparticles. Serum IgG titers were determined using anti-mouse IgG staining, as this staining was shown to be the most sensitive.

Generation of 'Immune' Phage Antibody Repertoires by RT-PCR Cloning of VH Genes

From successfully immunized mice, the inguinal lymph nodes were used for the construction of 'immune' phage antibody repertoires. RNA was extracted from the lymphoid tissue using Trizol LS and 1 μg of total RNA was used in a RT reaction using an IgG-CH1 specific primer. The resulting cDNA was then used to amplify the polyclonal pool of VH-encoding cDNA using in-house developed VH-specific primers essentially as described in Marks et al. (J Mol Biol. 1991 Dec. 5; 222(3):581-97). The resulting PCR product was then cloned in a phagemid vector for the display of Fab fragments on phage, as described in de Haard et al. (J Biol Chem. 1999 Jun. 25; 274(26):18218-30) with the exception that the light chain was the same for every antibody and was encoded by the vector. After ligation, the phagemids were used to transform *E. coli* TG1 bacteria and transformed bacteria were plated onto LB-agar plates containing ampicillin and glucose. All phage libraries contained >10e6 transformants and had an insert frequency of >80%. Bacteria were harvested after overnight growth and used to prepare phage according to established protocols (de Haard et al., J Biol Chem. 1999 Jun. 25; 274(26):18218-30).

Selection of Phage Carrying Fab Fragments Specifically Binding to Human CD3.

Phage libraries were rescued according to standardized procedures (J Mol Biol. 1991 Dec. 5; 222(3):581-97; J Biol Chem. 1999 Jun. 25; 274(26):18218-30) and phage were selected with one or more rounds of selection of the immune phage antibody repertoires. In the first round, recombinant CD3 protein was coated onto the wells of a Maxisorp™ ELISA plate or to a NUNC immuno-tube, whereas in the second round, either recombinant CD3 protein or cells over-expressing the human CD3 protein were used. The Maxisorp™ ELISA plates or immuno-tubes were blocked with 4% ELK. Phage antibody libraries were also blocked with 4% ELK and excess of human IgG to deplete for Fc region binders prior to the addition of the phage library to the coated antigen.

Incubation with the phage library with the coated protein was performed for 2 hrs at room temperature under shaking conditions. Plates or tubes were then washed with 0.05% Tween-20 in PBS followed by 5 to 10 times washing with PBS. Bound phage were eluted using 50 mM glycine (pH 2.2) and added to *E. coli* TG-1 and incubated at 37° C. for phage infection.

Subsequently infected bacteria were plated on agar plates containing Ampicillin, and glucose and incubated at 37° C. overnight. After the first round of selection, colonies were scraped off the plates and combined and thereafter rescued and amplified to prepare an enriched first round phage pool for the synthetic repertoires. For the 'immune' repertoires, single clones were screened for target binding after the first round of phage selection.

Antibody Cloning and Production

Bispecific antibodies as used herein typically differ from each other only in the particular amino acid sequence of the heavy chain variable region of one or both variable domains. The antibodies were produced by cloning the heavy chain variable regions into expression vectors for the expression of heavy and light chains. Methods for the production of bispecific antibodies are known in the art.

Briefly, DNA encoding the heavy chain variable region for the CD3 targeted variable domain was cloned into MV1624 vector (see FIG. 10*a*), encoding the KK residues (L351K, T366K) in the CH3 region for the generation of IgG heavy chain heterodimers (WO2013/157954 and WO2013/157953). The Fc constant regions contains mutation in the CH2 to silence the Fc effector function. The DNA encoding the heavy chain variable region replaces the stuffer region in the construct. The variable region is preceded by an encoded HC signal peptide (not shown). The DNA encoding the heavy chain variable region for the EGFR targeted variable domain was cloned into vector MV1625 (FIG. 10*b*) expressing the second heavy chain of the base antibody portion of the bispecific antibodies, bearing the L351D-L368E mutations in the CH3 region (WO2013/157954 and WO2013/157953). The DNA encoding the heavy chain variable region replaces the stuffer region in the construct. The variable region is preceded by an encoded HC signal peptide (not shown). Both constructs also contain an expression cassette for expression of the IGKV1-39/jk1 light chain.

Expression of the two heavy chains together with the mentioned light chain leads to the production of the bispecific antibody.

293-F cells were used for expression of the designed antibodies in a 24 wells plate format. Two days before transfection, 293-F cell stock was split in 293-F culture medium in a 1:1 ratio and incubated overnight at 37° C. and 8% C02 at an orbital shaking speed of 155 rpm. Cells were diluted on the day before transfection to a density of $5\times10^5$ cells/mL. 4 ml of the suspension cells were seeded into a 24 deep wells plate, covered with a breathable seal and incubated overnight at 37° C. and 8% $CO_2$ at an orbital shaking speed of 285 rpm. On transfection day, 4.8 ml 293-F culture medium were mixed with 240 μg of polyethylenimine (PEI) linear (MW 25,000). For each IgG to be produced, 200 μL of the 293F culture medium-PEI mix was added to 8 μl of DNA (for IgG heterodimers 4 μl of DNA encoding each heavy chain). The mixture was incubated for 20 minutes at room temperature before gently adding to the cells. On the day after transfection Penicillin-Streptomycin (Pen Strep) diluted in 500 μL 293F medium was added to each well. The plates were incubated at 37° C. and 8% $CO_2$ at an orbital shaking speed of 285 rpm until harvest seven days after transfection. Plates were centrifuged 5 min at 500 g, supernatants containing IgGs were filtered using 10-12 μm melt blown polypropylene filter plates and stored at −20° C. prior to purification.

Purification of Antibodies from Culture Supernatant

Medium containing antibodies is harvested and centrifuged to remove the cell debris. Subsequently Protein A Sepharose beads are added to the medium. Medium and Protein A Sepharose beads are incubated with the antibodies to allow binding.

After incubation the beads are isolated from the medium and washed, by a vacuum filter. The antibodies are eluted from the beads by incubation with elution buffer. Optionally, the buffer of the purified IgG is exchanged/desalted.

Buffer Exchange

In order to desalt the purified antibodies the antibody fraction is centrifuged using a filter plate or filter column. The plate or column is centrifuged to reduce the volume of the antibody fraction. Subsequently, PBS or the required buffer is added to the fraction to replace the buffer with a low salt buffer. Optionally this centrifugation step followed by adding buffer is repeated in order to further desalt the storage buffer of the antibodies.

Antibody tumor antigen specific T cell activation and lysis of BxPC3 cells or of HTC-116 cells.

The capacity of the particular CD3 x tumor antigen bispecific IgG combinations to induce tumor antigen-specific T cell activation and lysis of tumor antigen positive target cells in a cytotoxicity assay was tested. The effector cells were healthy donor-derived resting T cells and the target cells were BxPC3 cells or HTC-116 cells.

Using Ficoll and EasySep human T cell isolation kit according to standard techniques resting T cells were isolated from whole blood from healthy donors, checked for >95% T cell purity by anti-CD3 antibody using flow cytometric analysis and subsequently cryopreserved. For a cytotoxicity assay the cryopreserved T cells were thawed and used if their viability was >90% upon thawing, determined by standard Trypan Blue staining. Cytotoxicity assay in short, thawed resting T cells and BxPC3 or HCT116 target cells were co-cultured in an E:T ratio of 5:1 for 48 hours. Antibodies were tested in a dilution range. a CD3 monospecific antibody and an EGFR monospecific antibody, as well as an irrelevant IgG1 isotype control mAb are included in the assay as controls (e.g., an antibody which binds CD3 and another antigen such as tetanus toxin (TT)). T cell activation was quantified using flow cytometry; CD8 T cells were gated based on CD8 expression and subsequently analyzed for their activation status by measuring CD69 expression on T cells. Target cell lysis was determined by measuring the fraction of alive cells by measuring ATP levels assessed by CellTiterGlo (Promega). ATP levels, measured by luminescence on an Envision Microplate reader results in Relative light unit (RLU) values, which were analyzed using GraphPad Prism.

Target cell lysis for each sample was calculated as follows:

$$\%\ \text{Killing}=(100-(\text{RLU sample}/\text{RLU no IgG})\times100).$$

In this assay, the bispecific antibodies have two binding domains. One of the binding domains is targeted towards EGFR and the other to CD3. Both binding domains have the same (common) light chain variable region (VL) and a different heavy chain variable region (VH). The EGFR targeted binding domain has a VH with the amino acid sequence of MF8233. The CD3 targeted binding domain has a VH with an amino acid sequence of one of the MFs indicated for CD3. The bispecific antibody contain mutation in the CH2 to silence the Fc effector function.

Figure 4:
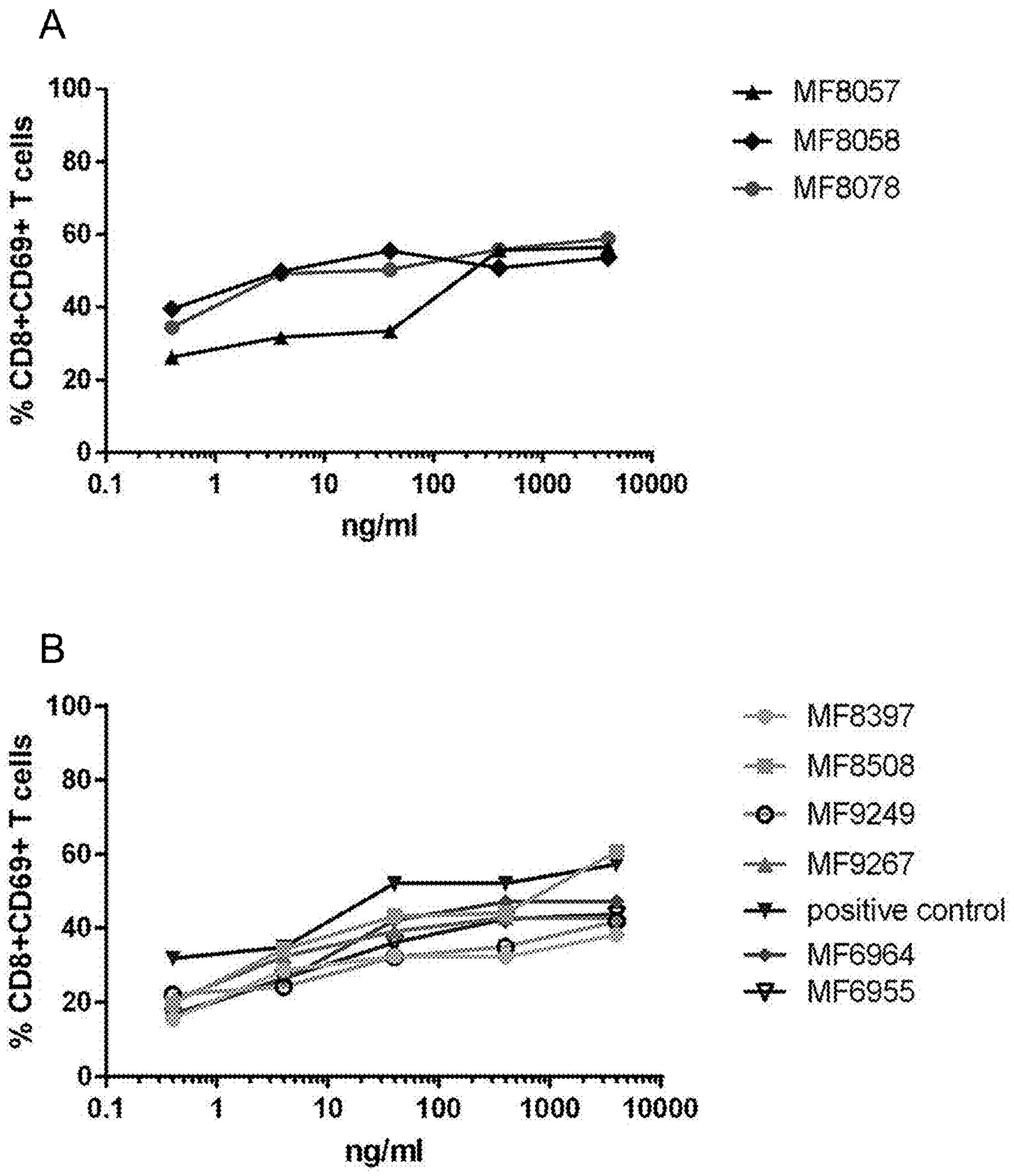
Figure 6:
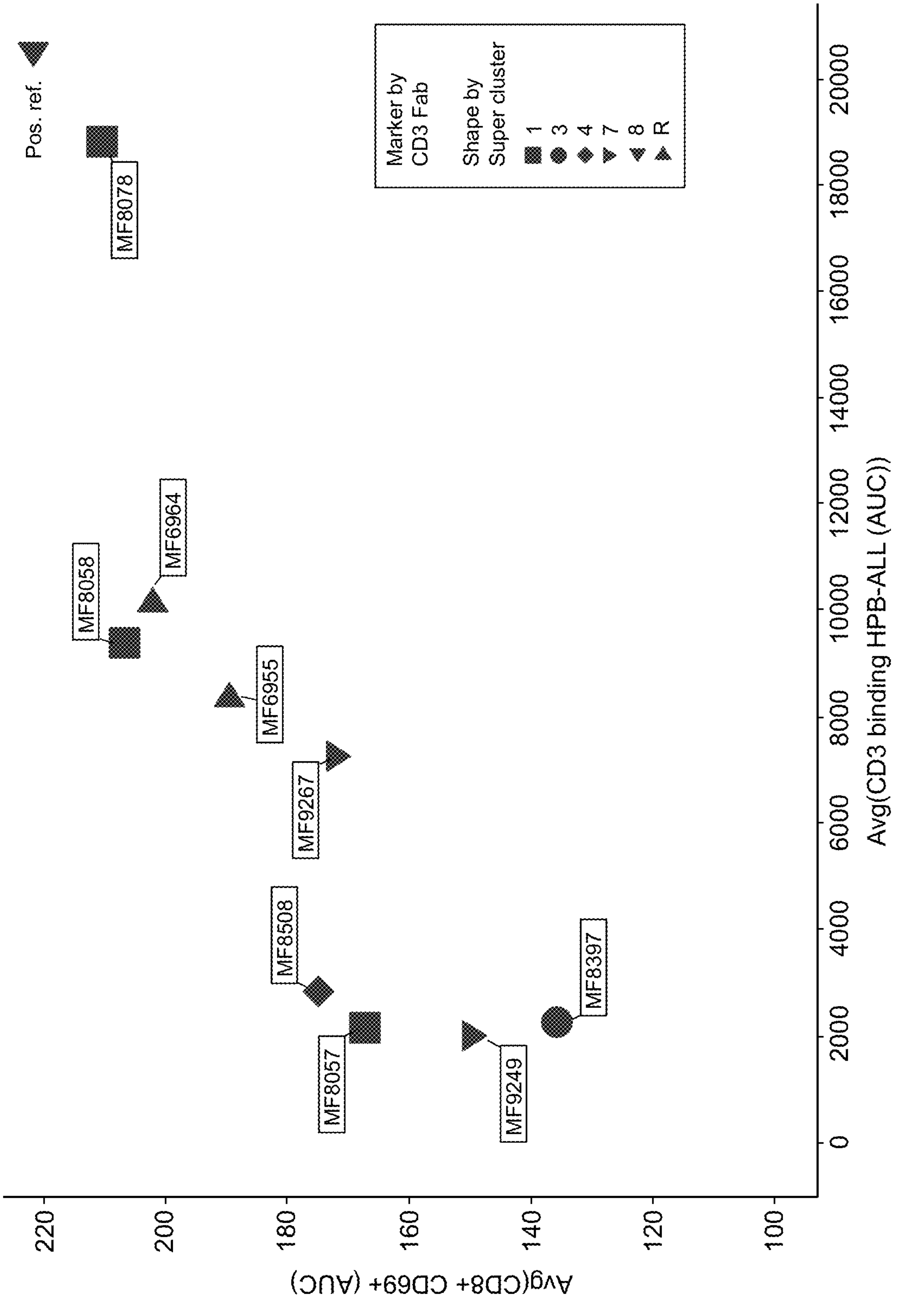
Figure 7:
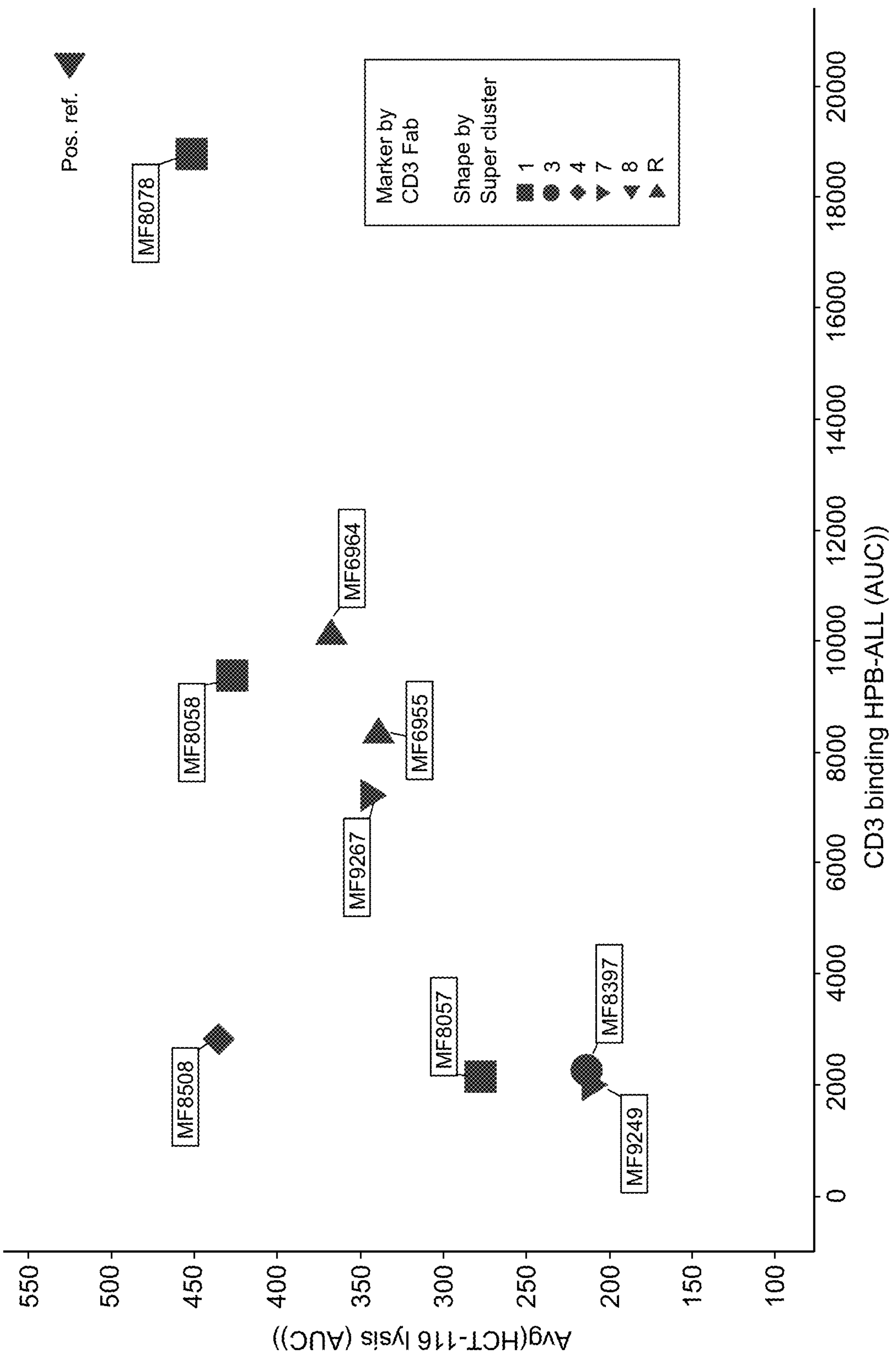

The antibody MF8233xMF8397 induced upregulation of CD69 (FIG. 4-6) and CD25 (FIG. 4-6) on CD4 and CD8 T cells, determined after 48 hours of co-culture at an E±T ratio of 5:1. T cell-mediated lysis was measured after 48 hours.

CD3 Bispecific Antibody Characterization

A candidate EGFR/CD3 IgG bispecific antibody can be tested for binding using any suitable assay. For example, binding to membrane-expressed CD3 on HPB-ALL cells (DSMZ, ACC 483) can be assessed by flow cytometry (according to the FACS procedure as previously described in WO2014/051433). In one embodiment, the binding of a candidate EGFR/CD3 bispecific antibody to CD3 on HPB ALL cells is demonstrated by flow cytometry, performed according to standard procedures known in the art. Binding to cell expressed CD3 can be confirmed using CHO cell transfected with CD3δ/ε or CD3γ/ε. The binding of the candidate bispecific IgG1 to EGFR can be determined using BxPC3 and HCT-116 as well as CHO cells transfected with an EGFR expression construct; a CD3 monospecific antibody and an EGFR monospecific antibody, as well as an irrelevant IgG1 isotype control mAb are included in the assay as controls (e.g., an antibody which binds CD3 and another antigen such as tetanus toxin (TT)).

Generation of Further Clones from Superclusters 1, 3 and 4

From the immune phage library screening (as described in section 'Selection of phage carrying Fab fragments specifically binding to human CD3'), additional clones were characterized carrying Fab fragments specifically binding to human CD3. From supercluster 1, additional clones were identified, including MF8048, MF8101 and MF8056. Additional clones were identified from supercluster 3 and supercluster 4, including MF8562 of supercluster 3 and MF8998 of supercluster 4.

From supercluster 4, further new clones were identified using next-generation sequencing (NGS) analysis. NGS was performed on the VH gene pools present from MeMo® mice that were used to generate the anti-CD3 panel. To this aim, the sequence data sets obtained from different mice were compared with an MF sequence belonging to supercluster 4 MF. This led to identification of sequence variants clones MF10401 and MF10428 that belong to supercluster 4.

Several different mutations were found in the HCDR1 and HCDR2 for different sequences.

VH sequences of all additional clones from supercluster 1, 3 and 4 were cloned into MV1624 (DM-KK) vector and expressed as CD3xEGFR bispecific format for further characterization, as described in section 'Antibody cloning and Production' above.

Characterization of Further Clones from Superclusters 1 and 4

Additional clones from supercluster 1 were characterized with respect to their functional activity in a bispecific format. The EGFR binding domain of the bispecific CD3xEGFR antibody has the amino acid sequence encoded by MF8233. As a control, these CD3 clones were also tested with another antigen (e.g. Tetanus toxin) with the amino acid sequence encoded by MF1337. Reference MFs from supercluster 1 (MF8057 and MF8058) were included to directly compare the affinity of the sequence variant to that of already characterized MF clones from supercluster 1 according to sections: 'Antibody tumor antigen specific T cell activation and lysis of BxPC3 cells or of HTC-116 Cells' and 'CD3 Bispecific Antibody Characterization' as described above. Binding affinity to HPB-All cells expressing human CD3-TCR complex using flow cytometry (FIG. 14 A and FIG. 18) and T-cell activation and lysis of tumor antigen positive target cells (HCT-116) in a cytotoxicity assay (FIG. 14 B-E) assays were performed. No target cell lysis was observed with bispecific antibodies having the MF1337 control arm. For the different CD3 clones tested, target cell lysis was observed in a dose dependent manner. Low target cell lysis was observed for MF8048. Expression levels of activation markers CD69 and CD25 on CD4 and CD8 T cells were measured in FACS staining for the evaluation of T-cell activation. Dose-dependent T-cell activation was observed for all clones, and no T-cell activation was observed for negative control. Finally, cytokine production of IFN-γ and TNF-α was determined in the supernatant derived from the EGFRxCD3 cytotoxicity assay with HCT-116 cells after 48 hrs using Luminex® Assays (eBiosciences™) following standard manufacturer's instructions (FIG. 14 F-G).

Figure 15E:
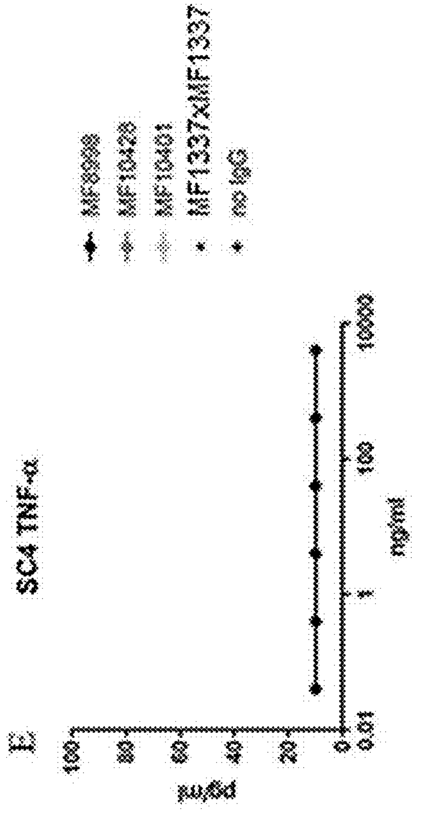

For characterization of additional clones belonging to supercluster 4, binding affinity was determined in FACS to HPB-ALL cells (FIG. 15). PG1337, a monovalent antibody with two identical MF1337 arms specific for tetanus toxin, was used as a negative control. For cytotoxicity assay, HCT-116 cells and BxPC3 cells were used as target cells to test activity of MF8998 and BxPC3 target cells were used to test activity of MF10401 and MF10428. A CD3xTAA bispecific antibody with known high activity was included as positive control. Target cell lysis was quantified using cell viability measurements. Supernatant from the cytotoxicity assay was used to measure cytokine levels for IL-6, IFN-γ and TNF-α using Luminex® assays.

The three supercluster 4 clones tested were thus found to exhibit different binding but similar lysis activity. Although the lysis activity of these clones was similar, reduced cytokine production was observed.

TABLE 1

AUC values for binding of the indicated CD3 clones mentioned in FIG. 15A

| MF combination | AUC |
|---|---|
| MF8233 × MF8998 | 13630 |
| MF8233 × MF10428 | 2700 |
| MF8233 × MF10401 | 9646 |
| MF1337 × MF1337 | 255 |

TABLE 2

AUC and EC50 values for target cell lysis of the indicated CD3 clones mentioned in FIG. 15A.

| MF combination | Target | AUC | EC50 (ng/mL) |
|---|---|---|---|
| MF8233 × MF8998 | EGFR | 253 | 6.9 |
| MF8233 × MF10428 | EGFR | 216 | 10.7 |
| MF8233 × MF10401 | EGFR | 241 | 4.6 |
| CD3 × Mock: −ctrl | Mock | 11 | — |
| CD3 × TAA: +ctrl | TAA | 369 | 4.5 |

TABLE 3

AUC and EC50 values for the amount of indicated cytokines and CD3 clones mentioned in FIG. 15A.

| MF combination | Cytokine | AUC | EC50 (ng/mL) |
|---|---|---|---|
| MF8233 × MF8998 | IL-6 | 858 | 51.2 |
| MF8233 × MF10428 | IL-6 | 659 | 8.6 |
| MF8233 × MF10401 | IL-6 | 657 | 3.1 |
| MF8233 × MF8998 | IFNγ | 311 | >400 |
| MF8233 × MF10428 | IFNγ | 107 | >4000 |
| MF8233 × MF10401 | IFNγ | 114 | >4000 |
| MF8233 × MF8998 | TNFα | 50 | — |
| MF8233 × MF10428 | TNFα | 50 | — |
| MF8233 × MF10401 | TNFα | 50 | — |

Figure 16A:
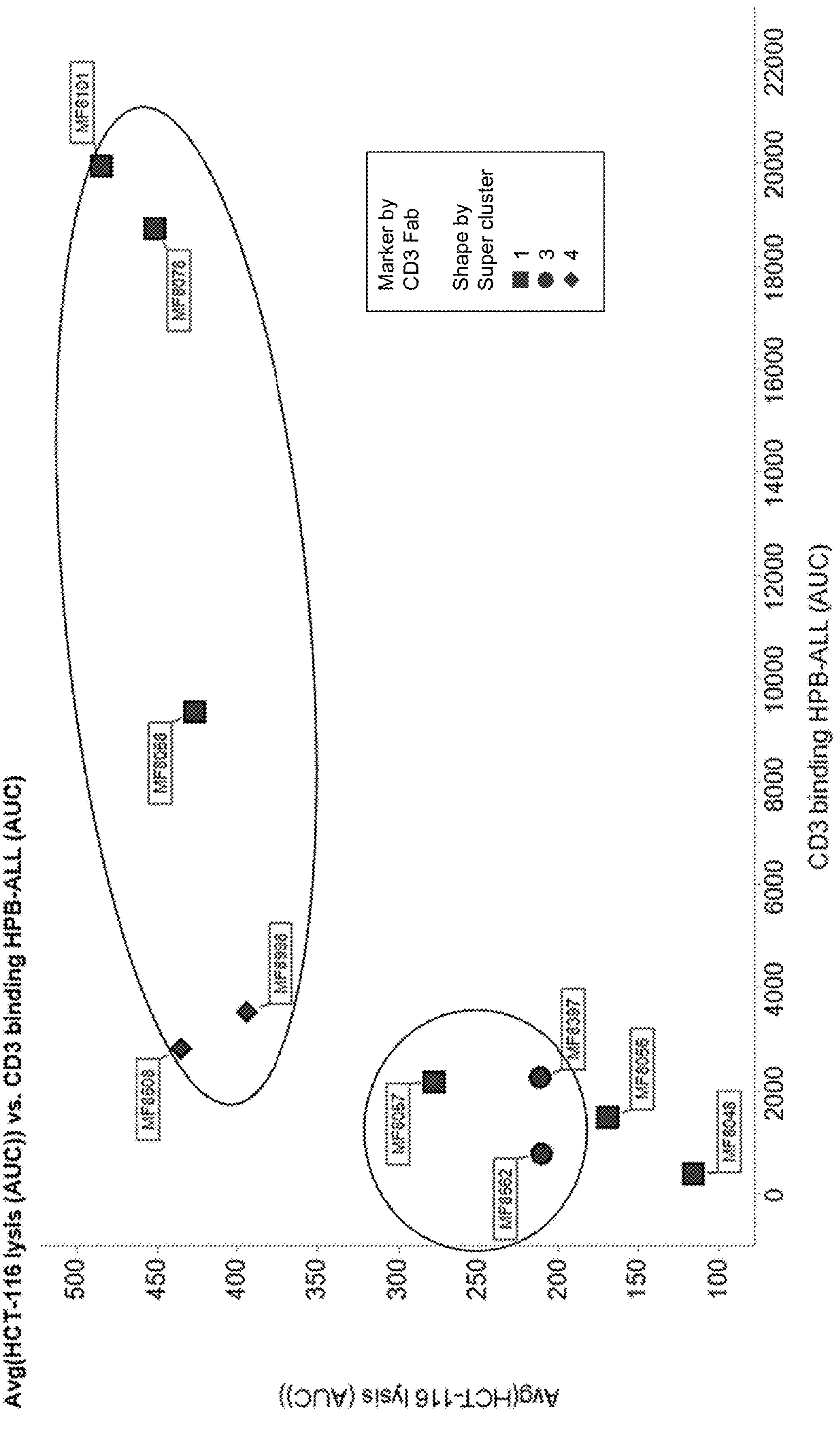
Figure 16B:
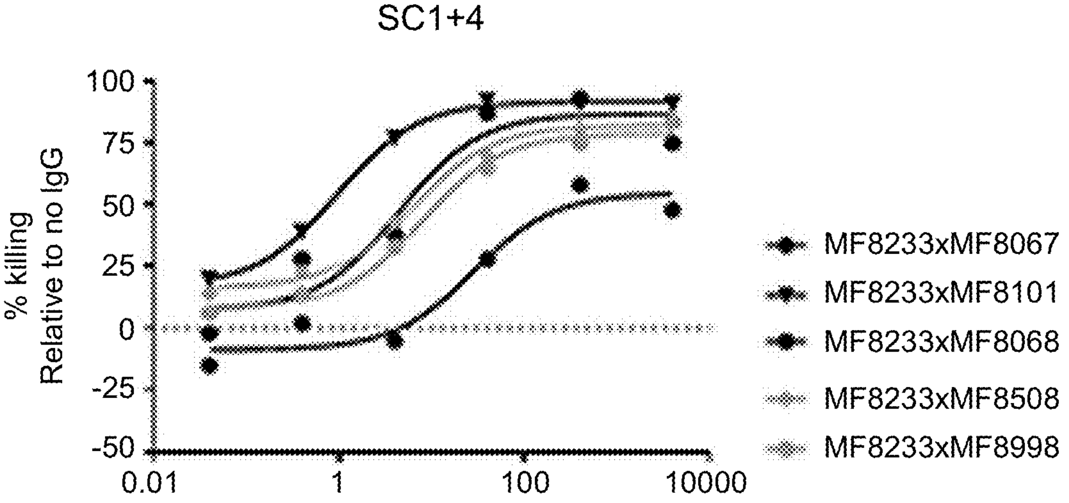

As evaluated by the cytotoxicity assay, it was observed that all further identified MFs are functional. Next, a graph was plotted between lysis on Y-axis and binding affinity on X-axis (FIG. 16A) to understand the relation within and across superclusters between lysis and affinity. Overall, a diverse panel of anti-CD3 Fabs was generated composed of multiple superclusters and covering a range of affinities. Interestingly, clones were identified in supercluster 1 and 4 which exhibit similar activity but different CD3 binding (FIG. 16B). Comparison of superclusters 1 and 3 revealed clones which exhibit similar CD3 binding and differential activity (FIG. 16C).

TABLE 4

Figure 16C:
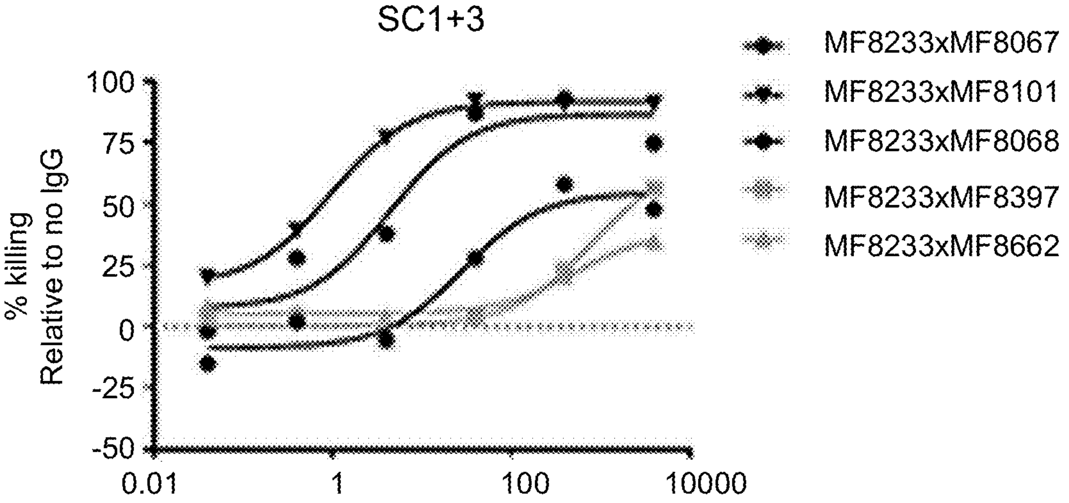

AUC and EC50 values for target cell lysis of the indicated CD3 clones mentioned in FIGS. 16B and 16C.

| MF combination | AUC | EC50 (ng/mL) |
|---|---|---|
| MF8233 × MF8057 | 117 | 28.5 |
| MF8233 × MF8058 | 283 | 4.4 |
| MF8233 × MF8101 | 355 | 1.0 |
| MF8233 × MF8508 | 267 | 6.4 |
| MF8233 × MF8998 | 232 | 8.0 |
| MF8233 × MF8397 | 62 | >400 |
| MF8233 × MF8562 | 57 | >400 |

Characterization of CD3 Antigens

Figure 17:
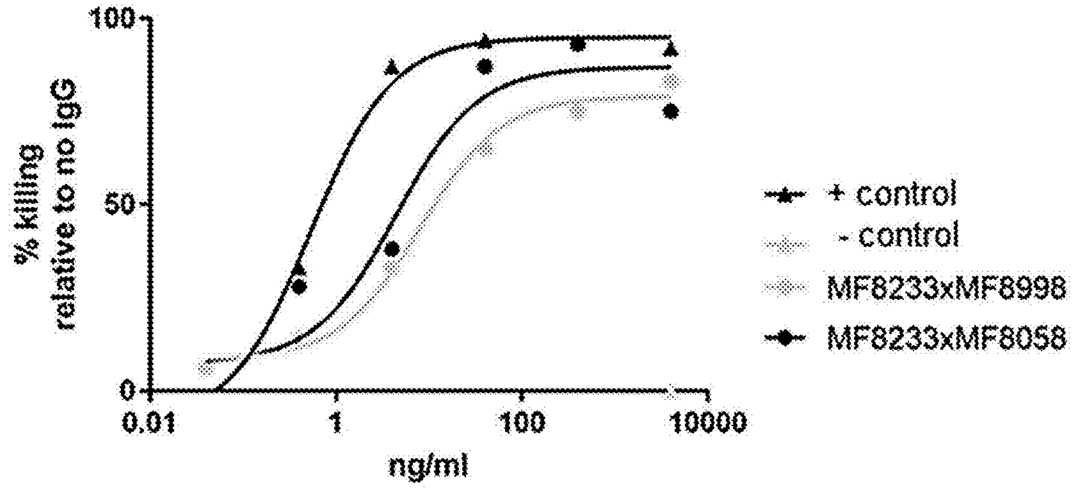

As described above, two clones from supercluster 1 and supercluster 4, i.e. MF8058 and MF8998 respectively, were found to have similar lysis activity in a bispecific format with clone MF8233 as Fab arm binding EGFR as the tumor-cell antigen (FIG. 17). For this experiment, lysis activity against HCT-116 cells was measured as described herein above. MF9257xMF8233 was used as a positive control and MF9257xMF1337 was the negative control. As can be seen from FIG. 17 and Table 5, dose-dependent and high killing percentage were observed for multiple tested bispecific antibodies.

TABLE 5

AUC and EC50 values for target cell lysis for the indicated bispecific antibodies mentioned in FIG. 17. Negative controls displayed no significant measurable activity.

| Cytoxicity assay/ target cell | Tumor target and immune cell engaging target if applicable | MF combination | AUC | EC50 (ng/mL) |
|---|---|---|---|---|
| HCT116 | EGFR × CD3 | MF8233 × MF8058 | 283 | 4.4 |
| HCT116 | EGFR × CD3 | MF8233 × MF8998 | 232 | 8.0 |
| HCT116 | EGFR | +control | 354 | 0.5 |

Binding Affinity

Figure 18:
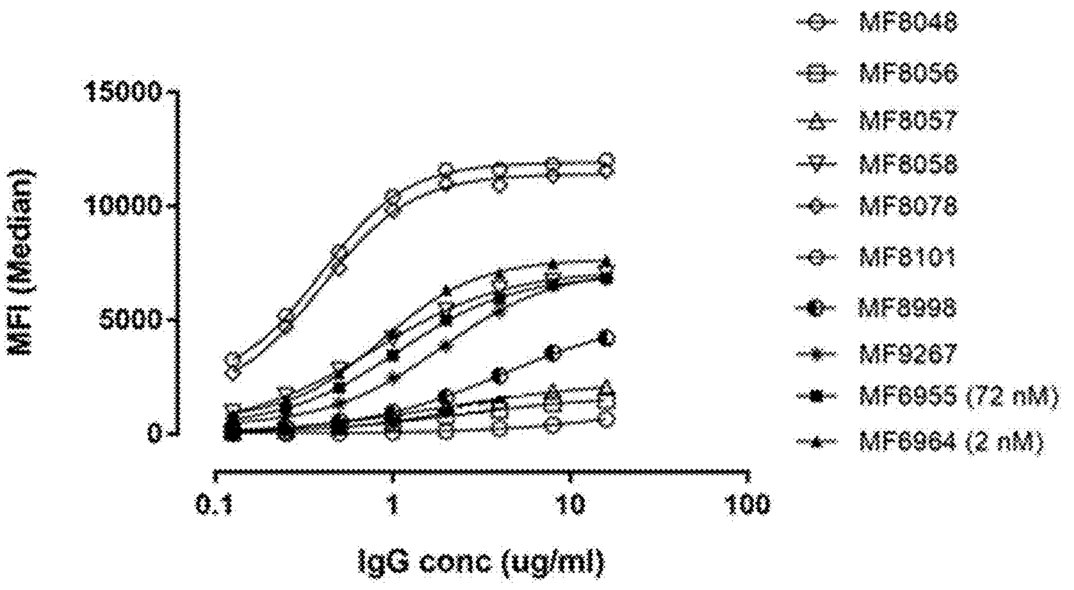

As described in section 'CD3 Bispecific antibody characterization', the binding affinity of additional CD3 clones was analyzed in FACS on HPB-ALL cells expressing human CD3. The affinities of MF6955 and MF6964 for CD3 were measured by surface plasmon resonance (SPR) technology using a BIAcore™ T100. An anti-human IgG mouse monoclonal antibody (Becton and Dickinson, cat. Nr. 555784) was coupled to the surfaces of a CM5 sensor chip using free amine chemistry (NHS/EDC). Then the CD3xTAA bispecific antibody was captured onto this sensor surface. Subsequently the recombinant purified antigen human CD3δε-Fc was run over the sensor surface in a concentration range to measure on- and off-rates. After each cycle, the sensor surface was regenerated by a pulse of HCl and CD3xTAA bispecific antibody was captured again. From the obtained sensograms, on-and off-rates were determined using the BIAevaluation software. FIG. 18 describes the binding affinity range of the CD3 panel generated.

The invention claimed is:

1. An antigen-binding protein that binds human CD3 comprising an antibody variable domain comprising a heavy chain variable region and a light chain variable region wherein the heavy chain variable region comprises:

a CDR1, CDR2 and CDR3 comprising the amino acid sequence:

CDR1: (SEQ ID NO: 42)
SFGIS

CDR2: (SEQ ID NO: 43)
GFIPVLGTANYAQKFQG

CDR3: (SEQ ID NO: 44)
RGNWNPFDP;

or comprising the amino acid sequence:

CDR1: (SEQ ID NO: 51)
SKTFTIS;

CDR2: (SEQ ID NO: 52)
GIIPLFGTITYAQKFQG;

CDR3: (SEQ ID NO: 53)
RGNWNPFDP;

or comprising the amino acid sequence:

CDR1: (SEQ ID NO: 60)
SRTFTIS;

CDR2: (SEQ ID NO: 61)
SIIPIFGTITYAQKFQG;

CDR3: (SEQ ID NO: 62)
RGNWNPFDP;

or comprising the amino acid sequence:

CDR1: (SEQ ID NO: 84)
SKTLTIS;

CDR2: (SEQ ID NO: 85)
GIIPIFGSITYAQKFQD;

CDR3: (SEQ ID NO: 86)
RGNWNPFDP, or comprising the amino acid sequence:

CDR1: (SEQ ID NO: 68)
GSGIS;

CDR2: (SEQ ID NO: 69)
GFIPFFGSANYAQKFRD;

CDR3: (SEQ ID NO: 70)
RGNWNPLDP;

or comprising the amino acid sequence:

CDR1: (SEQ ID NO: 100)
GSGIS;

CDR2: (SEQ ID NO: 101)
GFIPFFGSANYAQKFRD;

CDR3: (SEQ ID NO: 102)
RGNWNPFDP;

or comprising the amino acid sequence:

CDR1: (SEQ ID NO: 199)
RFWIG;

CDR2: (SEQ ID NO: 200)
IIYPGDSDTRYSPSFQG;

-continued

CDR3: (SEQ ID NO: 201)
HIRYFDWSEDYHYYLDV;

or comprising the amino acid sequence:

CDR1: (SEQ ID NO: 208)
RYWIG;

CDR2: (SEQ ID NO: 209)
IIYPGDSDTRYSPSFQG;

CDR3: (SEQ ID NO: 210)
NIRYFVWSEDYHYYMDV;

or comprising the amino acid sequence:

CDR1: (SEQ ID NO: 117)
SYALS;

CDR2: (SEQ ID NO: 118)
GISGSGRTTWYADSVKG;

CDR3: (SEQ ID NO: 119)
DGGYSYGPYWYFDL;

or comprising the amino acid sequence:

CDR1: (SEQ ID NO: 125)
SYALS;

CDR2: (SEQ ID NO: 126)
AISGSGRTTWYADSVKG;

CDR3: (SEQ ID NO: 127)
DGGYTYGPYWYFDL;

or comprising the amino acid sequence:

CDR1: (SEQ ID NO: 142)
DYTMH;

CDR2: (SEQ ID NO: 143)
DISWSSGSIGYADSVKG;

CDR3: (SEQ ID NO: 144)
DHRGYGDYEGGGFDY;

or comprising the amino acid sequence:

CDR1: (SEQ ID NO: 150)
DYTMH;

-continued

CDR2: (SEQ ID NO: 151)
DISWSSGSIGYADSVKG;

CDR3: (SEQ ID NO: 152)
DHRGYGDYEGGGFDH;

or comprising the amino acid sequence:

CDR1: (SEQ ID NO: 166)
DYTMH;

CDR2: (SEQ ID NO: 167)
DISWSGGSIYYADSVKG;

CDR3: (SEQ ID NO: 168)
DHRGYGDYEGGGFDY;

or comprising the amino acid sequence:

CDR1: (SEQ ID NO: 182)
DYTMH;

CDR2: (SEQ ID NO: 183)
DISWSSGTTGYADSVKG;

CDR3: (SEQ ID NO: 184)
DHMGYGDYEGGGFDY;

and wherein the light chain variable region comprises a CDR1, CDR2, and CDR3 region comprising the amino acid sequence:

CDR1: (SEQ ID NO: 21)
QSISSY;

CDR2: (SEQ ID NO: 22)
AAS;

CDR3: (SEQ ID NO: 299)
QQSYSTPPT.

2. The antigen-binding protein of claim 1, wherein said light chain variable region is a germline IgVκ1-39*01 variable region.

3. The antigen-binding protein of claim 1, wherein said light chain variable region comprises the kappa light chain IgVκ1-39*01/IGJκ1*01.

4. The antigen-binding protein of claim 1, wherein said light chain variable region comprises the germline kappa light chain IgVκ1-39*01/IGJκ1*01.

5. The antigen-binding protein of claim 1, which is an antibody.

6. The antigen-binding protein of claim 5, wherein said antibody is a human or humanized antibody.

7. The antigen-binding protein of claim 1, wherein said light chain variable region comprises the amino acid sequence (SEQ ID NO: 16)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPPTFGQ

GTKVEIK with 0-5 amino acid variations, insertions, deletions, substitutions, additions or a combination thereof at one or more positions other than the CDRs.

8. The antigen-binding protein of claim 7, wherein said heavy chain variable region comprises the amino acid sequence:

(SEQ ID NO: 45)
EVQLVQSGAEVKKPGSSVKVSCKASGGTFRSFGISWVRQAPGQGLEWMGG

FIPVLGTANYAQKFQGRVTIIADKSTNTAYMELSSLRSEDTAVYYCARRG

NWNPFDPWGQGTLVTVSS, with 0-10 or 0-5 amino acid variations, insertions, deletions, substitutions, additions or a combination thereof at one or more positions other than the CDRs.

9. The antigen-binding protein of claim 7, wherein said heavy chain variable region comprises the amino acid sequence:

(SEP ID NO: 54)
QVQLVQSGAEVKKPGSSVKVSCKASGDAFKSKTFTISWVRQAPGQGLEWL

GGIIPLFGTITYAQKFQGRVTITADKSTNTAFMELSSLRSEDTAMYYCTR

RGNWNPFDPWGQGTLVTVSS, with 0-10 or 0-5 amino acid variations, insertions, deletions, substitutions, additions or a combination thereof at one or more positions other than the CDRs.

10. The antigen-binding protein of claim 7, wherein said heavy chain variable region comprises the amino acid sequence:

(SEQ ID NO: 63)
EVQLVQSGSELKKPGSSVKVSCKASGVTGNSRTFTISWVRQAPGQGLEWL

GSIIPIFGTITYAQKFQGRVTITADKSTSTAFMELTSLRSEDTAIYYCTR

RGNWNPFDPWGQGTLVTVSS, with 0-10 or 0-5 amino acid variations, insertions, deletions, substitutions, additions or a combination thereof at one or more positions other than the CDRs.

11. The antigen-binding protein of claim 7, wherein said heavy chain variable region comprises the amino acid sequence:

(SEQ ID NO: 71)
QVQLVQSGAEVKKPGSSVKVSCKASGGTFRGSGISWVRQAPGQGLEWVGG

FIPFFGSANYAQKFRDRVTITADKSATTAYMELSSLRSEDTAIYYCAKRG

NWNPLDPWGQGTLVTVSS, with 0-10 or 0-5 amino acid variations, insertions, deletions, substitutions, additions or a combination thereof at one or more positions other than the CDRs.

12. The antigen-binding protein of claim 7, wherein said heavy chain variable region comprises the amino acid sequence:

(SEQ ID NO: 87)
QVQLVQSGAEVKKPGSSVKVSCKASGVTFKSKTLTISWVRQAPGQGLEWL

GGIIPIFGSITYAQKFQDRVSITADKSTNTAYLELNSLRSEDTAIYYCAR

RGNWNPFDPWGQGTLVTVSS, with 0-10 or 0-5 amino acid variations, insertions, deletions, substitutions, additions or a combination thereof at one or more positions other than the CDRs.

13. The antigen-binding protein of claim 7, wherein said heavy chain variable region comprises the amino acid sequence:

(SEQ ID NO: 103)
EVQLVQSGAEVKKPGSSVKVSCKASGGTFRGSGISWVRQAPGQGLEWVGG

FIPFFGSANYAQKFRDRVTITADKSATTAYMELSSRSEDTAIYYCAKRGN

WNPFDPWGQGTLVTVSS, with 0-10 or 0-5 amino acid variations, insertions, deletions, substitutions, additions or a combination thereof at one or more positions other than the CDRs.

14. The antigen-binding protein of claim 7, wherein said heavy chain variable region comprises the amino acid sequence:

(SEQ ID NO: 202)
EVQLVQSGAEVKKPGESLKISCKGSGYSFTRFWIGWVRQMPGKGLEWMGI

IYPGDSDTRYSPSFQGQVTISADKSTSTAYLQWSSLKASDTGMYYCVRHI

RYFDWSEDYHYYLDVWGKGTTVTVSS, with 0-10 or 0-5 amino acid variations, insertions, deletions, substitutions, additions or a combination thereof at one or more positions other than the CDRs.

15. The antigen-binding protein of claim 7, wherein said heavy chain variable region comprises the amino acid sequence:

(SEQ ID NO: 211)
EVQLVESGAEVKKPGESLKISCKGSGYSFTRYWIGWVRQMPGKGLEWMGI

IYPGDSDTRYSPSFQGQVTISADKSISTAYLQWSSLKASDTAMYYCVRNI

RYFVWSEDYHYYMDVWGKGTTVTVSS, with 0-10 or 0-5 amino acid variations, insertions, deletions, substitutions, additions or a combination thereof at one or more positions other than the CDRs.

16. The antigen-binding protein of claim 7, wherein said heavy chain variable region comprises the amino acid sequence:

(SEQ ID NO: 145)
EVQLVESGGGLVQPGRSLRLSCATSGFNFDDYTMHWVRQAPGKGLEWVSD

ISWSSGSIGYADSVKGRFTISRDNAKNSLWLQMNSLRTEDTALYFCAKDH

RGYGDYEGGGFDYWGQGTLVTVSS, with 0-10 or 0-5 amino acid variations, insertions, deletions, substitutions, additions or a combination thereof at one or more positions other than the CDRs.

17. The antigen-binding protein of claim 7, wherein said heavy chain variable region comprises the amino acid sequence:

(SEQ ID NO: 153)
EVQLVESGGGLVQPGRSLRLSCATSGFTFDDYTMHWVRQAPGKGLEWVSD
ISWSSGSIGYADSVKGRFTISRDNAKNSLYLQMNSLRAEDTALYFCAKDH
RGYGDYEGGGFDHWGQGTLVTVSS, with 0-10 or 0-5 amino acid variations, insertions, deletions, substitutions, additions or a combination thereof at one or more positions other than the CDRs.

18. The antigen-binding protein of claim 7, wherein said heavy chain variable region comprises the amino acid sequence:

(SEQ ID NO: 185)
EVQLVESGGGLVQPGRSLRLSCVTSGFTFDDYTMHWVRQAPGKGLEWVS
DISWSSGTTGYADSVKGRFTISRDNAKDSLYLQMNSLRTEDTALYYCAK
DHMGYGDYEGGGFDYWGQGTLVTVSS, with 0-10 or 0-5 amino acid variations, insertions, deletions, substitutions, additions or a combination thereof at one or more positions other than the CDRs.

19. The antigen-binding protein of claim 7, wherein said heavy chain variable region comprises the amino acid sequence:

(SEQ ID NO: 169)
EVQLVESGGVVVQPGGSLRLSCAASGFTFDDYTMHWVRQAPGKGLEWVS
DISWSGGSIYYADSVKGRFTISRDNSKNSLYLQMNSLRTEDTALYYCAK
DHRGYGDYEGGGFDYWGRGTLVTVSS, with 0-10 or 0-5 amino acid variations, insertions, deletions, substitutions, additions or a combination thereof at one or more positions other than the CDRs.

20. The antigen-binding protein of claim 7, wherein said light heavy chain variable region comprises a common light chain variable region with the amino acid sequence:

(SEQ ID NO: 120)
QVQLVQSGGGLVQPGGSLRLSCATSGFKFSSYALSWVRQAPGKGLEWVSG
ISGSGRTTWYADSVKGRFTISRDNSKNTLYLQMNSLRAEDTAVYYCARDG
GYSYGPYWYFDLWGRGTLVTVSS, with 0-10 or 0-5 amino acid variations, insertions, deletions, substitutions, additions or a combination thereof at one or more positions other than the CDRs.

21. The antigen-binding protein of claim 7, wherein said heavy chain variable region comprises a common light chain variable region with the amino acid sequence:

(SEQ ID NO: 128)
QVQLVESGGGLVQPGGSLRLSCATSGFTFISYALSWVRQAPGKGLEWVS
AISGSGRTTWYADSVKGRFTISRDNSKNTLFLQMNSLRAEDTAVYYCAR
DGGYTYGPYWYFDLWGRGTLVTVSS, with 0-10 or 0-5 amino acid variations, insertions, deletions, substitutions, additions or a combination thereof at one or more positions other than the CDRs.

22. A bispecific antibody comprising an antigen-binding protein of claim 1.

23. The bispecific antibody of claim 22, further comprising a H/L chain combination that binds a tumor-antigen.

24. The bispecific antibody of claim 23, wherein said H/L chain combination that binds a tumor-antigen binds human BCMA, CD19, CD20, CD30, CD33, CD38, CD44, CD123, CD138, CEA, CLEC12A, CS-1, EGFR, EGFRvIII, EPCAM, DLL3, LGR5, MSLN, FOLR1, FOLR3, HER2, HM1.24, MCSP, PD-L1, PSMA protein or a variant thereof.

25. The bispecific antibody of claim 22, which is a human or humanized antibody.

26. The bispecific antibody of claim 22, comprising two different immunoglobulin heavy chains with compatible heterodimerization domains.

27. The bispecific antibody of claim 26, wherein said compatible heterodimerization domains are compatible immunoglobulin heavy chain CH3 heterodimerization domains.

28. The bispecific antibody of claim 22, wherein said bispecific antibody is an IgG antibody with a mutant CH2 and/or lower hinge domain such that interaction of the bispecific IgG antibody to a Fc-gamma receptor is reduced.

29. The bispecific antibody of claim 28, wherein said mutant CH2 and/or lower hinge domain comprise an amino substitution at position 235 and/or 236, according to EU numbering.

30. The bispecific antibody of claim 22, comprising a common light chain.

* * * * *

SEQUENCE LISTING

```
<160> NUMBER OF SEQ ID NOS: 300

<210> SEQ ID NO 1
<211> LENGTH: 43942
<212> TYPE: DNA
<213> ORGANISM: Homo sapiens

<400> SEQUENCE: 1

ctatttagca ttgctgctgc cagccccaac cacatttctg attgcctagg aagaacagcc     60

tttcaaattt gacttctgca tgtggatagg tgagtgtctt ttgtggatac cgacagtggg    120

aatggctcct ctcaatttga gaaattctga aggaatttcc attggcaagt tcagcaaggc    180

caactgacgg agagaggaag caccctgact gttccagttc agacactctt ggggcttgtt    240

agtaattgag tatgtgtctg gataagtgag tgtcatttgt gggtccagac agcaggatct    300

gcttttctca atttgagaaa ttccgaagga atctccattt gcagattgaa ctagcccaac    360

aaacagggag aaagcaactc aactgtttca gtttggactc tcttgggact tgcttattgt    420

tgcagcagtt agattgtatt ctggtggttg tttgtgtgtt gatgtagttg tgggagatca    480

gggtttgatc tgagtgcaga ccgcttgggt gtattcttca gggttggtct gcatgtggct    540

gtgggccagt ggagtgaggg aacatctcta cccgtatcac gctgaacatg cccaatctca    600

tctgatctca gacagtcttt gaattgtagc actgccttat atttggattt attttgctgt    660

tgaatgtgaa tatgggatgg aagtccatgt ctccaggctt ctatgctgct gctctaagga    720

caggcaggcc tgattagtat gtgctgctgt ttggctacag agttctttgg agtctggaga    780

gatttggcct ttaaaaatca aactgtcaga ccctgtctca aggaaaaaaa aaaaaaacagg    840

atgtgagcgc tctccctctc cctctccctc tccctctccg tctccctctc cctctccctc    900

tccgtctccc tctccctctc cctctccgtc tccctctccc tctccccacg gtctccctct    960

catgtggagc cgaagctgga ctgtactgct gccatctcgg ctcactgcaa cctccctgcc   1020

tgattctcct gcctcagcct gccgagtgcc tgcgattgca ggcacgcacc accacgcctg   1080

actggttttg gtggagacgg ggtttcgctg tgttggccgg gccggtctcc agcccctaac   1140

cgcgagtgat ccgccagcct tggcctcccg aggtgccggg attgcagacg gagtctcgtt   1200
```

```
cactcagtgc tcaatggtgc ccaggctgga gtgcagtggc gtgatctcgg ctcactacaa   1260
cctacacctc ccagcaacct gccttggcct cccaaagtgc cgagattgca gcctctgccc   1320
ggccgccacc ccgtctggga agtgaggagt gtctccgcct ggccacccat cgtctgggat   1380
gtgaggagcc cctctgcctg gctgcccagt ctggaaagtg aggagcgtct ccgcccggcc   1440
gccatcccat ctaggaagtg aggagcgcct cttcccagcc gccatcacat ctaggaagtg   1500
aggagcgtct ctgcccggcc gcccatcgtc tgagatgtgg ggagcgcctc tgccccgccg   1560
ccccatctgg gatgtgagga gcgcctctgc ccggccgaga ccccgtctgg gaggtgagga   1620
gcgtctctgc ccggccgccc cgtctgagaa gtgaggagac cctctgcctg gcaaccaccc   1680
cgtctgagaa gtgaggagcc cctccgcccg gcagccgccc cgtctgagaa gtgaggagcc   1740
tctccgcccg gcagccaccc catctgggaa gtgaggagcg tctccgccca gcagccaccc   1800
cgtccgggag ggaggtgggg ggggttagcc ctccgcccgg ccagccgccc catccgggag   1860
ggaggtgggg ggtcagcccc ccgcctggcc agccatgccg tccgggaggg aggtgggggg   1920
gtcagccccc tgcccggcca gccgccccgt ccaggaggtg aggggcgcct ctgcccgccc   1980
ccccctactg ggaagtgagg agcccctcag cccggccagc caccccgtct gggacggaga   2040
tggggggtca gcccccccgc ccagccagct gccccgtccg ggagggaggt ggggggggtca   2100
gccccccgcc tggccagccg ccccgtccgg gagggaggtg ggggggtcag ccccccgcct   2160
ggccagccgc cccgtccggg agggaggtgg ggggggtcag ccccccccgcc cagccagccg   2220
ccccgtccgg gaggtgaggg gcgcctctgc ccggccgccc cctactggga agtgaggagc   2280
ccctctgcct ggccagccgc cccgtccggg agggaggtgg gggggtcagc cccctgcccg   2340
gccagccgcc ccgtccggga ggtgaggggc gcctctgccc ggccgcccct actgggaagt   2400
gaggagcccc tctgcccggc caccaccccg tctgggaggt gtgcccagca gctcattgag   2460
aacgggccag gatgacaatg gcggctttgt ggaatagaaa ggcgggaaag gtggggaaaa   2520
gattgagaaa tgggatggtt gccgtgtctg tgtagaaaga agtagacatg ggagactttt   2580
cattttgttc tgcactaaga aagattcttc tgccttggga tcctgttgat ctgtgacctt   2640
acccccaacc ctgtgctctc tgaaacatgt gctgtgtcca ctcagggtta aatggattaa   2700
gggcggtgca agatgtgctt tgttaaacag atgcttgaag gcagcatgct cgttaagagt   2760
catcaccaat ccctaatctc aagtaatcag ggacacaaac actgcggaag gccgcagggt   2820
cctctgccta ggaaaaccag agacctttgt tcacttgttt atctgctgac cttccctcca   2880
ctattgtccc atgaccctgc caaatcccct ctgtgagaaa cacccaagaa ttatcaataa   2940
aaaaaaaaaa aaaaaaaaaa aaaaaatcaa actgtcagct gggcgcaaga aactgaggtg   3000
ggcagatact tgagcccagg agttcgagac cagcctgggc aacatggtga aaccctgtct   3060
ctacaaaaaa tacaaatatt agctgggtgt aatggtgcat acctgtagtc ccagctactc   3120
aggaggctga ggtgggagga ttacctgagc ctgggaggtt gaggctgcag tgagccttga   3180
tcacaccact gcacttccag cctgggtgac ggagatcctg tctcaaaaaa aaaaataatc   3240
aaactatcat ggaaactgct ttattcaaaa ttttgtttca caacctttat tggattacct   3300
atcagaacaa ataaagttca accatgtgaa catgttcata aaccagtgag tttgcattgc   3360
tatctcatgg ctggaattta aaggtaaaag ctattggatc tttgtgtgta tgtaggtata   3420
tgtgtctaga tgttacgtgt tgtttttaga gggtagcaaa ttggcttata aattaaaaag   3480
cgttcataaa ttaagtaaat gagtctaagc atttttcaag tttacatgac ttaagtaaat   3540
```

```
ctttaataaa caagagagct tttagatcat ttgtaaaata aaaatagaaa tgcctttgga   3600
attgtcagca tacttttttt gtttgggttt tacatttgtc tctgctagat atttaaaggt   3660
gtcagggttt gacaaagaga ttataagact ataaacccag ccaagaacaa aattatcttt   3720
gtgtgatttt ttgataaata agactaattt aatgtcgtta ggttaataaa aatagctgaa   3780
acttttgcat tattggtgca agtatccatg tattttactt tatgtttctt tttttaaaa    3840
acggagtctc actctgtcgc ccaggctgga gtgcagtggc ccgatctcgg ctcactgcaa   3900
gctctgcctc ccgggttcac gccattctcc tgcctcagcc tcctgagtag ctgggaccac   3960
aggcgcccgc caccacgccc ggctaatttt ttgtattttt tagtagagaa gaggtttcac   4020
catgttagcc aggatggtct tgatctcctg acctcatgat cctcctgcct cagcctccca   4080
aagtgctggg attacaggtg taagcaatca tgcccagcca actttatgtt tcttacttag   4140
gtgaacatct aatatataca agttataaaa atggttaaca aggaaataat gaatagcttt   4200
gatatctctt ttctcataag taatatagat aattgctaaa aaagtgaatg aaatataaat   4260
ggcataaatg ctctaagtga actttttgtg taatttaata tcttgaagtt attttggatg   4320
ctcatgagat gtgtgggtca tttccaatta tgaaagggtt tcaatacaga aagttaaatg   4380
atgtaaaaac cttaattcct ttaaatctca gttttcctaa gcaatcaaaa acccaataac   4440
aatgacatag aaattatttt gataaaatgt aaaatttgtt tctcaggtca gttaccaaaa   4500
ggcaaagaaa aacctcctgc agtgtgattg cttctcctat cagagtccca tctcgaaaac   4560
ctgaaaatca aacctgataa atgatgtaga catatcaaga aaagccaaga ggacagaatc   4620
aagctatact ggaggaaaac gttgcttctc tagaatttta aaataaatat ttcagcatca   4680
gaccatgaca gcagttaagg caagagggaa aaaaaagata caagaactga caaagttgaa   4740
ggagatagtt tcatttcagg ttccttcaag gggagacaag ctgacagcaa caaaacacaa   4800
gaaagctgca ctttggagat atagatctga gaagtattca aaaagtaaca gattatagag   4860
tcaaaatcaa aacctctcat ccaatcaata ttttaagaaa accttgttct aacccagggg   4920
actaatctat atctctctcc cctagttact ggatcctttc taccctgttt cataaacaac   4980
ctaagtctat aatttgaatt aacctttaga taacttctga gttaaacaaa attatttctt   5040
taatcaataa gaacacatct tctttggcac attgtacatg gaatcataca atttgctgga   5100
attcttattc ttagtaatcc taaattttaa tggaaaccta ggaagcaaga aatcctgggc   5160
tgtctatcag atattaacat tttatagatg agaaacatga atgttctcag gcccagaaaa   5220
ctcaagttgt tttgggacct caagaaaaga ggaattcacc caattcatac aggtatctgc   5280
aagcacagat caattattgg ttgtgctcga gaggccttta aaaatcaaat ctgagattcc   5340
ttatgaaaag ttccagcaaa gccaatttaa aaaagcctat atgaacaata attcttgctt   5400
cagtttatgc aaataatcag gcaaactata ataagattaa aacagatttt gcaaataaat   5460
tggtcctact gtgatttgcc tttcatggaa atggggagct ggagagagaa acattatgtt   5520
ttggaagaaa actgcagtac acctgttatt agattaatct ttgacctatg gcaacctggt   5580
catccatggt atggagatac atctgtgctg tgctgcattc agttattaaa agtataagtt   5640
accagtggaa tttagatatg gattcatcac ctcagaagtt ggttcactgg atgcataagg   5700
aaataaaaac taatttttaa aaaagcaaaa ttttcaatcc cttggttttt gttatcgata   5760
taaaccaaaa tgtatctgag gtaggtctca attaatttca aagtttattt tgccaagggt   5820
agggatatgt gcctgaaaca caagtctgtg cctttctcca aagatgcttt tgagggcttc   5880
aatatttaaa ggggaaaggg cagatattgg ggaaagagga agaaatttta aaaaggtgtg   5940
```

```
ggtagggcgg tggctcatgc ctgtaatccc agtaatttgg gaggccaagg tgggcagatc   6000
acctgaggtc aggagtttga gactagcctg accaacatgg acaaacccca tctctactaa   6060
aaatacaaaa attagctggg tgtggtggtg cacggctgta atcccagcta ctcaggaggc   6120
tgaggcagga gaatcacttg aactcgggag acagaggttg cagtgagcca aaatcgtgcc   6180
actgcattcc agcctgggtg atgacagagt gagacttcat ctcaaaaaaa aaaaaaacaa   6240
aaaaacaaaa aaaaggtgtg ggtagataag agacaaatgg ttgtattctt ttgagatttt   6300
gatcagactt tcactaaata cacaattaca tgtgagagtg gggtaaagaa atagtcactt   6360
atgcctcagt ctagatcagt gaatctgcat ttttatacaa acgaaagggc agaggaagca   6420
atcagatatg catttgtttc agatgagcag agggttgact tcaagttcta tcctttgtcc   6480
catacctgtg aagataagct atcaatttac attgccaggg tgaaattcaa tcgaataaaa   6540
tgggagccag gtttgcctga cacaattccc agcttgactt ctctctttgg cttagtgatt   6600
tggggacccc aagatttatt ttcctttcac atctgtaata gctaaaatta aagtaggaga   6660
atattgggtc aggctttgag gccaaaccaa gcctagatgt gggtctgtct gaactcagat   6720
cactagcctc aaggctgctc atgaagaaga aaattatgcc aggaaaccag aaagtacctc   6780
tgagatctgt ggtttcctgg aaggtagtca atgtggggaa ggagtgaatt aaagtgactt   6840
ctgaaactag agggtataat gtgaaggaat tgttctattt tgcaaatcag tatcattagc   6900
ttcctgaacc tttactaaaa taaattgtga gagtaattac tttaggcaca atgtctttgg   6960
ttttaaatgc tgcagagtgg aagatccggt tgatacagaa cccacggctc acaattgaac   7020
agttgcagat gggtacatat aatccgggca cacaggaggt tattcccaaa agaacagcct   7080
acttggtgga ctggataaaa cactgtgaga actatttact ctgagaagga gaattgtccc   7140
actccaccta taaatgccaa gtggagcact ccagatgaag caacagatat gcttcaaatg   7200
taagccacgg gggactggct ttataatgat gtggcaggcc aggtcactaa tgcaggcctc   7260
cataacaact gtttcagtac tgactgagtg gttaagttaa atgttaaaag gtaaaaaagc   7320
cagtggcctt atacaaactc tggattgtaa caaaagccca ccacgagttt tgcctaggac   7380
tttcctgggg cttggaccca tgacaagata atgaaggaat tcttaacagg accagattag   7440
gattaaacaa gttttaccgg cagtctgaag aaacttccca ggcttccaca gacaagttta   7500
ttggagatct caaggaagtt cccaaacctc catgatttag caggagacaa gatagggtaa   7560
tcaccccagc acctggaccc atatagatta agtaaattta ctaagcctcc agaggaaggt   7620
cttcagaact cagatctcag ttatagatta caagaagtta atcactcatg tttttagatg   7680
aatgcactta cacacagaca tataacttag aaggtaataa gctctggaag actttgtaat   7740
tttgagttgg tctggcaata ttttccaggc cttctcccta taacttgtta aagaaataaa   7800
aactcttcct ccccagttca tctgcatctt gttactgggc tggaagaaat agcagtctga   7860
ccctcagttt ggtccaggaa caatgataga aatattaact tggctgggcg tggtggctca   7920
ctcctgtgat ccctgcactt tgggaggctg aggcgggtgg atcacatgag gtcaggagtt   7980
tgagaccagc ctggccaaca tgatgaaacc ccatgtctac taaaaataca aaaaattagc   8040
tgggcgtggt ggcgggcacc tgtaacccca gctactctgg aggctgaggc aggagaatct   8100
cttgaaccag tgaggcggag gttgcagtga gtagagattg tgccactgca ctccagcctg   8160
ggagagaaga gcgaaactct gtctcaaaaa aaaaaaaaaa gaagaaagaa atattaacct   8220
tactttttgg tttttggctc tttcgttgct ttgagtttta atggtaatga gtccctggca   8280
```

```
cctctattct tgtgtggcct agaatgttta attgactata agtctttttt gactctaagt   8340
cccttggtta caggggtccc actgacgaac aggatggact cggggcaggt agtcatacca   8400
ccttggaaat gatatggaac aaaataaagt ttggcaatca atgctccctc tggcatattc   8460
caaggagacc tcagtttcca agagataaat cttacctggg aaaaggtctt gccccttgcc   8520
ctgctgaggg tactggtagc tcccagaaat ggattagctc ttagcccctt tcaaaatgtt   8580
tacttggaga ctgttttcct ggactctctg atgcttgagg atttttttcct ccccctgaaac  8640
agaagctatg tcatacatga aacaattagg gaatatatta actagtctct ccaacagact   8700
tcatttctgt atggacttgc ctcttccctg tttgaaacca gggaatcgaa tcatactgaa   8760
gacctggaaa tcccatcagg ctgaagacta gctgcaacca caataggtca gtctttttaa   8820
ggtgctgctg accacccact cgtctatcaa gttagccagt gttaaaccat gaattcaaca   8880
tactcagtaa aactagtcac tgtgggatcc ctccagggga aacagtcatg ctcttgtgaa   8940
cctatacatg gccttaagtt aatattgaaa gcccagccaa agatcctaga taagaaactg   9000
taaaaggaat atgcattttt cagttattat tctctttaaa cccacagctt ttcacatata   9060
agatataatg aatcaggaat actttttggt aggcttagga ttgttctctt ggattcccca   9120
agggatccac tccaaattct ctggtatttt aaaattggtt tatctatatt atttatcatc   9180
cttgttcaat gtggcctaaa acgttgttct aaaactgaaa taaaagtacc cagatcatag   9240
tgctccaatg actacttctg attatagtgc cacatttcca ttccttatca ttattccacc   9300
tcacacgtcc tcagcatgaa gcagccagaa ggatcaatga ccagattctc catgattgag   9360
gaagtgataa atagaaaaga gagactgaaa ccggccccgt tatcttatag aactaatatt   9420
tacagttgtt tttgtttgtt ttgctttgga acatagaaat ggaccctgtc tggtcttaaa   9480
acttgaaact tgtttgtttt cctgagtttc ttgcttagaa aaccgacttt caggcaagga   9540
actgaaactc atcagagcac cacacccagg caatgagact gcagatcctt cacccagcat   9600
gatttttcc ctacctctgc ctaatttcta tttttcccct gtccacgtag catcaaactc   9660
tgtaaaatat ttgaagagat ttattctgag ccaaatatga gtgaccatgc ccgtgacaca   9720
gccctcagga ggccctgcga acatgcaccc aaggtggttc aggtacacat tggttttgta   9780
cattttaggg agacacgagg cttcaatcaa ctataaacat ttactgattg gcaattggtt   9840
gagtttatct aaaggtctgg aatcaataga aaagaaatgt ctgggttgtg gtaagaggtt   9900
gtagagacca aggttttatc atgcaaatga agcctccaga cagcagactt gagagagact   9960
taagtattaa tgcctgagag atataatgaa gcgtgttcga cacgcacttc ctgtcatggc  10020
ctgaacccat ctctcaggtt aaattttcaa agagctgtgg ttgaagaggg agtccattca  10080
gatggttgag ggccttaga atttcatttt tggtttacac tccccacaca gctacatttc  10140
tgcctgcaca tagctacatt ccttcctcac tatataacct cccaatttta gtttgttgga  10200
gaacaaagcc agaataaagc caatcctagt catagcattg caacttgtat cagatgaaag  10260
aaacctacaa aaagataatt ataaaattta gataaaatgt ataaaacaac tgagaaggca  10320
aaatttgagg ggctccaatt aatcaaggtt taccgcttat attctgtgtg actgccagaa  10380
aaaaagaaac aaaacttttt ggtaggaaga tcatttaaaa tttctgtttt taatacataa  10440
ggcctgttat ttaataaaaa attatgagac aacctaaaaa aaaagaatta aatatcaaaa  10500
caccaattga caagccaaat gataaaaact ggcctacata tggttcagaa aatgatttca  10560
ataaatctac tcttcaccat tctaatccct ttgcagtgcc ctaggatggt gactgactct  10620
catgtataat atccctggac actattgtcc tgaagctcta ggtatgtttg tgctaatagg  10680
```

```
aagaataggc aaaagattta aaggtgggag aatccttccc tacagcacta ggaaatggat  10740
atggagttgt tctcgctgag tgtacctcca gggaggcagc cttcatcagc tatagtttct  10800
gctgcttcag ttaattgcta ccagcaatgt tctctcaggc ctaatgtagt aatggcttcc  10860
ggcagtagct agccctgggg tatttcacta tccctcatgg tttcctttgg tcttatctct  10920
atcttgtaaa ttgtcctgtt attttatctt cttaaatttt ccttttaatg tataaccggt  10980
tttttctttt ttttttttt ttttggatcc caagtgtgtg tttctttttg gtacctgagt  11040
atatcactgt cactgtggtc tctcaacttt taaattatgt gactctgaag gtgtgtgtct  11100
ccaaattttt atccctgtgc acttttcttc acctgtcttc atttctttcc cttttttccg  11160
ttataacttt cactcacatc cgtgtgaaga gaccaccaaa caggctttgt gtgagcaaca  11220
aggctgttta tttcacctgg gtgcaggtgg gctgagtccg aaaagagagt cagcgaaggg  11280
agataggggt ggagctgttt tataagattt gggtaggtag tgggaaatta cagtcaaagg  11340
gggcttgttc tctggcggac aggagtgggg gccacaaggt gctcagtggg ggagcttttg  11400
agccaggatg agccaggaga aggaatttta taatgtcatc agttaaggca ggaacagacc  11460
attttcactt cttttgtagt ggaatgtcat ctgttaaggc aggaaccggc catctggatg  11520
tgtatgtgca ggtcacaggg gataggatgg tttagcttgg gctcagaggc ctgacattcc  11580
tgtctcctta tattaataag aaaataaaaa tgaaatagtg gtaaagtgtt gggacggcaa  11640
aaattttggg ggcttggtat ggagagataa cgggcgatat ttctcagggc tgcttccagc  11700
gggattaggg gcgatgtggg aacctagagt gggagagatt aagctgaagg aagatttcat  11760
gctaaggggt gatattgtgg agttgctaga agaaacattt gtcatttaga attattcgtg  11820
atggcctgga tacggttttg tatgaattga aaaactaaac agaataagag aaggagaaaa  11880
acaggtatta aaggactaag aattgggagg acctaggaca tctaattaga gagtgtccaa  11940
gggggttcag cataattact tacttggttg gcaagttttt gggctctatc cttgagtttt  12000
ttatgttgtc atacaccagg ccagattgat ttaggtagaa acaacactct tcatttaaga  12060
atatacagag tcctcctttt tcagcagtga ctaagtcaag gcctcagcgg ttttggagga  12120
caactgcagc taaagagtca acttgggcct ggaggactga taaagtttgt gatatgtctg  12180
tgatgctagc agagaagaca ctagagaggc tatggaaggt cgtgacagag gttgaaatgc  12240
ctcctattcc agtaccgaga gcaatagtgg aggcagaaag tcttaaactg ataagcaagg  12300
gaattagtgg aataactctt ttttgtcgtg tcggtgtcat gaggggaaca gggagctctt  12360
cggtcctatt tgcaaattga attttaggag taaggaaaac tagtgtgcat gtacctgtcc  12420
aattagcagg tagacacatg gaggtagagg atccacagag gaagaagaga ccttgtgcga  12480
ggcaaaactg gagaagcaaa gtaaaaagat gagaaggagt gctgaaaggg gtgtcttgta  12540
cccagactcc tggggatcca gctagggcag cagccatcag aggttgtaat ggggactggt  12600
ggggtaactg cgtagagggg gaggttcgat tttcatggtg tatgagaaaa tgttgagtgt  12660
ctatgagcta cctttcactg ttatttatgg ggctgggtat aagtaaacaa caagagggct  12720
ttggagatga agagtaaagg aacatcaaag tgaaaggtta cccaggggaa ttccagtggg  12780
tctttgctga gagatacata aaggagcagc cacaggaata gtagtttgtg ttgtgagagg  12840
taaatacggg gggagtagag ttgatacaag gagaaaggtt ttttaagtaa gtgtggagga  12900
gggcggcagc ttgctgacgt gaaatgtctg gggaggtcta gctggacctg tctagaaagt  12960
aaatgagttc atcaggaggg taaaggtgag ggctgttaaa ggaagtttgg aggtgtagga  13020
```

gacaggagat gttgcctagt ctgcatgtaa ggtggggaca gctgtgtagg cattggaaga 13080
aagggaaatg caaagctaga gtttgttcgc taaggaggga ttagaaacag ctaggagaga 13140
atgagtaatg tttatagtgt ggtggagata gctggggaga ggtagagggt ggcataagaa 13200
tgggaatgag aataagattg agtataaaag taaagaatag aacttcatca gggtgaaagt 13260
attggagggt cccctgccag caaagattat ctatcccctc tgagagggag ttaagagttg 13320
ccagtcctgg gtgggggcaa atcctcgagc ttgatgtgta gggaaaggag ggggcctgaa 13380
taatctatga ggaggagtag aatagtagat ggaacagaag ttatttcctt gaggatagat 13440
ttccacgatg gaaaggaaat gagaggttct aagaggtggg ctggtgactt gtactatagc 13500
atagcctgcc tttgctggtg tgtggcgatt aggcctggtg gaactactat gaataaacta 13560
agtgtgttca gggtgaggaa cacgaaagaa ggaaatatga ggaaaagggg tgaatgtcag 13620
gtgaatcaga gagatacagt catagggtc aggtgtggta tccagaatac tgtgggaggc 13680
tggattgaag tctgggccag gaacaatggt aattgtcaga gacttaacaa aaagggagtg 13740
tagctgaagg agccagggag cagaaagtgt atgcgtcagg tgggagaaag aaaatagatt 13800
ttggaaatta tgagaaccgt agagaatgag ttgggcatag tttgtgattt tttgggcctc 13860
taaaagtatt aaagcagcgg cagccactgc atgcagacat gagggctagg ctaaaatggt 13920
aaggtcaagt tgtttggaca gaaaggctac agggtgcggt cccagctctt gtgtaagaat 13980
tctgactgcc ctaaccatgc ctaggaagga aaggagttgt tgttttgtag aagggattgg 14040
ggtttgggaa attagccgga catgatcagc agggagagca catgtgtttt tatgagaatt 14100
atgctgagat aggtaagaga tgaggaagaa atttgggctt gactgaagta atgggggctg 14160
tctgtgaagc cttgcggcaa tacagcctag gtaatttgct gagtctgatg ggtgtcaggg 14220
tcagtccaag tgaaagtgaa gagaggctgg gatgacgggt gcaaaggaat agtaaagaaa 14280
gcatgtttga gacccagaac agaataatgg gttgtggagg gagatattga ggataggaga 14340
gtatatggat ttggcaccat ggggtggtta ggcaaaacaa tttggttgat aaggcacaga 14400
tcctgaacta acctgtaagc cttgtctggt tttaggacag gtaaaatggg ggaattgtaa 14460
ggggagttta taggctttaa aaggccatgc tgtagcagga gagtgataat aggctgtaat 14520
ccttttaaag cgtgctgtgg gataggatat tggcattgag cggggtaagg tgattaggtt 14580
ttaatgggat ggtaaggggt gcaggatcag tcgctaagga ggcagtagag gtgtcctata 14640
cttgtgggtt aaggtgggga gatacaaggg gaggatgtga aggaggcttt gacctggggg 14700
aaaaggtggc aatgaggtgt ggctgtagcc taggaatagt tagggaagca gataatttag 14760
ttaaagtgtc tcagcctaat aagggaacta ggcaggtggg gataactaaa aaggagtgct 14820
taaaagagta ttgtctaagt tggcacaaga gttggggagt tttaagaggt ttagaagcct 14880
ggccatcagt acttacaaca gttatgaagg caagggaaac aggcctttga aaagaaggta 14940
atgtggagtg ggtagcctcc gtattgatta agaaggggac gggcttaccc tccactgtga 15000
gagttaccta gagtgtctgt gatggtcctg taggcttctg aggtgattgg gcagtgacag 15060
tcttcagttg ttaagccgag aagatctggg aaggagtcag tcagagagcc ttggggcaga 15120
gttccagggg ctatgggagt ggctgccggt gagatggaca gtctgatttc cagtggggtc 15180
ttgcacagat gggacatggc ttaggaggaa tcttgggctg cgggcattct ctggccaggt 15240
ggccagattt ctggcacttt tagcaagctc ctgggggagg caggcctgga ggaatgcctg 15300
gccactgtgg tttaggcgtt tggaagttct tgcgtgctgg agatgtggct ggggtttgtc 15360
tcacagtgga ggcaaggaat tgcaactcag aaatatgttg ctactttgct gcctctactt 15420
tattattgta cactttgaag gcgaggttaa ttaagtcctg ttgtggggtt tgaggactgg 15480
aatttaattt ttggagtttt atttaatgtc gggagcagat tgggtaataa aatgtatatt 15540
gagaataaga cggccttttg accttttagg atctagggct gtaaagcgtc tcagggttgc 15600
tgccaaacga gccatgaact gggctgggtt attatatttg atgaaaaaga gcctaaacgc 15660
tatctgattt gggataaaga aaaaggaaca ttaaccttga ctatgccttt agctccagcc 15720
accttttttaa gaggaaattg ctgaacaggt tggggagggc tagtcatgga atgaaactgt 15780
aagctgggcc aggtgtgagg agaggaggtg ataaaaggat tacagggtgg agaagtggag 15840
gctgaggaag aattgggacc tagctcggcc tggtgaggag gcgagaggtc acatgggttt 15900
gtagaaaagg aagattagaa agactcagcg atgcttgggg ttgggactga ggggacaggc 15960
gggagggaaa gaaggaagat ttgggatgag ttgcattggg aacagagact agggagggac 16020
caatgtgtaa aagaatgcct ggacgtcagg cacctcagac cgtttgccta ttttacaaca 16080
agaattattt agatcttgta ggatggaaaa atggaaagtg acattttctg gctatgtgga 16140
actactgtcg agtttgtatt ggggtcaagt ggcattgcag aagaaaataa ggcatttagg 16200
ttttaggtca gctgtgaatt gaagaggttt taggttttta agagcacagg ctaagggaga 16260
agaaggggga atggagggcg gaagcttgcc catagtgaag gaggcaagcc cagagagaag 16320
agagagtaga gacatggaga gaaggggttg gggttcttg cccccaagaa gagcggtact 16380
tgccgctaag ggtgaaggag aaggggttgg ggggttcttg ccccccagaa aagcggagaa 16440
ggggtagaga catggagaaa agcggtgggg ttcttgcccc ccagaaaagc agagaaggag 16500
tagagacacg gagagaaggg gttgggggtt cttgctccca agaaaagcag tacttgtcgc 16560
taagggtgaa ggaccaaggc aggtgtcccc acatggtcag acacctctga aacatgggtg 16620
aataatcagg caggcatccc tgcctgattc caaagggaag actgtcttcc caattccgtg 16680
actggtgccg gagttttggg tctatgaata aaacgcgtct ccttcatctc tgtcagaaaa 16740
ggaaaggaac tgaaattaag agagagattg aagggtgatg ccaagattga aaggagaaag 16800
aggttgaggg atagtgagag aggttggaga agagagtaaa aagaggccac ttactggatt 16860
taaaattggt gagatgttcc ttgggctagt tggtctgagg accagaggtc ataggtggat 16920
ctttctcatg gaataaagag caggaggaca ggggattgat ctcccaaggg aggtcccctg 16980
atccgagtca cagcaccaaa tttcactcgc atccgtgtga agagaccaca aaacaggctt 17040
tgtgtgagca acaaggctgt ttatttcacc tgggtgcagg tgggctgagt ctgcaaagag 17100
agtcagcgaa gggagatggg gtggggctgt tttataagat ttgggtaggt aaaggaaaat 17160
tacatcaaag gggggttgtt ctctggcggg caggagtggg ggtaacaagg tgctcaatag 17220
gggagctttt gagccaagat gagccaggag aaggaatttc agaagataat gtcatcagtt 17280
aaggcaggaa caggccattt tcacttcttt tgtggtggaa tgtcatcagt taacgcagga 17340
accggccatc tggatgtgta catgcaggtc ataggcatat acacaggcat atgatggctt 17400
agcttgggct cagaggcctg acaataacaa cccacaaaaa atatataatt taggtaatgg 17460
ataatgtatc acttatgttt aatattggaa gacatctgta attatatttg cagattgtct 17520
cttagtattc aactagaatg aaaattgata taggttgatt tcatatcttg tctattgcaa 17580
atagtgctgc aataaacatg ggagtgcagg tatctatagt atatatacac aatggaatat 17640
tatttggcca tagaaggaaa tgaaatcctg tcatttgcag aaacaggagt ggaactgaag 17700
gtcattatgt taactgaaat aagccaggca cagaaagaca aatatcacat gtttccactc 17760

-continued atatgtgaga gctaaaagaa tgaatctcat ggaagcagag agtagaattg tggttaccag 17820
aggcttagaa aggggtggtg ggggataaag ataagttggt tgggtacaaa aataaaatta 17880
gatagaagga acaaattcta gtatttgata gtacagtggg aaaactatag ttgacaataa 17940
tttattgtat atttcaaaat agctaaaaga gaagaaatgt actattccca acagaaggaa 18000
aaggtaagtg tttgacggaa tgaatattct tattaccctg atttggtcat tacacattgt 18060
atacaggttt caaaatatca catgtacctc caaaatacat acaactattt tgtatcaata 18120
acaaaatttt taaaaaactg atataggctg tgaagggcaa accatgtagt catctcagag 18180
ctcagcttat tcttgtggat ataaatgttt tagctggctc taaaccaagg attttgtatg 18240
aagtaatact tattcaaata ttttcaacaa aatagagtac cttgcaaaca ggactttgag 18300
atttttcatt tgtttccctt tacagttcgt catatacgct tcatcttcta gtgttgattg 18360
atgaaacaac gttccacatg agacagcaga gcaatagaac acagaacagg actctgcctg 18420
tgtggtggcc ggtttccatc ctttcacaaa caaagagata tttataaaca aatatttata 18480
tgcaaatatt tgatccacct aggaaaaata gagggctact ctttcccacc aggagaggcc 18540
ttatagcctg tgcacatatt tgaacaaggc aaccagagac tttgatggtc tcaactctac 18600
cactcaccaa ctgtgtgatg ttggatacaa acttaaccac tttgcaactc acttccgcat 18660
ctgtaaaata agggtgataa taatagcacc tggtttagag agttgtaaag ataaaagcaa 18720
cattagtaaa gtacttagga tgaagtaatc atgttttgaa tatattttcc tttaaatgtg 18780
gctgccaata ttttcatggt aatattttca aatgtattca atagcttttt ctttatcagg 18840
agaaaatcag ttgttttaat taaattgaca ttgaattttt gatacattta ggagaattta 18900
gtttcttttt atacagtatt gacgcttcta atcccacagc atgtttttct attttttttct 18960 tttcttcaat agttttaaaa tttttttgtt cattttggtt atgcaaatat ctagttaatt 19020
tctatctgta atattttcct atttattttt agtagctctt ataaagggag cattttgttt 19080
ttcctgtcta tcctgacata ataaagcaat tagtttttaa ttgattttta aaaatattta 19140
tgcattctct ttcatatgta taataataat acctaaccat tttatgattt acatgtggca 19200
atgtcaagaa gaattttaaa gtaagattta ctaacgaata ttagagaaca tgctcaaaaa 19260
cagtcctctc cacccccctca cttccacttg cattcttgat caagaagtga aataaaaaat 19320
actaagacta ttgagtcaaa ctaataagac acaaatctgg actttggaga ctcatttccc 19380
tcccactttt gatagcttag ctgaggagga gatcaaatgg ttgagtcagt ctgtagagag 19440
atagcaaggc tgattatagt tttcctggcc tgcaaagctg tttccagagc cctcagtata 19500
cagaccttgg ccatcagtat gcatactctc tggtgtggtt tctgggcatc agatccctta 19560
atatataggt tggcgctaaa gtaattttgt aaacttttaa tggcaaaaac cacaattact 19620
tttgctttta atggcaaaaa ccagaattac tttagcacca acctatatat tgttatttag 19680
agaaactagg cattccctac ctctcttagg caaacctata gctatgtaac atggcaacgg 19740
aatgacacta actgtctcat tctccttggg agtgctctct gtatgttcag tctcccagtg 19800
aagagaaccc ttctatcagg accttcatca tcatacaaaa ggaatatcta tgccaggcca 19860
cagctgcaga ttagtgagtg tctgagaact gcatcttttc tgttattttt ctgcttgaaa 19920
gtttttcacc aataaatcct acactatgtc tgcaccatgt ggtgctagtt atttgtgttc 19980
tcttgcatga cactgatgat gttatccaaa cacaatttca aaaactactt tctgtagttg 20040
gtaaatatat agaaattgag aaaaaggaag aaatatgagg aagaaagatg ttatctgttg 20100
caacagttca atgttcttaa ctgaagccac agatgagatt tggctcattt gcagacatat 20160

```
gggtgattgg tacagtaggt ttataaacag aagtttaaac ttgtaagctt aagcttccgt  20220
ttataaacag aagtttaaaa ttataggtcc tgtttaacat tcagctctgt taactcactc  20280
atctttttgt gtttttacac tttgtcaaga tttctttaca tattcatcaa tgtctgaaga  20340
agttacttat gcagatcttc aattccagaa ctccagtgag atggaaaaaa tcccagaaat  20400
tggcaaattt ggggaaaaag gtaagatttt gagttatgga tgtgttgtaa gtttgtataa  20460
tagaagtggt tatagacttg catcttcaat attagtgata tagttactat tcaacttaaa  20520
ttttcaatta agtctcttat gtttaagcaa aggaacaaaa agtgtatgaa caaaatgatt  20580
agaaaaaagg gttttgtaaa aacacttatc tctgcattga ataatcaatc ttttacattt  20640
ttgaaatttt ttattatcac actcaatata attgggacag aatttttcaa atgattgggt  20700
tgtatgaaga ttttatttct ttatgagatg aagccatgga aaaagaaaca tgttcaggaa  20760
agtcatgatt tcatatgtgt gtgtgtgtgt gtgttttttt ttttataaga aaatgctttg  20820
tgtcagacag agagaccttt ataggatttc atttgactat ctaccaaact aagcataaat  20880
caccctaaaa tttctcctac ttcttttgga gatttttttac taacttacta aaaaataaaa  20940
catgttaagt taaatgaaat gaatcattaa ggaataaagg aagaaaagag gtaaagaaat  21000
atcagaagac ataatatatt cataatattc aaaaccacat tatatcaagt aactttgtat  21060
ttttcaattc aaattaaaat catgaaataa gtggtccatc tgtgttgact ttcacttaaa  21120
caaaactact cttcatctta ctcagaatcc tatagttttc ctattatgta tggttcttgc  21180
cttctggctc ctagcctttt gggagtgaaa tctgccctag cgaatccata gtttaaatca  21240
gtgtatttga gttaaaaata acttaaacag tgatagtgga gaacacaaag aagggtgata  21300
gaaacagaaa aataaggaga gaagagtgcc aaaattctca catattattt aagttgttgt  21360
cctctctcct ctccccacac agaatataac atctttaata ttctagcatt gctataaaca  21420
gaaatttcac tgttacatct tggatccatt tatgatgagc attgtaaatc ttgagaaagg  21480
atagcagatt aattctgttg gcttcttttt taatactgaa attttttttt agaaagaaga  21540
agggtttaag aattttacaa tattttctgt ctttatttcc ttgtttatat ttcttctttt  21600
atacactgaa agagaatggg catatcatga gcctaatatt accaacaatt gccctttact  21660
tgtcctctca cacccttcc cacctctttt cctgccaatc caccttaagt tcccaccaca  21720
agaattccct gaattcacgg aaatattgaa tccatgtctt cttcatgttc ttaatctcat  21780
ctaattttct cattatcgag cttagaatct acattatgta atataacatt gtattatgta  21840
atgtctactc ttagtctctt acacttctcc tcttcaatgt gtgttaattt ttccttaaaa  21900
actccagctc tggctaggtg cagtggctca tacccatagt cctagcactt tgagaggcca  21960
agatgggagg attatttgag gccagaagtt tgagaccagc ctggggaaag tagagatatg  22020
ccatgtctat aaaaaaaaaa tttttttaat taactgggca cccatagtct cagctgcttg  22080
ggaggctgag gaaagaggat tacttgagtc caggagttgg aggctctagt aagctaagat  22140
caggcgagtg tactccagtc tgggtgacac agcaagatcc tgcctcaaac aaatcaaaac  22200
aaaacaagac aaaaaccccca aaaacaaaca aataaaaaca actccagttc tggttaaacc  22260
cgaatatcca cccagtctgc cccagagttg aatattgctg gtgaaaaata cacaaatttt  22320
caaccccagt tactctcacc tttcctctgg taagaaaaaa gcatccatct acactttttt  22380
ttgttgttat ttaaatgtct atcctaccat gtccttactg atactctgct ttccttccag  22440
atagtattta cgataagtat gtacttatga agggacggct cctcattttg ctctgaattt  22500
```

cagtccatgt gtcgttttca aagacagact tccgtaattt tttcctttct ctcctgtgtc 22560
attattctct cttccttctc tgcttttcct ttttggtgca ccaacatact ctactactca 22620
ccaatatact ctgctactcc ttttataaca aaacacaatc cttgcttgac cacttaagcc 22680
tttccattat tatttaactt ctttgtttcc tttcacaact caacttttga aagcattttc 22740
tttggccact gactctcagt tcttcacctc tcattctgtt ctcaaccaac tctattaggc 22800
ttctgccccc ttggtgccat agagactgag ctttaggtca ctgatgtcct gcctgtttca 22860
tcccaatagt cacatgtctc ttccattact tcacttccct gcagcattga aaaagttgaa 22920
cagtcctcta aatgcttctt ttgcacatcc ctcctgacac atcctcatgg cttctcctgt 22980
caccatgcct gcctctcctc attctttgtt gattcctcct cctagatgaa actctacaag 23040
atggaatact ctgaagccct gtcctgggtc ccgttttatt gcatcactca gtacactctt 23100
ctaatctacc tcattcagtt gtttgacttt aaatagagtg actccccaat atctctgtat 23160
gacctttccc tgaatctcaa gactagaaaa tacatgtgcc actttcacat ttccataagg 23220
agttctaatc tcattttaaa cttaaaatgt caaaaatagt aatatttatt tttcttctaa 23280
aattgtctct ctctccagac agcctcatct cattaaatac acatataaat atatatttaa 23340
atacaatttt caagtgtttt ctctgtgcca gttctgttct aattgcatta taaatattaa 23400
attatttagt gtctgatact ttgcagtctt tctgtctccc atgctttaac catattgaaa 23460
ctcagacaca gagatgttaa aaggtgttaa ataatttcc cgaggtttca caagcaataa 23520
gcagcagaac cagaattcaa accaaaacat actgatatgg tttgactgtg tctccaccca 23580
aatctcatct tgaattgtag ctcccataag tcccacatgc tgtaggaggg acatggtggg 23640
aggtaattga atcatgggag cgggtttttc ccatgctgtt cttgtgatag tgaataagtc 23700
tcatgagatc tgatggtttt ataaagagga gttttcctgc acaagttctc tcttgtctgt 23760
ggccatgtga gatgtgcctt tcaccttcca ccatgagtgt gaggcctctc cagccacatg 23820
gaaccatgag tccattaaac ctctttttac ttataaatta cccagttgtg ggtatgtctt 23880
tatcagtcgt gtgaaaatga actaatgcag taaattggta ccaatagagt agggcgctgc 23940
tgtaaagata cccaaaaatc tgaaagagac tttgggactg ggcaacaggc agaggttgga 24000
atactttgga gggctcagaa gaagacagaa aaatgtggga cagtttggca cttcctagag 24060
acttcttgaa tggctttgac aaaaatggtg ataaggctga ggtggtctca gatggagatg 24120
aggaatttgt tgggaacggg agcaaaggtg actcttgtta tgttttagca aagtgactgg 24180
tagcattttg ctcctgccct agaaatttgt ggaacattga acttgagagg gatgatttag 24240
gatatctggc agaagaaatt tctaagcagc aaagcattaa agacgtgact cgggtgctgt 24300
taaaagcatt cagttttata agggaagcag agcataaaag ttcagaaaat ttgtggcttg 24360
acaatgataa ataaaagaaa atcccatttt ctgaggagaa attcaagcca gctgaagaaa 24420
tttctaaagt catgggaagc caaatgataa tcgccaaggc aatggggaaa atgactccag 24480
ggcatatcag aggtcttccc agcagcccct cccatcacat gcccagaggc ctaggaggaa 24540
taaatggtat tatggactga gcccagggtc cctctgctgt gtgcagtcta ggaacttggt 24600
gccctgcatc ccagctgctc cagccatgac taaaagaggc taaggtacag ctcaggtcat 24660
ggcttcggag agggtgcaaa ccccaagcct tggtagcttc catgtggtgt tgagcctttg 24720
agtgcacaga agtcaagagt tgggttttgg gaacctctgt ctagatttca gaggatgtat 24780
ggaaatgcct ggatgtccag gcagaagttt gctgcaggca tggggtgctc atggataacc 24840
tctgctagga cagtgcagaa gggaaatgtg aggtcagaag ctccacacag agtccccact 24900

```
ggggtactgt ccagtggagc agtgagaagt ggaccaccgt cctccagctc tcagaatggt  24960
agatccactg acagcatgca ctgtccactt ggaaaagctg cagacactca atatcagccc  25020
atgaaagcag ccatgaggga gactgtacct tgcaaagcca caggagcaga gctgcccaaa  25080
gacatgggag cctacctctt gcatcagcat gacctggatg tgagatatag agccaaagga  25140
gatgattttg gagctttaag atttggtgcc ctttggactt gcatggggcc tgtagcccct  25200
ttgttttggc caatttctcc catttggaat gaccgtattt atccaatgcc tgtactctca  25260
ttgtatctag gaagtaacta actttctttt gaatttactg gctcataggt ggaagggact  25320
tgccttgtct cagatggact gtggactttt gagttaatga tgaaatgagt taagtctttt  25380
ggggactgtt gggaaggcat gattggtttt gaaatgtgag acatgagatt tgggagaggt  25440
cagggtggaa tgatatggtt tggctgtgtc cacacccaaa tctcatcttg aattatagct  25500
cccacaattt ccacgtgttg ttggagggac ctcgtgggag gtaattgaat catatggtag  25560
gggtgtttct cgtgctgttc ctgtgatagt gaataagtgt catgagatct gatggtttta  25620
taaaggggag tttccctgca caagttcttt cttctcttgt ctgctgccat atgaggtgtg  25680
cctttcacct tccaccatga ttgtgaggcc tccccagccg cgtgaaactg tgaatccatt  25740
aaacctctct ttccttataa attgcccagt cttgggtatg tcttattagc aatgtgaaaa  25800
tggactaata cacatgctaa ccctaaagat ggtgttttgc tttttatcac tatgagatac  25860
tgcctacaaa tgtgcatatc taccaacttt ctctaaagaa aaatttcaga aatttttgca  25920
atagatttta gcttagaaat gtatacttaa tttatccatg ggtcatcaaa ttccctagta  25980
ctagctagtc aaacttctgt tctctttcac atgtcatact gtaacagatt tcttactgat  26040
aaaacaactc tgttattttg ccctcctaga ttaaattctt ccagtggttt ccccaaaaat  26100
ctaacttatt ctggctagaa aaggctgtaa ataatgtctc ctccttgtta ttttaaaaac  26160
aaaacaaaag aaaacaaata aaacctttaa catcattttt cacattggcc acaattcttc  26220
tgcccctctg aatatattct gtttttcaaa tagaaatctt ttccttaaat tattgtcttt  26280
gaacttcatg taattgctac ctgtaatgtt cttcctactt attttgcatg ctggttccta  26340
ttcataagat ttgaactgcc tgctctctat aacagcttag ttttaaatct ctgcacaaca  26400
tcgccaaatt tgagatcttt tctccctttc tttctttctc cctgtctcac ttatatatct  26460
atttatctat ttcctcctac aattaaaatt tatagctgtg aaaacaggaa cttgtacatc  26520
ttgctcactt tgatattgtt agcacccagg ataatgtcta ataaatacaa ggcactcaaa  26580
agataacttt tgaataattg aactttttaa taattgaata agttcattga ataaataaac  26640
ttgaataatt gaatacacat ataaataaga aaataatttt aagaaagata gcactggcat  26700
ttataattct aatcttagat aaaatcttga acatgtagtt ctttcagtag taactatttt  26760
ctaaagtcta tataagttaa gttttactat ttattagtaa ttgtctctgg atttcacaat  26820
attattgcac catcaactat gagatgtaag acatagctca gaagtatagt gagattatta  26880
tggtatccct gaattggatt ttcttgaaat atctagctag tctttaccta atgtataata  26940
gctttataca taatgatgat ttaaataaca tagtcacaat aataattcac tcacaaagtt  27000
tataattcct gtttttttt taaatagaga aatgatctat tctgggcttc actattcatt  27060
aaaaaggaag tattcaataa aagtttcttg caaaaacaca tgaaaatttt tttgaaaaat  27120
tgcaataaaa atggtgtaga tctggactga ttaagatcaa aagctaacgg gaggacaccc  27180
aaagacatta tgaaaagaca gcctatcttg ttcattctgc agctaaattc tcataattgc  27240
```

```
ctggggggat acataaacaa ctgaaactgt ttttcttgac atgccacaat tgtctactca  27300
agcaaagact tctcctattg gcttctctgt taatttccag ctactcactt ttcccaaatt  27360
tgtacaaaca aaatacacta tatctaggtt gactggtttt ctccattctc tattataaat  27420
tctgtttttg cttatctgtt tttttaaatc agtctaccag ttaacagctt ctcctgccag  27480
aatcaattta catacaaaac aattaagtga ttttgattta ttcttgacat attcttcaaa  27540
aatatttttt gaatattctt gaatggctag caaatccatt tctttccaat aggcatatta  27600
ggaaataaag gtaaaatgaa tgaatgaatg aatgagtaaa taatccaaat gaaagttata  27660
ccatttttag gcctctctgt taattttgct ttccacagca cctccagctc cctctcatgt  27720
atggcgtcca gcagccttgt ttctgactct tctgtgcctt ctgttgctca ttggattggg  27780
agtcttggca agcatgtgta tgtactgccc ctgtttttgt caagaggaag tatctagaat  27840
ttcaaatatt tagcaacaaa agtttattcc ttcagtggaa gatttataat aatgataggt  27900
gataggccca caaggaggac ttacaatgtg gaacttagtc tctttccctc actcctgtag  27960
agtaattgct ttccctaccc ctttaatctt tatactactt ctgcaaatga taaaggatga  28020
tggctctatt gagaatttac aattttttgt catttttttta atgtggagtt cacgtaactt  28080
tgaagataga aatgaaaaaa atgaacaaac tacaaaacat cagtgaagag ctccagagaa  28140
atatttctct acaactgatg agtaacatga atatctccaa caagatcagg aacctctcca  28200
ccacactgca aacaatagcc accaaattat gtcgtgagct atatagcaaa gaacaaggta  28260
atcttgtatt ctcttggagt tatttattgg acaataaact aaaccactga gtctcttaag  28320
aatcatttta taattagcta gcagcctttc tctagggagt cataatttgg gggaaagaat  28380
tacatgtggt tgatggagaa ttcattgata tttccacgca gttagaagaa aaacagaaaa  28440
agtagtaaca acaataggcc cccaaattat caggagataa tggttacata ataaaatgtt  28500
agacaagaca gtttctctaa tctgtcactt actataatta ttctgggcac tgaggttaat  28560
agaagacagg gaggaagtga cacctcttta caggtgactt cattcttaaa tttcagtcag  28620
tgattgataa caaagtccat agaaaaaaat aaattgagac ttcacctttg ggatcgggga  28680
gttggtcttt tagtgtctcc ataagtttct atagtcatag ttgctaaaac atattccttt  28740
tgctcctgag aaacctcaaa gtttcaacat ttcagagaac aaaaattaaa gaagataaga  28800
ttggtataga taggtggggt taattcttac tatacagaat gtttccagta attagttttt  28860
attgtcttta aagaatatac aaaataacaa agaggaattg acataggaag acacacttga  28920
atccaagtgc ttaatttgaa attttttttgt tcaagttatg tgtctgacac attatggtgg  28980
tatataagga actagaatac aggattcact tacttcccct tcgatgtaaa aaaaaaagaa  29040
acggcatgta atcccagcta cttgggtggc tgaggcagga gagtcacttg aatccaggag  29100
gtggaggctg ctgtgagctg agatcacgcc actgctctcc agtttgggca atagagcaag  29160
actctgtcaa aaaaaaaaaa agggggaaag agagaaagaa aaagaaagaa gaataaacag  29220
caaatgtgat caatgtcaca cagagaggaa aggaaataat aagaattatt atgactatca  29280
acaaaaccca aataaaacta tgttcttctt ccagagcaca aatgtaagcc ttgtccaagg  29340
agatggattt ggcataagga cagctgttat ttcctaagtg atgatgtcca aacatggcag  29400
gagagtaaaa tggcctgtgc tgctcagaat gccagcctgt tgaagataaa caacaaaaat  29460
gcattggtaa agcccaggtg tttctaccat catgggatag agaggggtgt ggcatgttgg  29520
agaagacttc aatcaaccca ctcatgattc tggtttattt cagttggggt gtgaagtgac  29580
tgaaactttg tacacttatc tcaagatatc ataggcaagg taaaacatac aagtttagga  29640
```

```
ccttagcata agagaaatat tactagctga caggtagatg agtattacag ggcacccaga  29700
atctataggt ctgtaagcat ttccaaatta gaatctagaa ccaaatctca gaacttaatt  29760
tataaacatt tatctaaaaa cagaggatac agagattatt ccccaggatt agcaattcca  29820
taagaactac atgggagaat atgttttgtt tctaccattt tgtatttttt aattcactaa  29880
gagaaatagg caagttatag taggttagca taaaatatgt acaaacaaga agaactgaag  29940
taagatggca caggcaagtg tcagatatat tgtactgagt ccttgaatcc caggaaaaat  30000
gtgttttctg gtagctttat tgatttattc attttcttag ttttccatgt ctaaataatg  30060
tttccatgtt acacttatta catagcattt ttggtctctc acatagcaat catatatttt  30120
taagcaaaat taccttttct aaaattctct gcttccccac aataagaaac tttcatcatc  30180
ctttatagaa gagagataaa tcaacccaca atctcttcct catcagatca ttgtcaagtg  30240
acccattcac agttacttac tctagaaaaa atttttaaag gctagaataa gaaaaaaacc  30300
tgttatttgg ctacaaaatt ctggactggt tctgaattct gttctgtaac cactcacatc  30360
tgagtgtgtg gcattttttt cctactcttt ctgtttctat taactcttgt ttatagccat  30420
tacccacctc ctttggccct ggacacaata tttactgctc aaattttttta atcttgaact  30480
tgtcattgtg aactcttcac tgactgtaaa ttaaggttgt acatggatta gtagggcctc  30540
tcttcttgtg agaccagcaa tgatattgtt aaaaatattg aaattttgta gtaaggagta  30600
ctttctttca atttcttata atgacattta atagtagtag tgcaatgtcc agtatgttac  30660
cttaaaacag caatttgtaa gaaattacat tataatgtaa aatacaaaag taggagactg  30720
tttcttaaac agactatctg tatttcctgt aggaatttat aaaatcccag agtagatcat  30780
atgactattg gctgggatta tctcctgaag aagattccac tcgtggtatg agagtggata  30840
atataatcaa ctcctctgcc tggtaagtgt ctattcttgt tagaatttta tagctgggtt  30900
tgagtagagg tattttcctt aggagcactg tagattcaaa ttaaaaccag cttcaattga  30960
aattgcatgc taaaagaacc cttttctatc atgcttcttt gatgtatttt ctaatacata  31020
aagttaccat aaatgccttc tcataatttt gacaagtaac taacaaaatt acagcagcca  31080
aattatggag aactctgtaa ataattttat ctaagaaaaa ttgtggaagc ccagaaaagt  31140
cattggacta acaagtactt aatattgtga taagttctag ggttcaaaga tgaatgaaat  31200
attgattcat cattaaagtt acttaaccat caattttatg tgcagactga ttgaattatg  31260
ctagagataa agagaatata gtgtgataaa tgcttcagta agaatacaca gactaacaaa  31320
acataaattt ttgcaatgat acttttgtta taaatgacac ttcaaatggg cattttaaaa  31380
agtttatgga tttagggggt acgattgcaa ttttgttata taaatatatt gcataatgat  31440
gaagtcagtg ttttcagtgt aaccataacc tggatagtgt acactgtacc caacaggtaa  31500
tttctcattc tttattttct tcccaccctc ctactttttg gagtctccaa tgtctattat  31560
tccacttttt atgtgcatgt gtacatatta tttagctccc acttaagtga gaatatgcag  31620
tatttaaatt tacgttcctg agttatttca tttaagagaa tggtctccag ctccatccat  31680
tttgctgcaa agtcatgatt tccttctttt ttatacttga gtagtatttc atggtgtata  31740
cactctaaaa gaaagcatgg tttcatgttt tcttatgcaa taatccgttg atggacactt  31800
aggacagttc catgactttg ctattgtaaa tagttctaca acaaacattt aagtgtaggt  31860
gtcttttttt taatataata attcctttcc ctttggttag atacccaata gtggaattgc  31920
tggatcaaat ggtaattcta tttttagttc tttgaaaaat tgccatagag tttacactaa  31980
```

cttccattct gaaatgggca tttttgaatg aaaaatttaa agactggttt agaagagcac 32040
ttcaggtgaa agaatataaa cttcagctta atatatcaca tatatagtat agataaaata 32100
atttgttgtg tagtataatg aggaatgtgg ttataaatat actattttaa gtggatttat 32160
acgttgtatt tgttctgctt ataatgggaa aaaaagtctt tacatataaa aatagtggca 32220
aattccattt gtattttta atctctgaaa tttgggaagc agaaaatatc aaacgaagaa 32280
agaaaccaga gtctcaacct gctggacact attggaagtc catcatttaa cacgttttta 32340
gtatatactt ttagcaggag acagctctga gtcaactgtg ttgaggtgcc accacagcga 32400
gtttaggcac tcagatccct gcatactcat cacattgggc cataatggca aatagaattt 32460
tttgttttgt tttgtttgtt tgctttttct ttcacataga aatagtaagt gtaggagtgt 32520
gggtcagaaa gaaaaggtgg ccctacctct gatggttggc aatgatagga tacaatggga 32580
gataagctat ctacaaatgg agtggagaag gatatatatt tcaaaggcct aatttgtagt 32640
gaaagactag agacaaaggt aatgtgtgtg tcaggagaga gtacagatgg aatcttgttt 32700
tgcaaacgta gaatatgtat gtgtttgtaa ttattgcaaa tggaatggta atctataatg 32760
gaatggaaaa cattgtagat attttcagtt atcaaaaaga aaactgaaaa agtatataat 32820
aattgtatgt atgatatata tatgtgtgtg tgtgtgtata tatatcttca ctttataact 32880
ctgtgttgtt ttggggtttg tttctgaaag gggggttgtaa taaatgacat ctgtactatg 32940
tcaccacaaa taaatctcat tcttaaacat ttaattgatg aacttattta ctggttgata 33000
tcattatttt tttacccaag tattgatgct aaattaatct aaaaggtaat atttttaatt 33060
tataaatttg tttttagtgc atagtccctg atcactaatc tagtatttat gggctggtca 33120
ttagaacttc agagtaaaat cttttgccaa gtgtcactta gagatgatgt tgaacttcag 33180
gtgtcatata tctcaggtga attcctgact ttgatgatta taaaaagcac ttgagggaga 33240
aagggtccaa gtcttactac tcctagccag ttagactagg agaatcttat ggaatggtat 33300
tattccaaat tatattatat atgaaggggc tggggtgcta actctgtaag caaaggacag 33360
caaatatcag atgttagaaa gtggaaaaag cagggagaaa tgaagcagta tttgacattg 33420
catatgtgtt aacataaaca attaactcgg acattcttga tactctgaac attaaattag 33480
atttagttta aacaacacag agtctagggc aataatatca tgttggaagt gtaatttttt 33540
tttctgtgaa tatgtttcaa atatctgact tgccaagtgt aattctttac tttctctttc 33600
agggttataa gaaacgcacc tgacttaaat aacatgtatt gtggatatat aaatagacta 33660
tatgttcaat attatcactg cacttataaa aaaagaatga tatgtgagaa gatggccaat 33720
ccagtgcagc ttggttctac atattttagg gaggcatgag gcatcaatca aatacattta 33780
aggagtgtag ggggtggggg ttctaggcta taggtaaatt taaatatttt ctggttgaca 33840
attagttgag tttgtctgaa gacctgggat tttatcatgc agatgaaaca tccaggtagc 33900
aagcttcaga gagaatagac tgtgaatgtt aatgccagag aggtataatg aagcatgtcc 33960
cacctcccac tttccatcat ggcctgaacc ctggaggaag aggaagtcca ttcagatagt 34020
tgtggggggc cttcgaattt tcattttcat ttacgttctt ccccttctgg ccaagatttg 34080
ccagaggcaa catcaaaaac cagcaaattt taattttgtc ccacagcgtt gctagggtgg 34140
catggctccc catctcgggt ccatcctata cttccatggg actccctatg gctgaaggcc 34200
ttatgagtca aaggacttat agccaattga ttgttctagg ccaggtaaga atggatatgg 34260
acatgcattt attacctctt aaaattatta ttttaagtaa aagccaataa acaaaaacga 34320
aaaggcaagt tacgagactg acttattttt aacttctgtg tgttgagcta ctgtaagctt 34380

```
ggcttttgtt aaagacatac agcaattagc tatgcaaaca taagcattgt tctgaaaaaa  34440
aatatataga tagatatgtt tatctccata actcataact gggagtatta tacccaagag  34500
gctttgttac aaggtatttt ttatcctgtt agtaaatatt ttcctgtaat tctataataa  34560
gcaaataaat tttcatggtt ggggtagatg caaaagtgac acataatcgt ttagaaagca  34620
actaaacttg ttttaccagc tgtttaggca tttttgtaac ccctccttga tttggaggtt  34680
tgaccttgac ctaatttttt tctttaaaac cagcccttac aatcttctgc cccctcctct  34740
tctgtgacag tagctgggcc tagagggaag ggggcttgta tagtttgtgc agcagagcat  34800
tctcagtgaa atacagatcc cggcccagtg ggatgccaaa atgacggaga gccacatctc  34860
tgatcttcaa aatatcatga tttgggtttt cctggaagta aaacaagaag agataaataa  34920
catttacagt ttgatcatta aaagagcaat ttgtgcgtca gaacagaaaa aggaacctat  34980
tccattaggg taccaactaa aaatacgaag aaaaattata atctggtact tgctagtgga  35040
ttaccatagc caaaaaatga tgtttcagtc tccactgaaa aaaaaaaaaa aaaagattag  35100
gactgaaatt gagtattaaa tgttttcctt tgaagcaatt cctttatccc cccccccctt  35160
tttttctatt aaagagaaat tatagcaaga ccaatttgtg tgcaaaataa gttttcggct  35220
tattatactt ggcctggtaa ttttgcataa aaggcagcaa gggttgggta tggtggctta  35280
tgcctgtaat cccagcacgt tgggaggcca aggcaggtgg attgcctgag gtcaggagtt  35340
caagaccaga ctggctaaca tggtgaaatc ccatttctac taaaaataca aaaatcagcc  35400
aggcgtggtg acacacgcct acagtcccag ctactcggga ggctgaggca ggagaatcgc  35460
ttgaacccgg gaggcaaagg tgccagtgag gtgagattgc accactgcac tccagcctgg  35520
gtgacagagc aagattccat ctccaaaaaa aattaattaa ttaatttaaa atgcagcaag  35580
aattgattgg ccatataggc ttctttaagt tgaccttgac tgaactttac ctaaaaatat  35640
gctattttag ttaaagtctt agtaaaataa ccagtgtctc aaattctttt attttaaaag  35700
atgcttttg aatttatgca aatgactata ctgtcataaa atcacaatcc aaattttaga  35760
actcaaagag aaatataaat ttgcttacaa aaacatactt cactcaaata actcaaaaga  35820
aaaagatttt gttgaccctg ctttaaccag agccagagct ttcaaacaat gtttatttgg  35880
gaaatgccat ttacaagcca acagctcatg aaagctgtct atcaggcatg gtagaatcta  35940
ggaaagaggc cccctactta tcagtatttt ctcctaatat ccccaggtag caagattcta  36000
tgtaaatcat ttttattttt ttatggaact cttttgggca ccatcatttt tattagcata  36060
ggggtggctt cagttaaaat tccatagcaa ggcagtacat ggctctcagg tggaaattct  36120
ctgttcaata ttgtcattgg gaaatattta cagtttttg ccatcagccc caataaatgt  36180
gccacaaatg ccacaaatga aatggaggat ttgtcctgac tagcgctcta gcttctaccc  36240
aatactttgt gggctgaggc aattttacta gttcccattc agcatgttca attaacattt  36300
actaaaagag cagattttta tgccttcagc tttatagtac tagaaagggg aaacatctcc  36360
cagtcagata tagtacccat tttcacatga catttaggta aagggcttac aactaccttc  36420
cataaagttt gtttaaacat cttaaatttt ataattctgt taacctgtat gtttttgttt  36480
gttttttgt tttgttttgt ttttagcccc agatcatttt accttttctt tctttctttt  36540
atttatttat tttttttga gacagagtct cgctcttgtc acccaggctg gagtgcagtg  36600
gcatgatctt ggctcactgc aacctccgcc tccttggttc aagtgattct cctgcctcag  36660
cctaccaact agctgggatt acaggtgccc accatcacac ctggctaatt tttgtatttt  36720
```

```
ttgggctgtg gactgttgag ttaatgctaa aatgagttaa gactttgggg gacttttggg  36780
aagacatgat tgattttgaa atgtgaggac atgagatttg ggaggtccag ggatggagtg  36840
atatggtttg gctgtgtctc cacccaaatc taatcttgaa ttgtagctcc cataattcaa  36900
catgatgcag gaggggacct ggtgggagat aattaaatca tgagggtggt tcccctatac  36960
tgttctcatg ttagacctaa aaccataaaa atcctagaag aaaacctagg cattaccatt  37020
caggacacag gcatgggcaa ggacttcatg tctaaaacac caaaagcaat ggcatcaaaa  37080
gccaaaattg acaaatggga tctaattaaa ctcaagagct tctgcacagc aaaagaaact  37140
accatcagag tgtacaggca acctacaaaa tgggagaaag tttttgcaat ctactcatct  37200
gacaaagggc taatatccag aatctacgaa gaactcaaac aaatttacaa gaaaaaacaa  37260
acaaccccat caaaaagtgg gcaaaggata tgaacagaca cttctcaaaa gaagacattt  37320
atgcagccaa aagacacatg taaaagtgct catcatcact ggccatcaga gaaatgcaaa  37380
tcaaaaccac aatgagatac catcccacac cagttagaat ggtgatcatt aaaaagtcag  37440
gagacaacag gtgctggaga ggatgtggag aaataggaac acttttacac tgttggtggg  37500
acgtaaacta gttcaaccat tatggaagtc agtgtggcga ttcctcaggg atctagaact  37560
agaaatacca tttgacccag ccatcccatt gctgggtata tacccaaagg attataaaac  37620
atgttgctat aaagacacat gcacatgtat gtttattgca gcactattca caatagcaaa  37680
gacttggaac caacccgaat gtccaacagt gatagactgg attaagaaaa tgtggcacat  37740
atacaccatg gaatactatg cagccataaa aaaggatgag ttcatgtcct ttgtagggac  37800
atggatgaag ctggaaacca tcattctcag caaagtattg caaggacaaa aaaccaaaca  37860
ccgcatgttc tcactcatag gtgggaattg aacaatgaga acacctggac acaggaaggg  37920
gaacatcaca caccggggcc tgttgtggga tggggggagg ggggagggat agcattagga  37980
gatacaccta atgttaaatg acgagttaat gggtgcagca caccaacatg gcacatgtat  38040
aaatatgtaa ctaacctgca cgttgtgcac atgtacccta aaacttaaag tataataata  38100
aaaaaaaaga aattacaagt gctgctccaa tgaacacaca aatagtaaga aaacaagata  38160
gccttattgc tgatatggag aaagtttggt ggtctggata caagacgaaa ccaatcacaa  38220
cgttctctta agtcaaagcc taatccagag caaggcccta actcttgtca attctgtgat  38280
gggtgagaga ggtgaagaag ctacagaaga aatgttggaa gctagcagag gttggttcat  38340
caggtttaag gaaagaagcc ttctctctaa cataaaaatg aaagatgaag cagcaagttg  38400
tgatgtagaa actggagcaa gttatccaga agatatagct aagatagctg aaggtgtcta  38460
gatgaaacag ctttgtattg gaaagacatg tcatctagga tttttatacc tagagaggaa  38520
aagtcaatgg ctggcttgaa agcttcaaag gacaagctga ctctcttgtt agggactaat  38580
gcagctgatg actttaagtt aaagccagta gtcttttatc atttcaaacg tcctagggac  38640
cttaataatt atgctaaatg tacctgccaa tgctctatga atgaaacaat gacgtctaga  38700
tgaaagcaca tttgtttata gcattgttta ctgagtattt taagcccatt gttgagaaac  38760
actgctcaga aaaaaaaaag gtcttttttt caaaatatta cagctcattg acaatgcacc  38820
tagtcaccca agagctctta tagacatgta ccgggaggtt aatgttttca gtcctgctaa  38880
cacagcatcc ttttctgcaa ccaacaaatc aaggagtaat tttgactttc aagttttatt  38940
ctttaagaaa tacacatcat aaggctataa ctcccacaga tactgattct tcttatatat  39000
cagagcaaag taaattgaaa accacctgga gacaacttac cattctagat gccattaaaa  39060
agatttgtga ttcatggaag gaagacaaag tgtcaacatt aacagacact tggaagaagt  39120
```

```
tgaatcaaac cctcatggat aacttgcagg cgttcaagac ttcagtggtg gaagtaactg  39180
cagatgtggt ggaaatagca agagaactag aactggaagt ggagcctgaa gatgtggctg  39240
aattgatgca attttatcag gaaactttaa caaatgagga gttgcttttt atggatgagc  39300
aaagaaaatg gttcttgaga caaatattat tcctggtgaa catgctgtga acattgttga  39360
aatgctaata aagtattctg aatattgcat aaacttagtt gataaagcag tagcaggatt  39420
tgagaggact gacttcaatt ttgaaagaag tttacgatga gtaaaatgct atttaacagc  39480
atcgcattct acagataaaa atttcataaa aggaagacta aattgatgct acaaacttca  39540
ccattgtctt attttaaaaa tagccacatc taccccatcc ttcagcaacc actgctgtga  39600
tccatcagca gccatcaaca tcaaggcaag acgctacacc agcaaaaaga ttttcactca  39660
ctaaagactc aaataatcag catttttagc aataaactat ttttaataaa actatgtaca  39720
ttttccagac ataatgctgt tgtatactta atagaagacg ttgtagctca aacataactt  39780
ttacacgaat tgggaaagca aataattaat gtgactcact ttattgcaat aattgcttta  39840
ttgtggtggt ctggaactga acccacaata tttccgaggc atgcctgtaa gttagtttta  39900
aattgaagaa gacagaagtc aaattttgct ggagttcact tagatgacat gtagaagatt  39960
tagtatttga aatgaggtgg tctgatctgt gctactaacg tttgtgctat tttgatttta  40020
tgtataagat actttagata tgaataccag aaaaagaatc acagtgattg gcctacattt  40080
ttaattgtat tgttgccatg cactaagata ttattcttct aagtttatgt gtgctatagg  40140
gatgtataca catatgtttt tccattttag ggagatgaaa caaagttgag ttgctaattt  40200
tgtacagttt tctgaattat tggttcctat ttagtttctc taaatagaca attcaaaata  40260
aaaaacatac tgataccatc acccaaatcc aagatctcca gacatttgaa gtaacaagta  40320
aaatttgagg tatttctatt atttttccta agccctccaa atctgcttaa ttattgatag  40380
gctagaaaaa agataaagat tcaagtgtct ttcagtgtta gcgcacaaag ctttaagagt  40440
aacacatatt tattgagtat gtattacata cttggtattc tgatcgatac tttatataat  40500
catattaaat gagcttcaca attaacttat gagcaaggta ataatattaa acccatttca  40560
aggtgagaac attacttatc caaagccaga tagagagtaa gttctaaagt agtgatattt  40620
ctctaactgt attaaagact acttgtatga gaattgtgtc gtgatgctgg taaaaaccca  40680
ggtctctgtg tctcctcagt cttcccactg agtaacatca gcatttgagt ttcctatttg  40740
gtttctctat gttttaacca aaacctccgt tgagatgttt gagaatcatg ttcgtaaatg  40800
gtagccacta gttaaaaaag ggaagctgtg ggaaagaaat gcaatttttt cctattatcc  40860
tgtaaaaggg tgcctttcca catattctgt aaatacttcc tgagttactc agcaaaaata  40920
aagcacagaa ctgttaggaa aatactaatt aaagcatttt tacttgtcct tctgtctagt  40980
agcctctgaa acttaagaag catttattca ttttacaaac ccagtgagtt ttcttgcaaa  41040
ctttcttttc cttctctagc gcagaaaatt actactgttg aatctaacca gaggtagact  41100
tggaatagta attctatttg cgtaatgttt taatgattga gctatttttc tcatgaacta  41160
tcttatacaa agagaaacaa atatctctct gttttgtgag ccagggtttc gggttggtgc  41220
tggtaagaga atagtgaatg gggaagtcat agtgttcgct ttcatggagt ttctggtaca  41280
gttaacactc taaagttcta ttttaggttg tagaactgtg agatataaaa gatggttgtt  41340
attattccta ttttaaatat gagaaaaggg aagttaaaga ggttatgaaa cttgttcatg  41400
attgtaattt agttaattga catctaaatt attttgctga ttctaagttt aatattcttt  41460
```

-continued

```
ttactatctt acaccgcctt tcaaacttag atattttgga cagatttcaa acatagatat  41520
tttgcacaac ttatattaat taagccctaa cctatattgg cctgattttg atgttatatg  41580
tgtatatctg aagatgcagt aaatcatacc atgttcaggt aattagaaat gaaggacaag  41640
aagaaagaaa attaaaggaa aatagaacaa ttgggaagca aatgataaac tcacgtgatg  41700
gcttctgtat attcaaagaa gggactaggt aattctgata ggaaagataa tattaaaaat  41760
aactccagtg agaagaaagg gagaaataag caattttcag ctactgatgc attcatacat  41820
atcttttatt gtacaataaa gcccttatct gtgttatcct gtccacctct ttgcattaag  41880
gtagttggtc caccttggtc atgccagcct tcctctcaca cattaaataa tgtttgttct  41940
cacagaaggt agggtgcatt ttcccattat gaaaataagc acaattcata tttccttttc  42000
catcttccaa aaactcaaac ctgtgaaggg aaagttagaa taaattcctt tgaaaactga  42060
gcaaacaatc agtaatcaga ctctgcgtat agtagtttga tgcaccaaat agagactgag  42120
gaaaatagga aaaaaaaaca aaaaaaaaaa cgattctcat tgttgagaaa gttccaccct  42180
gcttggcagt acaagatatg catatttaaa aagcccaata tcaatttcat ttagcataaa  42240
attaggagca agggaacagt aggtacaata ggagccctga agaagtgatg gagatggctc  42300
caaaataatg ggaaaacgca ttatctacaa gatcagactt tagttcggta ttgatggaag  42360
gtcaggactc agatgaactg acaggagatg gaagagccct acaggacaag tagctgcact  42420
agatgggaat acgctcatgg aaaagtgagt tgattcagta gttttgaaat caggatttat  42480
gttgcaagat aaatcatcta acacagcagg ctgtattgta attgtctgtt aagttatatt  42540
tctttctttc taaactgctt ataatgagat gacaaggaat atatacttat tggtttattt  42600
ggagaatacc tgcagaacta tgtgacaaag ttgttctatg tgctgaggat acactgataa  42660
agaaagacaa gaaagctaat gtctttcttg ttggggaact ttcatttaag tggggcgata  42720
ccggtaagaa gcccacaaaa aatagacaag aaaaattgag acagtggtaa gagttacaaa  42780
gaaacaaaac agtggtggac tgtatggata tgggtttaag ggaggctaat ttagtttggg  42840
tagagttagg ttcactgaag aagtgatgtt taaatagaga cttgagtctc agtggagaga  42900
tggtcatgga gttgtggagg cagagcattc tagaagaaaa tagcaagaca aaagccttaa  42960
ggtaacaaaa cgagtttgat ttgttggaag aatgtaaaga acactaagtt gcctgcaata  43020
ttgtaaatga ggcagcaagc aataggagat aggagataaa gcccaaggtc tgtgaagagg  43080
cttgcttgta gttgtagtat cctaagatcc tatctatagt aaatacttaa taaatatttg  43140
tttaaaaatt taattcataa tttgagtaat aatcagatta tataagtttt ggttatcagt  43200
ttaaatttta attgaagaga gactgcagtt ttgatataca ggatgaacaa aagatgttga  43260
gactgcagat tggaaagcca tataggaagc aactccactc aatgcaatca gtccctttgc  43320
ctggattgtt tgtagaagga caaagcttcg ttaatggaca ttggaattat cttgtgaaat  43380
acaatgtatc gaattcttgg agactcccag aatagaggaa taggcaaaac aatattgaaa  43440
actcaaaagg actctcaaga taacaacttt caactgtaaa ataatgatat gaaattttgt  43500
tttaaaaata tgtgaagata atcagaacaa gcaaaacaca aaaacacaca cacatgtgca  43560
tgcgcgcaca cacacacaca cactcacaca tacacataca tgcacacagt gttccatggt  43620
aaggttgaat gtaaaaatga atgggaataa tatcagagat aaaggtggat tgtggcttag  43680
ataaagagca aagtaatggg agagagggga aagaattgtc ttatgaccag cgctgtcttg  43740
tttgaattag caggtaagtg acccagctgc tgcttctata acccatagta gtgacttgga  43800
ctgagagaag agggaatctc aagaataaga gtttccagta ctccctccta ttctaagtgt  43860
```

ccagtgactt acatattttc tgagataacc gagccatcct cccacttcca gacctcattc 43920
gacttctggc gagataatcc ga 43942

<210> SEQ ID NO 2
<211> LENGTH: 182
<212> TYPE: PRT
<213> ORGANISM: Homo sapiens

<400> SEQUENCE: 2

Met Glu Gln Gly Lys Gly Leu Ala Val Leu Ile Leu Ala Ile Ile Leu
1 5 10 15

Leu Gln Gly Thr Leu Ala Gln Ser Ile Lys Gly Asn His Leu Val Lys
20 25 30

Val Tyr Asp Tyr Gln Glu Asp Gly Ser Val Leu Leu Thr Cys Asp Ala
35 40 45

Glu Ala Lys Asn Ile Thr Trp Phe Lys Asp Gly Lys Met Ile Gly Phe
50 55 60

Leu Thr Glu Asp Lys Lys Lys Trp Asn Leu Gly Ser Asn Ala Lys Asp
65 70 75 80

Pro Arg Gly Met Tyr Gln Cys Lys Gly Ser Gln Asn Lys Ser Lys Pro
85 90 95

Leu Gln Val Tyr Tyr Arg Met Cys Gln Asn Cys Ile Glu Leu Asn Ala
100 105 110

Ala Thr Ile Ser Gly Phe Leu Phe Ala Glu Ile Val Ser Ile Phe Val
115 120 125

Leu Ala Val Gly Val Tyr Phe Ile Ala Gly Gln Asp Gly Val Arg Gln
130 135 140

Ser Arg Ala Ser Asp Lys Gln Thr Leu Leu Pro Asn Asp Gln Leu Tyr
145 150 155 160

Gln Pro Leu Lys Asp Arg Glu Asp Asp Gln Tyr Ser His Leu Gln Gly
165 170 175

Asn Gln Leu Arg Arg Asn
180

<210> SEQ ID NO 3
<211> LENGTH: 171
<212> TYPE: PRT
<213> ORGANISM: Homo sapiens

<400> SEQUENCE: 3

Met Glu His Ser Thr Phe Leu Ser Gly Leu Val Leu Ala Thr Leu Leu
1 5 10 15

Ser Gln Val Ser Pro Phe Lys Ile Pro Ile Glu Glu Leu Glu Asp Arg
20 25 30

Val Phe Val Asn Cys Asn Thr Ser Ile Thr Trp Val Glu Gly Thr Val
35 40 45

Gly Thr Leu Leu Ser Asp Ile Thr Arg Leu Asp Leu Gly Lys Arg Ile
50 55 60

Leu Asp Pro Arg Gly Ile Tyr Arg Cys Asn Gly Thr Asp Ile Tyr Lys
65 70 75 80

Asp Lys Glu Ser Thr Val Gln Val His Tyr Arg Met Cys Gln Ser Cys
85 90 95

Val Glu Leu Asp Pro Ala Thr Val Ala Gly Ile Ile Val Thr Asp Val
100 105 110

Ile Ala Thr Leu Leu Leu Ala Leu Gly Val Phe Cys Phe Ala Gly His

```
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170


<210> SEQ ID NO 4
<211> LENGTH: 207
<212> TYPE: PRT
<213> ORGANISM: Homo sapiens

<400> SEQUENCE: 4

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205


<210> SEQ ID NO 5
<211> LENGTH: 164
<212> TYPE: PRT
<213> ORGANISM: Homo sapiens

<400> SEQUENCE: 5

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
```

```
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 6
<211> LENGTH: 7
<212> TYPE: PRT
<213> ORGANISM: Artificial Sequence
<220> FEATURE:
<223> OTHER INFORMATION: CDR1
<220> FEATURE:
<221> NAME/KEY: MISC_FEATURE
<222> LOCATION: (2)..(2)
<223> OTHER INFORMATION: is K or R

<400> SEQUENCE: 6

Ser Xaa Thr Phe Thr Ile Ser
1               5


<210> SEQ ID NO 7
<211> LENGTH: 17
<212> TYPE: PRT
<213> ORGANISM: Artificial Sequence
<220> FEATURE:
<223> OTHER INFORMATION: CDR2
<220> FEATURE:
<221> NAME/KEY: MISC_FEATURE
<222> LOCATION: (5)..(5)
<223> OTHER INFORMATION: is L or I

<400> SEQUENCE: 7

Gly Ile Ile Pro Xaa Phe Gly Thr Ile Thr Tyr Ala Gln Lys Phe Gln
1               5                   10                  15

Gly


<210> SEQ ID NO 8
<211> LENGTH: 9
<212> TYPE: PRT
<213> ORGANISM: Artificial Sequence
<220> FEATURE:
<223> OTHER INFORMATION: CDR3
<220> FEATURE:
<221> NAME/KEY: MISC_FEATURE
<222> LOCATION: (7)..(7)
<223> OTHER INFORMATION: is L or F

<400> SEQUENCE: 8

Arg Gly Asn Trp Asn Pro Xaa Asp Pro
1               5


<210> SEQ ID NO 9
<211> LENGTH: 5
<212> TYPE: PRT
<213> ORGANISM: Artificial Sequence
<220> FEATURE:
<223> OTHER INFORMATION: CDR1
```

```
<220> FEATURE:
<221> NAME/KEY: MISC_FEATURE
<222> LOCATION: (2)..(2)
<223> OTHER INFORMATION: is F or Y

<400> SEQUENCE: 9

Arg Xaa Trp Ile Gly
1               5


<210> SEQ ID NO 10
<211> LENGTH: 17
<212> TYPE: PRT
<213> ORGANISM: Artificial Sequence
<220> FEATURE:
<223> OTHER INFORMATION: CDR3
<220> FEATURE:
<221> NAME/KEY: MISC_FEATURE
<222> LOCATION: (1)..(1)
<223> OTHER INFORMATION: is H or N
<220> FEATURE:
<221> NAME/KEY: MISC_FEATURE
<222> LOCATION: (6)..(6)
<223> OTHER INFORMATION: is D or V
<220> FEATURE:
<221> NAME/KEY: MISC_FEATURE
<222> LOCATION: (15)..(15)
<223> OTHER INFORMATION: is L or M

<400> SEQUENCE: 10

Xaa Ile Arg Tyr Phe Xaa Trp Ser Glu Asp Tyr His Tyr Tyr Xaa Asp
1               5                   10                  15

Val


<210> SEQ ID NO 11
<211> LENGTH: 17
<212> TYPE: PRT
<213> ORGANISM: Artificial Sequence
<220> FEATURE:
<223> OTHER INFORMATION: CDR2
<220> FEATURE:
<221> NAME/KEY: MISC_FEATURE
<222> LOCATION: (6)..(6)
<223> OTHER INFORMATION: is S or G
<220> FEATURE:
<221> NAME/KEY: MISC_FEATURE
<222> LOCATION: (8)..(8)
<223> OTHER INFORMATION: is S or T
<220> FEATURE:
<221> NAME/KEY: MISC_FEATURE
<222> LOCATION: (9)..(9)
<223> OTHER INFORMATION: is I or T
<220> FEATURE:
<221> NAME/KEY: MISC_FEATURE
<222> LOCATION: (10)..(10)
<223> OTHER INFORMATION: is G or Y

<400> SEQUENCE: 11

Asp Ile Ser Trp Ser Xaa Gly Xaa Xaa Xaa Tyr Ala Asp Ser Val Lys
1               5                   10                  15

Gly


<210> SEQ ID NO 12
<211> LENGTH: 15
<212> TYPE: PRT
<213> ORGANISM: Artificial Sequence
<220> FEATURE:
<223> OTHER INFORMATION: CDR3
<220> FEATURE:
<221> NAME/KEY: MISC_FEATURE
<222> LOCATION: (3)..(3)
<223> OTHER INFORMATION: is R or M
```

<220> FEATURE:
<221> NAME/KEY: MISC_FEATURE
<222> LOCATION: (15)..(15)
<223> OTHER INFORMATION: is H or Y

<400> SEQUENCE: 12

Asp His Xaa Gly Tyr Gly Asp Tyr Glu Gly Gly Gly Phe Asp Xaa
1 5 10 15

<210> SEQ ID NO 13
<211> LENGTH: 267
<212> TYPE: PRT
<213> ORGANISM: Homo sapiens

<400> SEQUENCE: 13

Met Trp Gly Val Phe Leu Leu Tyr Val Ser Met Lys Met Gly Gly Thr
1 5 10 15

Thr Gly Gln Asn Ile Asp Gln Pro Thr Glu Met Thr Ala Thr Glu Gly
20 25 30

Ala Ile Val Gln Ile Asn Cys Thr Tyr Gln Thr Ser Gly Phe Asn Gly
35 40 45

Leu Phe Trp Tyr Gln Gln His Ala Gly Glu Ala Pro Thr Phe Leu Ser
50 55 60

Tyr Asn Val Leu Asp Gly Leu Glu Glu Lys Gly Arg Phe Ser Ser Phe
65 70 75 80

Leu Ser Arg Ser Lys Gly Tyr Ser Tyr Leu Leu Leu Lys Glu Leu Gln
85 90 95

Met Lys Asp Ser Ala Ser Tyr Leu Cys Ala Val Met Asp Ser Asn Tyr
100 105 110

Gln Leu Ile Trp Gly Ala Gly Thr Lys Leu Ile Ile Lys Pro Asp Ile
115 120 125

Gln Asn Pro Asp Pro Ala Val Tyr Gln Leu Arg Asp Ser Lys Ser Ser
130 135 140

Asp Lys Ser Val Cys Leu Phe Thr Asp Phe Asp Ser Gln Thr Asn Val
145 150 155 160

Ser Gln Ser Lys Asp Ser Asp Val Tyr Ile Thr Asp Lys Thr Val Leu
165 170 175

Asp Met Arg Ser Met Asp Phe Lys Ser Asn Ser Ala Val Ala Trp Ser
180 185 190

Asn Lys Ser Asp Phe Ala Cys Ala Asn Ala Phe Asn Asn Ser Ile Ile
195 200 205

Pro Glu Asp Thr Phe Phe Pro Ser Pro Glu Ser Ser Cys Asp Val Lys
210 215 220

Leu Val Glu Lys Ser Phe Glu Thr Asp Thr Asn Leu Asn Phe Gln Asn
225 230 235 240

Leu Ser Val Ile Gly Phe Arg Ile Leu Leu Leu Lys Val Ala Gly Phe
245 250 255

Asn Leu Leu Met Thr Leu Arg Leu Trp Ser Ser
260 265

<210> SEQ ID NO 14
<211> LENGTH: 310
<212> TYPE: PRT
<213> ORGANISM: Homo sapiens

<400> SEQUENCE: 14

Met Arg Ile Arg Leu Leu Cys Cys Val Ala Phe Ser Leu Leu Trp Ala
1 5 10 15

```
Gly Pro Val Ile Ala Gly Ile Thr Gln Ala Pro Thr Ser Gln Ile Leu
            20                  25                  30

Ala Ala Gly Arg Arg Met Thr Leu Arg Cys Thr Gln Asp Met Arg His
        35                  40                  45

Asn Ala Met Tyr Trp Tyr Arg Gln Asp Leu Gly Leu Gly Leu Arg Leu
    50                  55                  60

Ile His Tyr Ser Asn Thr Ala Gly Thr Thr Gly Lys Gly Glu Val Pro
65                  70                  75                  80

Asp Gly Tyr Ser Val Ser Arg Ala Asn Thr Asp Asp Phe Pro Leu Thr
                85                  90                  95

Leu Ala Ser Ala Val Pro Ser Gln Thr Ser Val Tyr Phe Cys Ala Ser
            100                 105                 110

Ser Glu Ala Gly Gly Asn Thr Gly Glu Leu Phe Phe Gly Glu Gly Ser
        115                 120                 125

Arg Leu Thr Val Leu Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310


<210> SEQ ID NO 15
<211> LENGTH: 321
<212> TYPE: DNA
<213> ORGANISM: Artificial Sequence
<220> FEATURE:
<223> OTHER INFORMATION: IGKV1-39/jk1
<220> FEATURE:
<221> NAME/KEY: CDS
<222> LOCATION: (1)..(321)

<400> SEQUENCE: 15

gac atc cag atg acc cag tct cca tcc tcc ctg tct gca tct gta gga       48
Asp Ile Gln Met Thr Gln Ser Pro Ser Ser Leu Ser Ala Ser Val Gly
1               5                   10                  15

gac aga gtc acc atc act tgc cgg gca agt cag agc att agc agc tac       96
Asp Arg Val Thr Ile Thr Cys Arg Ala Ser Gln Ser Ile Ser Ser Tyr
            20                  25                  30
```

```
tta aat tgg tat cag cag aaa cca ggg aaa gcc cct aag ctc ctg atc      144
Leu Asn Trp Tyr Gln Gln Lys Pro Gly Lys Ala Pro Lys Leu Leu Ile
        35                  40                  45

tat gct gca tcc agt ttg caa agt ggg gtc cca tca agg ttc agt ggc      192
Tyr Ala Ala Ser Ser Leu Gln Ser Gly Val Pro Ser Arg Phe Ser Gly
    50                  55                  60

agt gga tct ggg aca gat ttc act ctc acc atc agc agt ctg caa cct      240
Ser Gly Ser Gly Thr Asp Phe Thr Leu Thr Ile Ser Ser Leu Gln Pro
65                  70                  75                  80

gaa gat ttt gca act tac tac tgt caa cag agt tac agt acc cct cca      288
Glu Asp Phe Ala Thr Tyr Tyr Cys Gln Gln Ser Tyr Ser Thr Pro Pro
                85                  90                  95

acg ttc ggc caa ggg acc aag gtg gag atc aaa                          321
Thr Phe Gly Gln Gly Thr Lys Val Glu Ile Lys
            100                 105


<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105


<210> SEQ ID NO 17
<211> LENGTH: 324
<212> TYPE: DNA
<213> ORGANISM: Artificial Sequence
<220> FEATURE:
<223> OTHER INFORMATION: IGKV1-39/jk5
<220> FEATURE:
<221> NAME/KEY: CDS
<222> LOCATION: (1)..(321)

<400> SEQUENCE: 17

cga act gtg gct gca cca tct gtc ttc atc ttc ccg cca tct gat gag       48
Arg Thr Val Ala Ala Pro Ser Val Phe Ile Phe Pro Pro Ser Asp Glu
1               5                   10                  15

cag ttg aaa tct gga act gcc tct gtt gtg tgc ctg ctg aat aac ttc       96
Gln Leu Lys Ser Gly Thr Ala Ser Val Val Cys Leu Leu Asn Asn Phe
            20                  25                  30

tat ccc aga gag gcc aaa gta cag tgg aag gtg gat aac gcc ctc caa      144
Tyr Pro Arg Glu Ala Lys Val Gln Trp Lys Val Asp Asn Ala Leu Gln
        35                  40                  45

tcg ggt aac tcc cag gag agt gtc aca gag cag gac agc aag gac agc      192
Ser Gly Asn Ser Gln Glu Ser Val Thr Glu Gln Asp Ser Lys Asp Ser
    50                  55                  60
```

```
acc tac agc ctc agc agc acc ctg acg ctg agc aaa gca gac tac gag      240
Thr Tyr Ser Leu Ser Ser Thr Leu Thr Leu Ser Lys Ala Asp Tyr Glu
65                  70                  75                  80

aaa cac aaa gtc tac gcc tgc gaa gtc acc cat cag ggc ctg agc tcg      288
Lys His Lys Val Tyr Ala Cys Glu Val Thr His Gln Gly Leu Ser Ser
                85                  90                  95

ccc gtc aca aag agc ttc aac agg gga gag tgt tag                      324
Pro Val Thr Lys Ser Phe Asn Arg Gly Glu Cys
            100                 105


<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 19
<211> LENGTH: 108
<212> TYPE: PRT
<213> ORGANISM: Artificial Sequence
<220> FEATURE:
<223> OTHER INFORMATION: IGKV1-39/jk5 common light chain variable domain
      translation

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105


<210> SEQ ID NO 20
<211> LENGTH: 95
```

<212> TYPE: PRT
<213> ORGANISM: Artificial Sequence
<220> FEATURE:
<223> OTHER INFORMATION: V-region IGKV1-39A

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 21
<211> LENGTH: 6
<212> TYPE: PRT
<213> ORGANISM: Artificial Sequence
<220> FEATURE:
<223> OTHER INFORMATION: CDR1 common light chain

<400> SEQUENCE: 21

```
Gln Ser Ile Ser Ser Tyr
1               5
```

<210> SEQ ID NO 22
<211> LENGTH: 3
<212> TYPE: PRT
<213> ORGANISM: Artificial Sequence
<220> FEATURE:
<223> OTHER INFORMATION: CDR2 common light chain

<400> SEQUENCE: 22

```
Ala Ala Ser
1
```

<210> SEQ ID NO 23
<211> LENGTH: 7
<212> TYPE: PRT
<213> ORGANISM: Artificial Sequence
<220> FEATURE:
<223> OTHER INFORMATION: CDR3 common light chain

<400> SEQUENCE: 23

```
Gln Gln Ser Tyr Ser Thr Pro
1               5
```

<210> SEQ ID NO 24
<211> LENGTH: 294
<212> TYPE: DNA
<213> ORGANISM: Artificial Sequence
<220> FEATURE:
<223> OTHER INFORMATION: IgG heavy chain CH1 region
<220> FEATURE:
<221> NAME/KEY: CDS
<222> LOCATION: (1)..(294)

<400> SEQUENCE: 24

```
gct agc acc aag ggc cca tcg gtc ttc ccc ctg gca ccc tcc tcc aag       48
Ala Ser Thr Lys Gly Pro Ser Val Phe Pro Leu Ala Pro Ser Ser Lys
```

-continued

```
1               5                   10                  15

agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30

ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45

ggc gtg cac acc ttc ccg gct gtc cta cag tcc tca gga ctc tac tcc       192
Gly Val His Thr Phe Pro Ala Val Leu Gln Ser Ser Gly Leu Tyr Ser
    50                  55                  60

ctc agc agc gtc gtg acc gtg ccc tcc agc agc ttg ggc acc cag acc       240
Leu Ser Ser Val Val Thr Val Pro Ser Ser Ser Leu Gly Thr Gln Thr
65                  70                  75                  80

tac atc tgc aac gtg aat cac aag ccc agc aac acc aag gtg gac aag       288
Tyr Ile Cys Asn Val Asn His Lys Pro Ser Asn Thr Lys Val Asp Lys
                85                  90                  95

aga gtt                                                               294
Arg Val


<210> SEQ ID NO 25
<211> LENGTH: 98
<212> TYPE: PRT
<213> ORGANISM: Artificial Sequence
<220> FEATURE:
<223> OTHER INFORMATION: Synthetic Construct

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val


<210> SEQ ID NO 26
<211> LENGTH: 45
<212> TYPE: DNA
<213> ORGANISM: Artificial Sequence
<220> FEATURE:
<223> OTHER INFORMATION: IgG heavy chain hinge region
<220> FEATURE:
<221> NAME/KEY: CDS
<222> LOCATION: (1)..(45)

<400> SEQUENCE: 26

gag ccc aaa tct tgt gac aaa act cac aca tgc cca ccg tgc cca            45
Glu Pro Lys Ser Cys Asp Lys Thr His Thr Cys Pro Pro Cys Pro
1               5                   10                  15


<210> SEQ ID NO 27
<211> LENGTH: 15
<212> TYPE: PRT
<213> ORGANISM: Artificial Sequence
<220> FEATURE:
<223> OTHER INFORMATION: Synthetic Construct
```

<400> SEQUENCE: 27

```
Glu Pro Lys Ser Cys Asp Lys Thr His Thr Cys Pro Pro Cys Pro
1               5                   10                  15
```

<210> SEQ ID NO 28
<211> LENGTH: 330
<212> TYPE: DNA
<213> ORGANISM: Artificial Sequence
<220> FEATURE:
<223> OTHER INFORMATION: IgG heavy chain CH2 region
<220> FEATURE:
<221> NAME/KEY: CDS
<222> LOCATION: (1)..(330)

<400> SEQUENCE: 28

```
gca cct gaa ctc ctg ggg gga ccg tca gtc ttc ctc ttc ccc cca aaa       48
Ala Pro Glu Leu Leu Gly Gly Pro Ser Val Phe Leu Phe Pro Pro Lys
1               5                   10                  15

ccc aag gac acc ctc atg atc tcc cgg acc cct gag gtc aca tgc gtg       96
Pro Lys Asp Thr Leu Met Ile Ser Arg Thr Pro Glu Val Thr Cys Val
            20                  25                  30

gtg gtg gac gtg agc cac gaa gac cct gag gtc aag ttc aac tgg tac      144
Val Val Asp Val Ser His Glu Asp Pro Glu Val Lys Phe Asn Trp Tyr
        35                  40                  45

gtg gac ggc gtg gag gtg cat aat gcc aag aca aag ccg cgg gag gag      192
Val Asp Gly Val Glu Val His Asn Ala Lys Thr Lys Pro Arg Glu Glu
    50                  55                  60

cag tac aac agc acg tac cgt gtg gtc agc gtc ctc acc gtc ctg cac      240
Gln Tyr Asn Ser Thr Tyr Arg Val Val Ser Val Leu Thr Val Leu His
65                  70                  75                  80

cag gac tgg ctg aat ggc aag gag tac aag tgc aag gtc tcc aac aaa      288
Gln Asp Trp Leu Asn Gly Lys Glu Tyr Lys Cys Lys Val Ser Asn Lys
                85                  90                  95

gcc ctc cca gcc ccc atc gag aaa acc atc tcc aaa gcc aaa              330
Ala Leu Pro Ala Pro Ile Glu Lys Thr Ile Ser Lys Ala Lys
            100                 105                 110
```

<210> SEQ ID NO 29
<211> LENGTH: 110
<212> TYPE: PRT
<213> ORGANISM: Artificial Sequence
<220> FEATURE:
<223> OTHER INFORMATION: Synthetic Construct

<400> SEQUENCE: 29

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

```
<210> SEQ ID NO 30
<211> LENGTH: 330
<212> TYPE: DNA
<213> ORGANISM: Artificial Sequence
<220> FEATURE:
<223> OTHER INFORMATION: IgG heavy chain CH2 domain containing L235G and
      G236R silencing substitutions
<220> FEATURE:
<221> NAME/KEY: CDS
<222> LOCATION: (1)..(330)

<400> SEQUENCE: 30

gca cct gaa ctc ggc agg gga ccg tca gtc ttc ctc ttc ccc cca aaa       48
Ala Pro Glu Leu Gly Arg Gly Pro Ser Val Phe Leu Phe Pro Pro Lys
1               5                   10                  15

ccc aag gac acc ctc atg atc tcc cgg acc cct gag gtc aca tgc gtg       96
Pro Lys Asp Thr Leu Met Ile Ser Arg Thr Pro Glu Val Thr Cys Val
            20                  25                  30

gtg gtg gac gtg agc cac gaa gac cct gag gtc aag ttc aac tgg tac      144
Val Val Asp Val Ser His Glu Asp Pro Glu Val Lys Phe Asn Trp Tyr
        35                  40                  45

gtg gac ggc gtg gag gtg cat aat gcc aag aca aag ccg cgg gag gag      192
Val Asp Gly Val Glu Val His Asn Ala Lys Thr Lys Pro Arg Glu Glu
    50                  55                  60

cag tac aac agc acg tac cgt gtg gtc agc gtc ctc acc gtc ctg cac      240
Gln Tyr Asn Ser Thr Tyr Arg Val Val Ser Val Leu Thr Val Leu His
65                  70                  75                  80

cag gac tgg ctg aat ggc aag gag tac aag tgc aag gtc tcc aac aaa      288
Gln Asp Trp Leu Asn Gly Lys Glu Tyr Lys Cys Lys Val Ser Asn Lys
                85                  90                  95

gcc ctc cca gcc ccc atc gag aaa acc atc tcc aaa gcc aaa              330
Ala Leu Pro Ala Pro Ile Glu Lys Thr Ile Ser Lys Ala Lys
            100                 105                 110


<210> SEQ ID NO 31
<211> LENGTH: 110
<212> TYPE: PRT
<213> ORGANISM: Artificial Sequence
<220> FEATURE:
<223> OTHER INFORMATION: Synthetic Construct

<400> SEQUENCE: 31

Ala Pro Glu Leu Gly Arg Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 32
<211> LENGTH: 321
<212> TYPE: DNA
<213> ORGANISM: Artificial Sequence
<220> FEATURE:
<223> OTHER INFORMATION: IgG heavy chain CH3 domain containing
```

```
      substitutions L351K and T366K (KK)
<220> FEATURE:
<221> NAME/KEY: CDS
<222> LOCATION: (1)..(318)

<400> SEQUENCE: 32

ggg cag ccc cga gaa cca cag gtg tac acc aag ccc cca tcc cgg gag       48
Gly Gln Pro Arg Glu Pro Gln Val Tyr Thr Lys Pro Pro Ser Arg Glu
1               5                   10                  15

gag atg acc aag aac cag gtc agc ctg aag tgc ctg gtc aaa ggc ttc       96
Glu Met Thr Lys Asn Gln Val Ser Leu Lys Cys Leu Val Lys Gly Phe
            20                  25                  30

tat ccc agc gac atc gcc gtg gag tgg gag agc aat ggg cag ccg gag      144
Tyr Pro Ser Asp Ile Ala Val Glu Trp Glu Ser Asn Gly Gln Pro Glu
        35                  40                  45

aac aac tac aag acc acg cct ccc gtg ctg gac tcc gac ggc tcc ttc      192
Asn Asn Tyr Lys Thr Thr Pro Pro Val Leu Asp Ser Asp Gly Ser Phe
    50                  55                  60

ttc ctc tat agc aag ctc acc gtg gac aag agc agg tgg cag cag ggg      240
Phe Leu Tyr Ser Lys Leu Thr Val Asp Lys Ser Arg Trp Gln Gln Gly
65                  70                  75                  80

aac gtc ttc tca tgc tcc gtg atg cat gag gct ctg cac aac cac tac      288
Asn Val Phe Ser Cys Ser Val Met His Glu Ala Leu His Asn His Tyr
                85                  90                  95

acg cag aag agc ctc tcc ctg tct ccg ggt tga                          321
Thr Gln Lys Ser Leu Ser Leu Ser Pro Gly
            100                 105


<210> SEQ ID NO 33
<211> LENGTH: 106
<212> TYPE: PRT
<213> ORGANISM: Artificial Sequence
<220> FEATURE:
<223> OTHER INFORMATION: Synthetic Construct

<400> SEQUENCE: 33

Gly Gln Pro Arg Glu Pro Gln Val Tyr Thr Lys Pro Pro Ser Arg Glu
1               5                   10                  15

Glu Met Thr Lys Asn Gln Val Ser Leu Lys Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105


<210> SEQ ID NO 34
<211> LENGTH: 321
<212> TYPE: DNA
<213> ORGANISM: Artificial Sequence
<220> FEATURE:
<223> OTHER INFORMATION: IgG heavy chain CH3 region containing
      substitutions L351D and L368E (DE)
<220> FEATURE:
<221> NAME/KEY: CDS
<222> LOCATION: (1)..(318)

<400> SEQUENCE: 34
```

```
ggg cag ccc cga gaa cca cag gtg tac acc gac ccc cca tcc cgg gag       48
Gly Gln Pro Arg Glu Pro Gln Val Tyr Thr Asp Pro Pro Ser Arg Glu
1               5                   10                  15

gag atg acc aag aac cag gtc agc ctg acc tgc gag gtc aaa ggc ttc       96
Glu Met Thr Lys Asn Gln Val Ser Leu Thr Cys Glu Val Lys Gly Phe
            20                  25                  30

tat ccc agc gac atc gcc gtg gag tgg gag agc aat ggg cag ccg gag      144
Tyr Pro Ser Asp Ile Ala Val Glu Trp Glu Ser Asn Gly Gln Pro Glu
        35                  40                  45

aac aac tac aag acc acg cct ccc gtg ctg gac tcc gac ggc tcc ttc      192
Asn Asn Tyr Lys Thr Thr Pro Pro Val Leu Asp Ser Asp Gly Ser Phe
    50                  55                  60

ttc ctc tat agc aag ctc acc gtg gac aag agc agg tgg cag cag ggg      240
Phe Leu Tyr Ser Lys Leu Thr Val Asp Lys Ser Arg Trp Gln Gln Gly
65                  70                  75                  80

aac gtc ttc tca tgc tcc gtg atg cat gag gct ctg cac aac cac tac      288
Asn Val Phe Ser Cys Ser Val Met His Glu Ala Leu His Asn His Tyr
                85                  90                  95

acg cag aag agc ctc tcc ctg tct ccg ggt tga                          321
Thr Gln Lys Ser Leu Ser Leu Ser Pro Gly
            100                 105
```

<210> SEQ ID NO 35
<211> LENGTH: 106
<212> TYPE: PRT
<213> ORGANISM: Artificial Sequence
<220> FEATURE:
<223> OTHER INFORMATION: Synthetic Construct

<400> SEQUENCE: 35

```
Gly Gln Pro Arg Glu Pro Gln Val Tyr Thr Asp Pro Pro Ser Arg Glu
1               5                   10                  15

Glu Met Thr Lys Asn Gln Val Ser Leu Thr Cys Glu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 36
<211> LENGTH: 4
<212> TYPE: PRT
<213> ORGANISM: Artificial Sequence
<220> FEATURE:
<223> OTHER INFORMATION: CH# sequence

<400> SEQUENCE: 36

```
Asp Glu Lys Lys
1
```

<210> SEQ ID NO 37
<211> LENGTH: 373
<212> TYPE: DNA
<213> ORGANISM: Artificial Sequence
<220> FEATURE:

<223> OTHER INFORMATION: MF8057

<400> SEQUENCE: 37

```
ggcccagccg gccatggccg aggtgcagct ggtgcagtct ggagctgagg tgaagaagcc      60

tgggtcctcg gtgaaggtct cctgcaaggc ttctggaggc accttccgca gctttggtat     120

cagttgggtg cgacaggccc ctggacaagg acttgagtgg atgggaggat tcatccctgt     180

ccttggtaca gcaaactacg cacagaaatt ccagggcaga gtgacgatta tcgcggacaa     240

atccacgaac acagcctaca tggagctgag cagcctgaga tctgaggaca cggccgtgta     300

ttactgtgcg cgaaggggta actggaaccc gttcgacccc tggggccagg gaaccctggt     360

caccgtctcg agt                                                        373
```

<210> SEQ ID NO 38
<211> LENGTH: 30
<212> TYPE: PRT
<213> ORGANISM: Artificial Sequence
<220> FEATURE:
<223> OTHER INFORMATION: MF8057 FW1

<400> SEQUENCE: 38

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg
            20                  25                  30
```

<210> SEQ ID NO 39
<211> LENGTH: 14
<212> TYPE: PRT
<213> ORGANISM: Artificial Sequence
<220> FEATURE:
<223> OTHER INFORMATION: MF8057 FW2

<400> SEQUENCE: 39

```
Trp Val Arg Gln Ala Pro Gly Gln Gly Leu Glu Trp Met Gly
1               5                   10
```

<210> SEQ ID NO 40
<211> LENGTH: 32
<212> TYPE: PRT
<213> ORGANISM: Artificial Sequence
<220> FEATURE:
<223> OTHER INFORMATION: MF8057 FW3 -1AA in FW4

<400> SEQUENCE: 40

```
Arg Val Thr Ile Ile Ala Asp Lys Ser Thr Asn Thr Ala Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 41
<211> LENGTH: 11
<212> TYPE: PRT
<213> ORGANISM: Artificial Sequence
<220> FEATURE:
<223> OTHER INFORMATION: MF8057 FW4

<400> SEQUENCE: 41

```
Trp Gly Gln Gly Thr Leu Val Thr Val Ser Ser
1               5                   10
```

<210> SEQ ID NO 42
<211> LENGTH: 5

```
<212> TYPE: PRT
<213> ORGANISM: Artificial Sequence
<220> FEATURE:
<223> OTHER INFORMATION: MF8057 CDR1

<400> SEQUENCE: 42

Ser Phe Gly Ile Ser
1               5


<210> SEQ ID NO 43
<211> LENGTH: 17
<212> TYPE: PRT
<213> ORGANISM: Artificial Sequence
<220> FEATURE:
<223> OTHER INFORMATION: MF8057 CDR2

<400> SEQUENCE: 43

Gly Phe Ile Pro Val Leu Gly Thr Ala Asn Tyr Ala Gln Lys Phe Gln
1               5                   10                  15

Gly


<210> SEQ ID NO 44
<211> LENGTH: 9
<212> TYPE: PRT
<213> ORGANISM: Artificial Sequence
<220> FEATURE:
<223> OTHER INFORMATION: MF8057 CDR3

<400> SEQUENCE: 44

Arg Gly Asn Trp Asn Pro Phe Asp Pro
1               5


<210> SEQ ID NO 45
<211> LENGTH: 118
<212> TYPE: PRT
<213> ORGANISM: Artificial Sequence
<220> FEATURE:
<223> OTHER INFORMATION: MF8057 VH

<400> SEQUENCE: 45

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Phe
            20                  25                  30

Gly Ile Ser Trp Val Arg Gln Ala Pro Gly Gln Gly Leu Glu Trp Met
        35                  40                  45

Gly Gly Phe Ile Pro Val Leu Gly Thr Ala Asn Tyr Ala Gln Lys Phe
    50                  55                  60

Gln Gly Arg Val Thr Ile Ile Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asn Trp Asn Pro Phe Asp Pro Trp Gly Gln Gly Thr
            100                 105                 110

Leu Val Thr Val Ser Ser
        115


<210> SEQ ID NO 46
<211> LENGTH: 379
<212> TYPE: DNA
<213> ORGANISM: Artificial Sequence
<220> FEATURE:
<223> OTHER INFORMATION: MF8058
```

<400> SEQUENCE: 46

```
ggcccagccg gccatggccc aggtgcagct ggtgcagtct ggggctgagg tgaagaagcc     60

tgggtcctcg gtgaaggtct cctgcaaggc ttctggagac gccttcaaaa gcaaaacctt    120

tactatcagc tgggtgcgac aggcccctgg acaggggctt gagtggctgg gggggatcat    180

ccctcttttt ggtacaatta cctacgcaca gaagttccag ggcagagtca cgattaccgc    240

ggacaaatcc acgaacactg ccttcatgga actgagcagc ctgagatctg aggacacggc    300

catgtattat tgtacgcgac gggggaactg gaaccccttc gacccctggg gccagggaac    360

cctggtcacc gtctcgagt                                                 379
```

<210> SEQ ID NO 47
<211> LENGTH: 14
<212> TYPE: PRT
<213> ORGANISM: Artificial Sequence
<220> FEATURE:
<223> OTHER INFORMATION: MF8058 FW2

<400> SEQUENCE: 47

```
Trp Val Arg Gln Ala Pro Gly Gln Gly Leu Glu Trp Leu Gly
1               5                   10
```

<210> SEQ ID NO 48
<211> LENGTH: 30
<212> TYPE: PRT
<213> ORGANISM: Artificial Sequence
<220> FEATURE:
<223> OTHER INFORMATION: MF8058 FW1

<400> SEQUENCE: 48

```
Gln Val Gln Leu Val Gln Ser Gly Ala Glu Val Lys Lys Pro Gly Ser
1               5                   10                  15

Ser Val Lys Val Ser Cys Lys Ala Ser Gly Asp Ala Phe Lys
            20                  25                  30
```

<210> SEQ ID NO 49
<211> LENGTH: 32
<212> TYPE: PRT
<213> ORGANISM: Artificial Sequence
<220> FEATURE:
<223> OTHER INFORMATION: MF8058 FW3

<400> SEQUENCE: 49

```
Arg Val Thr Ile Thr Ala Asp Lys Ser Thr Asn Thr Ala Phe Met Glu
1               5                   10                  15

Leu Ser Ser Leu Arg Ser Glu Asp Thr Ala Met Tyr Tyr Cys Thr Arg
            20                  25                  30
```

<210> SEQ ID NO 50
<211> LENGTH: 11
<212> TYPE: PRT
<213> ORGANISM: Artificial Sequence
<220> FEATURE:
<223> OTHER INFORMATION: MF8058 FW4

<400> SEQUENCE: 50

```
Trp Gly Gln Gly Thr Leu Val Thr Val Ser Ser
1               5                   10
```

<210> SEQ ID NO 51
<211> LENGTH: 7
<212> TYPE: PRT

<213> ORGANISM: Artificial Sequence
<220> FEATURE:
<223> OTHER INFORMATION: MF8058 CDR1

<400> SEQUENCE: 51

Ser Lys Thr Phe Thr Ile Ser
1 5

<210> SEQ ID NO 52
<211> LENGTH: 17
<212> TYPE: PRT
<213> ORGANISM: Artificial Sequence
<220> FEATURE:
<223> OTHER INFORMATION: MF8058 CDR2

<400> SEQUENCE: 52

Gly Ile Ile Pro Leu Phe Gly Thr Ile Thr Tyr Ala Gln Lys Phe Gln
1 5 10 15

Gly

<210> SEQ ID NO 53
<211> LENGTH: 9
<212> TYPE: PRT
<213> ORGANISM: Artificial Sequence
<220> FEATURE:
<223> OTHER INFORMATION: MF8058 CDR3

<400> SEQUENCE: 53

Arg Gly Asn Trp Asn Pro Phe Asp Pro
1 5

<210> SEQ ID NO 54
<211> LENGTH: 120
<212> TYPE: PRT
<213> ORGANISM: Artificial Sequence
<220> FEATURE:
<223> OTHER INFORMATION: MF8058 VH

<400> SEQUENCE: 54

Gln Val Gln Leu Val Gln Ser Gly Ala Glu Val Lys Lys Pro Gly Ser
1 5 10 15

Ser Val Lys Val Ser Cys Lys Ala Ser Gly Asp Ala Phe Lys Ser Lys
20 25 30

Thr Phe Thr Ile Ser Trp Val Arg Gln Ala Pro Gly Gln Gly Leu Glu
35 40 45

Trp Leu Gly Gly Ile Ile Pro Leu Phe Gly Thr Ile Thr Tyr Ala Gln
50 55 60

Lys Phe Gln Gly Arg Val Thr Ile Thr Ala Asp Lys Ser Thr Asn Thr
65 70 75 80

Ala Phe Met Glu Leu Ser Ser Leu Arg Ser Glu Asp Thr Ala Met Tyr
85 90 95

Tyr Cys Thr Arg Arg Gly Asn Trp Asn Pro Phe Asp Pro Trp Gly Gln
100 105 110

Gly Thr Leu Val Thr Val Ser Ser
115 120

<210> SEQ ID NO 55
<211> LENGTH: 379
<212> TYPE: DNA
<213> ORGANISM: Artificial Sequence
<220> FEATURE:
<223> OTHER INFORMATION: MF8078

<400> SEQUENCE: 55
ggcccagccg gccatggccg aggtgcagct ggtgcagtct gggtctgagt tgaagaagcc 60
tgggtcctcg gtgaaggtct cctgcaaggc ttctggagtc accttcaaca gcagaacctt 120
tactatcagt tgggtgcgac aggcccctgg acaagggctt gagtggctgg ggagtatcat 180
ccctattttt ggtacaataa cctacgcaca gaagttccag ggcagagtca cgattaccgc 240
ggacaaatcc acgagcactg ccttcatgga actgaccagc ctgagatctg aggacacggc 300
catatattat tgtacgagac gggggaactg gaaccccttc gacccctggg gccagggcac 360
cctggtcacc gtctcgagt 379

<210> SEQ ID NO 56
<211> LENGTH: 30
<212> TYPE: PRT
<213> ORGANISM: Artificial Sequence
<220> FEATURE:
<223> OTHER INFORMATION: MF8078 FW1

<400> SEQUENCE: 56

Glu Val Gln Leu Val Gln Ser Gly Ser Glu Leu Lys Lys Pro Gly Ser
1 5 10 15

Ser Val Lys Val Ser Cys Lys Ala Ser Gly Val Thr Phe Asn
20 25 30

<210> SEQ ID NO 57
<211> LENGTH: 14
<212> TYPE: PRT
<213> ORGANISM: Artificial Sequence
<220> FEATURE:
<223> OTHER INFORMATION: MF8078 FW2

<400> SEQUENCE: 57

Trp Val Arg Gln Ala Pro Gly Gln Gly Leu Glu Trp Leu Gly
1 5 10

<210> SEQ ID NO 58
<211> LENGTH: 32
<212> TYPE: PRT
<213> ORGANISM: Artificial Sequence
<220> FEATURE:
<223> OTHER INFORMATION: MF8078 FW3

<400> SEQUENCE: 58

Arg Val Thr Ile Thr Ala Asp Lys Ser Thr Ser Thr Ala Phe Met Glu
1 5 10 15

Leu Thr Ser Leu Arg Ser Glu Asp Thr Ala Ile Tyr Tyr Cys Thr Arg
20 25 30

<210> SEQ ID NO 59
<211> LENGTH: 11
<212> TYPE: PRT
<213> ORGANISM: Artificial Sequence
<220> FEATURE:
<223> OTHER INFORMATION: MF8078 FW4

<400> SEQUENCE: 59

Trp Gly Gln Gly Thr Leu Val Thr Val Ser Ser
1 5 10

<210> SEQ ID NO 60
<211> LENGTH: 7
<212> TYPE: PRT
<213> ORGANISM: Artificial Sequence

<220> FEATURE:
<223> OTHER INFORMATION: MF8078 CDR1

<400> SEQUENCE: 60

Ser Arg Thr Phe Thr Ile Ser
1 5

<210> SEQ ID NO 61
<211> LENGTH: 17
<212> TYPE: PRT
<213> ORGANISM: Artificial Sequence
<220> FEATURE:
<223> OTHER INFORMATION: MF8078 CDR2

<400> SEQUENCE: 61

Ser Ile Ile Pro Ile Phe Gly Thr Ile Thr Tyr Ala Gln Lys Phe Gln
1 5 10 15

Gly

<210> SEQ ID NO 62
<211> LENGTH: 9
<212> TYPE: PRT
<213> ORGANISM: Artificial Sequence
<220> FEATURE:
<223> OTHER INFORMATION: MF8078 CDR3

<400> SEQUENCE: 62

Arg Gly Asn Trp Asn Pro Phe Asp Pro
1 5

<210> SEQ ID NO 63
<211> LENGTH: 120
<212> TYPE: PRT
<213> ORGANISM: Artificial Sequence
<220> FEATURE:
<223> OTHER INFORMATION: MF8078 VH

<400> SEQUENCE: 63

Glu Val Gln Leu Val Gln Ser Gly Ser Glu Leu Lys Lys Pro Gly Ser
1 5 10 15

Ser Val Lys Val Ser Cys Lys Ala Ser Gly Val Thr Phe Asn Ser Arg
20 25 30

Thr Phe Thr Ile Ser Trp Val Arg Gln Ala Pro Gly Gln Gly Leu Glu
35 40 45

Trp Leu Gly Ser Ile Ile Pro Ile Phe Gly Thr Ile Thr Tyr Ala Gln
50 55 60

Lys Phe Gln Gly Arg Val Thr Ile Thr Ala Asp Lys Ser Thr Ser Thr
65 70 75 80

Ala Phe Met Glu Leu Thr Ser Leu Arg Ser Glu Asp Thr Ala Ile Tyr
85 90 95

Tyr Cys Thr Arg Arg Gly Asn Trp Asn Pro Phe Asp Pro Trp Gly Gln
100 105 110

Gly Thr Leu Val Thr Val Ser Ser
115 120

<210> SEQ ID NO 64
<211> LENGTH: 30
<212> TYPE: PRT
<213> ORGANISM: Artificial Sequence
<220> FEATURE:
<223> OTHER INFORMATION: FW1

<400> SEQUENCE: 64

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Arg
20 25 30

<210> SEQ ID NO 65
<211> LENGTH: 14
<212> TYPE: PRT
<213> ORGANISM: Artificial Sequence
<220> FEATURE:
<223> OTHER INFORMATION: FW2

<400> SEQUENCE: 65

Trp Val Arg Gln Ala Pro Gly Gln Gly Leu Glu Trp Val Gly
1 5 10

<210> SEQ ID NO 66
<211> LENGTH: 32
<212> TYPE: PRT
<213> ORGANISM: Artificial Sequence
<220> FEATURE:
<223> OTHER INFORMATION: FW3

<400> SEQUENCE: 66

Arg Val Thr Ile Thr Ala Asp Lys Ser Ala Thr Thr Ala Tyr Met Glu
1 5 10 15

Leu Ser Ser Leu Arg Ser Glu Asp Thr Ala Ile Tyr Tyr Cys Ala Lys
20 25 30

<210> SEQ ID NO 67
<211> LENGTH: 11
<212> TYPE: PRT
<213> ORGANISM: Artificial Sequence
<220> FEATURE:
<223> OTHER INFORMATION: FW4

<400> SEQUENCE: 67

Trp Gly Gln Gly Thr Leu Val Thr Val Ser Ser
1 5 10

<210> SEQ ID NO 68
<211> LENGTH: 5
<212> TYPE: PRT
<213> ORGANISM: Artificial Sequence
<220> FEATURE:
<223> OTHER INFORMATION: CDR1

<400> SEQUENCE: 68

Gly Ser Gly Ile Ser
1 5

<210> SEQ ID NO 69
<211> LENGTH: 17
<212> TYPE: PRT
<213> ORGANISM: Artificial Sequence
<220> FEATURE:
<223> OTHER INFORMATION: CDR2

<400> SEQUENCE: 69

Gly Phe Ile Pro Phe Phe Gly Ser Ala Asn Tyr Ala Gln Lys Phe Arg
1 5 10 15

Asp

<210> SEQ ID NO 70

<211> LENGTH: 9
<212> TYPE: PRT
<213> ORGANISM: Artificial Sequence
<220> FEATURE:
<223> OTHER INFORMATION: CDR3

<400> SEQUENCE: 70

Arg Gly Asn Trp Asn Pro Leu Asp Pro
1               5

<210> SEQ ID NO 71
<211> LENGTH: 118
<212> TYPE: PRT
<213> ORGANISM: Artificial Sequence
<220> FEATURE:
<223> OTHER INFORMATION: VH

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Gly Ser
            20                  25                  30

Gly Ile Ser Trp Val Arg Gln Ala Pro Gly Gln Gly Leu Glu Trp Val
        35                  40                  45

Gly Gly Phe Ile Pro Phe Phe Gly Ser Ala Asn Tyr Ala Gln Lys Phe
    50                  55                  60

Arg Asp Arg Val Thr Ile Thr Ala Asp Lys Ser Ala Thr Thr Ala Tyr
65                  70                  75                  80

Met Glu Leu Ser Ser Leu Arg Ser Glu Asp Thr Ala Ile Tyr Tyr Cys
                85                  90                  95

Ala Lys Arg Gly Asn Trp Asn Pro Leu Asp Pro Trp Gly Gln Gly Thr
            100                 105                 110

Leu Val Thr Val Ser Ser
        115

<210> SEQ ID NO 72
<211> LENGTH: 90
<212> TYPE: DNA
<213> ORGANISM: Artificial Sequence
<220> FEATURE:
<223> OTHER INFORMATION: FW1

<400> SEQUENCE: 72
caggtgcagc tggtgcagtc tggggctgag gtgaagaagc ctgggtcctc ggtgaaggtc     60
tcctgcaagg cttctggagg caccttcaga                                      90

<210> SEQ ID NO 73
<211> LENGTH: 42
<212> TYPE: DNA
<213> ORGANISM: Artificial Sequence
<220> FEATURE:
<223> OTHER INFORMATION: FW2

<400> SEQUENCE: 73
tgggtgcgac aggcccctgg acaagggctt gagtgggtgg gc                        42

<210> SEQ ID NO 74
<211> LENGTH: 96
<212> TYPE: DNA
<213> ORGANISM: Artificial Sequence
<220> FEATURE:
<223> OTHER INFORMATION: FW3

<400> SEQUENCE: 74
agagtcacga ttaccgcgga caaatccgcg accacagcct acatggaact gagcagcctg 60
agatctgagg acacggccat atattactgt gcgaaa 96

<210> SEQ ID NO 75
<211> LENGTH: 33
<212> TYPE: DNA
<213> ORGANISM: Artificial Sequence
<220> FEATURE:
<223> OTHER INFORMATION: FW4

<400> SEQUENCE: 75
tggggccagg gcaccctggt caccgtctcg agt 33

<210> SEQ ID NO 76
<211> LENGTH: 15
<212> TYPE: DNA
<213> ORGANISM: Artificial Sequence
<220> FEATURE:
<223> OTHER INFORMATION: CDR1

<400> SEQUENCE: 76
ggttctggta tcagc 15

<210> SEQ ID NO 77
<211> LENGTH: 51
<212> TYPE: DNA
<213> ORGANISM: Artificial Sequence
<220> FEATURE:
<223> OTHER INFORMATION: CDR2

<400> SEQUENCE: 77
gggttcatcc ctttctttgg ttcagcaaac tacgcacaga agttccggga c 51

<210> SEQ ID NO 78
<211> LENGTH: 27
<212> TYPE: DNA
<213> ORGANISM: Artificial Sequence
<220> FEATURE:
<223> OTHER INFORMATION: CDR3

<400> SEQUENCE: 78
agaggaaatt ggaacccgct cgacccc 27

<210> SEQ ID NO 79
<211> LENGTH: 354
<212> TYPE: DNA
<213> ORGANISM: Artificial Sequence
<220> FEATURE:
<223> OTHER INFORMATION: VH

<400> SEQUENCE: 79
caggtgcagc tggtgcagtc tggggctgag gtgaagaagc ctgggtcctc ggtgaaggtc 60
tcctgcaagg cttctggagg caccttcaga ggttctggta tcagctgggt gcgacaggcc 120
cctggacaag ggcttgagtg ggtgggcggg ttcatccctt tctttggttc agcaaactac 180
gcacagaagt tccgggacag agtcacgatt accgcggaca aatccgcgac cacagcctac 240
atggaactga gcagcctgag atctgaggac acggccatat attactgtgc gaaaagagga 300
aattggaacc cgctcgaccc ctggggccag ggcaccctgg tcaccgtctc gagt 354

<210> SEQ ID NO 80
<211> LENGTH: 30

```
<212> TYPE: PRT
<213> ORGANISM: Artificial Sequence
<220> FEATURE:
<223> OTHER INFORMATION: FW1

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Lys
            20                  25                  30


<210> SEQ ID NO 81
<211> LENGTH: 14
<212> TYPE: PRT
<213> ORGANISM: Artificial Sequence
<220> FEATURE:
<223> OTHER INFORMATION: FW2

<400> SEQUENCE: 81

Trp Val Arg Gln Ala Pro Gly Gln Gly Leu Glu Trp Leu Gly
1               5                   10


<210> SEQ ID NO 82
<211> LENGTH: 32
<212> TYPE: PRT
<213> ORGANISM: Artificial Sequence
<220> FEATURE:
<223> OTHER INFORMATION: FW3

<400> SEQUENCE: 82

Arg Val Ser Ile Thr Ala Asp Lys Ser Thr Asn Thr Ala Tyr Leu Glu
1               5                   10                  15

Leu Asn Ser Leu Arg Ser Glu Asp Thr Ala Ile Tyr Tyr Cys Ala Arg
            20                  25                  30


<210> SEQ ID NO 83
<211> LENGTH: 11
<212> TYPE: PRT
<213> ORGANISM: Artificial Sequence
<220> FEATURE:
<223> OTHER INFORMATION: FW4

<400> SEQUENCE: 83

Trp Gly Gln Gly Thr Leu Val Thr Val Ser Ser
1               5                   10


<210> SEQ ID NO 84
<211> LENGTH: 7
<212> TYPE: PRT
<213> ORGANISM: Artificial Sequence
<220> FEATURE:
<223> OTHER INFORMATION: CDR1

<400> SEQUENCE: 84

Ser Lys Thr Leu Thr Ile Ser
1               5


<210> SEQ ID NO 85
<211> LENGTH: 17
<212> TYPE: PRT
<213> ORGANISM: Artificial Sequence
<220> FEATURE:
<223> OTHER INFORMATION: CDr2

<400> SEQUENCE: 85

Gly Ile Ile Pro Ile Phe Gly Ser Ile Thr Tyr Ala Gln Lys Phe Gln
```

1 5 10 15

Asp

<210> SEQ ID NO 86
<211> LENGTH: 9
<212> TYPE: PRT
<213> ORGANISM: Artificial Sequence
<220> FEATURE:
<223> OTHER INFORMATION: CDR3

<400> SEQUENCE: 86

Arg Gly Asn Trp Asn Pro Phe Asp Pro
1 5

<210> SEQ ID NO 87
<211> LENGTH: 120
<212> TYPE: PRT
<213> ORGANISM: Artificial Sequence
<220> FEATURE:
<223> OTHER INFORMATION: VH

<400> SEQUENCE: 87

Gln Val Gln Leu Val Gln Ser Gly Ala Glu Val Lys Lys Pro Gly Ser
1 5 10 15

Ser Val Lys Val Ser Cys Lys Ala Ser Gly Val Thr Phe Lys Ser Lys
20 25 30

Thr Leu Thr Ile Ser Trp Val Arg Gln Ala Pro Gly Gln Gly Leu Glu
35 40 45

Trp Leu Gly Gly Ile Ile Pro Ile Phe Gly Ser Ile Thr Tyr Ala Gln
50 55 60

Lys Phe Gln Asp Arg Val Ser Ile Thr Ala Asp Lys Ser Thr Asn Thr
65 70 75 80

Ala Tyr Leu Glu Leu Asn Ser Leu Arg Ser Glu Asp Thr Ala Ile Tyr
85 90 95

Tyr Cys Ala Arg Arg Gly Asn Trp Asn Pro Phe Asp Pro Trp Gly Gln
100 105 110

Gly Thr Leu Val Thr Val Ser Ser
115 120

<210> SEQ ID NO 88
<211> LENGTH: 90
<212> TYPE: DNA
<213> ORGANISM: Artificial Sequence
<220> FEATURE:
<223> OTHER INFORMATION: FW1

<400> SEQUENCE: 88
caggtgcagc tggtgcagtc tggggctgag gtgaagaagc ctgggtcctc ggtgaaggtc 60
tcctgcaagg cttctggagt caccttcaaa 90

<210> SEQ ID NO 89
<211> LENGTH: 42
<212> TYPE: DNA
<213> ORGANISM: Artificial Sequence
<220> FEATURE:
<223> OTHER INFORMATION: FW2

<400> SEQUENCE: 89
tgggtgcgac aggcccctgg acaagggctt gagtggctgg ga 42

<210> SEQ ID NO 90

<211> LENGTH: 96
<212> TYPE: DNA
<213> ORGANISM: Artificial Sequence
<220> FEATURE:
<223> OTHER INFORMATION: FW3

<400> SEQUENCE: 90
agagtctcga ttaccgcgga caaatccacg aacacagcct acttggaact gaacagcctg 60
aggtctgagg acacggccat ttattattgt gcgaga 96

<210> SEQ ID NO 91
<211> LENGTH: 33
<212> TYPE: DNA
<213> ORGANISM: Artificial Sequence
<220> FEATURE:
<223> OTHER INFORMATION: FW4

<400> SEQUENCE: 91
tggggccagg gcaccctggt caccgtctcg agt 33

<210> SEQ ID NO 92
<211> LENGTH: 21
<212> TYPE: DNA
<213> ORGANISM: Artificial Sequence
<220> FEATURE:
<223> OTHER INFORMATION: CDR1

<400> SEQUENCE: 92
agcaaaacct taactatcag c 21

<210> SEQ ID NO 93
<211> LENGTH: 51
<212> TYPE: DNA
<213> ORGANISM: Artificial Sequence
<220> FEATURE:
<223> OTHER INFORMATION: CDR2

<400> SEQUENCE: 93
gggatcatcc ctatttttgg ttcaataacc tacgcacaga agttccagga c 51

<210> SEQ ID NO 94
<211> LENGTH: 27
<212> TYPE: DNA
<213> ORGANISM: Artificial Sequence
<220> FEATURE:
<223> OTHER INFORMATION: CDR3

<400> SEQUENCE: 94
cgggggaact ggaacccctt cgacccc 27

<210> SEQ ID NO 95
<211> LENGTH: 360
<212> TYPE: DNA
<213> ORGANISM: Artificial Sequence
<220> FEATURE:
<223> OTHER INFORMATION: VH

<400> SEQUENCE: 95
caggtgcagc tggtgcagtc tggggctgag gtgaagaagc ctgggtcctc ggtgaaggtc 60
tcctgcaagg cttctggagt caccttcaaa agcaaaacct taactatcag ctgggtgcga 120
caggcccctg gacaagggct tgagtggctg ggagggatca tccctatttt tggttcaata 180
acctacgcac agaagttcca ggacagagtc tcgattaccg cggacaaatc cacgaacaca 240
gcctacttgg aactgaacag cctgaggtct gaggacacgg ccatttatta ttgtgcgaga 300
cgggggaact ggaacccctt cgacccctgg ggccagggca ccctggtcac cgtctcgagt 360

<210> SEQ ID NO 96
<211> LENGTH: 30
<212> TYPE: PRT
<213> ORGANISM: Artificial Sequence
<220> FEATURE:
<223> OTHER INFORMATION: FW1

<400> SEQUENCE: 96

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg
            20                  25                  30

<210> SEQ ID NO 97
<211> LENGTH: 14
<212> TYPE: PRT
<213> ORGANISM: Artificial Sequence
<220> FEATURE:
<223> OTHER INFORMATION: FW2

<400> SEQUENCE: 97

Trp Val Arg Gln Ala Pro Gly Gln Gly Leu Glu Trp Val Gly
1               5                   10

<210> SEQ ID NO 98
<211> LENGTH: 32
<212> TYPE: PRT
<213> ORGANISM: Artificial Sequence
<220> FEATURE:
<223> OTHER INFORMATION: FW3

<400> SEQUENCE: 98

Arg Val Thr Ile Thr Ala Asp Lys Ser Ala Thr Thr Ala Tyr Met Glu
1               5                   10                  15

Leu Ser Ser Leu Arg Ser Glu Asp Thr Ala Ile Tyr Tyr Cys Ala Lys
            20                  25                  30

<210> SEQ ID NO 99
<211> LENGTH: 11
<212> TYPE: PRT
<213> ORGANISM: Artificial Sequence
<220> FEATURE:
<223> OTHER INFORMATION: FW4

<400> SEQUENCE: 99

Trp Gly Gln Gly Thr Leu Val Thr Val Ser Ser
1               5                   10

<210> SEQ ID NO 100
<211> LENGTH: 5
<212> TYPE: PRT
<213> ORGANISM: Artificial Sequence
<220> FEATURE:
<223> OTHER INFORMATION: CDR1

<400> SEQUENCE: 100

Gly Ser Gly Ile Ser
1               5

<210> SEQ ID NO 101
<211> LENGTH: 17
<212> TYPE: PRT
<213> ORGANISM: Artificial Sequence

<220> FEATURE:
<223> OTHER INFORMATION: CDR2

<400> SEQUENCE: 101

Gly Phe Ile Pro Phe Phe Gly Ser Ala Asn Tyr Ala Gln Lys Phe Arg
1               5                   10                  15

Asp

<210> SEQ ID NO 102
<211> LENGTH: 9
<212> TYPE: PRT
<213> ORGANISM: Artificial Sequence
<220> FEATURE:
<223> OTHER INFORMATION: CDR3

<400> SEQUENCE: 102

Arg Gly Asn Trp Asn Pro Phe Asp Pro
1               5

<210> SEQ ID NO 103
<211> LENGTH: 118
<212> TYPE: PRT
<213> ORGANISM: Artificial Sequence
<220> FEATURE:
<223> OTHER INFORMATION: VH

<400> SEQUENCE: 103

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Gly Ser
            20                  25                  30

Gly Ile Ser Trp Val Arg Gln Ala Pro Gly Gln Gly Leu Glu Trp Val
        35                  40                  45

Gly Gly Phe Ile Pro Phe Phe Gly Ser Ala Asn Tyr Ala Gln Lys Phe
    50                  55                  60

Arg Asp Arg Val Thr Ile Thr Ala Asp Lys Ser Ala Thr Thr Ala Tyr
65                  70                  75                  80

Met Glu Leu Ser Ser Leu Arg Ser Glu Asp Thr Ala Ile Tyr Tyr Cys
                85                  90                  95

Ala Lys Arg Gly Asn Trp Asn Pro Phe Asp Pro Trp Gly Gln Gly Thr
            100                 105                 110

Leu Val Thr Val Ser Ser
        115

<210> SEQ ID NO 104
<211> LENGTH: 90
<212> TYPE: DNA
<213> ORGANISM: Artificial Sequence
<220> FEATURE:
<223> OTHER INFORMATION: FW1

<400> SEQUENCE: 104
gaggtgcagc tggtgcagtc tggagctgag gtgaagaagc ctgggtcctc ggtgaaggtc     60
tcctgcaagg cttctggagg caccttcaga                                      90

<210> SEQ ID NO 105
<211> LENGTH: 42
<212> TYPE: DNA
<213> ORGANISM: Artificial Sequence
<220> FEATURE:
<223> OTHER INFORMATION: FW2

<400> SEQUENCE: 105
tgggtgcgac aggcccctgg acaagggctt gagtgggtgg gc 42

<210> SEQ ID NO 106
<211> LENGTH: 96
<212> TYPE: DNA
<213> ORGANISM: Artificial Sequence
<220> FEATURE:
<223> OTHER INFORMATION: FW3

<400> SEQUENCE: 106
agagtcacga ttaccgcgga caaatccgcg accacagcct acatggaact gagcagcctg 60
agatctgagg acacggccat atattactgt gcgaaa 96

<210> SEQ ID NO 107
<211> LENGTH: 33
<212> TYPE: DNA
<213> ORGANISM: Artificial Sequence
<220> FEATURE:
<223> OTHER INFORMATION: FW4

<400> SEQUENCE: 107
tggggccagg gcaccctggt caccgtctcg agt 33

<210> SEQ ID NO 108
<211> LENGTH: 15
<212> TYPE: DNA
<213> ORGANISM: Artificial Sequence
<220> FEATURE:
<223> OTHER INFORMATION: CDR1

<400> SEQUENCE: 108
ggttctggta tcagc 15

<210> SEQ ID NO 109
<211> LENGTH: 51
<212> TYPE: DNA
<213> ORGANISM: Artificial Sequence
<220> FEATURE:
<223> OTHER INFORMATION: CDR2

<400> SEQUENCE: 109
gggttcatcc ctttctttgg ttcagcaaac tacgcacaga agttccggga c 51

<210> SEQ ID NO 110
<211> LENGTH: 27
<212> TYPE: DNA
<213> ORGANISM: Artificial Sequence
<220> FEATURE:
<223> OTHER INFORMATION: CDR3

<400> SEQUENCE: 110
agaggaaatt ggaacccgtt cgacccc 27

<210> SEQ ID NO 111
<211> LENGTH: 354
<212> TYPE: DNA
<213> ORGANISM: Artificial Sequence
<220> FEATURE:
<223> OTHER INFORMATION: FW

<400> SEQUENCE: 111
gaggtgcagc tggtgcagtc tggagctgag gtgaagaagc ctgggtcctc ggtgaaggtc 60
tcctgcaagg cttctggagg caccttcaga ggttctggta tcagctgggt gcgacaggcc 120
cctggacaag ggcttgagtg ggtgggcggg ttcatccctt tctttggttc agcaaactac 180
gcacagaagt tccgggacag agtcacgatt accgcggaca aatccgcgac cacagcctac 240
atggaactga gcagcctgag atctgaggac acggccatat attactgtgc gaaaagagga 300
aattggaacc cgttcgaccc ctggggccag ggcaccctgg tcaccgtctc gagt 354

<210> SEQ ID NO 112
<211> LENGTH: 379
<212> TYPE: DNA
<213> ORGANISM: Artificial Sequence
<220> FEATURE:
<223> OTHER INFORMATION: MF8397

<400> SEQUENCE: 112
caggtgcagc tggtgcagtc tgggggaggc ctggtacagc ctggggggtc cctgagactc 60
tcctgtgcaa cctctggatt caaattcagt agctatgccc tgagctgggt ccgccaggca 120
ccagggaagg gactggagtg ggtctcaggt attagtggta gtggtcgcac cacatggtat 180
gcagactccg tgaagggccg gttcaccatc tccagagaca attccaagaa cacgctgtat 240
ctgcaaatga acagcctgag agccgaggac acggccgtat attactgtgc gagagacggt 300
ggatacagct atggccctta ctggtacttc gatctctggg gccgtggaac cctggtcacc 360
cctggtcacc gtctccagt 379

<210> SEQ ID NO 113
<211> LENGTH: 30
<212> TYPE: PRT
<213> ORGANISM: Artificial Sequence
<220> FEATURE:
<223> OTHER INFORMATION: MF8397 FW1

<400> SEQUENCE: 113

Gln Val Gln Leu Val Gln Ser Gly Gly Gly Leu Val Gln Pro Gly Gly
1 5 10 15

Ser Leu Arg Leu Ser Cys Ala Thr Ser Gly Phe Lys Phe Ser
20 25 30

<210> SEQ ID NO 114
<211> LENGTH: 14
<212> TYPE: PRT
<213> ORGANISM: Artificial Sequence
<220> FEATURE:
<223> OTHER INFORMATION: MF8397 FW2

<400> SEQUENCE: 114

Trp Val Arg Gln Ala Pro Gly Lys Gly Leu Glu Trp Val Ser
1 5 10

<210> SEQ ID NO 115
<211> LENGTH: 32
<212> TYPE: PRT
<213> ORGANISM: Artificial Sequence
<220> FEATURE:
<223> OTHER INFORMATION: MF8397 FW3

<400> SEQUENCE: 115

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 116
<211> LENGTH: 11
<212> TYPE: PRT
<213> ORGANISM: Artificial Sequence
<220> FEATURE:
<223> OTHER INFORMATION: MF8397 FW4

<400> SEQUENCE: 116

Trp Gly Arg Gly Thr Leu Val Thr Val Ser Ser
1 5 10

<210> SEQ ID NO 117
<211> LENGTH: 5
<212> TYPE: PRT
<213> ORGANISM: Artificial Sequence
<220> FEATURE:
<223> OTHER INFORMATION: MF8397 CDR1

<400> SEQUENCE: 117

Ser Tyr Ala Leu Ser
1 5

<210> SEQ ID NO 118
<211> LENGTH: 17
<212> TYPE: PRT
<213> ORGANISM: Artificial Sequence
<220> FEATURE:
<223> OTHER INFORMATION: MF8397 CDR2

<400> SEQUENCE: 118

Gly Ile Ser Gly Ser Gly Arg Thr Thr Trp Tyr Ala Asp Ser Val Lys
1 5 10 15

Gly

<210> SEQ ID NO 119
<211> LENGTH: 14
<212> TYPE: PRT
<213> ORGANISM: Artificial Sequence
<220> FEATURE:
<223> OTHER INFORMATION: MF8397 CDR3

<400> SEQUENCE: 119

Asp Gly Gly Tyr Ser Tyr Gly Pro Tyr Trp Tyr Phe Asp Leu
1 5 10

<210> SEQ ID NO 120
<211> LENGTH: 123
<212> TYPE: PRT
<213> ORGANISM: Artificial Sequence
<220> FEATURE:
<223> OTHER INFORMATION: MF8397 VH

<400> SEQUENCE: 120

Gln Val Gln Leu Val Gln Ser Gly Gly Gly Leu Val Gln Pro Gly Gly
1 5 10 15

Ser Leu Arg Leu Ser Cys Ala Thr Ser Gly Phe Lys Phe Ser Ser Tyr
20 25 30

Ala Leu Ser Trp Val Arg Gln Ala Pro Gly Lys Gly Leu Glu Trp Val
35 40 45

Ser Gly Ile Ser Gly Ser Gly Arg Thr Thr Trp Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys

```
                85                  90                  95

Ala Arg Asp Gly Gly Tyr Ser Tyr Gly Pro Tyr Trp Tyr Phe Asp Leu
            100                 105                 110

Trp Gly Arg Gly Thr Leu Val Thr Val Ser Ser
        115                 120


<210> SEQ ID NO 121
<211> LENGTH: 30
<212> TYPE: PRT
<213> ORGANISM: Artificial Sequence
<220> FEATURE:
<223> OTHER INFORMATION: FW1

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ile
            20                  25                  30


<210> SEQ ID NO 122
<211> LENGTH: 14
<212> TYPE: PRT
<213> ORGANISM: Artificial Sequence
<220> FEATURE:
<223> OTHER INFORMATION: FW2

<400> SEQUENCE: 122

Trp Val Arg Gln Ala Pro Gly Lys Gly Leu Glu Trp Val Ser
1               5                   10


<210> SEQ ID NO 123
<211> LENGTH: 32
<212> TYPE: PRT
<213> ORGANISM: Artificial Sequence
<220> FEATURE:
<223> OTHER INFORMATION: FW3

<400> SEQUENCE: 123

Arg Phe Thr Ile Ser Arg Asp Asn Ser Lys Asn Thr Leu Phe Leu Gln
1               5                   10                  15

Met Asn Ser Leu Arg Ala Glu Asp Thr Ala Val Tyr Tyr Cys Ala Arg
            20                  25                  30


<210> SEQ ID NO 124
<211> LENGTH: 11
<212> TYPE: PRT
<213> ORGANISM: Artificial Sequence
<220> FEATURE:
<223> OTHER INFORMATION: FW4

<400> SEQUENCE: 124

Trp Gly Arg Gly Thr Leu Val Thr Val Ser Ser
1               5                   10


<210> SEQ ID NO 125
<211> LENGTH: 5
<212> TYPE: PRT
<213> ORGANISM: Artificial Sequence
<220> FEATURE:
<223> OTHER INFORMATION: CDR1

<400> SEQUENCE: 125

Ser Tyr Ala Leu Ser
1               5
```

<210> SEQ ID NO 126
<211> LENGTH: 17
<212> TYPE: PRT
<213> ORGANISM: Artificial Sequence
<220> FEATURE:
<223> OTHER INFORMATION: CDR2

<400> SEQUENCE: 126

Ala Ile Ser Gly Ser Gly Arg Thr Thr Trp Tyr Ala Asp Ser Val Lys
1               5                   10                  15

Gly

<210> SEQ ID NO 127
<211> LENGTH: 14
<212> TYPE: PRT
<213> ORGANISM: Artificial Sequence
<220> FEATURE:
<223> OTHER INFORMATION: CDR3

<400> SEQUENCE: 127

Asp Gly Gly Tyr Thr Tyr Gly Pro Tyr Trp Tyr Phe Asp Leu
1               5                   10

<210> SEQ ID NO 128
<211> LENGTH: 123
<212> TYPE: PRT
<213> ORGANISM: Artificial Sequence
<220> FEATURE:
<223> OTHER INFORMATION: VH

<400> SEQUENCE: 128

Gln Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ile Ser Tyr
            20                  25                  30

Ala Leu Ser Trp Val Arg Gln Ala Pro Gly Lys Gly Leu Glu Trp Val
        35                  40                  45

Ser Ala Ile Ser Gly Ser Gly Arg Thr Thr Trp Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Gly Gly Tyr Thr Tyr Gly Pro Tyr Trp Tyr Phe Asp Leu
            100                 105                 110

Trp Gly Arg Gly Thr Leu Val Thr Val Ser Ser
        115                 120

<210> SEQ ID NO 129
<211> LENGTH: 90
<212> TYPE: DNA
<213> ORGANISM: Artificial Sequence
<220> FEATURE:
<223> OTHER INFORMATION: FW1

<400> SEQUENCE: 129
caggtgcagc tggtggagtc tgggggaggc ctggtacagc ctgggggtc cctgagactc     60 tcctgtgcaa cctctggatt cacctttatc                                     90

<210> SEQ ID NO 130
<211> LENGTH: 42

<212> TYPE: DNA
<213> ORGANISM: Artificial Sequence
<220> FEATURE:
<223> OTHER INFORMATION: FW2

<400> SEQUENCE: 130
tgggtccgcc aggctccagg gaaggggctg gaatgggtct ca 42

<210> SEQ ID NO 131
<211> LENGTH: 96
<212> TYPE: DNA
<213> ORGANISM: Artificial Sequence
<220> FEATURE:
<223> OTHER INFORMATION: FW3

<400> SEQUENCE: 131
cggttcacca tctccagaga caattccaag aacacgctgt ttctgcaaat gaacagcctg 60
agagccgagg acacggccgt atattactgt gcgaga 96

<210> SEQ ID NO 132
<211> LENGTH: 33
<212> TYPE: DNA
<213> ORGANISM: Artificial Sequence
<220> FEATURE:
<223> OTHER INFORMATION: FW4

<400> SEQUENCE: 132
tggggccgtg gcaccctggt caccgtctcg agt 33

<210> SEQ ID NO 133
<211> LENGTH: 15
<212> TYPE: DNA
<213> ORGANISM: Artificial Sequence
<220> FEATURE:
<223> OTHER INFORMATION: CDR1

<400> SEQUENCE: 133
agctatgccc tgagc 15

<210> SEQ ID NO 134
<211> LENGTH: 51
<212> TYPE: DNA
<213> ORGANISM: Artificial Sequence
<220> FEATURE:
<223> OTHER INFORMATION: CDR2

<400> SEQUENCE: 134
gctattagtg gtagtggtcg taccacatgg tacgcagact ccgtgaaggg c 51

<210> SEQ ID NO 135
<211> LENGTH: 42
<212> TYPE: DNA
<213> ORGANISM: Artificial Sequence
<220> FEATURE:
<223> OTHER INFORMATION: CDR3

<400> SEQUENCE: 135
gacggtggat acacctatgg cccttactgg tacttcgatc tc 42

<210> SEQ ID NO 136
<211> LENGTH: 369
<212> TYPE: DNA
<213> ORGANISM: Artificial Sequence
<220> FEATURE:
<223> OTHER INFORMATION: VH

<400> SEQUENCE: 136

```
caggtgcagc tggtggagtc tgggggaggc ctggtacagc ctggggggtc cctgagactc     60
tcctgtgcaa cctctggatt cacctttatc agctatgccc tgagctgggt ccgccaggct    120
ccagggaagg ggctggaatg ggtctcagct attagtggta gtggtcgtac cacatggtac    180
gcagactccg tgaagggccg gttcaccatc tccagagaca attccaagaa cacgctgttt    240
ctgcaaatga acagcctgag agccgaggac acggccgtat attactgtgc gagagacggt    300
ggatacacct atggccctta ctggtacttc gatctctggg gccgtggcac cctggtcacc    360
gtctcgagt                                                            369
```

<210> SEQ ID NO 137
<211> LENGTH: 391
<212> TYPE: DNA
<213> ORGANISM: Artificial Sequence
<220> FEATURE:
<223> OTHER INFORMATION: MF8508

<400> SEQUENCE: 137

```
ggcccagccg gccatggccg aggtgcagct ggtggagtct gggggaggat tggtacagcc     60
tggcaggtcc ctgagactct cctgtgcaac ctctggattc aactttgatg attataccat    120
gcactgggtc cggcaagctc cagggaaggg cctggagtgg gtctcagata ttagttggag    180
tagtggtagc ataggctatg cggactctgt gaagggccga ttcaccatct ccagagacaa    240
cgccaagaac tccctgtggc tgcaaatgaa cagtctgaga actgaggaca cggccttgta    300
tttctgtgca aaagatcata gggggtacgg tgactacgag ggtggtggct ttgactactg    360
gggccaggga accctggtca ccgtctccag t                                   391
```

<210> SEQ ID NO 138
<211> LENGTH: 30
<212> TYPE: PRT
<213> ORGANISM: Artificial Sequence
<220> FEATURE:
<223> OTHER INFORMATION: MF8508 FW1

<400> SEQUENCE: 138

```
Glu Val Gln Leu Val Glu Ser Gly Gly Gly Leu Val Gln Pro Gly Arg
1               5                   10                  15

Ser Leu Arg Leu Ser Cys Ala Thr Ser Gly Phe Asn Phe Asp
            20                  25                  30
```

<210> SEQ ID NO 139
<211> LENGTH: 14
<212> TYPE: PRT
<213> ORGANISM: Artificial Sequence
<220> FEATURE:
<223> OTHER INFORMATION: MF8508 FW2

<400> SEQUENCE: 139

```
Trp Val Arg Gln Ala Pro Gly Lys Gly Leu Glu Trp Val Ser
1               5                   10
```

<210> SEQ ID NO 140
<211> LENGTH: 32
<212> TYPE: PRT
<213> ORGANISM: Artificial Sequence
<220> FEATURE:
<223> OTHER INFORMATION: MF8508 FW3

<400> SEQUENCE: 140

-continued

Arg Phe Thr Ile Ser Arg Asp Asn Ala Lys Asn Ser Leu Trp Leu Gln
1 5 10 15

Met Asn Ser Leu Arg Thr Glu Asp Thr Ala Leu Tyr Phe Cys Ala Lys
20 25 30

<210> SEQ ID NO 141
<211> LENGTH: 11
<212> TYPE: PRT
<213> ORGANISM: Artificial Sequence
<220> FEATURE:
<223> OTHER INFORMATION: MF8508 FW4

<400> SEQUENCE: 141

Trp Gly Gln Gly Thr Leu Val Thr Val Ser Ser
1 5 10

<210> SEQ ID NO 142
<211> LENGTH: 5
<212> TYPE: PRT
<213> ORGANISM: Artificial Sequence
<220> FEATURE:
<223> OTHER INFORMATION: MF8508 CDR1

<400> SEQUENCE: 142

Asp Tyr Thr Met His
1 5

<210> SEQ ID NO 143
<211> LENGTH: 17
<212> TYPE: PRT
<213> ORGANISM: Artificial Sequence
<220> FEATURE:
<223> OTHER INFORMATION: MF8508 CDR2

<400> SEQUENCE: 143

Asp Ile Ser Trp Ser Ser Gly Ser Ile Gly Tyr Ala Asp Ser Val Lys
1 5 10 15

Gly

<210> SEQ ID NO 144
<211> LENGTH: 15
<212> TYPE: PRT
<213> ORGANISM: Artificial Sequence
<220> FEATURE:
<223> OTHER INFORMATION: MF8508 CDR3

<400> SEQUENCE: 144

Asp His Arg Gly Tyr Gly Asp Tyr Glu Gly Gly Gly Phe Asp Tyr
1 5 10 15

<210> SEQ ID NO 145
<211> LENGTH: 124
<212> TYPE: PRT
<213> ORGANISM: Artificial Sequence
<220> FEATURE:
<223> OTHER INFORMATION: MF8508 VH

<400> SEQUENCE: 145

Glu Val Gln Leu Val Glu Ser Gly Gly Gly Leu Val Gln Pro Gly Arg
1 5 10 15

Ser Leu Arg Leu Ser Cys Ala Thr Ser Gly Phe Asn Phe Asp Asp Tyr
20 25 30

Thr Met His Trp Val Arg Gln Ala Pro Gly Lys Gly Leu Glu Trp Val
35 40 45

```
Ser Asp Ile Ser Trp Ser Ser Gly Ser Ile Gly Tyr Ala Asp Ser Val
    50                  55                  60

Lys Gly Arg Phe Thr Ile Ser Arg Asp Asn Ala Lys Asn Ser Leu Trp
65                  70                  75                  80

Leu Gln Met Asn Ser Leu Arg Thr Glu Asp Thr Ala Leu Tyr Phe Cys
                85                  90                  95

Ala Lys Asp His Arg Gly Tyr Gly Asp Tyr Glu Gly Gly Gly Phe Asp
            100                 105                 110

Tyr Trp Gly Gln Gly Thr Leu Val Thr Val Ser Ser
        115                 120
```

<210> SEQ ID NO 146
<211> LENGTH: 30
<212> TYPE: PRT
<213> ORGANISM: Artificial Sequence
<220> FEATURE:
<223> OTHER INFORMATION: FW1

<400> SEQUENCE: 146

```
Glu Val Gln Leu Val Glu Ser Gly Gly Gly Leu Val Gln Pro Gly Arg
1               5                   10                  15

Ser Leu Arg Leu Ser Cys Ala Thr Ser Gly Phe Thr Phe Asp
            20                  25                  30
```

<210> SEQ ID NO 147
<211> LENGTH: 14
<212> TYPE: PRT
<213> ORGANISM: Artificial Sequence
<220> FEATURE:
<223> OTHER INFORMATION: FW2

<400> SEQUENCE: 147

```
Trp Val Arg Gln Ala Pro Gly Lys Gly Leu Glu Trp Val Ser
1               5                   10
```

<210> SEQ ID NO 148
<211> LENGTH: 32
<212> TYPE: PRT
<213> ORGANISM: Artificial Sequence
<220> FEATURE:
<223> OTHER INFORMATION: FW3

<400> SEQUENCE: 148

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr Phe Cys Ala Lys
            20                  25                  30
```

<210> SEQ ID NO 149
<211> LENGTH: 11
<212> TYPE: PRT
<213> ORGANISM: Artificial Sequence
<220> FEATURE:
<223> OTHER INFORMATION: FW4

<400> SEQUENCE: 149

```
Trp Gly Gln Gly Thr Leu Val Thr Val Ser Ser
1               5                   10
```

<210> SEQ ID NO 150
<211> LENGTH: 5
<212> TYPE: PRT
<213> ORGANISM: Artificial Sequence
<220> FEATURE:

<223> OTHER INFORMATION: CDR1

<400> SEQUENCE: 150

```
Asp Tyr Thr Met His
1               5
```

<210> SEQ ID NO 151
<211> LENGTH: 17
<212> TYPE: PRT
<213> ORGANISM: Artificial Sequence
<220> FEATURE:
<223> OTHER INFORMATION: CDR3

<400> SEQUENCE: 151

```
Asp Ile Ser Trp Ser Ser Gly Ser Ile Gly Tyr Ala Asp Ser Val Lys
1               5                   10                  15

Gly
```

<210> SEQ ID NO 152
<211> LENGTH: 15
<212> TYPE: PRT
<213> ORGANISM: Artificial Sequence
<220> FEATURE:
<223> OTHER INFORMATION: CDR3

<400> SEQUENCE: 152

```
Asp His Arg Gly Tyr Gly Asp Tyr Glu Gly Gly Gly Phe Asp His
1               5                   10                  15
```

<210> SEQ ID NO 153
<211> LENGTH: 124
<212> TYPE: PRT
<213> ORGANISM: Artificial Sequence
<220> FEATURE:
<223> OTHER INFORMATION: VH

<400> SEQUENCE: 153

```
Glu Val Gln Leu Val Glu Ser Gly Gly Gly Leu Val Gln Pro Gly Arg
1               5                   10                  15

Ser Leu Arg Leu Ser Cys Ala Thr Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Asp Ile Ser Trp Ser Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Phe Cys
                85                  90                  95

Ala Lys Asp His Arg Gly Tyr Gly Asp Tyr Glu Gly Gly Gly Phe Asp
            100                 105                 110

His Trp Gly Gln Gly Thr Leu Val Thr Val Ser Ser
        115                 120
```

<210> SEQ ID NO 154
<211> LENGTH: 90
<212> TYPE: DNA
<213> ORGANISM: Artificial Sequence
<220> FEATURE:
<223> OTHER INFORMATION: FW1

<400> SEQUENCE: 154
gaggtgcagc tggtggagtc tgggggaggc ttggtacagc ctggcaggtc cctgagactc 60
tcctgtgcaa cctctggatt cacctttgat 90

<210> SEQ ID NO 155
<211> LENGTH: 42
<212> TYPE: DNA
<213> ORGANISM: Artificial Sequence
<220> FEATURE:
<223> OTHER INFORMATION: FW2

<400> SEQUENCE: 155
tgggtccggc aagctccagg gaagggcctg gagtgggtct ca 42

<210> SEQ ID NO 156
<211> LENGTH: 96
<212> TYPE: DNA
<213> ORGANISM: Artificial Sequence
<220> FEATURE:
<223> OTHER INFORMATION: FW3

<400> SEQUENCE: 156
cgattcacca tctccagaga caacgccaag aactccctgt atctgcaaat gaacagtctg 60
agagctgagg acacggcctt gtatttctgt gcaaaa 96

<210> SEQ ID NO 157
<211> LENGTH: 33
<212> TYPE: DNA
<213> ORGANISM: Artificial Sequence
<220> FEATURE:
<223> OTHER INFORMATION: FW4

<400> SEQUENCE: 157
tggggccagg gaaccctggt caccgtctcc agt 33

<210> SEQ ID NO 158
<211> LENGTH: 15
<212> TYPE: DNA
<213> ORGANISM: Artificial Sequence
<220> FEATURE:
<223> OTHER INFORMATION: CDR1

<400> SEQUENCE: 158
gattatacca tgcac 15

<210> SEQ ID NO 159
<211> LENGTH: 51
<212> TYPE: DNA
<213> ORGANISM: Artificial Sequence
<220> FEATURE:
<223> OTHER INFORMATION: CDR2

<400> SEQUENCE: 159
gatattagtt ggagtagtgg tagcataggc tatgcggact ctgtgaaggg c 51

<210> SEQ ID NO 160
<211> LENGTH: 45
<212> TYPE: DNA
<213> ORGANISM: Artificial Sequence
<220> FEATURE:
<223> OTHER INFORMATION: MF8998_16

<400> SEQUENCE: 160
gatcataggg ggtacggtga ctacgagggt ggtggctttg accac 45

<210> SEQ ID NO 161
<211> LENGTH: 372
<212> TYPE: DNA
<213> ORGANISM: Artificial Sequence
<220> FEATURE:
<223> OTHER INFORMATION: VH

<400> SEQUENCE: 161
gaggtgcagc tggtggagtc tgggggaggc ttggtacagc ctggcaggtc cctgagactc 60
tcctgtgcaa cctctggatt cacctttgat gattatacca tgcactgggt ccggcaagct 120
ccagggaagg gcctggagtg ggtctcagat attagttgga gtagtggtag cataggctat 180
gcggactctg tgaagggccg attcaccatc tccagagaca acgccaagaa ctccctgtat 240
ctgcaaatga acagtctgag agctgaggac acggccttgt atttctgtgc aaaagatcat 300
agggggtacg gtgactacga gggtggtggc tttgaccact ggggccaggg aaccctggtc 360
accgtctcca gt 372

<210> SEQ ID NO 162
<211> LENGTH: 30
<212> TYPE: PRT
<213> ORGANISM: Artificial Sequence
<220> FEATURE:
<223> OTHER INFORMATION: FW1

<400> SEQUENCE: 162

Glu Val Gln Leu Val Glu Ser Gly Gly Val Val Val Gln Pro Gly Gly
1 5 10 15

Ser Leu Arg Leu Ser Cys Ala Ala Ser Gly Phe Thr Phe Asp
20 25 30

<210> SEQ ID NO 163
<211> LENGTH: 14
<212> TYPE: PRT
<213> ORGANISM: Artificial Sequence
<220> FEATURE:
<223> OTHER INFORMATION: FW2

<400> SEQUENCE: 163

Trp Val Arg Gln Ala Pro Gly Lys Gly Leu Glu Trp Val Ser
1 5 10

<210> SEQ ID NO 164
<211> LENGTH: 32
<212> TYPE: PRT
<213> ORGANISM: Artificial Sequence
<220> FEATURE:
<223> OTHER INFORMATION: FW3

<400> SEQUENCE: 164

Arg Phe Thr Ile Ser Arg Asp Asn Ser Lys Asn Ser Leu Tyr Leu Gln
1 5 10 15

Met Asn Ser Leu Arg Thr Glu Asp Thr Ala Leu Tyr Tyr Cys Ala Lys
20 25 30

<210> SEQ ID NO 165
<211> LENGTH: 11
<212> TYPE: PRT
<213> ORGANISM: Artificial Sequence
<220> FEATURE:
<223> OTHER INFORMATION: FW4

<400> SEQUENCE: 165

Trp Gly Arg Gly Thr Leu Val Thr Val Ser Ser 1 5 10

<210> SEQ ID NO 166
<211> LENGTH: 5
<212> TYPE: PRT
<213> ORGANISM: Artificial Sequence
<220> FEATURE:
<223> OTHER INFORMATION: CDR1

<400> SEQUENCE: 166

Asp Tyr Thr Met His
1 5

<210> SEQ ID NO 167
<211> LENGTH: 17
<212> TYPE: PRT
<213> ORGANISM: Artificial Sequence
<220> FEATURE:
<223> OTHER INFORMATION: CDR2

<400> SEQUENCE: 167

Asp Ile Ser Trp Ser Gly Gly Ser Ile Tyr Tyr Ala Asp Ser Val Lys
1 5 10 15

Gly

<210> SEQ ID NO 168
<211> LENGTH: 15
<212> TYPE: PRT
<213> ORGANISM: Artificial Sequence
<220> FEATURE:
<223> OTHER INFORMATION: CDR3

<400> SEQUENCE: 168

Asp His Arg Gly Tyr Gly Asp Tyr Glu Gly Gly Gly Phe Asp Tyr
1 5 10 15

<210> SEQ ID NO 169
<211> LENGTH: 124
<212> TYPE: PRT
<213> ORGANISM: Artificial Sequence
<220> FEATURE:
<223> OTHER INFORMATION: VH

<400> SEQUENCE: 169

Glu Val Gln Leu Val Glu Ser Gly Gly Val Val Val Gln Pro Gly Gly
1 5 10 15

Ser Leu Arg Leu Ser Cys Ala Ala Ser Gly Phe Thr Phe Asp Asp Tyr
20 25 30

Thr Met His Trp Val Arg Gln Ala Pro Gly Lys Gly Leu Glu Trp Val
35 40 45

Ser Asp Ile Ser Trp Ser Gly Gly Ser Ile Tyr Tyr Ala Asp Ser Val
50 55 60

Lys Gly Arg Phe Thr Ile Ser Arg Asp Asn Ser Lys Asn Ser Leu Tyr
65 70 75 80

Leu Gln Met Asn Ser Leu Arg Thr Glu Asp Thr Ala Leu Tyr Tyr Cys
85 90 95

Ala Lys Asp His Arg Gly Tyr Gly Asp Tyr Glu Gly Gly Gly Phe Asp
100 105 110

Tyr Trp Gly Arg Gly Thr Leu Val Thr Val Ser Ser
115 120

<210> SEQ ID NO 170

<211> LENGTH: 90
<212> TYPE: DNA
<213> ORGANISM: Artificial Sequence
<220> FEATURE:
<223> OTHER INFORMATION: FW1

<400> SEQUENCE: 170
gaggtgcagc tggtggagag cggcggcgtg gtggtgcagc ccggcggcag cctgagactg 60
agctgcgccg ccagcggctt caccttcgac 90

<210> SEQ ID NO 171
<211> LENGTH: 42
<212> TYPE: DNA
<213> ORGANISM: Artificial Sequence
<220> FEATURE:
<223> OTHER INFORMATION: FW2

<400> SEQUENCE: 171
tgggtgagac aggcccccgg caagggcctg gagtgggtga gc 42

<210> SEQ ID NO 172
<211> LENGTH: 96
<212> TYPE: DNA
<213> ORGANISM: Artificial Sequence
<220> FEATURE:
<223> OTHER INFORMATION: FW3

<400> SEQUENCE: 172
agattcacca tcagcagaga caacagcaag aacagcctgt acctgcagat gaacagcctg 60
agaaccgagg acaccgccct gtactactgc gccaag 96

<210> SEQ ID NO 173
<211> LENGTH: 33
<212> TYPE: DNA
<213> ORGANISM: Artificial Sequence
<220> FEATURE:
<223> OTHER INFORMATION: FW4

<400> SEQUENCE: 173
tggggcagag gcaccctggt caccgtctcg agc 33

<210> SEQ ID NO 174
<211> LENGTH: 15
<212> TYPE: DNA
<213> ORGANISM: Artificial Sequence
<220> FEATURE:
<223> OTHER INFORMATION: CDR1

<400> SEQUENCE: 174
gactacacca tgcac 15

<210> SEQ ID NO 175
<211> LENGTH: 51
<212> TYPE: DNA
<213> ORGANISM: Artificial Sequence
<220> FEATURE:
<223> OTHER INFORMATION: CDR2

<400> SEQUENCE: 175
gacatcagct ggagcggcgg cagcatctac tacgccgaca gcgtgaaggg c 51

<210> SEQ ID NO 176
<211> LENGTH: 45
<212> TYPE: DNA
<213> ORGANISM: Artificial Sequence

<220> FEATURE:
<223> OTHER INFORMATION: CDR3

<400> SEQUENCE: 176
gaccacagag gctacggcga ctacgagggc ggcggcttcg actac 45

<210> SEQ ID NO 177
<211> LENGTH: 372
<212> TYPE: DNA
<213> ORGANISM: Artificial Sequence
<220> FEATURE:
<223> OTHER INFORMATION: VH

<400> SEQUENCE: 177
gaggtgcagc tggtggagag cggcggcgtg gtggtgcagc ccggcggcag cctgagactg 60
agctgcgccg ccagcggctt caccttcgac gactacacca tgcactgggt gagacaggcc 120
cccggcaagg gcctggagtg ggtgagcgac atcagctgga gcggcggcag catctactac 180
gccgacagcg tgaagggcag attcaccatc agcagagaca acagcaagaa cagcctgtac 240
ctgcagatga acagcctgag aaccgaggac accgccctgt actactgcgc caaggaccac 300
agaggctacg gcgactacga gggcggcggc ttcgactact ggggcagagg caccctggtc 360
accgtctcga gc 372

<210> SEQ ID NO 178
<211> LENGTH: 30
<212> TYPE: PRT
<213> ORGANISM: Artificial Sequence
<220> FEATURE:
<223> OTHER INFORMATION: FW1

<400> SEQUENCE: 178

Glu Val Gln Leu Val Glu Ser Gly Gly Gly Leu Val Gln Pro Gly Arg
1 5 10 15

Ser Leu Arg Leu Ser Cys Val Thr Ser Gly Phe Thr Phe Asp
20 25 30

<210> SEQ ID NO 179
<211> LENGTH: 14
<212> TYPE: PRT
<213> ORGANISM: Artificial Sequence
<220> FEATURE:
<223> OTHER INFORMATION: FW2

<400> SEQUENCE: 179

Trp Val Arg Gln Ala Pro Gly Lys Gly Leu Glu Trp Val Ser
1 5 10

<210> SEQ ID NO 180
<211> LENGTH: 32
<212> TYPE: PRT
<213> ORGANISM: Artificial Sequence
<220> FEATURE:
<223> OTHER INFORMATION: FW3

<400> SEQUENCE: 180

Arg Phe Thr Ile Ser Arg Asp Asn Ala Lys Asp Ser Leu Tyr Leu Gln
1 5 10 15

Met Asn Ser Leu Arg Thr Glu Asp Thr Ala Leu Tyr Tyr Cys Ala Lys
20 25 30

<210> SEQ ID NO 181
<211> LENGTH: 11

<212> TYPE: PRT
<213> ORGANISM: Artificial Sequence
<220> FEATURE:
<223> OTHER INFORMATION: FW4

<400> SEQUENCE: 181

Trp Gly Gln Gly Thr Leu Val Thr Val Ser Ser
1               5                   10

<210> SEQ ID NO 182
<211> LENGTH: 5
<212> TYPE: PRT
<213> ORGANISM: Artificial Sequence
<220> FEATURE:
<223> OTHER INFORMATION: CDR1

<400> SEQUENCE: 182

Asp Tyr Thr Met His
1               5

<210> SEQ ID NO 183
<211> LENGTH: 17
<212> TYPE: PRT
<213> ORGANISM: Artificial Sequence
<220> FEATURE:
<223> OTHER INFORMATION: CDR2

<400> SEQUENCE: 183

Asp Ile Ser Trp Ser Ser Gly Thr Thr Gly Tyr Ala Asp Ser Val Lys
1               5                   10                  15

Gly

<210> SEQ ID NO 184
<211> LENGTH: 15
<212> TYPE: PRT
<213> ORGANISM: Artificial Sequence
<220> FEATURE:
<223> OTHER INFORMATION: CDR3

<400> SEQUENCE: 184

Asp His Met Gly Tyr Gly Asp Tyr Glu Gly Gly Gly Phe Asp Tyr
1               5                   10                  15

<210> SEQ ID NO 185
<211> LENGTH: 124
<212> TYPE: PRT
<213> ORGANISM: Artificial Sequence
<220> FEATURE:
<223> OTHER INFORMATION: VH

<400> SEQUENCE: 185

Glu Val Gln Leu Val Glu Ser Gly Gly Gly Leu Val Gln Pro Gly Arg
1               5                   10                  15

Ser Leu Arg Leu Ser Cys Val Thr Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Asp Ile Ser Trp Ser Ser Gly Thr Thr Gly Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Thr Glu Asp Thr Ala Leu Tyr Tyr Cys
                85                  90                  95

```
Ala Lys Asp His Met Gly Tyr Gly Asp Tyr Glu Gly Gly Gly Phe Asp
            100                 105                 110

Tyr Trp Gly Gln Gly Thr Leu Val Thr Val Ser Ser
        115                 120


<210> SEQ ID NO 186
<211> LENGTH: 90
<212> TYPE: DNA
<213> ORGANISM: Artificial Sequence
<220> FEATURE:
<223> OTHER INFORMATION: FW1

<400> SEQUENCE: 186

gaagtgcagc tggtggagtc tgggggaggc ttggtacagc ctggcaggtc cctgagactc     60

tcctgtgtaa cctctggatt cacctttgat                                      90


<210> SEQ ID NO 187
<211> LENGTH: 42
<212> TYPE: DNA
<213> ORGANISM: Artificial Sequence
<220> FEATURE:
<223> OTHER INFORMATION: FW2

<400> SEQUENCE: 187

tgggtccggc aagctccggg gaagggcctg gagtgggtct ca                        42


<210> SEQ ID NO 188
<211> LENGTH: 96
<212> TYPE: DNA
<213> ORGANISM: Artificial Sequence
<220> FEATURE:
<223> OTHER INFORMATION: FW3

<400> SEQUENCE: 188

cgattcacca tctccagaga caatgccaag gactccctgt atctgcaaat gaacagtctg     60

agaactgagg acacggcctt gtattactgt gcaaaa                               96


<210> SEQ ID NO 189
<211> LENGTH: 33
<212> TYPE: DNA
<213> ORGANISM: Artificial Sequence
<220> FEATURE:
<223> OTHER INFORMATION: FW4

<400> SEQUENCE: 189

tggggccagg gaaccctggt caccgtctcg agc                                  33


<210> SEQ ID NO 190
<211> LENGTH: 15
<212> TYPE: DNA
<213> ORGANISM: Artificial Sequence
<220> FEATURE:
<223> OTHER INFORMATION: CDR1

<400> SEQUENCE: 190

gattatacca tgcac                                                      15


<210> SEQ ID NO 191
<211> LENGTH: 51
<212> TYPE: DNA
<213> ORGANISM: Artificial Sequence
<220> FEATURE:
<223> OTHER INFORMATION: CDR2

<400> SEQUENCE: 191
```

gatattagtt ggagtagtgg caccactggc tatgcggact ctgtgaaggg c 51

<210> SEQ ID NO 192
<211> LENGTH: 45
<212> TYPE: DNA
<213> ORGANISM: Artificial Sequence
<220> FEATURE:
<223> OTHER INFORMATION: CDR3

<400> SEQUENCE: 192
gatcatatgg ggtacggtga ctacgagggt ggtggctttg actac 45

<210> SEQ ID NO 193
<211> LENGTH: 372
<212> TYPE: DNA
<213> ORGANISM: Artificial Sequence
<220> FEATURE:
<223> OTHER INFORMATION: VH

<400> SEQUENCE: 193
gaagtgcagc tggtggagtc tgggggaggc ttggtacagc ctggcaggtc cctgagactc 60
tcctgtgtaa cctctggatt cacctttgat gattatacca tgcactgggt ccggcaagct 120
ccggggaagg gcctggagtg ggtctcagat attagttgga gtagtggcac cactggctat 180
gcggactctg tgaagggccg attcaccatc tccagagaca atgccaagga ctccctgtat 240
ctgcaaatga acagtctgag aactgaggac acggccttgt attactgtgc aaaagatcat 300
atggggtacg gtgactacga gggtggtggc tttgactact ggggccaggg aaccctggtc 360
accgtctcga gc 372

<210> SEQ ID NO 194
<211> LENGTH: 397
<212> TYPE: DNA
<213> ORGANISM: Artificial Sequence
<220> FEATURE:
<223> OTHER INFORMATION: MF9249

<400> SEQUENCE: 194
ggcccagccg gccatggccg aggtgcagct ggtgcagtct ggagcagaag tgaaaaagcc 60
cggggagtct ctgaagatct cctgtaaggg ttctggatac agttttacta ggttttggat 120
cggctgggtg cgccagatgc ccgggaaagg cctggagtgg atggggatca tctatcctgg 180
tgactctgat accagataca gcccgtcctt ccaaggccag gtcaccatct cagccgacaa 240
gtccaccagt accgcctacc tgcagtggag cagcctgaag gcctcggaca ccggcatgta 300
ttattgtgtg agacatatac gatattttga ctggtcggaa gactaccact attacctgga 360
cgtctggggc aaagggacca cggtcaccgt ctccagt 397

<210> SEQ ID NO 195
<211> LENGTH: 30
<212> TYPE: PRT
<213> ORGANISM: Artificial Sequence
<220> FEATURE:
<223> OTHER INFORMATION: MF9249 FW1

<400> SEQUENCE: 195

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr
20 25 30

<210> SEQ ID NO 196
<211> LENGTH: 14
<212> TYPE: PRT
<213> ORGANISM: Artificial Sequence
<220> FEATURE:
<223> OTHER INFORMATION: MF9249 FW2

<400> SEQUENCE: 196

Trp Val Arg Gln Met Pro Gly Lys Gly Leu Glu Trp Met Gly
1 5 10

<210> SEQ ID NO 197
<211> LENGTH: 32
<212> TYPE: PRT
<213> ORGANISM: Artificial Sequence
<220> FEATURE:
<223> OTHER INFORMATION: MF9249 FW3

<400> SEQUENCE: 197

Gln Val Thr Ile Ser Ala Asp Lys Ser Thr Ser Thr Ala Tyr Leu Gln
1 5 10 15

Trp Ser Ser Leu Lys Ala Ser Asp Thr Gly Met Tyr Tyr Cys Val Arg
20 25 30

<210> SEQ ID NO 198
<211> LENGTH: 11
<212> TYPE: PRT
<213> ORGANISM: Artificial Sequence
<220> FEATURE:
<223> OTHER INFORMATION: MF9249 FW4

<400> SEQUENCE: 198

Trp Gly Lys Gly Thr Thr Val Thr Val Ser Ser
1 5 10

<210> SEQ ID NO 199
<211> LENGTH: 5
<212> TYPE: PRT
<213> ORGANISM: Artificial Sequence
<220> FEATURE:
<223> OTHER INFORMATION: MF9249 CDR1

<400> SEQUENCE: 199

Arg Phe Trp Ile Gly
1 5

<210> SEQ ID NO 200
<211> LENGTH: 17
<212> TYPE: PRT
<213> ORGANISM: Artificial Sequence
<220> FEATURE:
<223> OTHER INFORMATION: MF9249 CDR2

<400> SEQUENCE: 200

Ile Ile Tyr Pro Gly Asp Ser Asp Thr Arg Tyr Ser Pro Ser Phe Gln
1 5 10 15

Gly

<210> SEQ ID NO 201
<211> LENGTH: 17
<212> TYPE: PRT
<213> ORGANISM: Artificial Sequence
<220> FEATURE:
<223> OTHER INFORMATION: MF9249 CDR3

<400> SEQUENCE: 201

```
His Ile Arg Tyr Phe Asp Trp Ser Glu Asp Tyr His Tyr Tyr Leu Asp
1               5                   10                  15

Val


<210> SEQ ID NO 202
<211> LENGTH: 126
<212> TYPE: PRT
<213> ORGANISM: Artificial Sequence
<220> FEATURE:
<223> OTHER INFORMATION: MF9249 VH

<400> SEQUENCE: 202

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Phe
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Thr Ser Thr Ala Tyr
65                  70                  75                  80

Leu Gln Trp Ser Ser Leu Lys Ala Ser Asp Thr Gly Met Tyr Tyr Cys
                85                  90                  95

Val Arg His Ile Arg Tyr Phe Asp Trp Ser Glu Asp Tyr His Tyr Tyr
            100                 105                 110

Leu Asp Val Trp Gly Lys Gly Thr Thr Val Thr Val Ser Ser
        115                 120                 125


<210> SEQ ID NO 203
<211> LENGTH: 378
<212> TYPE: DNA
<213> ORGANISM: Artificial Sequence
<220> FEATURE:
<223> OTHER INFORMATION: MF9267

<400> SEQUENCE: 203

gaggtgcagc tggtggagtc tggggcagag gtgaaaaagc ccggggagtc tctgaagatc      60

tcctgtaagg gttctggata cagttttact aggtattgga tcggctgggt gcgccagatg     120

cccgggaaag gcctggagtg gatggggatc atctatcctg gtgactctga taccagatac     180

agcccgtcct tccaaggcca ggtcaccatc tcagccgaca agtccatcag tactgcctac     240

ctgcagtgga gcagcctgaa ggcctcggac accgccatgt attattgtgt gagaaatata     300

cgatattttg tctggtcgga ggactaccac tactacatgg acgtctgggg caaagggacc     360

acggtcaccg tctccagt                                                   378


<210> SEQ ID NO 204
<211> LENGTH: 30
<212> TYPE: PRT
<213> ORGANISM: Artificial Sequence
<220> FEATURE:
<223> OTHER INFORMATION: MF9267 FW1

<400> SEQUENCE: 204

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30
```

<210> SEQ ID NO 205
<211> LENGTH: 14
<212> TYPE: PRT
<213> ORGANISM: Artificial Sequence
<220> FEATURE:
<223> OTHER INFORMATION: MF9267 FW2

<400> SEQUENCE: 205

Trp Val Arg Gln Met Pro Gly Lys Gly Leu Glu Trp Met Gly
1 5 10

<210> SEQ ID NO 206
<211> LENGTH: 32
<212> TYPE: PRT
<213> ORGANISM: Artificial Sequence
<220> FEATURE:
<223> OTHER INFORMATION: MF9267 FW3

<400> SEQUENCE: 206

Gln Val Thr Ile Ser Ala Asp Lys Ser Ile Ser Thr Ala Tyr Leu Gln
1 5 10 15

Trp Ser Ser Leu Lys Ala Ser Asp Thr Ala Met Tyr Tyr Cys Val Arg
20 25 30

<210> SEQ ID NO 207
<211> LENGTH: 11
<212> TYPE: PRT
<213> ORGANISM: Artificial Sequence
<220> FEATURE:
<223> OTHER INFORMATION: MF9267 FW4

<400> SEQUENCE: 207

Trp Gly Lys Gly Thr Thr Val Thr Val Ser Ser
1 5 10

<210> SEQ ID NO 208
<211> LENGTH: 5
<212> TYPE: PRT
<213> ORGANISM: Artificial Sequence
<220> FEATURE:
<223> OTHER INFORMATION: MF9267 CDR1

<400> SEQUENCE: 208

Arg Tyr Trp Ile Gly
1 5

<210> SEQ ID NO 209
<211> LENGTH: 17
<212> TYPE: PRT
<213> ORGANISM: Artificial Sequence
<220> FEATURE:
<223> OTHER INFORMATION: MF9267 CDR2

<400> SEQUENCE: 209

Ile Ile Tyr Pro Gly Asp Ser Asp Thr Arg Tyr Ser Pro Ser Phe Gln
1 5 10 15

Gly

<210> SEQ ID NO 210
<211> LENGTH: 17
<212> TYPE: PRT
<213> ORGANISM: Artificial Sequence
<220> FEATURE:
<223> OTHER INFORMATION: MF9267 CDR3

<400> SEQUENCE: 210

Asn Ile Arg Tyr Phe Val Trp Ser Glu Asp Tyr His Tyr Tyr Met Asp
1 5 10 15

Val

<210> SEQ ID NO 211
<211> LENGTH: 126
<212> TYPE: PRT
<213> ORGANISM: Artificial Sequence
<220> FEATURE:
<223> OTHER INFORMATION: MF9267 VH

<400> SEQUENCE: 211

Glu Val Gln Leu Val Glu Ser Gly Ala Glu Val Lys Lys Pro Gly Glu
1 5 10 15

Ser Leu Lys Ile Ser Cys Lys Gly Ser Gly Tyr Ser Phe Thr Arg Tyr
20 25 30

Trp Ile Gly Trp Val Arg Gln Met Pro Gly Lys Gly Leu Glu Trp Met
35 40 45

Gly Ile Ile Tyr Pro Gly Asp Ser Asp Thr Arg Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Val Arg Asn Ile Arg Tyr Phe Val Trp Ser Glu Asp Tyr His Tyr Tyr
100 105 110

Met Asp Val Trp Gly Lys Gly Thr Thr Val Thr Val Ser Ser
115 120 125

<210> SEQ ID NO 212
<211> LENGTH: 363
<212> TYPE: DNA
<213> ORGANISM: Artificial Sequence
<220> FEATURE:
<223> OTHER INFORMATION: MF5377

<400> SEQUENCE: 212
gaggtgcagc tggtgcagtc tggagctgag gtgaagaagc ctgggtcctc ggtgaaggtc 60
tcctgcaagg cttctggagg catcttcagc acctatgcta tcagctgggt gcgacaggcc 120
cctggacaag ggcttgagtg gatgggaggg atcatcccta tctttgatac accaaactac 180
gcacagaagt tccagggcag agtcacgatt accgcggaca aatccacgag cacagcctac 240
atggacctga gcagcctgag atctgaggac acggccgtat attactgtgc gaaaaacgtg 300
cgtggatata gtgcctacga ccttgactac tggggccagg gcaccctggt caccgtctcc 360
agt 363

<210> SEQ ID NO 213
<211> LENGTH: 30
<212> TYPE: PRT
<213> ORGANISM: Artificial Sequence
<220> FEATURE:
<223> OTHER INFORMATION: MF5377 FW1

<400> SEQUENCE: 213

Glu Val Gln Leu Val Gln Ser Gly Ala Glu Val Lys Lys Pro Gly Ser
1 5 10 15

Ser Val Lys Val Ser Cys Lys Ala Ser Gly Gly Ile Phe Ser 20 25 30

<210> SEQ ID NO 214
<211> LENGTH: 14
<212> TYPE: PRT
<213> ORGANISM: Artificial Sequence
<220> FEATURE:
<223> OTHER INFORMATION: MF5377 FW2

<400> SEQUENCE: 214

Trp Val Arg Gln Ala Pro Gly Gln Gly Leu Glu Trp Met Gly
1 5 10

<210> SEQ ID NO 215
<211> LENGTH: 32
<212> TYPE: PRT
<213> ORGANISM: Artificial Sequence
<220> FEATURE:
<223> OTHER INFORMATION: MF5377 FW3

<400> SEQUENCE: 215

Arg Val Thr Ile Thr Ala Asp Lys Ser Thr Ser Thr Ala Tyr Met Asp
1 5 10 15

Leu Ser Ser Leu Arg Ser Glu Asp Thr Ala Val Tyr Tyr Cys Ala Lys
20 25 30

<210> SEQ ID NO 216
<211> LENGTH: 11
<212> TYPE: PRT
<213> ORGANISM: Artificial Sequence
<220> FEATURE:
<223> OTHER INFORMATION: MF5377 FW4

<400> SEQUENCE: 216

Trp Gly Gln Gly Thr Leu Val Thr Val Ser Ser
1 5 10

<210> SEQ ID NO 217
<211> LENGTH: 5
<212> TYPE: PRT
<213> ORGANISM: Artificial Sequence
<220> FEATURE:
<223> OTHER INFORMATION: MF5377 CDR1

<400> SEQUENCE: 217

Thr Tyr Ala Ile Ser
1 5

<210> SEQ ID NO 218
<211> LENGTH: 17
<212> TYPE: PRT
<213> ORGANISM: Artificial Sequence
<220> FEATURE:
<223> OTHER INFORMATION: MF5377 CDR2

<400> SEQUENCE: 218

Gly Ile Ile Pro Ile Phe Asp Thr Pro Asn Tyr Ala Gln Lys Phe Gln
1 5 10 15

Gly

<210> SEQ ID NO 219
<211> LENGTH: 12
<212> TYPE: PRT
<213> ORGANISM: Artificial Sequence
<220> FEATURE:
<223> OTHER INFORMATION: MF5377 CDR3

<400> SEQUENCE: 219

Asn Val Arg Gly Tyr Ser Ala Tyr Asp Leu Asp Tyr
1 5 10

<210> SEQ ID NO 220
<211> LENGTH: 121
<212> TYPE: PRT
<213> ORGANISM: Artificial Sequence
<220> FEATURE:
<223> OTHER INFORMATION: MF5377 VH

<400> SEQUENCE: 220

Glu Val Gln Leu Val Gln Ser Gly Ala Glu Val Lys Lys Pro Gly Ser
1 5 10 15

Ser Val Lys Val Ser Cys Lys Ala Ser Gly Gly Ile Phe Ser Thr Tyr
20 25 30

Ala Ile Ser Trp Val Arg Gln Ala Pro Gly Gln Gly Leu Glu Trp Met
35 40 45

Gly Gly Ile Ile Pro Ile Phe Asp Thr Pro Asn Tyr Ala Gln Lys Phe
50 55 60

Gln Gly Arg Val Thr Ile Thr Ala Asp Lys Ser Thr Ser Thr Ala Tyr
65 70 75 80

Met Asp Leu Ser Ser Leu Arg Ser Glu Asp Thr Ala Val Tyr Tyr Cys
85 90 95

Ala Lys Asn Val Arg Gly Tyr Ser Ala Tyr Asp Leu Asp Tyr Trp Gly
100 105 110

Gln Gly Thr Leu Val Thr Val Ser Ser
115 120

<210> SEQ ID NO 221
<211> LENGTH: 363
<212> TYPE: DNA
<213> ORGANISM: Artificial Sequence
<220> FEATURE:
<223> OTHER INFORMATION: MF5444

<400> SEQUENCE: 221
caggtgcagc tggtgcaatc tgggtctgag ttgaagaagc ctggggcctc agtgaaggtt 60
tcctgcaagg cttctggata caccttcact agctattcta tgaattgggt gcgacaggcc 120
cctggacaag ggcttgagtg gatgggatgg atcaacacca acactgggaa cccaacgtat 180
gcccagggct tcacaggacg gtttgtcttc tccttggaca cctctgtcag cacggcatat 240
ctgcagatca gcagcctaaa ggctgaggac actgccgtgt attactgtgc gagagatcac 300
gattttcgga ctgggagggc ttttgatatc tggggccaag ggaccacggt caccgtctcc 360
agt 363

<210> SEQ ID NO 222
<211> LENGTH: 30
<212> TYPE: PRT
<213> ORGANISM: Artificial Sequence
<220> FEATURE:
<223> OTHER INFORMATION: MF5444 FW1

<400> SEQUENCE: 222

Gln Val Gln Leu Val Gln Ser Gly Ser Glu Leu Lys Lys Pro Gly Ala
1 5 10 15

Ser Val Lys Val Ser Cys Lys Ala Ser Gly Tyr Thr Phe Thr
20 25 30

```
<210> SEQ ID NO 223
<211> LENGTH: 14
<212> TYPE: PRT
<213> ORGANISM: Artificial Sequence
<220> FEATURE:
<223> OTHER INFORMATION: MF5444 FW2

<400> SEQUENCE: 223

Trp Val Arg Gln Ala Pro Gly Gln Gly Leu Glu Trp Met Gly
1               5                   10


<210> SEQ ID NO 224
<211> LENGTH: 32
<212> TYPE: PRT
<213> ORGANISM: Artificial Sequence
<220> FEATURE:
<223> OTHER INFORMATION: MF5444 FW3

<400> SEQUENCE: 224

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30


<210> SEQ ID NO 225
<211> LENGTH: 11
<212> TYPE: PRT
<213> ORGANISM: Artificial Sequence
<220> FEATURE:
<223> OTHER INFORMATION: MF5444 FW4

<400> SEQUENCE: 225

Trp Gly Gln Gly Thr Thr Val Thr Val Ser Ser
1               5                   10


<210> SEQ ID NO 226
<211> LENGTH: 5
<212> TYPE: PRT
<213> ORGANISM: Artificial Sequence
<220> FEATURE:
<223> OTHER INFORMATION: MF5444 CDR1

<400> SEQUENCE: 226

Ser Tyr Ser Met Asn
1               5


<210> SEQ ID NO 227
<211> LENGTH: 17
<212> TYPE: PRT
<213> ORGANISM: Artificial Sequence
<220> FEATURE:
<223> OTHER INFORMATION: MF5444 CDR2

<400> SEQUENCE: 227

Trp Ile Asn Thr Asn Thr Gly Asn Pro Thr Tyr Ala Gln Gly Phe Thr
1               5                   10                  15

Gly


<210> SEQ ID NO 228
<211> LENGTH: 12
<212> TYPE: PRT
<213> ORGANISM: Artificial Sequence
<220> FEATURE:
<223> OTHER INFORMATION: MF5444 CDR3
```

<400> SEQUENCE: 228

```
Asp His Asp Phe Arg Thr Gly Arg Ala Phe Asp Ile
1               5                   10
```

<210> SEQ ID NO 229
<211> LENGTH: 121
<212> TYPE: PRT
<213> ORGANISM: Artificial Sequence
<220> FEATURE:
<223> OTHER INFORMATION: MF5444 VH

<400> SEQUENCE: 229

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ser Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp His Asp Phe Arg Thr Gly Arg Ala Phe Asp Ile Trp Gly
            100                 105                 110

Gln Gly Thr Thr Val Thr Val Ser Ser
        115                 120
```

<210> SEQ ID NO 230
<211> LENGTH: 372
<212> TYPE: DNA
<213> ORGANISM: Artificial Sequence
<220> FEATURE:
<223> OTHER INFORMATION: MF5380

<400> SEQUENCE: 230

```
gaggtgcagc tggtggagtc tgggggagac gtggtccagc ctgggaggtc cctgagactc      60

tcctgtgcag cctctggatt caccttcagt agctatggca tgcactgggt ccgccaggct     120

ccaggcaagg ggctggagtg ggtggcagtt atatcatatg atggaagtaa taaatactat     180

gcagactccg tgaagggccg attcaccatc tccagagaca actccaagag cacgctgttt     240

ctgcaaatga acagcctgag agctgaggac acggctgtgt atttctgtgt gagaggcctc     300

cccataacta tggttcgggg agcgtactcc tttgactact ggggccaggg caccctggtc     360

accgtctcca gt                                                         372
```

<210> SEQ ID NO 231
<211> LENGTH: 30
<212> TYPE: PRT
<213> ORGANISM: Artificial Sequence
<220> FEATURE:
<223> OTHER INFORMATION: MF5380 FW1

<400> SEQUENCE: 231

```
Glu Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser
            20                  25                  30
```

<210> SEQ ID NO 232
<211> LENGTH: 14
<212> TYPE: PRT
<213> ORGANISM: Artificial Sequence
<220> FEATURE:
<223> OTHER INFORMATION: MF5380 FW2

<400> SEQUENCE: 232

Trp Val Arg Gln Ala Pro Gly Lys Gly Leu Glu Trp Val Ala
1 5 10

<210> SEQ ID NO 233
<211> LENGTH: 32
<212> TYPE: PRT
<213> ORGANISM: Artificial Sequence
<220> FEATURE:
<223> OTHER INFORMATION: MF5380 FW3

<400> SEQUENCE: 233

Arg Phe Thr Ile Ser Arg Asp Asn Ser Lys Ser Thr Leu Phe Leu Gln
1 5 10 15

Met Asn Ser Leu Arg Ala Glu Asp Thr Ala Val Tyr Phe Cys Val Arg
20 25 30

<210> SEQ ID NO 234
<211> LENGTH: 11
<212> TYPE: PRT
<213> ORGANISM: Artificial Sequence
<220> FEATURE:
<223> OTHER INFORMATION: MF5380 FW4

<400> SEQUENCE: 234

Trp Gly Gln Gly Thr Leu Val Thr Val Ser Ser
1 5 10

<210> SEQ ID NO 235
<211> LENGTH: 5
<212> TYPE: PRT
<213> ORGANISM: Artificial Sequence
<220> FEATURE:
<223> OTHER INFORMATION: MF5380 CDR1

<400> SEQUENCE: 235

Ser Tyr Gly Met His
1 5

<210> SEQ ID NO 236
<211> LENGTH: 17
<212> TYPE: PRT
<213> ORGANISM: Artificial Sequence
<220> FEATURE:
<223> OTHER INFORMATION: MF5380 CDR2

<400> SEQUENCE: 236

Val Ile Ser Tyr Asp Gly Ser Asn Lys Tyr Tyr Ala Asp Ser Val Lys
1 5 10 15

Gly

<210> SEQ ID NO 237
<211> LENGTH: 15
<212> TYPE: PRT
<213> ORGANISM: Artificial Sequence
<220> FEATURE:
<223> OTHER INFORMATION: MF5380 CDR3

<400> SEQUENCE: 237

```
Gly Leu Pro Ile Thr Met Val Arg Gly Ala Tyr Ser Phe Asp Tyr
1               5                   10                  15


<210> SEQ ID NO 238
<211> LENGTH: 124
<212> TYPE: PRT
<213> ORGANISM: Artificial Sequence
<220> FEATURE:
<223> OTHER INFORMATION: MF5380 VH

<400> SEQUENCE: 238

Glu Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Val Tyr Phe Cys
                85                  90                  95

Val Arg Gly Leu Pro Ile Thr Met Val Arg Gly Ala Tyr Ser Phe Asp
            100                 105                 110

Tyr Trp Gly Gln Gly Thr Leu Val Thr Val Ser Ser
        115                 120


<210> SEQ ID NO 239
<211> LENGTH: 366
<212> TYPE: DNA
<213> ORGANISM: Artificial Sequence
<220> FEATURE:
<223> OTHER INFORMATION: MF8233

<400> SEQUENCE: 239

caggttcagc tggtgcagtc tggagctgag gtgaagaagc ctggggcctc agtgaaggtc      60

tcctgcaagg cttctggtta cacctttacc agctatggta tcagctgggt gcgacaggcc     120

cctggacaag ggcttgagtg gatgggatgg atcagcgctt acaatgccaa cacaaactat     180

gcacagaagc tccagggcag agtcaccatg accacagaca catccacgag cacagcctac     240

atggagctga ggagcctgag atctgacgac acggctgtgt attactgtgc aaaagatcgt     300

cattggcatt ggtggctgga cgcctttgat tattggggcc aaggtaccct ggtcaccgtc     360

tccagt                                                                366


<210> SEQ ID NO 240
<211> LENGTH: 30
<212> TYPE: PRT
<213> ORGANISM: Artificial Sequence
<220> FEATURE:
<223> OTHER INFORMATION: MF8233 FW1

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 241
<211> LENGTH: 14
<212> TYPE: PRT
<213> ORGANISM: Artificial Sequence
<220> FEATURE:
<223> OTHER INFORMATION: MF8233 FW2

<400> SEQUENCE: 241

Trp Val Arg Gln Ala Pro Gly Gln Gly Leu Glu Trp Met Gly
1               5                   10

<210> SEQ ID NO 242
<211> LENGTH: 32
<212> TYPE: PRT
<213> ORGANISM: Artificial Sequence
<220> FEATURE:
<223> OTHER INFORMATION: MF8233 FW3

<400> SEQUENCE: 242

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Lys
            20                  25                  30

<210> SEQ ID NO 243
<211> LENGTH: 11
<212> TYPE: PRT
<213> ORGANISM: Artificial Sequence
<220> FEATURE:
<223> OTHER INFORMATION: MF8233 FW4

<400> SEQUENCE: 243

Trp Gly Gln Gly Thr Leu Val Thr Val Ser Ser
1               5                   10

<210> SEQ ID NO 244
<211> LENGTH: 5
<212> TYPE: PRT
<213> ORGANISM: Artificial Sequence
<220> FEATURE:
<223> OTHER INFORMATION: MF8233 CDR1

<400> SEQUENCE: 244

Ser Tyr Gly Ile Ser
1               5

<210> SEQ ID NO 245
<211> LENGTH: 17
<212> TYPE: PRT
<213> ORGANISM: Artificial Sequence
<220> FEATURE:
<223> OTHER INFORMATION: MF8233 CDR2

<400> SEQUENCE: 245

Trp Ile Ser Ala Tyr Asn Ala Asn Thr Asn Tyr Ala Gln Lys Leu Gln
1               5                   10                  15

Gly

<210> SEQ ID NO 246
<211> LENGTH: 13
<212> TYPE: PRT
<213> ORGANISM: Artificial Sequence
<220> FEATURE:
<223> OTHER INFORMATION: MF8233 CDR3

<400> SEQUENCE: 246

Asp Arg His Trp His Trp Trp Leu Asp Ala Phe Asp Tyr
1 5 10

<210> SEQ ID NO 247
<211> LENGTH: 122
<212> TYPE: PRT
<213> ORGANISM: Artificial Sequence
<220> FEATURE:
<223> OTHER INFORMATION: MF8233 VH

<400> SEQUENCE: 247

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Ala Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Lys Asp Arg His Trp His Trp Trp Leu Asp Ala Phe Asp Tyr Trp
100 105 110

Gly Gln Gly Thr Leu Val Thr Val Ser Ser
115 120

<210> SEQ ID NO 248
<211> LENGTH: 366
<212> TYPE: DNA
<213> ORGANISM: Artificial Sequence
<220> FEATURE:
<223> OTHER INFORMATION: MF9891

<400> SEQUENCE: 248
caggttcagc tggtgcagtc tggagctgag gtgaagaagc ctggggcctc agtgaaggtc 60
tcctgcaagg cttctggtta cacctttacc agctatggta tcagctgggt gcgacaggcc 120
cctggacaag ggcttgagtg gatgggatgg atcagcgctt acaatgccaa cacaaactat 180
gcacagaagc tccagggcag agtcaccatg accacagaca catccacgag cacagcctac 240
atggagctga ggagcctgag atctgacgac acggctgtgt attactgtgc aaaagatctg 300
tacggtcatt ggtggctgga tgcctttgat tattggggcc aaggtaccct ggtcaccgtc 360
tccagt 366

<210> SEQ ID NO 249
<211> LENGTH: 30
<212> TYPE: PRT
<213> ORGANISM: Artificial Sequence
<220> FEATURE:
<223> OTHER INFORMATION: MF9891 FW1

<400> SEQUENCE: 249

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr
20 25 30

<210> SEQ ID NO 250

<211> LENGTH: 14
<212> TYPE: PRT
<213> ORGANISM: Artificial Sequence
<220> FEATURE:
<223> OTHER INFORMATION: MF9891 FW2

<400> SEQUENCE: 250

Trp Val Arg Gln Ala Pro Gly Gln Gly Leu Glu Trp Met Gly
1 5 10

<210> SEQ ID NO 251
<211> LENGTH: 32
<212> TYPE: PRT
<213> ORGANISM: Artificial Sequence
<220> FEATURE:
<223> OTHER INFORMATION: MF9891 FW3

<400> SEQUENCE: 251

Arg Val Thr Met Thr Thr Asp Thr Ser Thr Ser Thr Ala Tyr Met Glu
1 5 10 15

Leu Arg Ser Leu Arg Ser Asp Asp Thr Ala Val Tyr Tyr Cys Ala Lys
20 25 30

<210> SEQ ID NO 252
<211> LENGTH: 11
<212> TYPE: PRT
<213> ORGANISM: Artificial Sequence
<220> FEATURE:
<223> OTHER INFORMATION: MF9891 FW4

<400> SEQUENCE: 252

Trp Gly Gln Gly Thr Leu Val Thr Val Ser Ser
1 5 10

<210> SEQ ID NO 253
<211> LENGTH: 5
<212> TYPE: PRT
<213> ORGANISM: Artificial Sequence
<220> FEATURE:
<223> OTHER INFORMATION: MF9891 CDR1

<400> SEQUENCE: 253

Ser Tyr Gly Ile Ser
1 5

<210> SEQ ID NO 254
<211> LENGTH: 17
<212> TYPE: PRT
<213> ORGANISM: Artificial Sequence
<220> FEATURE:
<223> OTHER INFORMATION: MF9891 CDR2

<400> SEQUENCE: 254

Trp Ile Ser Ala Tyr Asn Ala Asn Thr Asn Tyr Ala Gln Lys Leu Gln
1 5 10 15

Gly

<210> SEQ ID NO 255
<211> LENGTH: 13
<212> TYPE: PRT
<213> ORGANISM: Artificial Sequence
<220> FEATURE:
<223> OTHER INFORMATION: MF9891 CDR3

<400> SEQUENCE: 255

Asp Leu Tyr Gly His Trp Trp Leu Asp Ala Phe Asp Tyr 1 5 10

<210> SEQ ID NO 256
<211> LENGTH: 122
<212> TYPE: PRT
<213> ORGANISM: Artificial Sequence
<220> FEATURE:
<223> OTHER INFORMATION: MF9891 VH

<400> SEQUENCE: 256

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Ala Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Lys Asp Leu Tyr Gly His Trp Trp Leu Asp Ala Phe Asp Tyr Trp
100 105 110

Gly Gln Gly Thr Leu Val Thr Val Ser Ser
115 120

<210> SEQ ID NO 257
<211> LENGTH: 366
<212> TYPE: DNA
<213> ORGANISM: Artificial Sequence
<220> FEATURE:
<223> OTHER INFORMATION: MF9886

<400> SEQUENCE: 257
caggttcagc tggtgcagtc tggagctgag gtgaagaagc ctggggcctc agtgaaggtc 60
tcctgcaagg cttctggtta cacctttacc agctatggta tcagctgggt gcgacaggcc 120
cctggacaag ggcttgagtg gatgggatgg atcagcgctt acaatgccaa cacaaactat 180
gcacagaagc tccagggcag agtcaccatg accacagaca catccacgag cacagcctac 240
atggagctga ggagcctgag atctgacgac acggctgtgt attactgtgc aaaaggtcca 300
ggttctcatt ggtggctgga tgcctttgat tattggggcc aaggtaccct ggtcaccgtc 360
tccagt 366

<210> SEQ ID NO 258
<211> LENGTH: 30
<212> TYPE: PRT
<213> ORGANISM: Artificial Sequence
<220> FEATURE:
<223> OTHER INFORMATION: MF9886 FW1

<400> SEQUENCE: 258

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr
20 25 30

<210> SEQ ID NO 259
<211> LENGTH: 14

<212> TYPE: PRT
<213> ORGANISM: Artificial Sequence
<220> FEATURE:
<223> OTHER INFORMATION: MF9886 FW2

<400> SEQUENCE: 259

Trp Val Arg Gln Ala Pro Gly Gln Gly Leu Glu Trp Met Gly
1 5 10

<210> SEQ ID NO 260
<211> LENGTH: 32
<212> TYPE: PRT
<213> ORGANISM: Artificial Sequence
<220> FEATURE:
<223> OTHER INFORMATION: MF9886 FW3

<400> SEQUENCE: 260

Arg Val Thr Met Thr Thr Asp Thr Ser Thr Ser Thr Ala Tyr Met Glu
1 5 10 15

Leu Arg Ser Leu Arg Ser Asp Asp Thr Ala Val Tyr Tyr Cys Ala Lys
20 25 30

<210> SEQ ID NO 261
<211> LENGTH: 11
<212> TYPE: PRT
<213> ORGANISM: Artificial Sequence
<220> FEATURE:
<223> OTHER INFORMATION: MF9886 FW4

<400> SEQUENCE: 261

Trp Gly Gln Gly Thr Leu Val Thr Val Ser Ser
1 5 10

<210> SEQ ID NO 262
<211> LENGTH: 5
<212> TYPE: PRT
<213> ORGANISM: Artificial Sequence
<220> FEATURE:
<223> OTHER INFORMATION: MF9886 CDR1

<400> SEQUENCE: 262

Ser Tyr Gly Ile Ser
1 5

<210> SEQ ID NO 263
<211> LENGTH: 17
<212> TYPE: PRT
<213> ORGANISM: Artificial Sequence
<220> FEATURE:
<223> OTHER INFORMATION: MF9886 CDR2

<400> SEQUENCE: 263

Trp Ile Ser Ala Tyr Asn Ala Asn Thr Asn Tyr Ala Gln Lys Leu Gln
1 5 10 15

Gly

<210> SEQ ID NO 264
<211> LENGTH: 13
<212> TYPE: PRT
<213> ORGANISM: Artificial Sequence
<220> FEATURE:
<223> OTHER INFORMATION: MF9886 CDR3

<400> SEQUENCE: 264

Gly Pro Gly Ser His Trp Trp Leu Asp Ala Phe Asp Tyr
1 5 10

<210> SEQ ID NO 265
<211> LENGTH: 122
<212> TYPE: PRT
<213> ORGANISM: Artificial Sequence
<220> FEATURE:
<223> OTHER INFORMATION: MF9886 VH

<400> SEQUENCE: 265

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Ala Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Lys Gly Pro Gly Ser His Trp Trp Leu Asp Ala Phe Asp Tyr Trp
100 105 110

Gly Gln Gly Thr Leu Val Thr Val Ser Ser
115 120

<210> SEQ ID NO 266
<211> LENGTH: 366
<212> TYPE: DNA
<213> ORGANISM: Artificial Sequence
<220> FEATURE:
<223> OTHER INFORMATION: MF9873

<400> SEQUENCE: 266
caggttcagc tggtgcagtc tggagctgag gtgaagaagc ctggggcctc agtgaaggtc 60
tcctgcaagg cttctggtta cacctttacc agctatggta tcagctgggt gcgacaggcc 120
cctggacaag ggcttgagtg gatgggatgg atcagcgctt acaatgccaa cacaaactat 180
gcacagaagc tccagggcag agtcaccatg accacagaca catccacgag cacagcctac 240
atggagctga ggagcctgag atctgacgac acggctgtgt attactgtgc aaaagataga 300
ggttggcatt ggtggctgga tgcctttgat tattggggcc aaggtaccct ggtcaccgtc 360
tccagt 366

<210> SEQ ID NO 267
<211> LENGTH: 30
<212> TYPE: PRT
<213> ORGANISM: Artificial Sequence
<220> FEATURE:
<223> OTHER INFORMATION: MF9873 FW1

<400> SEQUENCE: 267

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr
20 25 30

<210> SEQ ID NO 268
<211> LENGTH: 14
<212> TYPE: PRT

<213> ORGANISM: Artificial Sequence
<220> FEATURE:
<223> OTHER INFORMATION: MF9873 FW2

<400> SEQUENCE: 268

Trp Val Arg Gln Ala Pro Gly Gln Gly Leu Glu Trp Met Gly
1 5 10

<210> SEQ ID NO 269
<211> LENGTH: 32
<212> TYPE: PRT
<213> ORGANISM: Artificial Sequence
<220> FEATURE:
<223> OTHER INFORMATION: MF9873 FW3

<400> SEQUENCE: 269

Arg Val Thr Met Thr Thr Asp Thr Ser Thr Ser Thr Ala Tyr Met Glu
1 5 10 15

Leu Arg Ser Leu Arg Ser Asp Asp Thr Ala Val Tyr Tyr Cys Ala Lys
20 25 30

<210> SEQ ID NO 270
<211> LENGTH: 11
<212> TYPE: PRT
<213> ORGANISM: Artificial Sequence
<220> FEATURE:
<223> OTHER INFORMATION: MF9873 FW4

<400> SEQUENCE: 270

Trp Gly Gln Gly Thr Leu Val Thr Val Ser Ser
1 5 10

<210> SEQ ID NO 271
<211> LENGTH: 5
<212> TYPE: PRT
<213> ORGANISM: Artificial Sequence
<220> FEATURE:
<223> OTHER INFORMATION: MF9873 CDR1

<400> SEQUENCE: 271

Ser Tyr Gly Ile Ser
1 5

<210> SEQ ID NO 272
<211> LENGTH: 17
<212> TYPE: PRT
<213> ORGANISM: Artificial Sequence
<220> FEATURE:
<223> OTHER INFORMATION: MF9873 CDR2

<400> SEQUENCE: 272

Trp Ile Ser Ala Tyr Asn Ala Asn Thr Asn Tyr Ala Gln Lys Leu Gln
1 5 10 15

Gly

<210> SEQ ID NO 273
<211> LENGTH: 13
<212> TYPE: PRT
<213> ORGANISM: Artificial Sequence
<220> FEATURE:
<223> OTHER INFORMATION: MF9873 CDR3

<400> SEQUENCE: 273

Asp Arg Gly Trp His Trp Trp Leu Asp Ala Phe Asp Tyr
1 5 10

<210> SEQ ID NO 274
<211> LENGTH: 122
<212> TYPE: PRT
<213> ORGANISM: Artificial Sequence
<220> FEATURE:
<223> OTHER INFORMATION: MF9873 VH

<400> SEQUENCE: 274

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ala Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg Gly Trp His Trp Trp Leu Asp Ala Phe Asp Tyr Trp
            100                 105                 110

Gly Gln Gly Thr Leu Val Thr Val Ser Ser
        115                 120
```

<210> SEQ ID NO 275
<211> LENGTH: 375
<212> TYPE: DNA
<213> ORGANISM: Artificial Sequence
<220> FEATURE:
<223> OTHER INFORMATION: MF9988

<400> SEQUENCE: 275

```
caggttcagc tggtgcagtc tggagctgag gtgaagaagc ctggggcctc agtgaaggtc     60

tcctgcaagg cttctggtta cacctttacc agctatggta tcagctgggt gcgacaggcc    120

cctggacaag ggcttgagtg gatgggatgg atcagcgctt acaatgccaa cacaaactat    180

gcacagaagc tccagggcag agtcaccatg accacagaca catccacgag cacagcctac    240

atggagctga ggagcctgag atctgacgac acggctgtgt attactgtgc aaaagatcgt    300

cattggcatt ggtggctgga cggctttgat tattggggcc aaggtaccct ggtcaccgtc    360

tcgagtgtct ccagt                                                     375
```

<210> SEQ ID NO 276
<211> LENGTH: 30
<212> TYPE: PRT
<213> ORGANISM: Artificial Sequence
<220> FEATURE:
<223> OTHER INFORMATION: MF9988 FW1

<400> SEQUENCE: 276

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 277
<211> LENGTH: 14
<212> TYPE: PRT
<213> ORGANISM: Artificial Sequence

```
<220> FEATURE:
<223> OTHER INFORMATION: MF9988 FW2

<400> SEQUENCE: 277

Trp Val Arg Gln Ala Pro Gly Gln Gly Leu Glu Trp Met Gly
1               5                   10


<210> SEQ ID NO 278
<211> LENGTH: 32
<212> TYPE: PRT
<213> ORGANISM: Artificial Sequence
<220> FEATURE:
<223> OTHER INFORMATION: MF9988 FW3

<400> SEQUENCE: 278

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Lys
            20                  25                  30


<210> SEQ ID NO 279
<211> LENGTH: 11
<212> TYPE: PRT
<213> ORGANISM: Artificial Sequence
<220> FEATURE:
<223> OTHER INFORMATION: MF9988 FW4

<400> SEQUENCE: 279

Trp Gly Gln Gly Thr Leu Val Thr Val Ser Ser
1               5                   10


<210> SEQ ID NO 280
<211> LENGTH: 5
<212> TYPE: PRT
<213> ORGANISM: Artificial Sequence
<220> FEATURE:
<223> OTHER INFORMATION: MF9988 CDR1

<400> SEQUENCE: 280

Ser Tyr Gly Ile Ser
1               5


<210> SEQ ID NO 281
<211> LENGTH: 17
<212> TYPE: PRT
<213> ORGANISM: Artificial Sequence
<220> FEATURE:
<223> OTHER INFORMATION: MF9988 CDR2

<400> SEQUENCE: 281

Trp Ile Ser Ala Tyr Asn Ala Asn Thr Asn Tyr Ala Gln Lys Leu Gln
1               5                   10                  15

Gly


<210> SEQ ID NO 282
<211> LENGTH: 13
<212> TYPE: PRT
<213> ORGANISM: Artificial Sequence
<220> FEATURE:
<223> OTHER INFORMATION: MF9988 CDR3

<400> SEQUENCE: 282

Asp Arg His Trp His Trp Trp Leu Asp Gly Phe Asp Tyr
1               5                   10
```

<210> SEQ ID NO 283
<211> LENGTH: 122
<212> TYPE: PRT
<213> ORGANISM: Artificial Sequence
<220> FEATURE:
<223> OTHER INFORMATION: MF9988 VH

<400> SEQUENCE: 283

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Ala Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Lys Asp Arg His Trp His Trp Trp Leu Asp Gly Phe Asp Tyr Trp
100 105 110

Gly Gln Gly Thr Leu Val Thr Val Ser Ser
115 120

<210> SEQ ID NO 284
<211> LENGTH: 369
<212> TYPE: DNA
<213> ORGANISM: Artificial Sequence
<220> FEATURE:
<223> OTHER INFORMATION: MF6744 anti-CD127 antibody sequence

<400> SEQUENCE: 284
gaggtgcagc tggtgcagtc tggagcagag gtgaaaaagc ccggggagtc actgaaaatc 60
tcctgtaagg gttctggata cagctttacc agctactgga tcggctgggt gcgccagatg 120
cccgggaaag gcctggagtg gatggggatc atctttcctg atgactctga taccagatac 180
agtccgtcct tccaaggcca ggtcaccatc tcagccgaca agtccatcag taccgcctac 240
ctgcagtgga gcagcctgaa accctcggac accgccatgt attactgtgt gagacttggt 300
ggatatagtg gctacgctga ggattttgtt gacttctggg gccagggaac cctggtcacc 360
gtctccagt 369

<210> SEQ ID NO 285
<211> LENGTH: 30
<212> TYPE: PRT
<213> ORGANISM: Artificial Sequence
<220> FEATURE:
<223> OTHER INFORMATION: MF6744 FW1

<400> SEQUENCE: 285

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr
20 25 30

<210> SEQ ID NO 286
<211> LENGTH: 14
<212> TYPE: PRT
<213> ORGANISM: Artificial Sequence
<220> FEATURE:

<223> OTHER INFORMATION: MF6744 FW2

<400> SEQUENCE: 286

Trp Val Arg Gln Met Pro Gly Lys Gly Leu Glu Trp Met Gly
1 5 10

<210> SEQ ID NO 287
<211> LENGTH: 32
<212> TYPE: PRT
<213> ORGANISM: Artificial Sequence
<220> FEATURE:
<223> OTHER INFORMATION: MF6744 FW3

<400> SEQUENCE: 287

Gln Val Thr Ile Ser Ala Asp Lys Ser Ile Ser Thr Ala Tyr Leu Gln
1 5 10 15

Trp Ser Ser Leu Lys Pro Ser Asp Thr Ala Met Tyr Tyr Cys Val Arg
20 25 30

<210> SEQ ID NO 288
<211> LENGTH: 11
<212> TYPE: PRT
<213> ORGANISM: Artificial Sequence
<220> FEATURE:
<223> OTHER INFORMATION: MF6744 FW4

<400> SEQUENCE: 288

Trp Gly Gln Gly Thr Leu Val Thr Val Ser Ser
1 5 10

<210> SEQ ID NO 289
<211> LENGTH: 5
<212> TYPE: PRT
<213> ORGANISM: Artificial Sequence
<220> FEATURE:
<223> OTHER INFORMATION: MF6744 CDR1

<400> SEQUENCE: 289

Ser Tyr Trp Ile Gly
1 5

<210> SEQ ID NO 290
<211> LENGTH: 17
<212> TYPE: PRT
<213> ORGANISM: Artificial Sequence
<220> FEATURE:
<223> OTHER INFORMATION: MF6744 CDR2

<400> SEQUENCE: 290

Ile Ile Phe Pro Asp Asp Ser Asp Thr Arg Tyr Ser Pro Ser Phe Gln
1 5 10 15

Gly

<210> SEQ ID NO 291
<211> LENGTH: 14
<212> TYPE: PRT
<213> ORGANISM: Artificial Sequence
<220> FEATURE:
<223> OTHER INFORMATION: MF6744 CDR3

<400> SEQUENCE: 291

Leu Gly Gly Tyr Ser Gly Tyr Ala Glu Asp Phe Val Asp Phe
1 5 10

<210> SEQ ID NO 292

<211> LENGTH: 123
<212> TYPE: PRT
<213> ORGANISM: Artificial Sequence
<220> FEATURE:
<223> OTHER INFORMATION: MF6744 VH

<400> SEQUENCE: 292

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Phe Pro Asp Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Pro Ser Asp Thr Ala Met Tyr Tyr Cys
                85                  90                  95

Val Arg Leu Gly Gly Tyr Ser Gly Tyr Ala Glu Asp Phe Val Asp Phe
            100                 105                 110

Trp Gly Gln Gly Thr Leu Val Thr Val Ser Ser
        115                 120

<210> SEQ ID NO 293
<211> LENGTH: 118
<212> TYPE: PRT
<213> ORGANISM: Artificial Sequence
<220> FEATURE:
<223> OTHER INFORMATION: MF4327 CLEC12A

<400> SEQUENCE: 293

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Thr Thr Gly Asp Trp Phe Asp Tyr Trp Gly Gln Gly Thr
            100                 105                 110

Leu Val Thr Val Ser Ser
        115

<210> SEQ ID NO 294
<211> LENGTH: 393
<212> TYPE: DNA
<213> ORGANISM: Artificial Sequence
<220> FEATURE:
<223> OTHER INFORMATION: H1H7232B (1129) VH-MF6955 in combination with
      common light chain, VH gene: IGHV3-9

<400> SEQUENCE: 294
gcggcccagc cggccatggc cgaggtgcag ctggtggagt cgggggaggg cttggttcac     60

```
cctggcaggt ccctgagact ctcctgtgca gcctctggat tcacctttga tgattatacc    120

atgcactggg tccggcaagc tccagggaag ggcctggaat gggtctcaga tattagttgg    180

aatagtggta gcagaggcta tgcggactct gtgaagggcc gattcaccat ctccagagat    240

aatgccgaga actccctgta cctgcaaatg aacagtctga gagctgagga cacggccttg    300

tattactgtg caaaagataa aagtggctac ggccactact actactacgc tatggacgtc    360

tggggccaag ggaccacggt caccgtctcc tca                                 393


<210> SEQ ID NO 295
<211> LENGTH: 131
<212> TYPE: PRT
<213> ORGANISM: Artificial Sequence
<220> FEATURE:
<223> OTHER INFORMATION: H1H7232B (1129) VH - MF6955 in combination with
      common light chain VH gene: IGHV3-9

<400> SEQUENCE: 295

Ala Ala Gln Pro Ala Met Ala Glu Val Gln Leu Val Glu Ser Gly Gly
1               5                   10                  15

Gly Leu Val His Pro Gly Arg Ser Leu Arg Leu Ser Cys Ala Ala Ser
            20                  25                  30

Gly Phe Thr Phe Asp Asp Tyr Thr Met His Trp Val Arg Gln Ala Pro
        35                  40                  45

Gly Lys Gly Leu Glu Trp Val Ser Asp Ile Ser Trp Asn Ser Gly Ser
    50                  55                  60

Arg Gly Tyr Ala Asp Ser Val Lys Gly Arg Phe Thr Ile Ser Arg Asp
65                  70                  75                  80

Asn Ala Glu Asn Ser Leu Tyr Leu Gln Met Asn Ser Leu Arg Ala Glu
                85                  90                  95

Asp Thr Ala Leu Tyr Tyr Cys Ala Lys Asp Lys Ser Gly Tyr Gly His
            100                 105                 110

Tyr Tyr Tyr Tyr Ala Met Asp Val Trp Gly Gln Gly Thr Thr Val Thr
        115                 120                 125

Val Ser Ser
    130


<210> SEQ ID NO 296
<211> LENGTH: 390
<212> TYPE: DNA
<213> ORGANISM: Artificial Sequence
<220> FEATURE:
<223> OTHER INFORMATION: H1H7241B (1145) VH - MF6964 in combination with
      common light chain VH gene: IGHV3-9

<400> SEQUENCE: 296

gcggcccagc cggccatggc cgaggtgcag ctggtggagt ctgggggagg cttggttcag     60

cctggcaggt ccctgagact ctcctgtgca gcctctggat ttacctttgc tgactatacc    120

atgcactggg tccggcaagg tccagggaag ggcctggagt gggtctcaga tattggttgg    180

aatagtaata ctataggcta tgcggactct gtgaagggcc gattcgccat ctccagagac    240

aacgccaaga actccctgta tcttcaaatg aacagtctgc gacctgagga cacggcctta    300

tattactgtg taaaggataa aagtggctac gggaaattcc aatacggttt ggacgtctgg    360

ggccaaggga ccacggtcac cgtctcctca                                     390


<210> SEQ ID NO 297
<211> LENGTH: 130
<212> TYPE: PRT
```

```
<213> ORGANISM: Artificial Sequence
<220> FEATURE:
<223> OTHER INFORMATION: H1H7241B (1145) VH - MF6964 in combination with
      common light chain VH gene: IGHV3-9

<400> SEQUENCE: 297

Ala Ala Gln Pro Ala Met Ala Glu Val Gln Leu Val Glu Ser Gly Gly
1               5                   10                  15

Gly Leu Val Gln Pro Gly Arg Ser Leu Arg Leu Ser Cys Ala Ala Ser
            20                  25                  30

Gly Phe Thr Phe Ala Asp Tyr Thr Met His Trp Val Arg Gln Gly Pro
        35                  40                  45

Gly Lys Gly Leu Glu Trp Val Ser Asp Ile Gly Trp Asn Ser Asn Thr
    50                  55                  60

Ile Gly Tyr Ala Asp Ser Val Lys Gly Arg Phe Ala Ile Ser Arg Asp
65                  70                  75                  80

Asn Ala Lys Asn Ser Leu Tyr Leu Gln Met Asn Ser Leu Arg Pro Glu
                85                  90                  95

Asp Thr Ala Leu Tyr Tyr Cys Val Lys Asp Lys Ser Gly Tyr Gly Lys
            100                 105                 110

Phe Gln Tyr Gly Leu Asp Val Trp Gly Gln Gly Thr Thr Val Thr Val
        115                 120                 125

Ser Ser
    130


<210> SEQ ID NO 298
<211> LENGTH: 126
<212> TYPE: PRT
<213> ORGANISM: Artificial Sequence
<220> FEATURE:
<223> OTHER INFORMATION: VH

<400> SEQUENCE: 298

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Phe
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Thr Ser Thr Ala Tyr
65                  70                  75                  80

Leu Gln Trp Ser Ser Leu Lys Ala Ser Asp Thr Gly Met Tyr Tyr Cys
                85                  90                  95

Val Arg His Ile Arg Tyr Phe Asp Trp Ser Glu Asp Tyr His Tyr Tyr
            100                 105                 110

Leu Asp Val Trp Gly Lys Gly Thr Thr Val Thr Val Ser Ser
        115                 120                 125


<210> SEQ ID NO 299
<211> LENGTH: 9
<212> TYPE: PRT
<213> ORGANISM: Artificial Sequence
<220> FEATURE:
<223> OTHER INFORMATION: CDR3

<400> SEQUENCE: 299

Gln Gln Ser Tyr Ser Thr Pro Pro Thr
```

-continued

```
1               5


<210> SEQ ID NO 300
<211> LENGTH: 10
<212> TYPE: PRT
<213> ORGANISM: Artificial Sequence
<220> FEATURE:
<223> OTHER INFORMATION: CDR3

<400> SEQUENCE: 300

Gln Gln Ser Tyr Ser Thr Pro Pro Ile Thr
1               5                   10
```